US008466193B2

(12) United States Patent
Verner et al.

(10) Patent No.: US 8,466,193 B2
(45) Date of Patent: Jun. 18, 2013

(54) SELECTIVE INHIBITORS OF HISTONE DEACETYLASE

(75) Inventors: Erik Verner, Belmont, CA (US); Sriram Balasubramanian, San Carlos, CA (US); Joseph J. Buggy, Mountain View, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 237 days.

(21) Appl. No.: 12/988,271

(22) PCT Filed: Apr. 15, 2009

(86) PCT No.: PCT/US2009/040709
§ 371 (c)(1),
(2), (4) Date: Dec. 1, 2010

(87) PCT Pub. No.: WO2009/129335
PCT Pub. Date: Oct. 22, 2009

(65) Prior Publication Data
US 2011/0081409 A1  Apr. 7, 2011

Related U.S. Application Data

(60) Provisional application No. 61/045,198, filed on Apr. 15, 2008.

(51) Int. Cl.
*A01N 43/36* (2006.01)
(52) U.S. Cl.
USPC .......................................... 514/427; 548/561
(58) Field of Classification Search
USPC ........................................ 548/561; 514/427
See application file for complete search history.

(56) References Cited

U.S. PATENT DOCUMENTS

| 2005/0137234 A1 | 6/2005 | Bressi et al. |
| 2007/0281934 A1 | 12/2007 | Buggy et al. |

FOREIGN PATENT DOCUMENTS

| WO | 03083067 | * 10/2003 |
| WO | WO-2005-028447 A1 | 3/2005 |
| WO | WO-2007-109178 | 9/2007 |
| WO | WO-2009-129335 A2 | 10/2009 |
| WO | WO-2009-129335 A3 | 10/2009 |

OTHER PUBLICATIONS

Apte and Voronov, "Interleukin-1—a major pleiotropic cytokine in tumor-host interactions," Cancer Biol 12:277-290 (2002).
Dai et al., Bioorg Med Chem Ltrs 13:1897-1901 (2003).
Grignani et al., "Fusion proteins of the retinoic acid receptor-α recruit histone deacetylase in promyelocytic leukaemia," Nature 391:815-818 (1998).
Kelly et al., "Phase 1 Clinical Trial of Histone Deacetylase Inhibitor: Suberoylanilide Hydroxamic Acid Administered Intravenously," Clin Cancer Res 9:3578-3588 (2003).
Kramer et al., "Histone deacetylase as a therapeutic target," Trends in Endocrinology and Metabolism 12(7):294-300 (2001).
Lee et al., Bioorg Med Chem Ltrs 17(17):4895-4900 (2007).
Lin et al., "Role of the histone deacetylase complex in acute promyelocytic leukaemia," Nature 391:811-814 (1998).
Patnaik et al., "A Phase I Study of Pivaloyloxymethyl Butyrate, a Prodrug of the Differentiating Agent Butyric Acid, in Patients with Advanced Solid Malignancies," Clin Cancer Res 8:2142-2148 (2002).
Piekarz et al., "Phase II trial of depsipeptide in patients with T-cell lymphoma: Review of responses and surrogate marker analysis," Proc Amer Assoc Cancer Res 46, 2005 (Abstract only).
Warrell et al., "Therapeutic Targeting of Transcription in Acute Promyelocytic Leukemia by Use of an Inhibitor of Histone Deacetylase," J National Cancer Inst 90(21):1621-1625 (1998).
PCT/US09/40709 Search Report dated Feb. 1, 2010.
PCT/US09/40709 IPER dated Oct. 28, 2010.
Mai et al., "3-(4-Aroyl-1-methyl-1H-2-pyrrolyl)-N-hydroxy-2-propenamides as a New Class of Synthetic Histone Deacetylase Inhibitors," Journ. Med. Chem., vol. 47, No. 1, pp. 1098-1109 (2004).
CA 2,721,218 Exam Report dated Feb. 15, 2012.
EP 09733489 Search Report dated Mar. 23, 2012.

* cited by examiner

*Primary Examiner* — Niloofar Rahmani
(74) *Attorney, Agent, or Firm* — Wilson, Sonsini, Goodrich & Rosati

(57) ABSTRACT

Described herein are compounds and pharmaceutical compositions containing such compounds, which inhibit the activity of histone deacetylase 8 (HDAC8). Also described herein are methods of using such HDAC8 inhibitors, alone and in combination with other compounds, for treating diseases or conditions that would benefit from inhibition of HDAC8 activity.

17 Claims, 4 Drawing Sheets

SELECTIVE INHIBITORS OF HISTONE DEACETYLASE

RELATED APPLICATIONS

This application is filed pursuant to 35 U.S.C. §371 as a United States National Phase Application of International Application No. PCT/US09/40709 entitled "SELECTIVE INHIBITORS OF HISTONE DEACETYLASE" filed Apr. 15, 2009, which claims benefit of U.S. Provisional Application No. 61/045,198 entitled "SELECTIVE INHIBITORS OF HISTONE DEACETYLASE" filed Apr. 15, 2008, which are herein incorporated by reference.

FIELD OF THE INVENTION

Described herein are compounds, methods of making such compounds, pharmaceutical compositions and medicaments that include such compounds, and methods of using such compounds to inhibit the activity of histone deacetylase 8.

BACKGROUND OF THE INVENTION

Histone deacetylases (HDACs) catalyze the removal of acetyl groups from histones, proteins that organize and modulate the structure of chromatin in nucleosomes. HDAC-mediated deacetylation of chromatin-bound histones regulates the expression of a variety of genes throughout the genome. Importantly, HDACs have been linked to cancer, as well as other health conditions. To date, eleven major HDAC isoforms have been described (HDACs 1-11). HDACs are categorized into two classes. Class I HDACs include HDAC1, HDAC2, HDAC3, HDAC8 and HDAC11. Class II HDACs include HDAC4, HDAC5, HDAC6, HDAC7, HDAC9 and HDAC10. Small molecule HDAC inhibitors that are isoform-selective are useful as therapeutic agents with reduced toxicity and as tools for probing the biology of the HDAC isoforms.

SUMMARY OF THE INVENTION

In one aspect provided herein are 1,2-disubstituted-1H-benzimidazole-6-carboxylic acid hydroxyamide compounds, 1,3-disubstituted-indole-6-carboxylic acid hydroxyamide compounds, 1,3-disubstituted-azaindole-6-carboxylic acid hydroxyamide compounds, substituted-1H-pyrrole-2-yl-N-hydroxyacrylamide compounds, and other selective HDAC8 inhibitors, pharmaceutically acceptable salts, pharmaceutically acceptable N-oxides, pharmaceutically active metabolites, pharmaceutically acceptable prodrugs, and pharmaceutically acceptable solvates thereof, which selectively inhibit HDAC8 activity and are used to treat mammals where inhibition of HDAC8 activity would provide benefit. Compounds described herein are selective HDAC8 inhibitors.

In one aspect, described herein is a compound having a structure of Formula I:

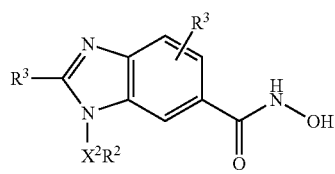

Formula I wherein:
X$^2$ is a bond, —C$_1$-C$_6$alkylene-, —C$_2$-C$_6$alkenylene-, —C$_2$-C$_6$alkynylene-, —C$_1$-C$_6$heteroalkylene-, C$_1$-C$_6$fluoroalkylene, C$_2$-C$_6$fluoroalkenylene, C$_1$-C$_6$haloalkylene, C$_2$-C$_6$haloalkenylene, —C$_1$-C$_6$alkylene-O—, —C$_1$-C$_3$alkylene-O—C$_1$-C$_3$alkylene-, —C$_1$-C$_6$alkylene-NH—, —C$_1$-C$_3$alkylene-NH—C$_1$-C$_3$alkylene-, —C$_1$-C$_6$alkylene-C(=O)NH—, —C$_1$-C$_3$alkylene-C(=O)NH—C$_1$-C$_3$alkylene-, —C$_1$-C$_6$alkylene-NHC(=O)—, —C$_1$-C$_3$alkylene-NHC(=O)—C$_1$-C$_3$alkylene-, —C$_1$-C$_6$alkylene-S—, —C$_1$-C$_3$alkylene-S—C$_1$-C$_3$alkylene-, —C$_1$-C$_6$alkylene-S(=O)—, —C$_1$-C$_3$alkylene-S(=O)—C$_1$-C$_3$alkylene, —C$_1$-C$_6$alkylene-S(=O)$_2$—, —C$_1$-C$_3$alkylene-S(=O)$_2$—C$_1$-C$_3$alkylene, —C(=O)—, or —C(=O)—C$_1$-C$_6$alkylene;

R$^2$ is a substituted or unsubstituted group selected from among aryl, heteroaryl, C$_3$-C$_{10}$cycloalkyl, and C$_2$-C$_{10}$heterocycloalkyl; where if R$^2$ is substituted, then R$^2$ is substituted with 1, 2, or 3 groups selected from among halogen, C$_1$-C$_6$alkoxy, C$_1$-C$_6$fluoroalkoxy, aminoC$_1$-C$_6$alkoxy, C$_1$-C$_3$alkylaminoC$_1$-C$_3$alkoxy, hydroxyC$_1$-C$_3$alkylaminoC$_1$-C$_3$alkoxy, C$_2$-C$_8$heterocycloalkylC$_1$-C$_3$alkoxy, C$_2$-C$_8$heterocycloalkylC$_1$-C$_2$alkyl, —CN, —NO$_2$, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=O)$_2$—R$^{11}$, OC(=O)N(R$^{10}$)$_2$, —NR$^{10}$C(=O)O—R$^{11}$, —OC(=O)O—R$^{11}$, —NHC(=O)NH—R$^{11}$, —OC(=O)—R$^{11}$, —N(R$^{10}$)$_2$, —C$_1$-C$_2$alkylN(R$^{10}$)$_2$, C$_1$-C$_6$alkyl, C$_1$-C$_6$fluoroalkyl, C$_2$-C$_6$alkenyl, C$_2$-C$_6$alkynyl, C$_1$-C$_6$heteroalkyl, C$_3$-C$_8$cycloalkyl, substituted or unsubstituted C$_2$-C$_{10}$heterocycloalkyl, substituted or unsubstituted aryl, and substituted or unsubstituted heteroaryl;

R$^{10}$ is hydrogen, or a substituted or unsubstituted group selected from among C$_1$-C$_6$alkyl, C$_1$-C$_6$fluoroalkyl, C$_1$-C$_6$heteroalkyl, C$_3$-C$_8$cycloalkyl, C$_2$-C$_8$heterocycloalkyl, aryl, and heteroaryl;

R$^{11}$ is a substituted or unsubstituted group selected from among C$_1$-C$_6$alkyl, C$_1$-C$_6$fluoroalkyl, C$_3$-C$_8$cycloalkyl, C$_2$-C$_8$heterocycloalkyl, aryl, and heteroaryl;

each R$^3$ is independently hydrogen, C$_1$-C$_6$alkyl, C$_2$-C$_6$alkenyl, C$_2$-C$_6$alkynyl, C$_1$-C$_6$alkoxy, C$_1$-C$_6$fluoroalkoxy, C$_1$-C$_6$heteroalkyl, substituted or unsubstituted phenyl, or C$_1$-C$_6$aminoalkyl;

or a pharmaceutically acceptable salt, pharmaceutically acceptable N-oxide, or pharmaceutically acceptable prodrug thereof.

For any and all of the embodiments, substituents are selected from among from a subset of the listed alternatives. For example, in some embodiments, each R$^3$ is hydrogen or C$_1$-C$_4$alkyl. In some other embodiments, each R$^3$ is hydrogen.

In some embodiments, X$^2$ is —C$_1$-C$_4$alkylene-, —C$_1$-C$_4$alkylene-O—, —C$_1$-C$_4$alkylene-NH—, —C$_1$-C$_4$alkylene-C(=O)NH—, —C$_1$-C$_4$alkylene-NHC(=O)—, —C$_1$-C$_4$alkylene-S—, —C$_1$-C$_4$alkylene-S(=O)—, —C$_1$-C$_4$alkylene-S(=O)$_2$—, —C(=O)—, or —C(=O)—C$_1$-C$_4$alkylene.

In some embodiments, R$^2$ is a substituted or unsubstituted group selected from among phenyl, monocyclic heteroaryl, C$_3$-C$_6$cycloalkyl, and C$_2$-C$_6$heterocycloalkyl.

In some embodiments, each R$^3$ is hydrogen; X$^2$ is —C$_1$-C$_4$alkylene-, —C$_1$-C$_4$alkylene-O—, —C$_1$-C$_4$alkylene- NH—, or —C$_1$-C$_4$alkylene-C(=O)NH—; R$^2$ is a substituted or unsubstituted phenyl or a substituted or unsubstituted monocyclic heteroaryl; where if R$^2$ is substituted, then R$^2$ is substituted with 1 or 2 groups selected from among halogen, C$_1$-C$_4$alkoxy, C$_1$-C$_4$fluoroalkoxy, (C$_3$-C$_6$heterocycloalkyl)C$_1$-C$_2$alkyl, —CN, —CO$_2$R$^{10}$, —C(=O)R$^{11}$, —NHC(=O)—R$^{11}$, —C(=O)N(R$^{10}$)$_2$, —S(=O)$_2$N(R$^{10}$)$_2$, —NHS(=O)$_2$—R$^{11}$, —N(R$^{10}$)$_2$, —C$_1$-C$_2$alkylN(R$^{10}$)$_2$, N(R$^{10}$)$_2$, C$_1$-C$_4$fluoroalkyl, and C$_1$-C$_4$heteroalkyl.

In some embodiments, X$^2$ is —C$_1$-C$_4$alkylene- or —C$_1$-C$_4$alkylene-O—.

In some embodiments, R$^2$ is a substituted or unsubstituted phenyl, a substituted or unsubstituted pyridinyl, a substituted or unsubstituted pyrimidinyl, a substituted or unsubstituted triazinyl, a substituted or unsubstituted pyrrolyl, a substituted or unsubstituted thiophenyl, or a substituted or unsubstituted furanyl.

In some embodiments, R$^2$ is a substituted or unsubstituted phenyl.

In some embodiments, R$^2$ is a substituted or unsubstituted phenyl; where if R$^2$ is substituted, then R$^2$ is substituted with 1 or 2 groups selected from among halogen, C$_1$-C$_4$alkoxy, C$_1$-C$_4$fluoroalkoxy, (C$_3$-C$_5$heterocycloalkyl)C$_1$-C$_2$alkyl, —NHC(=O)—R$^{11}$, —C(=O)N(R$^{10}$)$_2$, —S(=O)$_2$N(R$^{10}$)$_2$, —NHS(=O)$_2$—R$^{11}$, —C$_1$-C$_2$alkylN(R$^{10}$)$_2$, C$_1$-C$_4$alkyl, C$_1$-C$_4$fluoroalkyl, and C$_1$-C$_4$heteroalkyl.

In some embodiments, X$^2$ is —C$_1$-C$_3$alkylene-.

In some embodiments, X$^2$ is —C$_1$-C$_3$alkylene-O—.

In one aspect is a compound having a structure of Formula II:

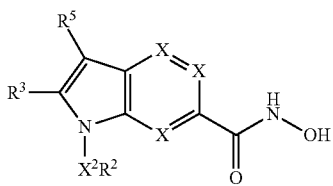

Formula II wherein:

each X is CR$^3$ or N, wherein one X is N;

X$^2$ is a bond, —C$_1$-C$_6$alkylene-, —C$_2$-C$_6$alkenylene-, —C$_2$-C$_6$alkynylene-, —C$_1$-C$_6$heteroalkylene-, C$_1$-C$_6$fluoroalkylene, C$_2$-C$_6$fluoroalkenylene, C$_1$-C$_6$haloalkylene, C$_2$-C$_6$haloalkenylene, —C$_1$-C$_6$alkylene-O—, —C$_1$-C$_3$alkylene-O—C$_1$-C$_3$alkylene-, —C$_1$-C$_6$alkylene-NH—, —C$_1$-C$_3$alkylene-NH—C$_1$-C$_3$alkylene-, —C$_1$-C$_6$alkylene-C(=O)NH—, —C$_1$-C$_3$alkylene-C(=O)NH—C$_1$-C$_3$alkylene-, —C$_1$-C$_6$alkylene-NHC(=O)—, —C$_1$-C$_3$alkylene-NHC(=O)—C$_1$-C$_3$alkylene-, —C$_1$-C$_6$alkylene-S—, —C$_1$-C$_3$alkylene-S—C$_1$-C$_3$alkylene-, —C$_1$-C$_6$alkylene-S(=O)—, —C$_1$-C$_3$alkylene-S(=O)—C$_1$-C$_3$alkylene-, —C$_1$-C$_6$alkylene-S(=O)$_2$—, —C$_1$-C$_3$alkylene-S(=O)$_2$—C$_1$-C$_3$alkylene-, —C(=O)—, or —C(=O)—C$_1$-C$_6$alkylene;

R$^2$ is a substituted or unsubstituted group selected from among aryl, heteroaryl, C$_3$-C$_{10}$cycloalkyl, and C$_2$-C$_{10}$heterocycloalkyl; where if R$^2$ is substituted, then R$^2$ is substituted with 1, 2, or 3 groups selected from among halogen, C$_1$-C$_6$alkoxy, C$_1$-C$_6$fluoroalkoxy, aminoC$_1$-C$_6$alkoxy, C$_1$-C$_3$alkylaminoC$_1$-C$_3$alkoxy, hydroxyC$_1$-C$_3$ alkylaminoC$_1$-C$_3$ alkoxy, C$_2$-C$_8$hetero cycloalkylC$_1$-C$_3$alkoxy, C$_2$-C$_8$heterocycloalkylC$_1$-C$_2$alkyl, —CN, —NO$_2$, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$NR$^{10}$)$_2$, —NR$^{10}$S(=O)$_2$—R$^{11}$, —OC(=O)N(R$^{10}$)$_2$, —NR$^{10}$C(=O)O—R$^{11}$, —OC(=O)O—R$^{11}$, —NHC(=O)NH—R$^{11}$, —OC(=O)—R$^{11}$, —N(R$^{10}$)$_2$, —C$_1$-C$_2$alkylN(R$^{10}$)$_2$, C$_1$-C$_6$alkyl, C$_1$-C$_6$fluoroalkyl, C$_2$-C$_6$alkenyl, C$_2$-C$_6$alkynyl, C$_1$-C$_6$heteroalkyl, C$_3$-C$_8$cycloalkyl, substituted or unsubstituted C$_2$-C$_{10}$heterocycloalkyl, substituted or unsubstituted aryl, substituted or unsubstituted heteroaryl;

R$^{10}$ is hydrogen, or a substituted or unsubstituted group selected from among C$_1$-C$_6$alkyl, C$_1$-C$_6$fluoroalkyl, C$_1$-C$_6$heteroalkyl, C$_3$-C$_8$cycloalkyl, C$_2$-C$_8$heterocycloalkyl, aryl, and heteroaryl;

R$^{11}$ is a substituted or unsubstituted group selected from among C$_1$-C$_6$alkyl, C$_1$-C$_6$fluoroalkyl, C$_3$-C$_8$cycloalkyl, C$_2$-C$_8$heterocycloalkyl, aryl, and heteroaryl;

each R$^3$ is independently hydrogen, C$_1$-C$_4$alkyl, C$_1$-C$_4$alkoxy, C$_1$-C$_4$fluoroalkoxy, or C$_1$-C$_4$heteroalkyl;

R$^5$ is hydrogen, C$_1$-C$_6$alkyl, C$_2$-C$_6$alkenyl, C$_2$-C$_6$alkynyl, C$_1$-C$_6$alkoxy, C$_1$-C$_6$fluoroalkoxy, C$_1$-C$_6$heteroalkyl, substituted or unsubstituted phenyl, C$_1$-C$_6$aminoalkyl, or —X$^6$—R$^6$;

X$^6$ is C$_1$-C$_6$alkylene, C$_1$-C$_6$fluoroalkylene, C$_2$-C$_6$alkenylene, or C$_2$-C$_6$heteroalkylene;

R$^6$ is hydrogen, halogen, —CN, hydroxy, amino, C$_1$-C$_6$alkylamino, di(C$_1$-C$_6$alkyl)amino, C$_1$-C$_6$alkoxy, C$_3$-C$_8$cycloalkyl, substituted or unsubstituted C$_2$-C$_8$heterocycloalkyl, substituted or unsubstituted phenyl, substituted or unsubstituted heteroaryl, or —X$^7$—R$^7$;

X$^7$ is a bond, —O—, —S—, —S(=O)—, —S(=O)$_2$—, —C(=O)—, —C(=O)O—, —OC(=O)—, —NHC(=O)—, —C(=O)NR$^a$—, —S(=O)$_2$NR$^a$—, —NHS(=O)$_2$—, —OC(=O)NR$^a$—, —NHC(=O)O—, —OC(=O)O—, —NHC(=O)NR$^a$—; wherein R$^a$ is selected from among hydrogen and C$_1$-C$_4$alkyl;

R$^7$ is hydrogen, C$_1$-C$_6$alkyl, C$_2$-C$_6$alkenyl, C$_1$-C$_6$heteroalkyl, C$_1$-C$_6$haloalkyl, C$_3$-C$_8$cycloallyl, (C$_3$-C$_8$cycloallyl)C$_1$-C$_2$alkylene, substituted or unsubstituted C$_2$-C$_8$heterocycloalkyl, (substituted or unsubstituted C$_2$-C$_8$heterocycloalkyl)C$_1$-C$_2$alkylene, substituted or unsubstituted phenyl, (substituted or unsubstituted phenyl)C$_1$-C$_2$alkylene, substituted or unsubstituted heteroaryl, (substituted or unsubstituted heteroaryl)C$_1$-C$_2$alkylene;

or a pharmaceutically acceptable salt, pharmaceutically acceptable N-oxide, or pharmaceutically acceptable prodrug thereof.

In some embodiments, each R$^3$ is independently hydrogen or C$_1$-C$_4$alkyl.

In some embodiments, X$^2$ is —C$_1$-C$_4$alkylene-, —C$_1$-C$_4$alkylene-O—, —C$_1$-C$_4$alkylene-NH—, —C$_1$-C$_4$alkylene-C(=O)NH—, —C$_1$-C$_4$alkylene-NHC(=O)—, —C$_1$-C$_4$alkylene-S—, —C$_1$-C$_4$alkylene-S(=O)—, —C$_1$-C$_4$alkylene-S(=O)$_2$—, —C(=O)—, or —C(=O)—C$_1$-C$_4$alkylene.

In some embodiments, R$^2$ is a substituted or unsubstituted group selected from among phenyl, monocyclic heteroaryl, C$_3$-C$_6$cycloalkyl, and C$_2$-C$_6$heterocycloalkyl; where if R$^2$ is substituted, then R$^2$ is substituted with 1 or 2 groups selected from among halogen, C$_1$-C$_4$alkoxy, C$_1$-C$_4$fluoroalkoxy, C$_2$-C$_8$heterocycloalkylC$_1$-C$_3$alkoxy, C$_2$-C$_8$heterocycloalkylC$_1$-C$_2$alkyl, —CN, —NO$_2$, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=O)$_2$—R$^{11}$, —OC(=O)N(R$^{10}$)$_2$, —NR$^{10}$C(=O)O—R$^{11}$, —OC(=O)O—R$^{11}$, —NHC(=O)NH—R$^{11}$, —OC(=O)—R$^{11}$, —N(R$^{10}$)$_2$, —C$_1$-C$_2$alkylN(R$^{10}$)$_2$, C$_1$-C$_4$alkyl, C$_1$-C$_4$fluoroalkyl, C$_2$-C$_4$alkenyl, C$_2$-C$_4$alkynyl, and C$_1$-C$_4$heteroalkyl.

In some embodiments, each R$^3$ is hydrogen.

In some embodiments, R$^5$ is hydrogen, C$_1$-C$_6$alkyl, C$_1$-C$_6$heteroalkyl, C$_1$-C$_6$aminoalkyl, or —X$^6$—R$^6$; X$^6$ is C$_1$-C$_4$alkylene; R$^6$ is amino, C$_1$-C$_4$alkylamino, di(C$_1$-C$_4$alkyl)amino, C$_1$-C$_4$alkoxy, C$_3$-C$_6$cycloalkyl, C$_2$-C$_6$heterocycloalkyl, substituted or unsubstituted phenyl, substituted or unsubstituted monocyclic heteroaryl, or —X$^7$—R$^7$; X$^7$ is a bond, —O—, —S—, —S(=O)—, —S(=O)$_2$—, —NH—, —C(=O)—, —C(=O)O—, —OC(=O)—, —NHC(=O)—, —C(=O)NH—, —S(=O)$_2$NH—, —NHS(=O)$_2$—, —OC(=O)NH—, —NHC(=O)O—, —OC(=O)O—, or —NHC(=O)NH—; R$^7$ is hydrogen, C$_1$-C$_6$alkyl, C$_3$-C$_8$cycloalkyl, (C$_3$-C$_8$cycloalkyl)C$_1$-C$_2$alkylene, substituted or unsubstituted C$_2$-C$_8$heterocycloalkyl, (substituted or unsubstituted C$_2$-C$_8$heterocycloalkyl)C$_1$-C$_2$alkylene, substituted or unsubstituted phenyl, (substituted or unsubstituted phenyl)C$_1$-C$_2$alkylene, substituted or unsubstituted monocyclic heteroaryl, or (substituted or unsubstituted monocyclic heteroaryl)C$_1$-C$_2$alkylene.

In some embodiments, X$^2$ is —C$_1$-C$_4$alkylene-, —C$_1$-C$_4$alkylene-O—, —C$_1$-C$_4$alkylene-NH—, or —C$_1$-C$_4$alkylene-C(=O)NH—.

In some embodiments, R$^2$ is a substituted or unsubstituted phenyl or a substituted or unsubstituted monocyclic heteroaryl; where if R$^2$ is substituted, then R$^2$ is substituted with 1 or 2 groups selected from among halogen, C$_1$-C$_4$alkoxy, C$_1$-C$_4$fluoroalkoxy, C$_3$-C$_6$heterocycloalkylC$_1$-C$_2$alkyl, —NHC(=O)—R$^{11}$, —C(=O)N(R$^{10}$)$_2$, —NHS(=O)$_2$N(R$^{10}$)$_2$, —R$^{11}$, —N(R$^{10}$)$_2$, —C$_1$-C$_2$alkylN(R$^{10}$)$_2$, C$_1$-C$_4$fluoroalkyl, and C$_1$-C$_4$heteroalkyl.

In some embodiments, R$^5$ is hydrogen, C$_1$-C$_4$alkyl, or C$_1$-C$_4$heteroalkyl.

In some embodiments, X$^2$ is —C$_1$-C$_4$alkylene- or —C$_1$-C$_4$alkylene-O—.

In some embodiments, R$^2$ is a substituted or unsubstituted phenyl, a substituted or unsubstituted pyridinyl, a substituted or unsubstituted pyrimidinyl, a substituted or unsubstituted triazinyl, a substituted or unsubstituted pyrrolyl, a substituted or unsubstituted thiophenyl, or a substituted or unsubstituted furanyl.

In some embodiments, R$^2$ is a substituted or unsubstituted phenyl.

In some embodiments, the compound of Formula II has the structure of Formula IId:

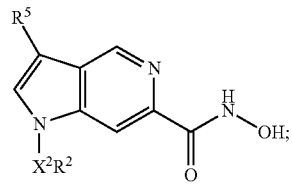

Formula IId or a pharmaceutically acceptable salt, pharmaceutically acceptable N-oxide, or pharmaceutically acceptable prodrug thereof.

In some embodiments, the compound of Formula II has the structure of Formula IIe:

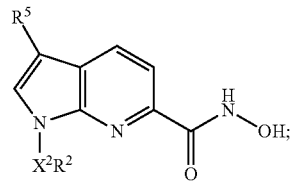

Formula IIe or a pharmaceutically acceptable salt, pharmaceutically acceptable N-oxide, or pharmaceutically acceptable prodrug thereof.

In some embodiments, the compound of Formula II has the structure of Formula IIf:

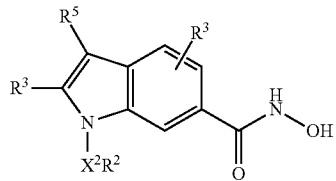

Formula IIf or a pharmaceutically acceptable salt, pharmaceutically acceptable N-oxide, or pharmaceutically acceptable prodrug thereof.

In one aspect, is a compound having the structure of Formula V:

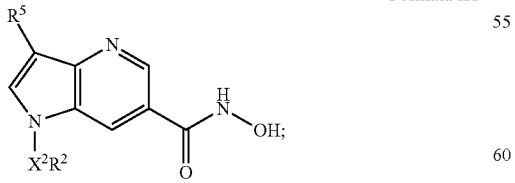

Formula V wherein:
X$^2$ is —C$_1$-C$_6$alkylene-O—, —C$_1$-C$_3$alkylene-O—C$_1$-C$_3$alkylene-, —C$_1$-C$_6$alkylene-NH—, —C$_1$-C$_3$alkylene-NH—C$_1$-C$_3$alkylene-, —C$_1$-C$_6$alkylene-C(=O)NH—, —C$_1$-C$_3$alkylene-C(=O)NH—C$_1$-C$_3$alkylene-, —C$_1$-C$_6$alkylene-NHC(=O)—, —C$_1$-C$_3$alkylene-NHC(=O)—C$_1$-C$_3$alkylene-, —C$_1$-C$_6$alkylene-S—, —C$_1$-C$_3$alkylene-S—C$_1$-C$_3$alkylene-, —C$_1$-C$_6$alkylene-S(=O)—, —C$_1$-C$_3$alkylene-S(=O)—C$_1$-C$_3$alkylene, —C$_1$-C$_6$alkylene-S(=O)$_2$—, or —C$_1$-C$_3$alkylene-S(=O)$_2$—C$_1$-C$_3$alkylene;

R$^2$ is a substituted or unsubstituted group selected from among aryl, heteroaryl, C$_3$-C$_{10}$cycloalkyl, and C$_2$-C$_{10}$heterocycloalkyl; where if R$^2$ is substituted, then R$^2$ is substituted with 1, 2, or 3 groups selected from among halogen, C$_1$-C$_6$alkoxy, C$_1$-C$_6$fluoroalkoxy, aminoC$_1$-C$_6$alkoxy, C$_1$-C$_3$alkylaminoC$_1$-C$_3$alkoxy, hydroxyC$_1$-C$_3$alkylaminoC$_1$-C$_3$alkoxy, C$_2$-C$_8$heterocycloalkylC$_1$-C$_3$alkoxy, C$_2$-C$_8$heterocycloalkylC$_1$-C$_2$alkyl, —CN, —NO$_2$, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$—R$^{11}$, —OC(=O)N(R$^{10}$)$_2$, —NR$^{10}$C(=O)O—R$^{11}$, —OC(=O)O—R$^{11}$, —NHC (=O)NH—$R^{11}$, —OC(=O)—$R^{11}$, —N($R^{10}$)$_2$, —$C_1$-$C_2$alkylN($R^{10}$)$_2$, $C_1$-$C_6$alkyl, $C_1$-$C_6$fluoroalkyl, $C_2$-$C_6$alkenyl, $C_2$-$C_6$alkynyl, $C_1$-$C_6$heteroalkyl, $C_3$-$C_8$cycloalkyl, substituted or unsubstituted $C_2$-$C_{10}$heterocycloalkyl, substituted or unsubstituted aryl, substituted or unsubstituted heteroaryl;

$R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

each $R^3$ is independently hydrogen, $C_1$-$C_4$alkyl, $C_1$-$C_4$alkoxy, $C_1$-$C_4$fluoroalkoxy, or $C_1$-$C_4$heteroalkyl;

$R^5$ is hydrogen, $C_1$-$C_6$alkyl, $C_2$-$C_6$alkenyl, $C_2$-$C_6$alkynyl, $C_1$-$C_6$alkoxy, $C_1$-$C_6$fluoroalkoxy, $C_1$-$C_6$heteroalkyl, substituted or unsubstituted phenyl, $C_1$-$C_6$aminoalkyl, or —$X^6$—$R^6$;

$X^6$ is $C_1$-$C_6$alkylene, $C_1$-$C_6$fluoroalkylene, $C_2$-$C_6$alkenylene, or $C_2$-$C_6$heteroalkylene;

$R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, substituted or unsubstituted $C_2$-$C_8$heterocycloalkyl, substituted or unsubstituted phenyl, substituted or unsubstituted heteroaryl, or $X^7$—$R^7$;

$X^7$ is a bond, —O—, —S—, —S(=O)—, —S(=O)$_2$—, —C(=O)—, —C(=O)O—, —OC(=O)—, —NHC(=O)—, —C(=O)NR$^a$—, —S(=O)$_2$NR$^a$—, —NHS(=O)$_2$—, —OC(=O)NR$^a$—, —NHC(=O)O—, —OC(=O)O—, —NHC(=O)NR$^a$; wherein R$^a$ is selected from among hydrogen and $C_1$-$C_4$alkyl;

$R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, ($C_3$-$C_8$cycloalkyl)$C_1$-$C_2$alkylene, substituted or unsubstituted $C_2$-$C_8$heterocycloalkyl, (substituted or unsubstituted $C_2$-$C_8$heterocycloalkyl)$C_1$-$C_2$alkylene, substituted or unsubstituted phenyl, (substituted or unsubstituted phenyl)$C_1$-$C_2$alkylene, substituted or unsubstituted heteroaryl, (substituted or unsubstituted heteroaryl)$C_1$-$C_2$alkylene;

or a pharmaceutically acceptable salt, pharmaceutically acceptable N-oxide, or pharmaceutically acceptable prodrug thereof.

In some embodiments, $X^2$ is —$C_1$-$C_4$alkylene-O—, —$C_1$-$C_4$alkylene-NH—, —$C_1$-$C_4$alkylene-C(=O)NH—, —$C_1$-$C_4$alkylene-NHC(=O)—, —$C_1$-$C_4$alkylene-S—, —$C_1$-$C_4$alkylene-S(=O)—, or —$C_1$-$C_4$alkylene-S(=O)$_2$—.

In some embodiments, each $R^3$ is independently hydrogen or $C_1$-$C_4$alkyl.

In some embodiments, $R^2$ is a substituted or unsubstituted group selected from among phenyl and monocyclic heteroaryl; where if $R^2$ is substituted, then $R^2$ is substituted with 1 or 2 groups selected from among halogen, $C_1$-$C_4$alkoxy, $C_1$-$C_4$fluoroalkoxy, $C_2$-$C_6$heterocycloalkyl$C_1$-$C_3$alkoxy, $C_2$-$C_6$heterocycloalkyl$C_1$-$C_2$alkyl, —CN, —NO$_2$, —CO$_2$$R^{10}$, —C(=O)$R^{11}$, —S—$R^{11}$, —S(=O)—$R^{11}$, —S(=O)$_2$—$R^{11}$, —NR$^{10}$C(=O)—$R^{11}$, —C(=O)N(R$^{10}$)$_2$, —S(=O)$_2$N(R$^{10}$)$_2$, NR$^{10}$S(=O)$_2$—$R^{11}$, —OC(=O)N(R$^{10}$)$_2$, —NR$^{10}$C(=O)O—$R^{11}$, —OC(=O)O—$R^{11}$, —NHC(=O)NH—$R^{11}$, —OC(=O)—$R^{11}$)—N(R$^{10}$)$_2$, —$C_1$-$C_2$alkylN(R$^{10}$)$_2$, $C_1$-$C_4$alkyl, $C_1$-$C_4$fluoroalkyl, $C_2$-$C_4$alkenyl, $C_2$-$C_4$alkynyl, $C_1$-$C_4$heteroalkyl, $C_3$-$C_6$cycloalkyl, substituted or unsubstituted $C_2$-$C_6$heterocycloalkyl, substituted or unsubstituted phenyl, substituted or unsubstituted monocyclic heteroaryl.

In some embodiments, $R^5$ is hydrogen, $C_1$-$C_6$alkyl, $C_1$-$C_6$heteroalkyl, $C_1$-$C_6$aminoalkyl, or —$X^6$—$R^6$; $X^6$ is $C_1$-$C_4$alkylene; $R^6$ is hydrogen, halogen, —CN, hydroxy, amino, $C_1$-$C_4$alkylamino, di($C_1$-$C_4$alkyl)amino, $C_1$-$C_4$alkoxy, $C_3$-$C_6$cycloalkyl, $C_2$-$C_6$heterocycloalkyl, substituted or unsubstituted phenyl, substituted or unsubstituted heteroaryl, or —$X^7$—$R^7$; $X^7$ is a bond, —O—, —S—, —S(=O)—, —S(=O)$_2$—, —NH—, —C(=O)—, —C(=O)O—, —OC(=O)—, —NHC(=O)—, —C(=O)NH—, —S(=O)$_2$NH—, —NHS(=O)$_2$—, —OC(=O)NH—, —NHC(=O)O—, —OC(=O)O—, —NHC(=O)NH—; $R^7$ is hydrogen, $C_1$-$C_6$alkyl, $C_3$-$C_8$cycloalkyl, ($C_3$-$C_8$cycloalkyl)$C_1$-$C_2$alkylene, substituted or unsubstituted $C_2$-$C_8$heterocycloalkyl, (substituted or unsubstituted $C_2$-$C_8$heterocycloalkyl)$C_1$-$C_2$alkylene, substituted or unsubstituted phenyl, (substituted or unsubstituted phenyl)$C_1$-$C_2$alkylene, substituted or unsubstituted monocyclic heteroaryl, (substituted or unsubstituted monocyclic heteroaryl) $C_1$-$C_2$alkylene.

In some embodiments, $R^2$ is a substituted or unsubstituted group selected from among phenyl and monocyclic heteroaryl; where if $R^2$ is substituted, then $R^2$ is substituted with 1 or 2 groups selected from among halogen, $C_1$-$C_4$alkoxy, $C_1$-$C_4$fluoroalkoxy, $C_2$-$C_6$heterocycloalkyl$C_1$-$C_3$alkoxy, $C_2$-$C_6$heterocycloalkyl$C_1$-$C_2$alkyl, —CN, —NO$_2$, —C(=O)$R^{11}$, —NHC(=O)—$R^{11}$, —C(=O)N(R$^{10}$)$_2$, —S(=O)$_2$N(R$^{10}$)$_2$, —NHS(=O)$_2$—$R^{11}$, —N(R$^{10}$)$_2$, —$C_1$-$C_2$alkylN(R$^{10}$)$_2$, $C_1$-$C_4$alkyl, $C_1$-$C_4$fluoroalkyl, $C_1$-$C_4$heteroalkyl, $C_3$-$C_6$cycloalkyl, substituted or unsubstituted $C_2$-$C_6$heterocycloalkyl, substituted or unsubstituted phenyl, substituted or unsubstituted monocyclic heteroaryl.

In some embodiments, each $R^3$ is hydrogen.

In some embodiments, $R^5$ is hydrogen, $C_1$-$C_4$alkyl, $C_1$-$C_4$heteroalkyl, $C_1$-$C_4$-aminoalkyl, or —$X^6$—$R^6$;

$X^6$ is $C_1$-$C_4$alkylene; $R^6$ is hydroxy, amino, $C_1$-$C_4$alkylamino, di($C_1$-$C_4$alkyl)amino, $C_1$-$C_4$alkoxy, $C_3$-$C_6$cycloalkyl, $C_2$-$C_6$heterocycloalkyl, substituted or unsubstituted phenyl, substituted or unsubstituted monocyclic heteroaryl, or —$X^7$—$R^7$; $X^7$ is a bond, —O—, —NH—, —NHC(=O)—, —C(=O)NH—, —S(=O)$_2$NH—, —NHS(=O)$_2$—; $R^7$ is $C_1$-$C_4$alkyl, $C_3$-$C_6$cycloalkyl, ($C_3$-$C_6$cycloalkyl)$C_1$-$C_2$alkylene, substituted or unsubstituted $C_2$-$C_6$heterocycloalkyl, (substituted or unsubstituted $C_2$-$C_6$heterocycloalkyl)$C_1$-$C_2$alkylene, substituted or unsubstituted phenyl, (substituted or unsubstituted phenyl)$C_1$-$C_2$alkylene, substituted or unsubstituted monocyclic heteroaryl, (substituted or unsubstituted monocyclic heteroaryl) $C_1$-$C_2$alkylene.

In some embodiments, $X^2$ is —$C_1$-$C_2$alkylene-O—, —$C_1$-$C_2$alkylene-NH—, or —$C_1$-$C_2$alkylene-C(=O)NH—.

In some embodiments, $R^2$ is a substituted or unsubstituted group selected from among phenyl and monocyclic heteroaryl; where if $R^2$ is substituted, then $R^2$ is substituted with 1 or 2 groups selected from among halogen, $C_1$-$C_4$alkoxy, $C_1$-$C_4$fluoroalkoxy, $C_2$-$C_6$heterocycloalkyl$C_1$-$C_2$alkyl, —C(=O)$R^{11}$, —NHC(=O)—$R^{11}$, —C(=O)N(R$^{10}$)$_2$, —S(=O)$_2$N(R$^{10}$)$_2$, —NHS(=O)$_2$—$R^{11}$, —N(R$^{10}$)$_2$, —$C_1$-$C_2$alkylN(R$^{10}$)$_2$, $C_1$-$C_4$alkyl, $C_1$-$C_4$fluoroalkyl, $C_1$-$C_4$heteroalkyl.

In some embodiments, $R^2$ is a substituted or unsubstituted group selected from phenyl, pyridinyl, pyrimidinyl, triazinyl, pyrrolyl, thiophenyl, and furanyl.

In some embodiments, $R^2$ is a substituted or unsubstituted phenyl.

In some embodiments, $R^5$ is hydrogen or $C_1$-$C_4$alkyl.

In one aspect is a compound of Formula B:

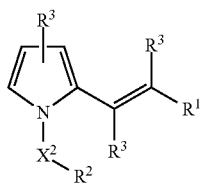

Formula B wherein:
R$^1$ is —C(=O)NHOH;
X$^2$ is a bond, —C$_1$-C$_6$alkylene-, —C$_2$-C$_6$alkenylene-, —C$_2$-C$_6$alkynylene-, —C$_1$-C$_6$heteroalkylene-, C$_1$-C$_6$fluoroalkylene, C$_2$-C$_6$fluoroalkenylene, C$_1$-C$_6$haloalkylene, C$_2$-C$_6$haloalkenylene, —C$_1$-C$_6$alkylene-O—, —C$_1$-C$_3$alkylene-O—C$_1$-C$_3$alkylene-, —C$_1$-C$_6$alkylene-NH—, —C$_1$-C$_3$alkylene-NH—C$_1$-C$_3$alkylene-, —C$_1$-C$_6$alkylene-C(=O)NH—, —C$_1$-C$_3$alkylene-C(=O)NH—C$_1$-C$_3$alkylene-, —C$_1$-C$_6$alkylene-NHC(=O)—, —C$_1$-C$_3$alkylene-NHC(=O)—C$_1$-C$_3$alkylene-, —C$_1$-C$_6$alkylene-S—, —C$_1$-C$_3$alkylene-S—C$_1$-C$_3$alkylene-, —C$_1$-C$_6$alkylene-S(=O)—, —C$_1$-C$_3$alkylene-S(=O)—C$_1$-C$_3$alkylene, —C$_1$-C$_6$alkylene-S(=O)$_2$—, —C$_1$-C$_3$alkylene-S(=O)$_2$—C$_1$-C$_3$alkylene, —C(=O)—, or —C(=O)—C$_1$-C$_6$alkylene;
R$^2$ is a substituted or unsubstituted group selected from aryl, heteroaryl, C$_3$-C$_{10}$cycloalkyl, and C$_2$-C$_{10}$heterocycloalkyl; where if R$^2$ is substituted, then R$^2$ is substituted with 1, 2, or 3 groups selected from among halogen, C$_1$-C$_6$alkoxy, C$_1$-C$_6$fluoroalkoxy, aminoC$_1$-C$_6$alkoxy, C$_1$-C$_3$alkylaminoC$_1$-C$_3$alkoxy, hydroxyC$_1$-C$_3$alkylaminoC$_1$-C$_3$alkoxy, C$_2$-C$_8$heterocycloalkylC$_1$-C$_3$alkoxy, C$_2$-C$_8$heterocycloalkylC$_1$-C$_2$alkyl, —CN, —NO$_2$, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=O)$_2$—R$^{11}$, —OC(=O)N(R$^{10}$)$_2$, —NR$^{10}$C(=O)O—R$^{11}$, —OC(=O)O—R$^{11}$, —NHC(=O)NH—R$^{11}$, —OC(=O)—R$^{11}$, —N(R$^1$)$_2$, —C$_1$-C$_2$alkylN(R$^{10}$)$_2$, C$_1$-C$_6$alkyl, C$_1$-C$_6$fluoroalkyl, C$_2$-C$_6$alkenyl, C$_2$-C$_6$alkynyl, C$_1$-C$_6$heteroalkyl, C$_3$-C$_8$cycloalkyl, substituted or unsubstituted C$_2$-C$_{10}$heterocycloalkyl, substituted or unsubstituted aryl, substituted or unsubstituted heteroaryl;
R$^{10}$ is hydrogen, or a substituted or unsubstituted group selected from among C$_1$-C$_6$alkyl, C$_1$-C$_6$fluoroalkyl, C$_1$-C$_6$heteroalkyl, C$_3$-C$_8$cycloalkyl, C$_2$-C$_8$heterocycloalkyl, aryl, and heteroaryl;
R$^{11}$ is a substituted or unsubstituted group selected from among C$_1$-C$_6$alkyl, C$_1$-C$_6$fluoroalkyl, C$_3$-C$_8$cycloalkyl, C$_2$-C$_8$heterocycloalkyl, aryl, and heteroaryl;
each R$^3$ is independently hydrogen, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$alkoxy, substituted or unsubstituted C$_1$-C$_6$fluoroalkoxy, substituted or unsubstituted C$_1$-C$_6$heteroalkyl, substituted or unsubstituted phenyl, or C$_1$-C$_6$aminoalkyl;
or a pharmaceutically acceptable salt, pharmaceutically acceptable N-oxide, or pharmaceutically acceptable prodrug thereof.

In some embodiments, each R$^3$ is independently hydrogen or C$_1$-C$_4$alkyl.

In some embodiments, each R$^3$ is hydrogen.

In some embodiments, the compound of Formula B has the structure of Formula IIIb:

Formula IIIb

In some embodiments, X$^2$ is a bond, —C$_1$-C$_6$alkylene-, —C$_1$-C$_6$alkylene-O—, —C$_1$-C$_3$alkylene-O—C$_1$-C$_3$alkylene-, —C$_1$-C$_6$alkylene-NH—, —C$_1$-C$_3$alkylene-NH—C$_1$-C$_3$alkylene-, —C$_1$-C$_6$alkylene-C(=O)NH—, —C$_1$-C$_3$alkylene-C(=O)NH—C$_1$-C$_3$alkylene-, —C$_1$-C$_6$alkylene-NHC(=O)—, —C$_1$-C$_3$alkylene-NHC(=O)—C$_1$-C$_3$alkylene-, —C$_1$-C$_6$alkylene-S—, —C$_1$-C$_3$alkylene-S—C$_1$-C$_3$alkylene-, —C$_1$-C$_6$alkylene-S(=O)—, —C$_1$-C$_3$alkylene-S(=O)—C$_1$-C$_3$alkylene, —C$_1$-C$_6$alkylene-S(=O)$_2$—, —C$_1$-C$_3$alkylene-S(=O)$_2$—C$_1$-C$_3$alkylene, —C(=O)—, or —C(=O)—C$_1$-C$_6$alkylene.

In some embodiments, R$^2$ is a substituted or unsubstituted group selected from phenyl, monocyclic heteroaryl, C$_3$-C$_6$cycloalkyl, and monocyclic C$_2$-C$_6$heterocycloalkyl; where if R$^2$ is substituted, then R$^2$ is substituted with 1 or 2 groups selected from among halogen, C$_1$-C$_4$alkoxy, C$_1$-C$_4$fluoroalkoxy, C$_3$-C$_6$heterocycloalkylC$_1$-C$_2$alkyl, —CN, —NO$_2$, —CO$_2$R$^{10}$, —C(=O)R$^{11}$, —S—R$^{11}$, —S(=O)—R$^{11}$, —S(=O)$_2$—R$^{11}$, —NHC(=O)—R$^{11}$, —C(=O)N(R$^{10}$)$_2$, —S(=O)$_2$N(R$^{10}$)$_2$, —NHS(=O)$_2$—R$^{11}$, —OC(=O)N(R$^{10}$)$_2$, —NHC(=O)O—R$^{11}$, —OC(=O)O—R$^{11}$, —NHC(=O)NH—R$^{11}$, —OC(=O)—R$^{11}$, —N)(R$^{10}$)$_2$, —C$_1$-C$_2$alkylN(R$^{10}$)$_2$, C$_1$-C$_4$alkyl, C$_1$-C$_4$fluoroalkyl, C$_1$-C$_4$heteroalkyl, C$_3$-C$_6$cycloalkyl, substituted or unsubstituted C$_2$-C$_6$heterocycloalkyl, substituted or unsubstituted phenyl, substituted or unsubstituted monocyclic heteroaryl.

In some embodiments, X$^2$ is a bond, —C$_1$-C$_4$alkylene-, —C$_1$-C$_4$alkylene-O—, —C$_1$-C$_4$alkylene-C(=O)NH—, —C$_1$-C$_4$alkylene-NHC(=O)—, —C$_1$-C$_4$alkylene-S—, —C$_1$-C$_4$alkylene-S(=O)—, —C$_1$-C$_4$alkylene-S(=O)$_2$—, or —C(=O)—C$_1$-C$_4$alkylene.

In some embodiments, X$^2$ is —C$_1$-C$_4$alkylene- or —C$_1$-C$_4$alkylene-O—.

In some embodiments, R$^2$ is a substituted or unsubstituted group selected from among phenyl and monocyclic heteroaryl.

In some embodiments, R$^2$ is a substituted or unsubstituted phenyl, or a substituted or unsubstituted 5- or 6-membered monocyclic heteroaryl group; where if R$^2$ is substituted, then R$^2$ is substituted with 1 or 2 groups selected from among halogen, C$_1$-C$_4$alkoxy, C$_1$-C$_4$fluoroalkoxy, C$_3$-C$_6$heterocycloalkylC$_1$-C$_2$alkyl, —CN, —CO$_2$R$^{10}$, —C(=O)R$^{11}$, —NHC(=O)—R$^{11}$, —C(=O)N(R$^{10}$)$_2$, —S(=O)$_2$N(R$^{10}$)$_2$, —NHS(=O)$_2$—R$^{11}$, —N(R$^{10}$)$_2$, —C$_1$-C$_2$alkylN(R$^{10}$)$_2$, C$_1$-C$_4$fluoroalkyl, and C$_1$-C$_4$heteroalkyl.

In some embodiments, R$^2$ is a substituted or unsubstituted group selected from phenyl, pyridinyl, pyrimidinyl, triazinyl, pyrrolyl, thiophenyl, and furanyl.

In some embodiments, R$^2$ is a substituted or unsubstituted 5- or 6-membered monocyclic heteroaryl group.

In some embodiments, R$^2$ is a substituted or unsubstituted phenyl.

In some embodiments, $X^2$ is —$C_1$-$C_4$alkylene-.

In some embodiments, $X^2$ is $C_1$-$C_4$alkylene-O—.

In a further aspect is a pharmaceutical composition comprising a HDAC8 inhibitor compound described herein, or a pharmaceutically acceptable salt, pharmaceutically acceptable N-oxide, or pharmaceutically acceptable prodrug thereof and a pharmaceutically acceptable diluent, excipient, or carrier.

In one aspect, the pharmaceutical composition is formulated for intravenous injection, subcutaneous injection, oral administration, inhalation, nasal administration, topical administration, ophthalmic administration or otic administration.

In one aspect, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In one aspect, HDAC8 8 inhibitor compounds described herein are for treating T-cell lymphoma or leukemia in a mammal.

In one aspect is the use of a HDAC8 8 inhibitor compound described herein in the manufacture of a medicament for treating T-cell lymphoma or leukemia in a mammal.

Also described is a a method of treating a disease or condition mediated by interleukin-1 beta (IL-1b) or IL-18 in a mammal, comprising administering to the mammal a therapeutically effective amount of a HDAC8 8 inhibitor compound described herein, or a pharmaceutically acceptable salt, pharmaceutically acceptable N-oxide, pharmaceutically active metabolite, pharmaceutically acceptable prodrug, or pharmaceutically acceptable solvate thereof. In one aspect, the disease or condition is selected from among osteoarthritis, rheumatoid arthritis, septic arthritis, gout, pseudogout, juvenile arthritis, Still's disease, Ankylosing spondylitis, systemic lupus erythematosus (SLE), Henoch-Schönlein purpura, psoriatic arthritis, reactive arthritis (Reiter's syndrome), hemochromatosis, hepatitis, Wegener's granulomatosis, Familial Mediterranean fever (FMF), HIDS (hyperimmunoglobulinemia D and periodic fever syndrome), TRAPS (TNF-alpha receptor associated periodic fever syndrome), inflammatory bowel disease, Crohn's Disease, ulcerative colitis, recurrent fever, anemia, leukocytosis, asthma, chronic obstructive pulmonary disease, and myalgia.

In one aspect, the method further comprises administering to the mammal a second therapeutic agent, selected from among tacrolimus, cyclosporin, rapamicin, methotrexate, cyclophosphamide, azathioprine, mercaptopurine, mycophenolate, or FTY720, prednisone, cortisone acetate, prednisolone, methylprednisolone, dexamethasone, betamethasone, triamcinolone, beclometasone, fludrocortisone acetate, deoxycorticosterone acetate, aldosterone, aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketolorac tromethamine, naproxen, oxaprozin, diclofenac, etodolac, indomethacin, sulindac, tolmetin, meclofenamate, meclofenamate sodium, mefenamic acid, piroxicam, meloxicam, celecoxib, rofecoxib, valdecoxib, parecoxib, etoricoxib, lumiracoxib, CS-502, JTE-522, L-745,337 and NS398, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, allergy vaccines, antihistamines, antileukotrienes, beta-agonists, theophylline, and anticholinergics.

In one aspect, HDAC8 8 inhibitor compounds described herein are for treating a disease or condition mediated by interleukin-1 beta (IL-1b) or IL-18 in a mammal.

In one aspect is the use of a HDAC8 8 inhibitor compounds described herein in the manufacture of a medicament for treating a disease or condition mediated by interleukin-1 beta (IL-1b) or IL-18 in a mammal.

In one aspect, the mammal is a human.

In any of the aforementioned embodiments involving the treatment with a HDAC8 inhibitor compound are further embodiments comprising administering at least one additional agent in addition to the administration of a HDAC8 inhibitor compound. Each agent is administered in any order, including simultaneously.

In some embodiments, compounds described herein are administered to a human.

In some embodiments, compounds described herein are orally administered.

In some embodiments, compounds described herein are used for inhibiting the activity of HDAC8 or for the treatment of a disease or condition that would benefit from inhibition of the activity of HDAC8.

In some embodiments, compounds described herein are used for the formulation of a medicament for the inhibition of HDAC8 activity.

Articles of manufacture, which include packaging material, a HDAC8 inhibitor compound described herein, within the packaging material, and a label that indicates that the compound or composition, or pharmaceutically acceptable salt, pharmaceutically acceptable N-oxide, prodrug, or pharmaceutically acceptable solvate thereof, is used for inhibiting the activity of HDAC8, or for the treatment, prevention or amelioration of one or more symptoms of a disease or condition that would benefit from inhibition of the activity of HDAC8, are provided.

Other objects, features and advantages of the methods, compounds, and compositions described herein will become apparent from the following detailed description. It should be understood, however, that the detailed description and the specific examples, while indicating specific embodiments, are given by way of illustration only, since various changes and modifications within the spirit and scope of the disclosure will become apparent from this detailed description.

INCORPORATION BY REFERENCE

Figure 1:
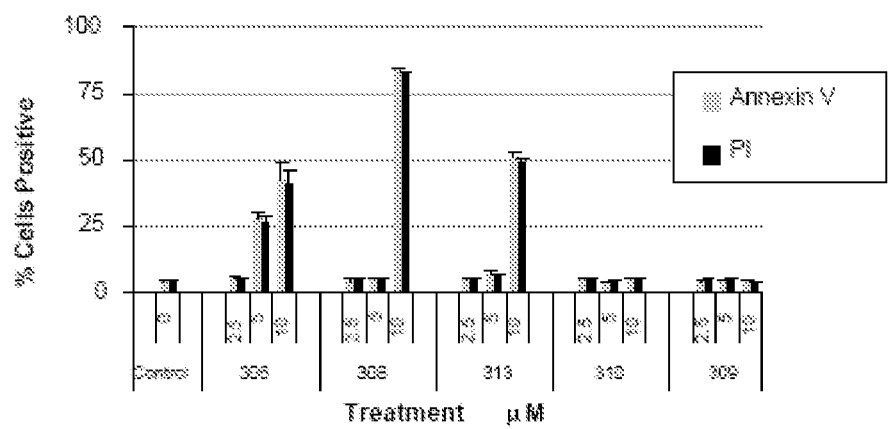
FIG. 1 is an illustrative panel of scatter plots showing the effect of HDAC8 selective inhibitor compounds on cell proliferation in Jurkat cells. Apoptosis was measured by Annexin-V flow cytommetry.
Figure 2:
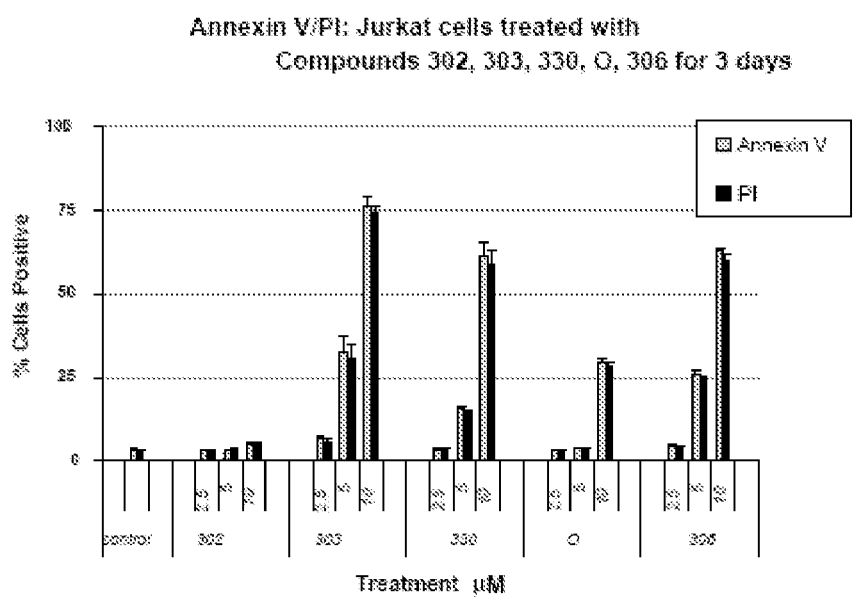
FIG. 2 is an illustrative panel of scatter plots showing the effect of HDAC8 selective inhibitors compounds on cell proliferation in Jurkat cells. Apoptosis was measured by Annexin-V flow cytommetry. Compound O is 3-(benzyloxy)-N-hydroxylbenzamide.

All publications, patents, and patent applications mentioned in this specification are herein incorporated by reference for the disclosure for which the item is being cited.

DETAILED DESCRIPTION

Covalent modification of histone proteins through acetylation and deacetylation is an important determinant of chromatin structure and a regulator of gene expression. Acetylation of histone proteins occurs on lysine residues near the N-termini of these proteins. In conjunction with other modifications of histone proteins and DNA, the acetylation state of histones determines whether the chromatin is in a condensed, transcriptionally silent state or in a form more accessible to the transcription machinery of the cell. In general, hyperacetylation of histone proteins is associated with transcriptional activation of genes. The steady-state histone acetylation level arises from the opposing action of histone acetyltransferase (HAT) and histone deacetylase (HDAC) enzymes.

Histone deacetylases (HDACs) catalyze the removal of acetyl groups from lysine ε-amino groups near the N-termini of histones. This reaction promotes the condensation of chromatin, leading to repression of transcription.

HDAC inhibitors (HDIs) modify gene expression positively or negatively in a cell- and gene-specific manner. HDIs increase the accumulation of acetylated histones, directly influencing chromatin structure and, thereby, the relationship of the nucleosome to gene promoter elements.

Histone deacetylase (HDAC) enzymes modulate gene expression through the deacetylation of acetylated lysine residues on histone proteins. They operate in biological systems as part of multiprotein corepressor complexes. Histone deacetylases have been grouped into three classes. Class I and class II histone deacetylases (HDACs) are zinc containing hydrolase enzymes. The division of the proteins into classes I and II is based on protein size, sequence similarity, and organization of the protein domains.

Members of class I are related to the yeast RPD3 gene product. Class I HDACs include: HDAC1; HDAC2; HDAC3; HDAC8; HDAC11.

HDAC8 is a 377 residue, 42 kDa protein localized to the nucleus of a wide array of tissues, as well as several human tumor cell lines. The wild-type form of full length HDAC8 is described in GenBank Accession Number NP 060956; Buggy, J. J. et al., *Biochem. J.*, 350 (Pt 1), 199-205 (2000). The HDAC8 structure was solved with four different hydroxamate inhibitors bound (Somoza et al., *Structure*, 2004, 12, 1325)

Class II are homologues of the yeast HDA1 protein, and include: HDAC4; HDAC5; HDAC6; HDAC7; HDAC9; HDAC10.

Class II HDACs have been further subdivided into classes IIa (HDACs 4, 5, 7, and 9) and IIb (HDACs 6 and 10).

The third class of deacetylases consists of the members of the Sir2 family of enzymes. These enzymes have histone deacetylase activity but are structurally and evolutionarily unrelated to the class I and class II proteins. They are (nicotinamide adenine dinucleotide) NAD-dependent and unlike class I HDACs and class II HDACs, they do not contain a catalytic zinc site.

In the cell, HDAC proteins are recruited as part of multicomponent repressor complexes. Several HDAC containing complexes have been characterized, including the N-CoR/SMRT, Sin3, NuRD, and CoREST complexes. Within these complexes, HDACs 1 and 2 typically interact with the mSin3, Mi-2, or CoREST proteins. HDAC3 and the class IIa HDACs have been shown to interact with SMRT and the related N-CoR protein. A large number of transcription factors have been shown to bind to one of the corepressor complexes as a means of regulating transcription. The recruitment of HDACs by DNA-binding proteins allows histone deacetylation to be directed toward specific regions of the chromatin in order to promote targeted transcriptional repression.

HDAC proteins are promising therapeutic targets on account of their involvement in regulating genes involved in cell cycle progression and control. Inhibition of HDACs has been shown to upregulate genes, including p21WAF/CIP1, p27, p53, and cyclin E, and to down-regulate genes such as cyclin A and cyclin D. Growth inhibition in several lines of cancer cells has been observed upon treatment with HDAC inhibitors, and in vivo studies have shown that some of these inhibitors are efficacious in slowing tumor growth. The biological activity of each of the HDAC isozymes is determined by a combination of the intrinsic activity of the enzyme and the effects of cofactor binding on reactivity and substrate recognition (Schultz et al., *Biochemistry*, 2004, 43, 11083-11091).

Non-selective HDAC inhibitors inhibit the deacetylase activity of most, if not all, of the HDACs with equal potency. The mechanisms of the anticancer effects of SAHA, a non-selective HDAC inhibitor, are not completely understood, and likely result from both altered gene expression and altered function of proteins regulating cell proliferation and cell death pathways. Non-selective HDAC inhibitors, such as SAHA, induce the accumulation of acetylated histone proteins and non histone proteins. Non-histone proteins that are acetylated include, but are not limited to:

Bcl-6 (Oncoprotein); LEF/TCF (Lymphoid enhancer factor); P53 (Tumor suppressor); Ku70 (Autoantigen with multiple function, including DNA repair); H1F-1α (angiogenesis); GATA-1 (Transcription factor); WRN (Werner helicase); E2F-1 (Transcription factor); Smad7 (Transcription factor); Rb (Tumor suppressor); TFIIF (Transcription machinery); c-Jun (Transcription factor); α-Tubulin (Structural protein); HMGI(Y) (Chromatin structure); ACTR (Nuclear receptor coactivator); Androgen Receptor (Signal transduction); EKLF (Erythroid kruppel-like factor); YY-1 (Transcription factor); NF-κB (RelA) (Transcription factor); MyoD (Transcription factor); Importin a7 (Nuclear pore protein); Hsp90 (Chaperone protein); THEE (Transcription machinery); b-Catenin (Signaltransduction); TFJB (Transcription factor).

Genes whose transcription is altered by histone deacetylase inhibitors include:

1) Genes that are induced by HDAC inhibitors: Cell cycle (p1 and cyclin E); Proapoptotic (Bak, BAX, CD95, and its ligand gelsolin, GADD45β, p53, Apaf-1 DFF45a, Bim, BAD, TRAIL, DR5, Fas and its ligand, and Caspase 9, -8 and -3); Redox Components (Thioredoxin-binding protein-1, thioredoxin, glutaredoxin and methallothionein 1 L); Chromatin structure (Histone $H_2B$); Retinoic acid pathway (RARβ).

2) Genes that are repressed by HDAC inhibitors: Cell cycle (Cyclin D1 and A, and thymidylate synthase); Antiapoptotic (Bcl-2, Bcl-XL, c-FLIP, survivin, XIAP); Angiogenic factor (Vascular endothelial growth factor and HIF-Loc); Lipopolysaccharide-induced inflammatory cytokines (TNF-a, IFN-g and IL-1b and -6); Signal transducer and activator of transcription 5-controlled genes (STAT5).

HDAC enzymes or isoforms appear to be involved in many different types of cancer. Inhibition of HDACs with HDAC inhibitors results in multiple and desirable anti-cancer effects such as, but not limited to, (i) the inhibition of cancer cell proliferation, (ii) the induction of apoptosis (cell death) of cancer cells, (iii) cell cycle regulation, (iv) the induction of tumour suppressor genes, and (v) the blocking of tumour angiogenesis (development of new tumour blood vessels). These multiple effects provided by HDAC inhibitors provide a method of treating cancer.

Interest in histone deacetylase enzymes (HDACs) as targets for pharmaceutical development has centered on the role of HDACs in regulating genes associated with cell-cycle progression and the development and progression of cancer (Kramer et. al. *Trends Endocrinol. Metab.* 12, 294-300, (2001)). Several studies have shown that treatment of various cell lines with HDAC inhibitors leads to hyper acetylation of histone proteins and cell-cycle arrest in late $G_1$ phase or at the $G_2$/M transition. Genes involved in the cell cycle that have been shown to be up regulated by HDAC inhibitors include p21, p27, p53 and cyclin E. Cyclin A and cyclin D have been reported to be down regulated by HDAC inhibitors. In tumor cell lines, several studies have shown that treatment with HDAC inhibitors lead to growth inhibition, growth arrest, terminal differentiation and/or apoptosis. In vivo studies have demonstrated growth inhibition of tumors and a reduction in tumor metastasis as a result of treatment with HDAC inhibitors.

The clearest link between abnormal HDAC activity and cancer occurs in acute promyelocytic leukemia. In this condition, a chromosomal translocation leads to the fusion of the retinoic acid receptor RARα with the promyelocytic leukemia (PML) or promyelocytic leukemia zinc-finger (PLZF) proteins. Both PML-RARα and PLZF-RARα promote the progression of leukemia by repressing retinoic acid-regulated genes through the abnormal recruitment of SMRT-mSin3-HDAC complex (Lin et. al. *Nature* 391, 811-814 (1998)); Grignani et al. *Nature* 391, 815-818 (1998)). Whereas the PML-RARα form of the disease is treatable with retinoic acid, the PLZF-RARα form is resistant to this treatment. For a patient with the retinoic acid-resistant form of the disease, the addition of the HDAC inhibitor sodium butyrate to the dosing regimen led to complete clinical and cytogenic remission (Warren et al. *J. Natl. Cancer. Inst.* 90, 1621-1625, (1998)). HDACs have also been associated with Huntington's disease (Steffan, et al., *Nature* 413:739-744, "Histone deacetylase inhibitors arrest polyglutamine-dependent neurodegeneration in *Drosophila*").

In general, almost all of the inhibitors targeting HDACs are broad spectrum compounds, inhibiting all of the HDAC isoforms with equal potency. These broad spectrum HDAC inhibitors cause the induction of differentiation, growth arrest and/or apoptosis in a large number of tumor cell lines in vitro.

Clinical administration of broad spectrum HDAC inhibitors (pan HDAC inhibitors) has been associated with many dose limiting toxicities. These include thrombocytopenia, and other hematological toxicities, QTc prolongation and other cardiac toxicities, nausea, fever, fatigue, and anorexia (For example, see *Clinical Cancer Research* 2003, 9(10), 3578-3588; *Clinical Cancer Research* 2002, 8(7), 2142-2148; and *Proceedings of the American Association of Cancer Research* 2005, 46, Abs 3978). Selective HDAC inhibitors that selectively inhibit only one HDAC isoform, as opposed to a pan-selective inhibitor, is expected to produce a drug with an improved toxicity profile.

Adverse effects in humans have been reported in several clinical trials using pan-HDAC inhibitors. Originally designed for oncological applications, such toxicities might not be crucial when taking into consideration their therapeutic effects and the high mortality rate of cancer.

Described herein are selective HDAC8 inhibitor compounds. Compounds described herein selectively inhibit HDAC8 over other HDAC isoforms (e.g. HDACs 1, 2, 3, 6, 10, and 11).

As described herein, HDAC8 is expressed primarily in delta cells of the islets of Langerhans in the pancreas; in small intestinal epithelial cells; and in neuroendocrine cells. Of note, delta cells express and secrete somatostatin, a peptide hormone that inhibits the secretion of insulin and growth hormone. Without being bound by theory, it is believed that HDAC8 activity drives the expression of somatostatin in delta cells. Thus, inhibiting HDAC8 activity is expected to decrease somatostatin expression and secretion from delta cells, and consequently increase systemic insulin and growth hormone levels.

Described herein are methods for inhibiting somatostatin expression in a subject by administering to the subject a selective HDAC8 inhibitor composition. Further, described herein are methods for treating a subject suffering from an insulin deficiency or a growth hormone deficiency by administering a selective HDAC8 inhibitor to the subject.

T-Cell Lymphomas or Leukemias

HDAC8 is expressed at unusually high levels in tumor cell lines, e.g., Jurkat, HuT78, K562, PC3, and OVCR-3. In fact, as described herein, inhibiting HDAC8 activity decreases proliferation of T-cell derived tumor cells (e.g., Jurkat cells) by apoptosis. In contrast, HDAC8 inhibition does not affect the proliferation of either non-cancerous cells (e.g., peripheral blood mononuclear cells) or tumor cell lines other than T-cell derived lines. Thus, selective HDAC8 inhibitors are useful for slowing or arresting the progression of T-cell derived cancers with lessened or no toxicity to non-cancerous cells.

Selective HDAC8 inhibitor compounds described herein were screened against tumor cell lines in vitro, and were found to induce apoptosis in cell lines derived from T-cell lymphomas or leukemias. Selective HDAC8 inhibitor compounds described herein inhibit the growth and induce apoptosis in Jurkat cells. Unlike broad spectrum inhibitors, selective HDAC8 inhibitor compounds described herein do not cause detectable histone or tubulin acetylation, but lead to a dose dependent decrease in HDAC8 protein levels in treated cells. Selective HDAC8 inhibitor compounds described herein activated caspases 3, 8 and 9, showing that both intrinsic and extrinsic apoptic pathways were involved; accordingly, apoptosis was blocked completely by pan-caspase inhibitors but only partially by inhibitors of specific caspases. Thus, selective HDAC8 inhibitor compounds described herein are of benefit in the treatment of T-cell lymphomas and leukemias.

Described herein are methods for treating a subject suffering from a T-cell lymphoma by administering to the subject a selective HDAC8 inhibitor composition. Also described herein are methods for treating a subject suffering from a T-cell lymphoma by administering to the subject a population of autologous T-cells that have been exposed to a selective HDAC8 inhibitor composition ex vivo.

In some embodiments, selective HDAC8 inhibitor compounds and compositions thereof are used to treat a subject suffering from a T-cell lymphoma, e.g., a peripheral T-cell lymphoma, a lymphoblastic lymphoma, a cutaneous T-cell lymphoma, or an adult T-cell lymphoma.

In some embodiments, the T-cell lymphoma treatment method includes administering to a subject a therapeutically effective amount of a selective HDAC8 inhibitor pharmaceutical composition.

In other embodiments, the T-cell lymphoma treatment includes administering, in addition to a selective HDAC8 inhibitor pharmaceutical composition, one or more additional anti-cancer agents described herein in any combination.

The methods described herein include administering a pharmaceutical composition containing a selective HDAC8 inhibitor in a quantity sufficient to decrease HDAC8 deacetylase activity in vivo by a therapeutically effective amount. In some embodiments, cells derived from a subject to be treated (i.e. autologous cells) are exposed, ex vivo, to a pharmaceutical composition containing a selective HDAC8 inhibitor composition in a quantity sufficient to decrease HDAC8 deacetylase activity in vitro.

In one embodiment, T-cells from a donor subject suffering a T-cell lymphoma are cultured and expanded, ex vivo, in the presence of a selective HDAC8 inhibitor at a concentration that is effective for selectively killing transformed T-cells. Afterwards, the expanded T-cell population, free of transformed T-cells, are introduced into the donor subject. T-cell culture, in vitro expansion, and in vivo transfer is described in, e.g., Porter et al. (2006), *Blood*, 107(4):1325-1331; Rapoport et al. (2005), *Nat. Med.*, 1230-1237; Laport et al. (2003), *Blood*, 102(6):2004-2013.

Cytokine-Modulated Health Conditions

In some embodiments, a subject is administered a therapeutically effective amount of a selective HDAC8 inhibitor to decrease secretion of one or more inflammatory cytokines (e.g., IL-1β).

In some embodiments a selective HDAC8 inhibitor compound is administered to a subject to decrease the systemic levels of one or more inflammatory cytokines including, e.g., IL-1β, IL-6, IL-18, TNF-α, MCP-1, or MIP-1a.

As described herein, selective HDAC8 inhibitor compounds described herein reduce the secretion of proinflammatory cytokines including but not limited to interleukin-1 beta (IL-1β). Thus, HDAC8 is the HDAC enzyme involved in cytokine secretion. The use of selective HDAC8 inhibitor compounds provides a method of reducing cytokine secretion with reduced toxicity, due to the selective inhibition of one HDAC isoform (vs. the use of pan-HDAC inhibitors that inhibit all of the HDAC isoforms).

Selective HDAC8 inhibitor compounds described herein inhibit, in a dose dependent fashion, lipopolysaccharide (LPS) and/or ATP stimulated secretion of IL-1β from purified human peripheral blood mononuclear cells (PBMCs) as well as from the monocyte cell line THP-1. In some embodiments, the $EC_{50}$ for inhibition ranges from about 0.5 micromolar to about 5 micromolar.

The production and secretion of IL-1β is via a non-classical pathway of protein secretion, involving potassium efflux, the autocatalytic processing of procaspase-1, the cleavage by active caspase-1 of the IL-1β precursor, the influx of calcium ions, and the activation of specific phospholipases including PLA-2. In some embodiments, selective HDAC8 inhibitor compounds described herein inhibit one or more steps in this secretory pathway.

As described herein, selective HDAC8 inhibitors are used to treat diseases or conditions that are mediated or linked to IL-β secretion and activity. In certain autoimmune diseases or conditions, IL-1β is contributes to the signs and symptoms of the diseases or conditions (for examples of such Burger et al., *Best Practice & Research Clinical Rheumatology*, Vol. 20, No. 5, pp. 879-896, 2006; Dayer et al., *Current Opinions in Rheum.*, 2001, 13:170-176; Abramson et al., *Rheumatology*, 2002; 41; 972-980); selective HDAC8 inhibitor compounds are used to treat such diseases or conditions. As described herein, selective HDAC8 inhibitor compounds are used to inhibit IL-1β secretion and thus find utility in the treatment of diseases or conditions that are linked to IL-1β secretion and activity, which include, but are not limited to, osteoarthritis, rheumatoid arthritis, septic arthritis, gout, pseudogout, juvenile arthritis, Still's disease, Ankylosing spondylitis, systemic lupus erythematosus (SLE), Henoch-Schönlein purpura, psoriatic arthritis, reactive arthritis (Reiter's syndrome), hemochromatosis, hepatitis, Wegener's granulomatosis, Familial Mediterranean fever (FMF), HIDS (hyperimmunoglobulinemia D and periodic fever syndrome), TRAPS (TNF-alpha receptor associated periodic fever syndrome), inflammatory bowel disease, Crohn's Disease, ulcerative colitis, recurrent fever, anemia, leukocytosis, asthma, chronic obstructive pulmonary disease, myalgia; Adult Still's disease, Systemic-onset juvenile idiopathic arthritis, Lupus arthritis, Ankylosing spondylitis, familial Mediterranean fever (FMF), TNF receptor-associated periodic syndrome (TRAPS), hyperimmunoglobulinemia D with periodic fever syndrome (HIDS), Blau syndrome, FCAS, MWS, neonatal-onset multisystem inflammatory disease (NOMID) and cryopyrin-associated periodic syndrome (CAPS), familial cold autoinflammatory syndrome (FCAS); Muckle-Wells syndrome (MWS); neonatal-onset multisystem inflammatory disease (NOMID); chronic infantile neurologic, cutaneous, articular syndrome (CINCA); cryopyrin-associated periodic syndrome (CAPS); pyogenic sterile arthritis, pyoderma gangrenosum, and acne syndrome (PAPA).

In further embodiments, the methods described herein are used to treat an inflammatory disease, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In yet other embodiments, the methods described herein are used to treat an inflammatory skin condition. Inflammatory skin conditions are those conditions of the skin in which inflammatory cells (e.g., polymorphonuclear neutrophils and lymphocytes) infiltrate the skin with no overt or known infectious etiology. Symptoms of inflammatory skin conditions generally include erythema (redness), edema (swelling), pain, pruritus, increased surface temperature and loss of function. As used herein, inflammatory skin conditions include, but are not limited to, allergic contact dermatitis, urticarial dermatitis, psoriasis, eczema and related conditions, insect bites, erythroderma, mycosis fungoides and related conditions, pyoderma gangrenosum, erythema multiforme, rosacea, onychomycosis, and acne and related conditions, but excluding psoriasis and its related conditions.

In some embodiments, the methods described herein are used to treat an autoimmune disease, which includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

In some embodiments, the methods described herein are used to treat heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Chronic inflammation in patients has been linked to cancer development (Coussens et al., *Nature*, 420, 860-867, 2002). Cancers associated with chronic inflammation include, but are not limited to, lung, esophageal, gastric, pancreatic, cervical, bladder, prostate and colorectal cancers. The role of the inflammatory microenvironment as a causative factor in the etiology of cancer is also supported by findings that regular use of non-steroidal anti-inflammatory drugs (NSAIDs) is associated with a reduced incidence of colorectal, breast and gastric cancer. Pro-inflammatory cytokines are mediators of chronic inflammatory responses, and have effects on malignant processes.

Pro-inflammatory cytokines are involved in carcinogenesis and malignant transformation, tumor growth, invasion and metastasis. Persistent expression of proinflammatory cytokines, in or near tumors, exerts a range of effects, including but not limited to, increasing growth and invasiveness of the malignant cells, metastsis, tumorigenesis, to activation of immune-mediated mechanisms, leading to the destruction of tumor cells and inhibition of tumor growth. IL-1β-transfected tumor cells have been reported to fail to induce effective antitumor immune responses. In several human cancers, local IL-1β expression by the malignant cells or the microenvironment has been associated with aggressive tumor growth and poor prognosis.

In IL-1β-transfected fibrosarcoma cells, an up-regulation of MMP-2 and MMP-9 and TGFβ, genes that are involved in invasiveness, was observed, as opposed to the shut-off of these genes in IL-1α-transfected fibrosarcomas cells. IL-1β is thought to also enhance the invasiveness of already existing tumor cells by switching on angiogenesis and by the induction of inflammatory molecules, such as MMPs, heparanase, chemokines or integrins on the malignant cells or endothelial cells, leading to tumor dissemination and metastasis. IL-1β induces secretion of growth and invasiveness-promoting factors, e.g. matrix metalloproteinases and angiogenic factors (i.e. VEGF and bFGF and ELR-positive CXC chemokines, i.e. IL-8 and MCP-1). (Apte et al., seminars in *Cancer Biology*, vol. 12, 2002, 277-290).

Secreted IL-1β has been implicated in tumor growth and invasion. Inhibition of IL-1β secretion, e.g. by using selective HDAC8 compounds, in malignant cells, or in the tumor's microenvironment provides a method for cancer therapy.

Thus in one embodiment, selective HDAC8 compounds described herein, are used in cancer therapy. In one embodiment, selective HDAC8 compounds described herein, are used in the treatment of sarcomas. In another embodiment, selective HDAC8 compounds described herein, are used in the treatment of sarcomas selected from among alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, malignant fibrous histiocytoma, neurofibrosarcoma, rhabdomyosarcoma, synovial sarcoma, askin's tumor, ewing's, malignant hemangioendothelioma, malignant schwannoma, osteosarcoma, chondrosarcoma.

Symptoms, diagnostic tests, and prognostic tests for each of the above-mentioned conditions are known. See, e.g., "Harrison's Principles of Internal Medicine©," 16th ed., 2004, The McGraw-Hill Companies, Inc.

In various embodiments described herein, a subject suffers from more than one condition that is treated by administration of a therapeutically effective amount of a selective HDAC8 inhibitor composition. Thus, it is to be understood that the methods described herein are effective for treating a subject suffering from any combination of health conditions amenable to treatment by administration of a selective HDAC8 inhibitor composition. For example, in some embodiments, a subject suffering from a T-cell lymphoma also suffers from an inflammatory condition and vice versa.

Compounds

Compounds described herein, pharmaceutically acceptable salts, pharmaceutically acceptable N-oxides, pharmaceutically active metabolites, pharmaceutically acceptable prodrugs, or pharmaceutically acceptable solvates thereof, inhibit HDAC8 activity, and are used to treat patients where inhibition of HDAC8 activity provides benefit. Compounds described herein are selective HDAC8 inhibitor compounds.

In some embodiments of the methods described herein, the selective HDAC8 inhibitor has an $IC_{50}$ for HDAC8 that is at least about 10 fold lower than the $IC_{50}$ for HDAC1, HDAC2, HDAC3, HDAC6, HDAC10, or HDAC11. In some embodiments of any of the methods described herein, the selective HDAC8 inhibitor has an $IC_{50}$ for HDAC8 that is less than about 100 nM and that is at least about 10 fold lower than the $IC_{50}$ for HDAC1, HDAC2, HDAC3, HDAC6, HDAC10, or HDAC11. In some embodiments of any of the methods described herein, the selective HDAC8 inhibitor has an $IC_{50}$ for HDAC8 that is less than about 50 nM and that is at least about 10 fold lower than the $IC_{50}$ of the selective inhibitor for HDAC1, HDAC2, HDAC3, HDAC6, HDAC10, or HDAC11.

In some embodiments, selective HDAC8 inhibitors described herein have an $IC_{50}$ for HDAC8 that is at least about 15 fold lower than the $IC_{50}$ for HDAC1, HDAC2, HDAC3, HDAC6, and HDAC10. In some embodiments, selective HDAC8 inhibitors described herein have an $IC_{50}$ for HDAC8 that is at least about 20 fold lower than the $IC_{50}$ for HDAC1, HDAC2, HDAC3, HDAC6, and HDAC10. In some embodiments, selective HDAC8 inhibitors described herein have an $IC_{50}$ for HDAC8 that is at least about 100 fold lower than the $IC_{50}$ for HDAC1, HDAC2, HDAC3, HDAC6, and HDAC10. In addition, selective HDAC8 inhibitors described herein have an $IC_{50}$ for HDAC8 that is less than about 100 nM while the $IC_{50}$ for HDAC1, HDAC2, HDAC3, HDAC6, and HDAC10 is greater than about 100 nM.

In some embodiments, selective HDAC8 inhibitors described herein have an $IC_{50}$ for HDAC8 that is at least about 10 fold lower than the $IC_{50}$ for HDAC1. In some embodiments, selective HDAC8 inhibitors described herein have an $IC_{50}$ for HDAC8 that is at least about 20 fold lower than the $IC_{50}$ for HDAC1. In some embodiments, selective HDAC8 inhibitors described herein have an $IC_{50}$ for HDAC8 that is at least about 40 fold lower than the $IC_{50}$ for HDAC1. In some embodiments, selective HDAC8 inhibitors described herein have an $IC_{50}$ for HDAC8 that is at least about 100 fold lower than the $IC_{50}$ for HDAC1. In some embodiments, selective HDAC8 inhibitors described herein have an $IC_{50}$ for HDAC8 that is at least about 150 fold lower than the $IC_{50}$ for HDAC1. In yet other embodiments, selective HDAC8 inhibitors described herein have an $IC_{50}$ for HDAC8 that is at least about 200 fold lower than the $IC_{50}$ for HDAC1.

In some embodiments, selective HDAC8 inhibitors described herein have $IC_{50}$ for HDAC8 that is less than about 100 nM and that is at least about 20 fold lower than the $IC_{50}$ for other HDAC isoforms (HDAC1, HDAC2, HDAC3, HDAC6, HDAC10), wherein the $IC_{50}$ for the other HDAC isoforms is greater than about 100 nM.

In one embodiment, described herein are substituted benzimidazole-6-carboxylic acid hydroxyamide compounds, substituted azaindole-6-carboxylic acid hydroxyamide compounds, substituted-1H-pyrrole-2-yl-N-hydroxyacrylamide compounds, and substituted benzofuran, benzothiophene and indole compounds that are selective HDAC8 inhibitors. Compounds described herein are selective histone deacetylase 8 (HDAC8) inhibitors. In one embodiment, the selective HDAC8 inhibitor has an $IC_{50}$ for histone deacetylase 8 activity that is at least about 10 fold lower than the $IC_{50}$ of the selective HDAC8 inhibitor for activity of histone deacetylase 1, histone deacetylase 2, histone deacetylase 3, histone deacetylase 6, histone deacetylase 10, or histone deacetylase 11.

In one aspect is a compound of Formula A:

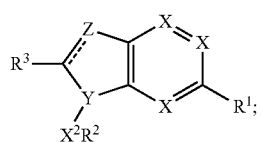

Formula A wherein:

$R^1$ is C(O)NHOH;

X is $CR^3$ or N, wherein at least two X are $CR^3$;

Z is $CR^5$, N, O or S; wherein if only one X is N then Z is $CR^5$;

Y is $CR^3$ or N;

╱╱ represents a double bond when Z is $CR^5$ or N; or is a single bond when Z is O or S;

$X^2$ is a bond, or a substituted or unsubstituted group selected from among $C_1$-$C_6$alkylene, $C_2$-$C_6$alkenylene, $C_2$-$C_6$ alkynylene, $C_1$-$C_6$heteroalkylene; $C_1$-$C_6$alkoxy; $C_1$-$C_6$amine; $C_1$-$C_6$amide; $C_1$-$C_6$sulfide; $C_1$-$C_6$sulfoxide; $C_1$-$C_6$sulfonyl; $C_1$-$C_6$fluoroalkylene, $C_2$-$C_6$fluoroalkenylene, $C_1$-$C_6$haloalkylene, $C_2$-$C_6$haloalkenylene, —C(=O)—, and —C(=O)—$C_1$-$C_6$alkylene;

$R^2$ is a substituted or unsubstituted group selected from among aryl, heteroaryl, cycloalkyl, and heterocycloalkyl;

where if $R^2$ is substituted, then each substituent on $R^2$ is selected from among halogen, sulfonyl, thiol, substituted or unsubstituted $C_1$-$C_6$alkoxy, $C_1$-$C_6$fluoroalkoxy, $C_1$-$C_6$aminoalkoxy, $C_1$-$C_6$alkylaminoalkoxy, $C_1$-$C_6$alkoxyaminoalkoxy, $C_1$-$C_6$hydroxyalkylaminoalkoxy, $C_1$-$C_6$heterocycloalkylalkoxy, substituted or unsubstituted heterocycloalkyl, substituted or unsubstituted heteroaryl; —CN, —$NO_2$, —$CO_2R^{10}$, —C(=O)$R^{11}$, —S—$R^{11}$, —S(=O)—$R^{11}$, S(=O)$_2$—$R^{11}$, —$NR^{10}$C(=O)—$R^{11}$, —C(=O)N($R^{10}$)$_2$, —S(=O)$_2$N($R^{10}$)$_2$, —$NR^{10}$S(=O)$_2$—$R^{11}$, —OC(=O)N($R^{10}$)$_2$, —$NR^{10}$C(=O)O—$R^{11}$, —OC(=O)O—$R^{11}$, —NHC(=O)NH—$R^{11}$, —OC(=O)—$R^{11}$; —N($R^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_6$cycloalkyl, and substituted or unsubstituted aryl, $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

each $R^3$ is independently hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $C_1$-$C_6$aminoallyl;

$R^5$ is hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, $C_1$-$C_6$aminoalkyl; or —$X^6$—$R^6$;

$X^6$ is a $C_1$-$C_6$alkylene, $C_1$-$C_6$fluoroalkylene, $C_2$-$C_6$alkenylene, $C_2$-$C_6$heteroalkylene;

$R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or —$X^7$—$R^7$;

$X^7$ is a bond, —O—, —S—, —S(=O)—, —S(=O)$_2$—, —$NR^a$—, —C(=O)—, —C(=O)O—, —OC(=O)—, —NHC(=O)—, —C(=O)$NR^a$—, —S(=O)$_2NR^a$—, —NHS(=O)$_2$—, —OC(=O)$NR^a$—, —NHC(=O)O—, —OC(=O)O—, —NHC(=O)$NR^a$—; wherein $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl;

$R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl;

or an active metabolite, pharmaceutically acceptable solvate, pharmaceutically acceptable salt, pharmaceutically acceptable N-oxide, or pharmaceutically acceptable prodrug thereof.

Benzimidazole Compounds

In one embodiment is a compound having a structure of Formula I:

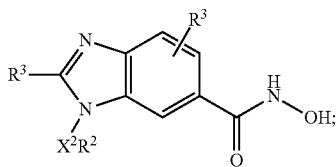

Formula I wherein:

X² is a bond, or a substituted or unsubstituted group selected from among $C_1$-$C_6$alkylene, $C_2$-$C_6$alkenylene, $C_2$-$C_6$ alkynylene, $C_1$-$C_6$heteroalkylene; $C_1$-$C_6$alkoxy; $C_1$-$C_6$amine; $C_1$-$C_6$amide; $C_1$-$C_6$sulfide; $C_1$-$C_6$sulfoxide; $C_1$-$C_6$sulfonyl; $C_1$-$C_6$fluoroalkylene, $C_2$-$C_6$fluoroalkenylene, $C_1$-$C_6$haloalkylene, $C_2$-$C_6$haloalkenylene, —C(=O)—, and —C(=O)—$C_1$-$C_6$alkylene;

R² is a substituted or unsubstituted group selected from among aryl, heteroaryl, cycloalkyl, and heterocycloalkyl;

where if R² is substituted, then each substituent on R² is selected from among halogen, sulfonyl, thiol, substituted or unsubstituted $C_1$-$C_6$alkoxy, $C_1$-$C_6$ fluoroalkoxy, $C_1$-$C_6$aminoalkoxy, $C_1$-$C_6$alkylaminoalkoxy, $C_1$-$C_6$alkoxyaminoalkoxy, $C_1$-$C_6$hydroxyalkylaminoalkoxy, $C_1$-$C_6$heterocycloalkylalkoxy, substituted or unsubstituted heterocycloalkyl, substituted or unsubstituted heteroaryl; —CN, —NO₂, —CO₂$R^{10}$, —C(=O)$R^{11}$, —S—$R^{11}$, —S(=O)—$R^{11}$, —S(=O)₂—$R^{11}$, —N$R^{10}$C(=O)—$R^{11}$, —C(=O)N($R^{10}$)₂, —S(=O)₂N($R^{10}$)₂, —N$R^{10}$S(=O)₂$R^{11}$, —OC(=O)N($R^{10}$)₂, —N$R^{10}$C(=O)O—$R^{11}$, —OC(=O)—$R^{11}$, —NHC(=O)NH—$R^{11}$, —OC(=O)—$R^{11}$; —N($R^{10}$)₂, substituted or unsubstituted $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_8$cycloalkyl, and substituted or unsubstituted aryl, $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloallyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

each R³ is independently hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $C_1$-$C_6$aminoalkyl;

or an active metabolite, pharmaceutically acceptable solvate, pharmaceutically acceptable salt, pharmaceutically acceptable N-oxide, or pharmaceutically acceptable prodrug thereof.

In one embodiment, is a 1,2-disubstituted-1H-benzimidazole-6-carboxylic acid hydroxyamide compound, wherein the substituent at the 1-position is —X²—R² and the substituent at the 2-position is R³, wherein:

X² is a bond, or a substituted or unsubstituted group selected from among $C_1$-$C_6$alkylene, $C_2$-$C_6$alkenylene, $C_2$-$C_6$ alkynylene, $C_1$-$C_6$heteroalkylene; $C_1$-$C_6$alkoxy; $C_1$-$C_6$amine; $C_6$amide; $C_1$-$C_6$sulfide; $C_1$-$C_6$sulfoxide; $C_1$-$C_6$sulfonyl; $C_1$-$C_6$fluoroalkylene, $C_2$-$C_6$fluoroalkenylene, $C_1$-$C_6$haloalkylene, $C_2$-$C_6$haloalkenylene, —C(=O)—, and —C(=O)—$C_1$-$C_6$alkylene;

R² is a substituted or unsubstituted group selected from among aryl, heteroaryl, cycloalkyl, and heterocycloalkyl;

where if R² is substituted, then each substituent on R² is selected from among halogen, sulfonyl, thiol, substituted or unsubstituted $C_1$-$C_6$alkoxy, $C_1$-$C_6$ fluoroalkoxy, $C_1$-$C_6$aminoalkoxy, $C_1$-$C_6$alkylaminoalkoxy, $C_1$-$C_6$alkoxyaminoalkoxy, $C_1$-$C_6$hydroxyalkylaminoalkoxy, $C_1$-$C_6$heterocycloalkylalkoxy, substituted or unsubstituted heterocycloalkyl, substituted or unsubstituted heteroaryl; —CN, —NO₂, —C(=O)$R^{10}$, —C(=O)$R^{11}$, —S—$R^{11}$, —S(=O)—$R^{11}$, —S(=O)₂—$R^{11}$, —N$R^{10}$C(=O)—$R^{11}$, —C(=O)N($R^{10}$)₂, —S(=O)₂ N($R^{10}$)₂, —N$R^{10}$S(=O)₂$R^{11}$, —OC(=O)N($R^{10}$)₂, —N$R^{10}$C(=O)O—$R^{11}$, —OC(=O)O—$R^{11}$, —NHC(=O)NH—$R^{11}$, —OC(=O)—$R^{11}$; —N($R^{10}$)₂, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_8$cycloalkyl, and substituted or unsubstituted aryl, $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

R³ is hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $C_1$-$C_6$aminoalkyl;

or an active metabolite, pharmaceutically acceptable solvate, pharmaceutically acceptable salt, pharmaceutically acceptable N-oxide, or pharmaceutically acceptable prodrug thereof.

For any and all of the embodiments, substituents are selected from among a subset of the listed alternatives. For example, in some embodiments, X² is a substituted or unsubstituted group selected from among $C_1$-$C_6$alkyl, $C_1$-$C_6$alkylene, $C_2$-$C_6$alkenylene, $C_1$-$C_6$alkoxy, $C_1$-$C_6$fluoroalkylene, $C_2$-$C_6$fluoroalkenylene, and $C_1$-$C_6$heteroalkylene. In other embodiments, X² is a substituted or unsubstituted group selected from among $C_1$-$C_6$alkyl, $C_1$-$C_6$alkylene, and $C_1$-$C_6$alkoxy. In some embodiments, X² is —CH₂—, —CH₂CH₂—, —(CH₂)₃—, —O(CH₂)—, —O(CH₂)₂— or —O(CH₂)₃—. In some embodiments, X² is —CH₂—.

In some embodiments, R² is an optionally substituted group selected from among phenyl, naphthyl, monocyclic heteroaryl, bicyclic heteroaryl, $C_3$-$C_8$ cycloalkyl, monocyclic heterocycloalkyl, and bicyclic heterocycloalkyl. In other embodiments, $R^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl, monocyclic heterocycloalkyl containing 0-2 N atoms, and bicyclic heterocycloalkyl 0-2 N atoms; where if $R^2$ is substituted, then each substituent on $R^2$ is selected from among halogen, sulfonyl, thiol, —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^{10}$C(=O)R$^{11}$, —C(=O)N(R$^{10}$)$_2$, —S(=O)$_2$N(R$^{10}$)$_2$, —NR S(=O)$_2$—R$^{11}$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, phenyl, and heteroaryl; $R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, phenyl, and heteroaryl.

In some embodiments, $R^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl; where if $R^2$ is substituted, then each substituent on $R^2$ is selected from among halogen, sulfonyl, thiol, —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, and phenyl; $R^{11}$ is a substituted or unsubstituted group selected from among $C_1$-$C_6$alkyl, $C_1$-$C_6$fluoroalkyl, and phenyl.

In some embodiments, $R^2$ is selected from among phenyl, 2-methylphenyl, 3-methylphenyl, 4-methylphenyl, 3,4-dimethylphenyl, 2-fluorophenyl, 3-fluorophenyl, 4-fluorophenyl, 3,4-difluorophenyl, 2-chlorophenyl, 3-chlorophenyl, 4-chlorophenyl, 2,4-dichlorophenyl, 3,4-dichlorophenyl, 3-methoxyphenyl, 3-methoxyphenyl, 4-methoxyphenyl, 3,5-dimethoxyphenyl, 3,4,5-trimethoxyphenyl, naphth-2-yl, cyclopentyl, cyclohexyl, cycloheptyl, 2-(trifluoromethyl)-phenyl, 3-(trifluoromethyl)-phenyl, 4-(trifluoromethyl)-phenyl, 2-(trifluoromethoxy)-phenyl, 3-(trifluoromethoxy)-phenyl, 4-(trifluoromethoxy)-phenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl) phenyl, 4-(methylsulfonyl)phenyl, 2-thiophenyl, 3-thiophenyl, 2-pyridyl, 3-pyridyl, 4-pyridyl, 2,3-difluorophenyl, 2,4-difluorophenyl, benzo[2,1,3]oxadiazol-5-yl, 3-fluoro-4-methoxy-phenyl, 2-(difluoromethoxy)-phenyl, 3-(difluoromethoxy)-phenyl, 4-(difluoromethoxy)-phenyl, N-(t-butoxycarbonyl)piperidin-4-yl, piperidin-4-yl, N-methylsulfonyl-2-aminophenyl, N-methylsulfonyl-3-aminophenyl, N-methylsulfonyl-4-aminophenyl, N-phenylsulfonyl-2-aminophenyl, N-phenylsulfonyl-3-aminophenyl, N-phenylsulfonyl-4-aminophenyl, 2-nitrophenyl, 3-nitrophenyl, 4-nitrophenyl, 2-aminophenyl, 3-aminophenyl, 4-aminophenyl, 2-dimethylaminophenyl, 3-dimethylaminophenyl, 4-dimethylaminophenyl, N-acetyl-2-aminophenyl, N-acetyl-3-aminophenyl, N-acetyl-4-aminophenyl, N-benzoyl-2-aminophenyl, N-benzoyl-3-aminophenyl, and N-benzoyl-4-aminophenyl.

In other embodiments, $R^2$ is selected from among phenyl, 3-methoxyphenyl, 4-methoxyphenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 3-fluoro-4-methoxyphenyl, 4-(trifluoromethoxy)-phenyl, 3,4-dichlorophenyl, 2,4-dichlorophenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl)phenyl, 4-(methylsulfonyl) phenyl, 2-thiophenyl, 3-thiophenyl, 2-pyridyl, 3-pyridyl, 4-pyridyl, 2,3-difluorophenyl, 2,4-difluorophenyl, 3,4-difluorophenyl.

In some embodiments, $R^3$ is hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $C_1$-$C_6$aminoalkyl;

In some embodiments, $R^3$ is selected from among hydrogen, methyl, ethyl, propyl, benzyl, dimethylaminomethyl, N-morpholinomethyl, N-pyrrolidinomethyl, N-piperidinomethyl, and N-benzylaminomethyl. In some embodiments, $R^3$ is selected from among hydrogen, methyl, ethyl, propyl, benzyl, dimethylaminomethyl, N-morpholinomethyl, N-pyrrolidinomethyl, and N-benzylaminomethyl.

Any combination of the groups described above for the various variables is contemplated herein.

In another embodiment, is a compound having a structure selected from among Formula (Ia):

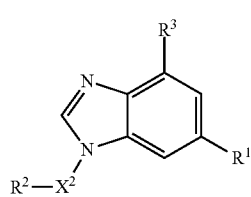

wherein:
$R^1$ is —C(O)NHOH;
$X^2$ is a bond, alkylene, alkenylene, or alkoxy;
$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, allylaminocarbonyl, dialkylaminocarbonyl, optionally substituted arylaminocarbonyl, optionally substituted heteroarylaminocarbonyl, carboxy, cyano, halo, haloalkoxy, or nitro;

R³ is hydrogen, alkyl, substituted alkyl, alkenyl, substituted alkenyl, hydroxy, alkoxy, or haloalkoxy; or an active metabolite, pharmaceutically acceptable solvate, pharmaceutically acceptable salt, pharmaceutically acceptable N-oxide, or pharmaceutically acceptable prodrug thereof.

In another embodiment, is a compound having a structure selected from among Formula Ia, wherein:

R¹ is —C(O)NHOH;

X² is a bond, alkylene, or alkoxy;

R² is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

R³ is hydrogen, alkenyl, substituted alkenyl, hydroxy, alkoxy, haloalkoxy, or —X⁶—R⁶ where X⁶ is alkylene or alkenylene and X⁶ is additionally optionally substituted with one, two, three, four, of five halo; and R⁶ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S(O)₀₋₂—, alkenyl-S(O)₀₋₂—, aminosulfonyl, alkylaminosulfonyl, dialkylaminosulfonyl, alkylsulfonyl-NR^c— (where R^b is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR^aR^b (where R^a and Rb are independently hydrogen, alkyl, substituted alkyl, alkenyl, alkynyl, substituted alkynyl, hydroxy, alkoxy, or alkenyloxy); or an active metabolite, pharmaceutically acceptable solvate, pharmaceutically acceptable salt, pharmaceutically acceptable N-oxide, or pharmaceutically acceptable prodrug thereof.

In one embodiment is a compound of Formula (Ia).

For any and all of the embodiments, substituents are selected from among from a subset of the listed alternatives. For example, in some embodiments, X² is a bond, alkylene, alkoxy, or alkenylene where the alkylene or alkenylene is optionally substituted with one, two, three, four, or five halogens. In another embodiment, X² is alkylene or alkenylene. In other embodiments, X² is —CH₂—, —CH₂CH₂—, —CH(CH₃)—, —(CH₂)₃—, —OCH₂—, —OCH₂CH₂—, or —CH₂CH=CH—. In some embodiments, X² is —CH₂—. In other embodiments, X² is —OCH₂CH₂—.

In some embodiments, R² is aryl, cycloalkyl, heteroaryl, or heterocycloalkyl where the aryl, cycloalkyl, heteroaryl, and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro. In other embodiments, R² is aryl, cycloalkyl, heteroaryl, or heterocycloalkyl, where the aryl, cycloalkyl, heteroaryl, and heterocycloalkyl are optionally substituted with one, two, or three substituents selected from among alkyl, alkoxy, alkoxycarbonyl, halogen, and haloalkoxy. In some other embodiments, R² is aryl, cycloalkyl, heteroaryl, or heterocycloalkyl, where the aryl is optionally substituted with one, two, or three substituents selected from among alkyl, alkoxy, halo, and haloalkoxy, and the heterocycloalkyl is optionally substituted with alkoxycarbonyl. In further embodiments, R² is cyclohexyl, benzooxadiazolyl, naphth-2-yl, phenyl, or piperidinyl, where the phenyl is optionally substituted with one, two, or three substituents selected from among methyl, methoxy, chloro, fluoro, trifluoromethoxy, and difluoromethoxy, and the piperidinyl is optionally substituted with t-butoxycarbonyl. In yet other embodiments, R² is cyclohexyl, benzo[2,1,3]oxadiazol-5-yl, phenyl, naphth-2-yl, 2-methylphenyl, 3-methylphenyl, 4-methylphenyl, 3-methoxyphenyl, 4-methoxyphenyl, 3,5-dimethoxyphenyl, 3,4,5-trimethoxyphenyl, 2-chlorophenyl, 3-chlorophenyl, 4-chlorophenyl, 3,4-dichlorophenyl, 2-fluorophenyl, 3-fluorophenyl, 4-fluorophenyl, 4-(difluoromethoxy)-phenyl, 4-(trifluoromethoxy)-phenyl, 3-fluoro-4-methoxy-phenyl, 4-(trifluoromethoxy)-phenyl, 3-fluoro-4-methoxy-phenyl, piperidin-4-yl, or N-(t-butoxycarbonyl)piperidin-4-yl.

In some embodiments, R² is benzo[2,1,3]oxadiazol-5-yl, 4-methoxyphenyl, 4-chlorophenyl, 4-(difluoromethoxy)-phenyl, or 3-fluoro-4-methoxy-phenyl.

In other embodiments, R² is 3,4-dichlorophenyl, 2,4-dichlorophenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl)phenyl, 4-(methylsulfonyl)phenyl, 2-thiophenyl, 3-thiophenyl, 2-pyridyl, 3-pyridyl, 4-pyridyl, 2,3-difluorophenyl, 2,4-difluorophenyl, 3,4-difluorophenyl.

In some embodiments, R³ is hydrogen, alkyl, substituted alkyl, alkenyl, substituted alkenyl, hydroxy, alkoxy, or haloalkoxy. In other embodiments, R³ is hydrogen.

In some embodiments, R² is aryl, cycloalkyl, heteroaryl, or heterocycloalkyl, where the aryl is substituted with one, two, or three substituents selected from among acyloxy, alkyl, substituted alkyl, alkenyl, substituted alkenyl, alkylamino, dialkylamino, and haloalkoxy; where the cycloalkyl is optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro; and where the heteroaryl and the heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, and nitro. In other embodiments, R² is aryl, cycloalkyl, heteroaryl, or heterocycloalkyl where the aryl is substituted with one, two, or three substituents selected from among alkyl and haloalkoxy, and the heterocycloalkyl is optionally substituted with alkoxycarbonyl. In yet other embodiments, R² is cyclohexyl; benzooxadiazolyl; phenyl substituted with one, two, or three substituents selected from among methyl, trifluoromethoxy, or difluoromethoxy; or piperidinyl optionally substituted with t-butoxycarbonyl.

In some embodiments, R² is cyclohexyl, benzo[2,1,3]oxadiazol-5-yl, 2-methylphenyl, 3-methylphenyl, 4-methylphenyl, 4-(difluoromethoxy)-phenyl, 4-(trifluoromethoxy)-phenyl, butoxycarbonyl)piperidin-4-yl, or piperidin-4-yl. In yet other embodiments, $R^2$ is benzo[2,1,3]oxadiazol-5-yl or 4-(difluoromethoxy)-phenyl.

In some embodiments, $R^3$ is hydrogen, alkenyl, substituted alkenyl, hydroxy, alkoxy, haloalkoxy, or —$X^6$—$R^6$, where $X^6$ is alkylene or alkenylene and $X^6$ is additionally optionally substituted with one, two, three, four, or five halogens; and $R^6$ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where R$^a$ handle are independently hydrogen, alkyl, substituted alkyl, alkenyl, alkynyl, substituted alkynyl, hydroxy, alkoxy, or alkenyloxy). In some embodiments, $R^3$ is hydrogen.

In some embodiments, $R^3$ is hydrogen; $X^2$ is alkylene or alkenylene; and $R^2$ is aryl, cycloalkyl, or heteroaryl, where the aryl, cycloalkyl, and heteroaryl are optionally substituted with one, two, or three substituents selected from among alkyl, alkoxy, alkoxycarbonyl, halogen, and haloalkoxy. In other embodiments, $R^3$ is hydrogen; $X^2$ is alkylene or alkenylene; and $R^2$ is naphthyl, phenyl, cycloalkyl, heteroaryl, or heterocycloalkyl optionally substituted with methyl, methoxy, t-butoxycarbonyl, chloro, fluoro, trifluoromethoxy, or difluoromethoxy. In some other embodiments, $R^3$ is hydrogen; $X^2$ is alkylene or alkenylene; and $R^2$ is phenyl where the phenyl is optionally substituted with one, two, or three substituents selected from among methyl, methoxy, chloro, fluoro, trifluoromethoxy, and difluoromethoxy; or $R^2$ is benzooxadiazolyl.

In some embodiments, $R^3$ is hydrogen; $X^2$ is alkylene or alkenylene; and $R^2$ is cycloalkyl, aryl, heteroaryl, or heterocycloalkyl, where the cycloalkyl is optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro; where the aryl is substituted with one, two, or three substituents selected from among acyloxy, alkyl, substituted alkyl, alkenyl, substituted alkenyl, alkylamino, dialkylamino, and haloalkoxy; where the heteroaryl and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, and nitro.

In some embodiments, $R^3$ is hydrogen; $X^2$ is alkylene or alkenylene; and $R^2$ is cycloalkyl; phenyl substituted with one, two, or three alkyl or haloalkoxy; benzooxadiazolyl; or piperidinyl optionally substituted with alkoxycarbonyl. In some other embodiments, $R^3$ is hydrogen; $X^2$ is alkylene or alkenylene; and $R^2$ is benzooxadiazolyl or phenyl where the phenyl is substituted with one, two, or three substituents selected from among methyl, chloro, fluoro, trifluoromethoxy, or difluoromethoxy.

Azaindole Compounds

In another embodiment is a compound having the structure of Formula II:

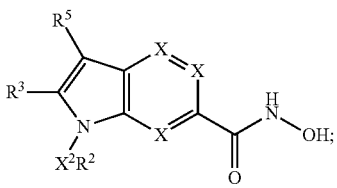

Formula II wherein:

X is CR$^3$ or N, wherein at least two X are CR$^3$;

$X^2$ is a bond, or a substituted or unsubstituted group selected from among $C_1$-$C_6$alkylene, $C_2$-$C_6$alkenylene, $C_2$-$C_6$ alkynylene, $C_1$-$C_6$heteroalkylene; $C_1$-$C_6$alkoxy; $C_1$-$C_6$amine; $C_1$-$C_6$amide; $C_1$-$C_6$sulfide; $C_1$-$C_6$sulfoxide; $C_1$-$C_6$sulfonyl; $C_1$-$C_6$fluoroalkylene, $C_2$-$C_6$fluoroalkenylene, $C_1$-$C_6$haloalkylene, $C_2$-$C_6$haloalkenylene, —C(=O)—, and —C(=O)—$C_1$-$C_6$alkylene;

$R^2$ is a substituted or unsubstituted group selected from among aryl, heteroaryl, cycloalkyl, and heterocycloalkyl;

where if $R^2$ is substituted, then each substituent on $R^2$ is selected from among halogen, sulfonyl, thiol, substituted or unsubstituted $C_1$-$C_6$alkoxy, $C_1$-$C_6$ fluoroalkoxy, $C_1$-$C_6$aminoalkoxy, $C_1$-$C_6$alkylaminoalkoxy, $C_1$-$C_6$alkoxyaminoalkoxy, $C_1$-$C_6$hydroxyalkylaminoalkoxy, $C_1$-$C_6$heterocycloalkylalkoxy, substituted or unsubstituted heterocycloalkyl, substituted or unsubstituted heteroaryl; —CN, —NO$_2$, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$; —NR$^{10}$S(=O)$_2$—R$^{11}$; —OC(=O)N(R$^{10}$)$_2$; —NR$^{10}$C(=O)O—R$^{11}$, —OC(=O)O—R$^{11}$, —NHC(=O)NH—R$^{11}$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_8$cycloalkyl, and substituted or unsubstituted aryl, $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

$R^5$ is hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, $C_1$-$C_6$aminoalkyl; or —X$^6$—R$^6$;

$X^6$ is a $C_1$-$C_6$alkylene, $C_1$-$C_6$fluoroalkylene, $C_2$-$C_6$alkenylene, $C_2$-$C_6$heteroalkylene;

$R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or —X$^7$—R$^7$;

$X^7$ is a bond, —O—, —S—, —S(=O)—, —S(=O)$_2$—, —NR$^a$—, —C(=O)—, —C(=O)O—, —OC(=O)—, —NHC(=O)—, —C(=O)NR$^a$—, —S(=O)$_2$NR$^a$—, —NHS(=O)$_2$—, —OC(=O)NR$^a$—, —NHC(=O)O—, —OC(=O)O—, —NHC(=O)NR$^a$—; wherein R$^a$ is selected from among hydrogen, C$_1$-C$_6$alkyl, C$_2$-C$_6$alkenyl, hydroxy, C$_1$-C$_6$alkoxy, C$_1$-C$_6$fluoroalkoxy, C$_1$-C$_6$heteroalkyl;

R$^7$ is hydrogen, C$_1$-C$_6$alkyl, C$_2$-C$_6$alkenyl, C$_1$-C$_6$heteroalkyl, C$_1$-C$_6$haloalkyl, C$_3$-C$_8$cycloalkyl, cycloalkylalkyl, C$_2$-C$_8$heterocycloalkyl, heterocycloalkylalkyl, aryl, arylalkyl, heteroaryl, heteroarylalkyl;

or an active metabolite, pharmaceutically acceptable solvate, pharmaceutically acceptable salt, pharmaceutically acceptable N-oxide, or pharmaceutically acceptable prodrug thereof.

In one embodiment, provided herein is a 1,3-disubstituted-azaindole-6-carboxylic acid hydroxyamide compound, wherein the substituent at the 1-position is —X$^2$—R$^2$ and the substituent at the 3-position is R$^5$, wherein:

X$^2$ is a bond, or a substituted or unsubstituted group selected from among, C$_1$-C$_6$alkylene, C$_2$-C$_6$alkenylene, C$_2$-C$_6$ alkynylene, C$_1$-C$_6$heteroalkylene; C$_1$-C$_6$alkoxy; C$_1$-C$_6$amine; C$_1$-C$_6$amide; C$_1$-C$_6$sulfide; C$_1$-C$_6$sulfoxide; C$_1$-C$_6$sulfonyl; C$_1$-C$_6$fluoroalkylene, C$_2$-C$_6$fluoroalkenylene, C$_1$-C$_6$haloalkylene, C$_2$-C$_6$haloalkenylene, C$_1$-C$_6$heteroalkylene; —C(=O)—, and —C(=O)—C$_1$-C$_6$alkylene;

R$^2$ is a substituted or unsubstituted group selected from among aryl, heteroaryl, cycloalkyl, and heterocycloalkyl;
  where if R$^2$ is substituted, then each substituent on R$^2$ is selected from among halogen, sulfonyl, thiol, substituted or unsubstituted C$_1$-C$_6$alkoxy, C$_1$-C$_6$ fluoroalkoxy, C$_1$-C$_6$aminoalkoxy, C$_1$-C$_6$alkylaminoalkoxy, C$_1$-C$_6$alkoxyaminoalkoxy, C$_1$-C$_6$hydroxyalkylaminoalkoxy, C$_1$-C$_6$heterocycloalkylalkoxy, substituted or unsubstituted heterocycloalkyl, substituted or unsubstituted heteroaryl; —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=O)$_2$—R$^{11}$, —OC(=O)N(R$^1$)$_2$, —NR$^{10}$C(=O)O—R$^{11}$, —OC(=O)O—R$^{11}$, —NHC(=O)NH—R$^{11}$, —OC(=O)—R$^{11}$; —N(R$^{10}$)$_2$, substituted or unsubstituted C$_1$-C$_6$alkyl, C$_1$-C$_6$fluoroalkyl, substituted or unsubstituted C$_2$-C$_6$alkenyl, substituted or unsubstituted C$_2$-C$_6$alkynyl, substituted or unsubstituted C$_1$-C$_6$heteroalkyl, substituted or unsubstituted C$_3$-C$_8$cycloalkyl, and substituted or unsubstituted aryl,
  R$^{10}$ is hydrogen, or a substituted or unsubstituted group selected from among C$_1$-C$_6$alkyl, C$_1$-C$_6$fluoroalkyl, C$_1$-C$_6$heteroalkyl, C$_3$-C$_8$cycloalkyl, C$_2$-C$_8$heterocycloalkyl, aryl, and heteroaryl;
  R$^{11}$ is a substituted or unsubstituted group selected from among C$_1$-C$_6$alkyl, C$_1$-C$_6$fluoroalkyl, C$_3$-C$_8$cycloalkyl, C$_2$-C$_8$heterocycloalkyl, aryl, and heteroaryl;

R$^5$ is hydrogen, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$alkoxy, substituted or unsubstituted C$_1$-C$_6$fluoroalkoxy, substituted or unsubstituted C$_1$-C$_6$heteroalkyl, substituted or unsubstituted phenyl, C$_1$-C$_6$aminoalkyl; or —X$^6$—R$^6$;

X$^6$ is a C$_1$-C$_6$alkylene, C$_1$-C$_6$fluoroalkylene, C$_2$-C$_6$alkenylene, C$_2$-C$_6$heteroalkylene;

R$^6$ is hydrogen, halogen, —CN, hydroxy, amino, C$_1$-C$_6$alkylamino, di(C$_1$-C$_6$alkylamino, C$_1$-C$_6$alkoxy, C$_3$-C$_8$cycloalkyl, C$_2$-C$_8$heterocycloalkyl, phenyl, heteroaryl, or —X$^7$—R$^7$;

X$^7$ is a bond, —O—, —S—, —S(=O)—, —S(=O)$_2$—, —NR$^a$—, —C(=O)—, —C(=O)O—, —OC(=O)—, —NHC(=O)—, —C(=O)NR$^a$—, —S(=O)$_2$NR$^a$—, —NHS(=O)$_2$—, —OC(=O)NR$^a$—, —NHC(=O)O—, —OC(=O)O—, —NHC(=O)NR$^a$—;

R$^7$ is hydrogen, C$_1$-C$_6$alkyl, C$_2$-C$_6$alkenyl, C$_1$-C$_6$heteroalkyl, C$_1$-C$_6$haloalkyl, C$_3$-C$_6$cycloalkyl, cycloalkylalkyl, C$_2$-C$_8$heterocycloalkyl, heterocycloalkylalkyl, aryl, arylalkyl, heteroaryl, heteroarylalkyl, R$^a$ is selected from among hydrogen, C$_1$-C$_6$alkyl, C$_2$-C$_6$alkenyl, hydroxy, C$_1$-C$_6$alkoxy, C$_1$-C$_6$fluoroalkoxy, C$_1$-C$_6$heteroalkyl; or R$^a$ and R$^7$ together with the N atom to which they are attached form a 5-, 6-, or 7-membered heterocycloalkyl;

or an active metabolite, pharmaceutically acceptable solvate, pharmaceutically acceptable salt, pharmaceutically acceptable N-oxide, or pharmaceutically acceptable prodrug thereof.

In some embodiments the azaindole moiety is selected from:

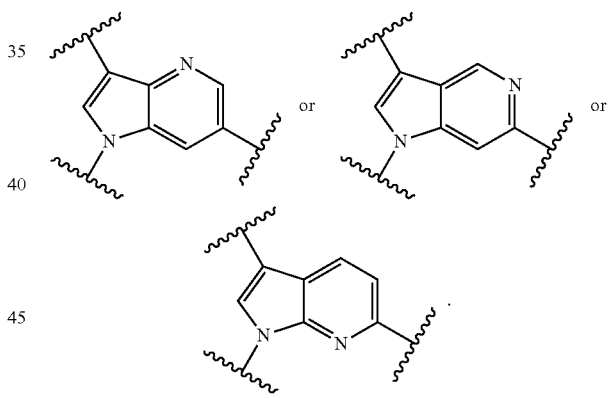

In other embodiments the azaindole moiety is selected from 4-azaindole, 5-azaindole, or 7-azaindole.

For any and all of the embodiments, substituents are selected from among from a subset of the listed alternatives. For example, in some embodiments, X$^2$ is a substituted or unsubstituted group selected from among C$_1$-C$_6$alkylene, C$_2$-C$_6$alkenylene, C$_1$-C$_6$alkoxy, C$_1$-C$_6$fluoroalkylene, C$_2$-C$_6$fluoroalkenylene, and C$_1$-C$_6$heteroalkylene. In other embodiments, X$^2$ is a substituted or unsubstituted group selected from among C$_1$-C$_6$alkylene, and C$_1$-C$_6$alkoxy. In some embodiments, X$^2$ is —CH$_2$—, —CH$_2$CH$_2$—, —(CH$_2$)$_3$—, —O(CH$_2$)—, —O(CH$_2$)$_2$— or —O(CH$_2$)$_3$—. In some embodiments, X$^2$ is —CH$_2$—.

In some embodiments, R$^2$ is an optionally substituted group selected from among phenyl, naphthyl, monocyclic heteroaryl, bicyclic heteroaryl, C$_3$-C$_8$ cycloalkyl, monocyclic heterocycloalkyl, and bicyclic heterocycloalkyl. In other embodiments, R$^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl, monocyclic heterocycloalkyl containing 0-2 N atoms, and bicyclic heterocycloalkyl 0-2 N atoms; where if $R^2$ is substituted, then each substituent on $R^2$ is selected from among halogen, sulfonyl, thiol, —CN, —$NO_2$, —$S(=O)_2NH_2$, —$CO_2H$, —$CO_2R^{10}$, —$C(=O)R^{11}$, —$S$—$R^{11}$, —$S(=O)$—$R^{11}$, —$S(=O)_2$—$R^{11}$, —$NR^{10}C(=O)$—$R^{11}$, —$C(=O)N(R^{10})_2$, —$S(=O)_2N(R^{10})_2$, —$NR^{10}S(=O)_2$—$R^{11}$, —$OC(=O)$—$R^{11}$; —$N(R')_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, phenyl, and heteroaryl; $R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, phenyl, and heteroaryl.

In some embodiments, $R^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl; where if $R^2$ is substituted, then each substituent on $R^2$ is selected from among halogen, sulfonyl, thiol, —CN, $NO_2$, —$S(=O)_2NH_2$, —$CO_2H$, —$CO_2R^{10}$, —$C(=O)R^{11}$, —$S(=O)$—$R^{11}$, —$S(=O)_2$, —$R^{11}$, —$NR^{10}C(=O)$—$R^{11}$, —$C(=O)N(R^{10})_2$, —$S(=O)_2N(R^{10})_2$, —$NR^{10}S(=O)_2$—$R^{11}$, —$OC(=O)$—$R^{11}$; —$N(R^{10})_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, and phenyl; $R^{11}$ is a substituted or unsubstituted group selected from among $C_1$-$C_6$alkyl, $C_1$-$C_6$fluoroalkyl, and phenyl.

In some embodiments, $R^2$ is selected from among phenyl, 2-methylphenyl, 3-methylphenyl, 4-methylphenyl, 3,4-dimethylphenyl, 2-fluorophenyl, 3-fluorophenyl, 4-fluorophenyl, 3,4-difluorophenyl, 2-chlorophenyl, 3-chlorophenyl, 4-chlorophenyl, 2,4-dichlorophenyl, 3,4-dichlorophenyl, 3-methoxyphenyl, 3-methoxyphenyl, 4-methoxyphenyl, 3,5-dimethoxyphenyl, 3,4,5-trimethoxyphenyl, naphth-2-yl, cyclopentyl, cyclohexyl, cycloheptyl, 2-(trifluoromethyl)-phenyl, 3-(trifluoromethyl)-phenyl, 4-(trifluoromethyl)-phenyl, 2-(trifluoromethoxy)-phenyl, 3-(trifluoromethoxy)-phenyl, 4-(trifluoromethoxy)-phenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl) phenyl, 4-(methylsulfonyl)phenyl, 2-thiophenyl, 3-thiophenyl, 2-pyridyl, 3-pyridyl, 4-pyridyl, 2,3-difluorophenyl, 2,4-difluorophenyl, benzo[2,1,3]oxadiazol-5-yl, 3-fluoro-4-methoxy-phenyl, 2-(difluoromethoxy)-phenyl, 3-(difluoromethoxy)-phenyl, 4-(difluoromethoxy)-phenyl, N-(t-butoxycarbonyl)piperidin-4-yl, piperidin-4-yl, N-methylsulfonyl-2-aminophenyl, N-methylsulfonyl-3-aminophenyl, N-methylsulfonyl-4-aminophenyl, N-phenylsulfonyl-2-aminophenyl, N-phenylsulfonyl-3-aminophenyl, N-phenylsulfonyl-4-aminophenyl, 2-nitrophenyl, 3-nitrophenyl, 4-nitrophenyl, 2-aminophenyl, 3-aminophenyl, 4-aminophenyl, 2-dimethylaminophenyl, 3-dimethylaminophenyl, 4-dimethylaminophenyl, N-acetyl-2-aminophenyl, N-acetyl-3-aminophenyl, N-acetyl-4-aminophenyl, N-benzoyl-2-aminophenyl, N-benzoyl-3-aminophenyl, and N-benzoyl-4-aminophenyl.

In other embodiments, $R^2$ is selected from among phenyl, 3-methoxyphenyl, 4-methoxyphenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 3-fluoro-4-methoxyphenyl, 4-(trifluoromethoxy)-phenyl, 3,4-dichlorophenyl, 2,4-dichlorophenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl)phenyl, 4-(methylsulfonyl) phenyl, 2-thiophenyl, 3-thiophenyl, 2-pyridyl, 3-pyridyl, 4-pyridyl, 2,3-difluorophenyl, 2,4-difluorophenyl, 3,4-difluorophenyl.

In some embodiments, $R^5$ is hydrogen, halogen, substituted or unsubstituted $C_1$-$C_6$alkyl, substituted or unsubstituted $C_2$-$C_6$alkenyl, substituted or unsubstituted $C_1$-$C_6$heteroalkyl, substituted or unsubstituted phenyl, or —$X^6$—$R^6$; $X^6$ is a $C_1$-$C_6$alkylene, $C_1$-$C_6$fluoroalkylene, $C_2$-$C_6$alkenylene, or $C_2$-$C_6$heteroalkylene; $R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_6$heterocycloalkyl, phenyl, heteroaryl, or —$X^7$—$R^7$; $X^7$ is a bond, —O—, —S—, —$S(=O)$—, —$S(=O)_2$—, —$C(=O)$—, —$C(=O)O$—, —$OC(=O)$—, —$NHC(=O)$—, —$C(=O)NR^a$—, —$S(=O)_2NR^a$—, —$NHS(=O)_2$—, —$OC(=O)NR^a$—, —$NHC(=O)O$—, —$OC(=O)O$—, —$NHC(=O)NR^a$—; $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl; r is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, 6-, or 7-membered heterocycloalkyl.

In some embodiments, $R^5$ is hydrogen, halogen, substituted or unsubstituted $C_1$-$C_6$alkyl, or —$X^6$—$R^6$.

In some embodiments, $X^6$ is $C_1$-$C_6$alkylene; $R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl containing 0-2 N atoms, phenyl, heteroaryl containing 0-2 N atoms, or —$X^7$—$R^7$; $X^7$ is a bond, —O—, —S—, —$S(=O)$—, —$S(=O)_2$—, —$C(=O)O$—, —$OC(=O)$—, —$NHC(=O)$—, —$C(=O)NR^a$—, —$S(=O)_2NR^a$—, —$NHS(=O)_2$—; $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl; $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, 6-, or 7-membered heterocycloalkyl.

In some embodiments, $R^6$ is —$X^7$—$R^7$.

In some embodiments, $X^7$ is a bond, —O—, —S—, —$S(=O)$—, —$S(=O)_2$—, —$NR^a$—, or —$C(=O)$—.

In some embodiments, $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, phenyl, phenyl$C_1$-$C_4$alkyl, heteroaryl, heteroaryl$C_1$-$C_4$alkyl; $R^a$ is selected from among hydrogen, $C_1$-$C_6$alkyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, or 6-membered heterocycloalkyl.

In some embodiments, $X^7$ is a bond, —O—, or —$NR^a$—. In some embodiments, $X^7$ is a bond, or -Me-.

In some embodiments, $R^a$ is selected from among hydrogen, $C_1$-$C_6$alkyl, hydroxy, $C_1$-$C_6$alkoxy, $C_1$-$C_6$heteroalkyl. In other embodiments, $R^a$ is selected from among hydrogen, $C_1$-$C_6$alkyl, and $C_1$-$C_6$heteroalkyl.

In some embodiments, $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, phenyl, phenyl$C_1$-$C_4$alkyl, heteroaryl, heteroaryl$C_1$-$C_4$alkyl; $R^a$ is selected from among hydrogen, $C_1$-$C_6$alkyl, hydroxy, $C_1$-$C_6$alkoxy, $C_1$-$C_6$heteroalkyl; or $R^a$ and $R^7$ together with the N atom to which they are attached form a 5-, or 6-membered heterocycloalkyl.

In some embodiments, $R^5$ is selected from among hydrogen, methyl, ethyl, propyl, benzyl, dimethylaminomethyl, N-morpholinomethyl, N-pyrrolidinomethyl, N-piperidinomethyl, and N-benzylaminomethyl. In some embodiments, $R^5$ is selected from among hydrogen, methyl, ethyl, propyl, benzyl, dimethylaminomethyl, N-morpholinomethyl, N-pyrrolidinomethyl, and N-benzylaminomethyl.

Any combination of the groups described above for the various variables is contemplated herein. It is understood that substituents and substitution patterns on the compounds provided herein are selected to provide compounds that are chemically stable and that are synthesized by techniques set forth herein.

In another embodiment, is a compound having a structure selected from among Formula (IIa), (IIb), and (IIc):

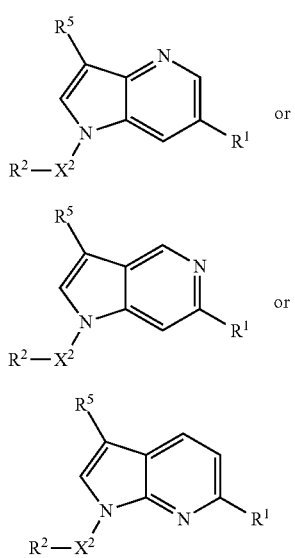

wherein:
$R^1$ is —C(O)NHOH;
$R^5$ is hydrogen, alkyl, substituted alkyl, alkenyl, substituted alkenyl, hydroxy, alkoxy, haloalkoxy, or optionally substituted phenyl;

$X^2$ is a bond, alkylene, or alkenylene where the alkylene or alkenylene is optionally substituted with halogen; and
$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or
an active metabolite, pharmaceutically acceptable solvate, pharmaceutically acceptable salt, pharmaceutically acceptable N-oxide, or pharmaceutically acceptable prodrug thereof.

In another embodiment, is a compound having a structure selected from among Formula (IIa), (IIb), or (IIc) wherein:
$R^1$ is —C(O)NHOH;
$R^5$ is hydrogen, alkyl, substituted alkyl, alkenyl, substituted alkenyl, hydroxy, alkoxy, haloalkoxy, or optionally substituted phenyl; and
$X^2$ is a bond; and $R^2$ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that $R^2$ is not optionally substituted pyrrole or optionally substituted 2,5-dioxo-pyrrole; or
$X^2$ is alkylene or alkenylene where the alkylene or alkenylene is optionally substituted with halo; and $R^2$ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or
an active metabolite, pharmaceutically acceptable solvate, pharmaceutically acceptable salt, pharmaceutically acceptable N-oxide, or pharmaceutically acceptable prodrug thereof.

In yet another embodiment, is a compound of Formula (IIa).

In a further embodiment, is a compound of Formula (IIb).

In yet another embodiment, is a compound of Formula (IIc).

In a further embodiment, is a compound of Formula (IId).

In yet another embodiment, is a compound of Formula (IIe).

In a further embodiment, is a compound of Formula (IIf).

In some embodiments, $R^5$ is hydrogen, alkyl, substituted alkyl, alkenyl, substituted alkenyl, hydroxy, alkoxy, haloalkoxy, or optionally substituted phenyl. In yet other embodiments, $R^2$ is alkyl or optionally substituted phenyl. In some other embodiments, $R^2$ is methyl, ethyl, isopropyl, or phenyl. In some embodiments, $R^2$ is methyl, ethyl, or isopropyl.

In some embodiments, $X^2$ is a bond, alkylene, alkoxy, or alkenylene where the alkylene or alkenylene is optionally substituted with halo. In other embodiments, $X^2$ is alkylene. In yet other embodiments, $X^5$ is —CH$_2$—.

In some embodiments, $R^2$ is aryl, cycloalkyl, heteroaryl, or heterocycloalkyl where the aryl, cycloalkyl, heteroaryl, and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro.

In yet other embodiments, $R^2$ is heterocycloalkyl optionally substituted with alkoxycarbonyl or $R^2$ is aryl optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carbonyl, cyano, halogen, haloalkoxy, and nitro. In some embodiments, $R^2$ is piperazinyl optionally substituted with t-butoxycarbonyl, or $R^2$ is phenyl optionally substituted with one, two, or three substituents selected from among acylamino, amino, halogen, and nitro. In some other embodiments, $R^2$ is 4-(t-butoxycarbonyl)piperazin-1-yl, phenyl, 4-aminophenyl, 4-(phenylcarbonylamino)-phenyl, 4-fluorophenyl, or 4-nitrophenyl. In yet other embodiments, $R^2$ is phenyl, 4-aminophenyl, 4-(phenylcarbonylamino)-phenyl, 4-fluorophenyl, or 4-nitrophenyl. In other embodiments, $R^2$ is 3,4-dichlorophenyl, 2,4-dichlorophenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl)phenyl, 4-(methylsulfonyl)phenyl, 2-thiophenyl, 3-thiophenyl, 2-pyridyl, 3-pyridyl, 4-pyridyl, 2,3-difluorophenyl, 2,4-difluorophenyl, 3,4-difluorophenyl.

In some embodiments, $X^2$ is a bond, or alkoxy; and $R^2$ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, or nitro; and the phenyl is substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro; provided that $R^2$ is not optionally substituted pyrrole or optionally substituted 2,5-dioxo-pyrrole; or $X^2$ is alkylene or alkenylene where the alkylene or alkenylene is optionally substituted with halogen; and $R^2$ is aryl, cycloalkyl, heteroaryl, or heterocycloalkyl where the cycloalkyl, heteroaryl, and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro; and the aryl is substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro.

In some embodiments, $X^2$ is alkylene or alkenylene; and $R^2$ is aryl substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro. In other embodiments, $R^2$ is phenyl substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro. In some other embodiments, $R^2$ is phenyl substituted with one, two, or three substituents selected from among optionally substituted arylcarbonylamino, amino, halo, and nitro. In yet other embodiments, $R^2$ is 4-(phenylcarbonylamino)-phenyl, 4-aminophenyl, 4-fluorophenyl, or 4-nitrophenyl.

Pyrrole Alkene Compounds

In one aspect, is a compound of Formula B:

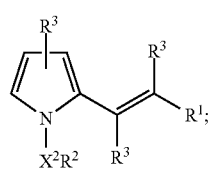

Formula B wherein:

$R^1$ is C(O)NHOH;

$X^2$ is a bond, or a substituted or unsubstituted group selected from among $C_1$-$C_6$alkylene, $C_2$-$C_6$alkenylene, $C_2$-$C_6$ alkynylene, $C_1$-$C_6$heteroalkylene; $C_1$-$C_6$alkoxy; $C_1$-$C_6$amine; $C_1$-$C_6$amide; $C_1$-$C_6$sulfide; $C_1$-$C_6$sulfoxide; $C_1$-$C_6$sulfonyl; $C_1$-$C_6$fluoroalkylene, $C_2$-$C_6$fluoroalkenylene, $C_1$-$C_6$haloalkylene, $C_2$-$C_6$haloalkenylene, —C(=O)—, and —C(=O)—$C_1$-$C_6$alkylene;

$R^2$ is a substituted or unsubstituted group selected from among aryl, heteroaryl, cycloalkyl, and heterocycloalkyl;

where if $R^2$ is substituted, then each substituent on $R^2$ is selected from among halogen, sulfonyl, thiol, substituted or unsubstituted $C_1$-$C_6$alkoxy, $C_1$-$C_6$ fluoroalkoxy, $C_1$-$C_6$aminoalkoxy, $C_1$-$C_6$alkylaminoalkoxy, $C_1$-$C_6$alkoxyaminoalkoxy, $C_1$-$C_6$hydroxyalkylaminoalkoxy, $C_1$-$C_6$heterocycloalkylalkoxy, substituted or unsubstituted heterocycloalkyl, substituted or unsubstituted heteroaryl; —CN, —NO$_2$, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=O)$_2$—R$^{11}$, —OC(=O)N(R$^{10}$)$_2$, —NR$^{10}$C(=O)O—R$^{11}$, —OC(=O)O—R$^{11}$, —NHC(=O)NH—R$^{11}$, —OC(=O)—R$^{11}$; —N(R$^{10}$)$_2$, substituted or =substituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_8$cycloalkyl, and substituted or unsubstituted aryl, $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

each $R^3$ is independently hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $C_1$-$C_6$aminoalkyl;

or an active metabolite, pharmaceutically acceptable solvate, pharmaceutically acceptable salt, pharmaceutically acceptable N-oxide, or pharmaceutically acceptable prodrug thereof.

In one embodiment, is a substituted-1H-pyrrole-2-yl-N-hydroxyacrylamide compound, wherein the substituent at the 1-position is —X$^2$—R$^2$, wherein:

$X^2$ is a bond, or a substituted or unsubstituted group selected from among $C_1$-$C_6$alkylene, $C_2$-$C_6$alkenylene, $C_2$-$C_6$ alkynylene, $C_1$-$C_6$heteroalkylene; $C_1$-$C_6$alkoxy; $C_1$-$C_6$amide; $C_1$-$C_6$amine; $C_1$-$C_6$sulfide; $C_1$-$C_6$sulfoxide; $C_1$-$C_6$sulfonyl; $C_1$-$C_6$fluoroalkyl; $C_2$-$C_6$fluoroalkenylene, $C_1$-$C_6$haloalkylene, $C_2$-$C_6$haloalkenylene, —C(=O)—, and —C(=O)—$C_1$-$C_6$alkylene;

$R^2$ is a substituted or unsubstituted group selected from among aryl, heteroaryl, cycloalkyl, and heterocycloalkyl;

where if $R^2$ is substituted, then each substituent on $R^2$ is selected from among halogen, sulfonyl, thiol, substituted or unsubstituted $C_1$-$C_6$alkoxy, $C_1$-$C_6$ fluoroalkoxy, $C_1$-$C_6$aminoalkoxy, $C_1$-$C_6$alkylaminoalkoxy, $C_1$-$C_6$alkoxyaminoalkoxy, $C_1$-$C_6$hydroxyalkylaminoalkoxy, $C_1$-$C_6$heterocycloalkylalkoxy, substituted or unsubstituted heterocycloalkyl, substituted or unsubstituted heteroaryl; —CN, —NO$_2$, —CO$_2$R$^{10}$, —C(=O)R$^{11}$, —S—R$^{11}$, C(=O)—R$^{11}$, —S(=O)$_2$—R$^{11}$, —NR$^{10}$C(=O)—R$^{11}$, —C(=O)N(R$^{10}$)$_2$, —S(=O)$_2$ N(R$^{10}$)$_2$, —NR$^{10}$S(=O)$_2$—R$^{11}$, —OC (=O)N(R$^{10}$)$_2$, —NR$^{10}$C(=O)O—R$^{11}$, —OC(=O)O—R$^{11}$, —NHC(=O)NH—R$^{11}$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_8$cycloalkyl, and substituted or unsubstituted aryl, $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

For any and all of the embodiments, substituents are selected from among from a subset of the listed alternatives. For example, in some embodiments, $X^2$ is a substituted or unsubstituted group selected from among $C_1$-$C_6$alkylene, $C_2$-$C_6$alkenylene, $C_1$-$C_6$alkoxy, $C_1$-$C_6$fluoroalkylene, $C_2$-$C_6$fluoroalkenylene, and $C_1$-$C_6$heteroalkylene. In other embodiments, $X^2$ is a substituted or unsubstituted group selected from among $C_1$-$C_6$alkylene, and $C_1$-$C_6$alkoxy. In some embodiments, $X^2$ is —CH$_2$—, —CH$_2$CH$_2$—, —(CH$_2$)$_3$—, —OCH$_2$—, —O(CH$_2$)$_2$— or —O(CH$_2$)$_3$—. In some embodiments, $X^2$ is —CH$_2$—.

In some embodiments, $R^2$ is an optionally substituted group selected from among phenyl, naphthyl, monocyclic heteroaryl, bicyclic heteroaryl, $C_3$-$C_8$ cycloalkyl, monocyclic heterocycloalkyl, and bicyclic heterocycloalkyl. In other embodiments, $R^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl, monocyclic heterocycloalkyl containing 0-2 N atoms, and bicyclic heterocycloalkyl 0-2 N atoms; where if $R^2$ is substituted, then each substituent on $R^2$ is selected from among hydrogen, halogen, sulfonyl, thiol, —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=O)$_2$—R$^{11}$; —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, phenyl, and heteroaryl; $R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, phenyl, and heteroaryl.

In some embodiments, $R^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl; where if $R^2$ is substituted, then each substituent on $R^2$ is selected from among hydrogen, halogen, sulfonyl, thiol, —CN, —NO$_2$, —S(=O)$_2$NH$_2$, —CO$_2$H, COR$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{14}$)$_2$, —S(=O)$_2$N(R$^{10}$)$_2$, —NR$^{10}$S(=O)$_2$—R$^{11}$, —OC(=O)—R$^{11}$; —N(R$^{10}$)$_2$, substituted or unsubstituted C₁-C₆alkyl, C₁-C₆fluoroalkyl, substituted or unsubstituted C₂-C₆alkenyl, substituted or unsubstituted C₁-C₆alkoxy, C₁-C₆ fluoroalkoxy, substituted or unsubstituted C₁-C₆heteroalkyl, substituted or unsubstituted C₃-C₈cycloalkyl, substituted or unsubstituted heterocycloalkyl, substituted or unsubstituted aryl, and substituted or unsubstituted heteroaryl; R¹⁰ is hydrogen, or a substituted or unsubstituted group selected from among C₁-C₆alkyl, C₁-C₆fluoroalkyl, C₁-C₆heteroalkyl, and phenyl; R¹¹ is a substituted or unsubstituted group selected from among C₁-C₆alkyl, C₁-C₆fluoroalkyl, and phenyl.

In some embodiments, R² is selected from among phenyl, 2-methylphenyl, 3-methylphenyl, 4-methylphenyl, 3,4-dimethylphenyl, 2-fluorophenyl, 3-fluorophenyl, 4-fluorophenyl, 3,4-difluorophenyl, 2-chlorophenyl, 3-chlorophenyl, 4-chlorophenyl, 2,4-dichlorophenyl, 3,4-dichlorophenyl, 3-methoxyphenyl, 3-methoxyphenyl, 4-methoxyphenyl, 3,5-dimethoxyphenyl, 3,4,5-trimethoxyphenyl, naphth-2-yl, cyclopentyl, cyclohexyl, cycloheptyl, 2-(trifluoromethyl)-phenyl, 3-(trifluoromethyl)-phenyl, 4-(trifluoromethyl)-phenyl, 2-(trifluoromethoxy)-phenyl, 3-(trifluoromethoxy)-phenyl, 4-(trifluoromethoxy)-phenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl) phenyl, 4-(methylsulfonyl)phenyl, 2-thiophenyl, 3-thiophenyl, 2-pyridyl, 3-pyridyl, 4-pyridyl, 2,3-difluorophenyl, 2,4-difluorophenyl, benzo[2,1,3]oxadiazol-5-yl, 3-fluoro-4-methoxy-phenyl, 2-(difluoromethoxy)-phenyl, 3-(difluoromethoxy)-phenyl, 4-(difluoromethoxy)-phenyl, N-(t-butoxycarbonyl)piperidin-4-yl, piperidin-4-yl, N-methylsulfonyl-2-aminophenyl, N-methylsulfonyl-3-aminophenyl, N-methylsulfonyl-4-aminophenyl, N-phenylsulfonyl-2-aminophenyl, N-phenylsulfonyl-3-aminophenyl, N-phenylsulfonyl-4-aminophenyl, 2-nitrophenyl, 3-nitrophenyl, 4-nitrophenyl, 2-aminophenyl, 3-aminophenyl, 4-aminophenyl, 2-dimethylaminophenyl, 3-dimethylaminophenyl, 4-dimethylaminophenyl, N-acetyl-2-aminophenyl, N-acetyl-3-aminophenyl, N-acetyl-4-aminophenyl, N-benzoyl-2-aminophenyl, N-benzoyl-3-aminophenyl, and N-benzoyl-4-aminophenyl.

In other embodiments, R² is selected from among phenyl, 3-methoxyphenyl, 4-methoxyphenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 3-fluoro-4-methoxyphenyl, 4-(trifluoromethoxy)-phenyl, 3,4-dichlorophenyl, 2,4-dichlorophenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl)phenyl, 4-(methylsulfonyl) phenyl, 2-thiophenyl, 3-thiophenyl, 2-pyridyl, 3-pyridyl, 4-pyridyl, 2,3-difluorophenyl, 2,4-difluorophenyl, 3,4-difluorophenyl.

In one embodiment is a compound having the structure of Formula IIIb:

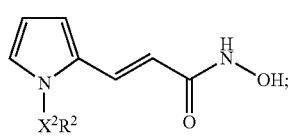

Formula IIIb wherein:
X² is a bond, or a substituted or unsubstituted group selected from among C₁-C₆alkylene, C₂-C₆alkenylene, C₂-C₆ alkynylene, C₁-C₆heteroalkylene; C₁-C₆alkoxy; C₁-C₆amine; C₁-C₆amide; C₁-C₆sulfide; C₁-C₆sulfoxide; C₁-C₆sulfonyl; C₁-C₆fluoroalkylene, C₂-C₆fluoroalkenylene, C₁-C₆haloalkylene, C₂-C₆haloalkenylene, —C(=O)—, and —C(=O)—C₁-C₆alkylene;

R² is a substituted or unsubstituted group selected from among aryl, heteroaryl, cycloalkyl, and heterocycloalkyl;

where if R² is substituted, then each substituent on R² is selected from among halogen, sulfonyl, thiol, substituted or unsubstituted C₁-C₆alkoxy, C₁-C₆ fluoroalkoxy, C₁-C₆aminoalkoxy, C₁-C₆alkylaminoalkoxy, C₁-C₆alkoxyaminoalkoxy, C₁-C₆hydroxyalkylaminoalkoxy, C₁-C₆heterocycloalkylalkoxy, substituted or unsubstituted heterocycloalkyl, substituted or unsubstituted heteroaryl; —CN, —NO₂, —CO₂R¹⁰, —C(=O)R¹¹, —S—R¹¹, —S(=O)—R¹¹, —S(=O)₂—R¹¹, —NR¹⁰C(=O)—R¹¹, —C(=O)N(R¹⁰)₂, —S(=O)₂N(R¹)₂, —NR¹⁰S(=O)₂—R¹¹, —OC(=O)N(R¹⁰)₂, —NR¹⁰C(=O)O—R¹¹, —OC(=O)O—R¹¹, —NHC(=O)NH—R¹¹, —OC(=O)—R¹¹; —N(R¹⁰)₂, substituted or unsubstituted C₁-C₆alkyl, C₁-C₆fluoroalkyl, substituted or unsubstituted C₂-C₆alkenyl, substituted or unsubstituted C₂-C₆alkynyl, substituted or unsubstituted C₁-C₆heteroalkyl, substituted or unsubstituted C₃-C₈cycloallyl, and substituted or unsubstituted aryl, R¹⁰ is hydrogen, or a substituted or unsubstituted group selected from among C₁-C₆alkyl, C₁-C₆fluoroalkyl, C₁-C₆heteroalkyl, C₃-C₈cycloalkyl, C₂-C₈heterocycloalkyl, aryl, and heteroaryl;

R¹¹ is a substituted or unsubstituted group selected from among C₁-C₆alkyl, C₁-C₆fluoroalkyl, C₃-C₈cycloalkyl, C₂-C₈heterocycloalkyl, aryl, and heteroaryl;

or an active metabolite, pharmaceutically acceptable solvate, pharmaceutically acceptable salt, pharmaceutically acceptable N-oxide, or pharmaceutically acceptable prodrug thereof.

In another embodiment, is a compound having a structure selected from among Formula (IIIa):

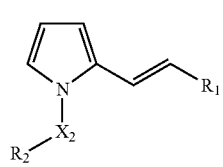

IIIa wherein:
R¹ is —C(O)NHOH;

X² is a bond, alkylene, alkenylene, or alkoxy;

R² is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or an active metabolite, pharmaceutically acceptable solvate, pharmaceutically acceptable salt, pharmaceutically acceptable N-oxide, or pharmaceutically acceptable prodrug thereof.

In another embodiment, is a compound having a structure selected from among Formula (IIIa) wherein:
- $R^1$ is —C(O)NHOH;
- $X^2$ is a bond, alkylene, or alkoxy;
- $R^2$ is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro; or
- an active metabolite, pharmaceutically acceptable solvate, pharmaceutically acceptable salt, pharmaceutically acceptable N-oxide, or pharmaceutically acceptable prodrug thereof.

In one embodiment, is a compound of Formula (IIIa).

In another embodiment, is a compound of Formula (IIIb).

For any and all of the embodiments, substituents are selected from among from a subset of the listed alternatives. For example, in some embodiments, $X^2$ is a bond, alkylene, alkoxy, or alkenylene where the alkylene or alkenylene is optionally substituted with one, two, three, four, or five halogens. In another embodiment, $X^2$ is alkylene or alkenylene. In other embodiments, $X^2$ is —CH$_2$CH$_2$—, —CH(CH$_3$)—, —(CH$_2$)$_3$—, —OCH$_2$—, —OCH$_2$CH$_2$—, or —CH$_2$CH=CH—. In some embodiments, $X^2$ is —CH$_2$—. In other embodiments, $X^2$ is —OCH$_2$CH$_2$—.

In some embodiments, $R^2$ is aryl, cycloalkyl, heteroaryl, or heterocycloalkyl where the aryl, cycloalkyl, heteroaryl, and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro. In other embodiments, $R^2$ is aryl, cycloalkyl, heteroaryl, or heterocycloalkyl, where the aryl, cycloalkyl, heteroaryl, and heterocycloalkyl are optionally substituted with one, two, or three substituents selected from among alkyl, alkoxy, alkoxycarbonyl, halogen, and haloalkoxy. In some other embodiments, $R^2$ is aryl, cycloalkyl, heteroaryl, or heterocycloalkyl, where the aryl is optionally substituted with one, two, or three substituents selected from among alkyl, alkoxy, halo, and haloalkoxy, and the heterocycloalkyl is optionally substituted with alkoxycarbonyl. In further embodiments, $R^2$ is cyclohexyl, benzooxadiazolyl, naphth-2-yl, phenyl, or piperidinyl, where the phenyl is optionally substituted with one, two, or three substituents selected from among methyl, methoxy, chloro, fluoro, trifluoromethoxy, and difluoromethoxy, and the piperidinyl is optionally substituted with t-butoxycarbonyl. In yet other embodiments, $R^2$ is cyclohexyl, benzo[2,1,3]oxadiazol-5-yl, phenyl, naphth-2-yl, 2-methylphenyl, 3-methylphenyl, 4-methylphenyl, 3-methoxyphenyl, 4-methoxyphenyl, 3,5-dimethoxyphenyl, 3,4,5-trimethoxyphenyl, 2-chlorophenyl, 3-chlorophenyl, 4-chlorophenyl, 3,4-dichlorophenyl, 2-fluorophenyl, 3-fluorophenyl, 4-fluorophenyl, 4-(difluoromethoxy)-phenyl, 4-(trifluoromethoxy)-phenyl, 3-fluoro-4-methoxy-phenyl, piperidin-4-yl, or N-(t-butoxycarbonyl)piperidin-4-yl.

In some embodiments, $R^2$ is benzo[2,1,3]oxadiazol-5-yl, 4-methoxyphenyl, 4-chlorophenyl, 4-(difluoromethoxy)-phenyl, or 3-fluoro-4-methoxy-phenyl.

In other embodiments, $R^2$ is 3,4-dichlorophenyl, 2,4-dichlorophenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl)phenyl, 4-(methylsulfonyl)phenyl, 2-thiophenyl, 3-thiophenyl, 2-pyridyl, 3-pyridyl, 4-pyridyl, 2,3-difluorophenyl, 2,4-difluorophenyl, 3,4-difluorophenyl.

In some embodiments, $R^2$ is aryl, cycloalkyl, heteroaryl, or heterocycloalkyl, where the aryl is substituted with one, two, or three substituents selected from among acyloxy, alkyl, substituted alkyl, alkenyl, substituted alkenyl, alkylamino, dialkylamino, and haloalkoxy; where the cycloalkyl is optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro; and where the heteroaryl and the heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, and nitro. In other embodiments, $R^2$ is aryl, cycloalkyl, heteroaryl, or heterocycloalkyl where the aryl is substituted with one, two, or three substituents selected from among alkyl and haloalkoxy, and the heterocycloalkyl is optionally substituted with alkoxycarbonyl. In yet other embodiments, $R^2$ is cyclohexyl; benzooxadiazolyl; phenyl substituted with one, two, or three substituents selected from among methyl, trifluoromethoxy, or difluoromethoxy; or piperidinyl optionally substituted with t-butoxycarbonyl.

In some embodiments, $R^2$ is cyclohexyl, benzo[2,1,3]oxadiazol-5-yl, 2-methylphenyl, 3-methylphenyl, 4-methylphenyl, 4-(difluoromethoxy)-phenyl, 4-(trifluoromethoxy)-phenyl, N-(t-butoxycarbonyl)piperidin-4-yl, or piperidin-4-yl. In yet other embodiments, $R^2$ is benzo[2,1,3]oxadiazol-5-yl or 4-(difluoromethoxy)-phenyl.

In some embodiments, $X^2$ is alkylene or alkenylene; and $R^2$ is aryl, cycloalkyl, or heteroaryl, where the aryl, cycloalkyl, and heteroaryl are optionally substituted with one, two, or three substituents selected from among alkyl, alkoxy, alkoxycarbonyl, halogen, and haloalkoxy. In other embodiments, $X^2$ is alkylene or alkenylene; and $R^2$ is naphthyl, phenyl, cycloalkyl, heteroaryl, or heterocycloalkyl optionally substituted with methyl, methoxy, t-butoxycarbonyl, chloro, fluoro, trifluoromethoxy, or difluoromethoxy. In some other embodiments, $X^2$ is alkylene or alkenylene; and $R^2$ is phenyl where the phenyl is optionally substituted with one, two, or three substituents selected from among methyl, methoxy, chloro, fluoro, trifluoromethoxy, and difluoromethoxy; or $R^2$ is benzooxadiazolyl.

In some embodiments, $X^2$ is alkylene or alkenylene; and $R^2$ is cycloalkyl, aryl, heteroaryl, or heterocycloalkyl, where the cycloalkyl is optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro; where the aryl is substituted with one, two, or three substituents selected from among acyloxy, alkyl, substituted alkyl, alkenyl, substituted alkenyl, alkylamino, and haloalkoxy; where the heteroaryl and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, and nitro.

In some embodiments, $X^2$ is alkylene or alkenylene; and $R^2$ is cycloalkyl; phenyl substituted with one, two, or three alkyl or haloalkoxy; benzooxadiazolyl; or piperidinyl optionally substituted with alkoxycarbonyl. In some other embodiments, $X^2$ is alkylene or alkenylene; and $R^2$ is benzooxadiazolyl or phenyl where the phenyl is substituted with one, two, or three substituents selected from among methyl, chloro, fluoro, trifluoromethoxy, or difluoromethoxy.

Selective HDAC8 Miscellaneous Compounds

In one embodiment is a compound having the structure of Formula IV:

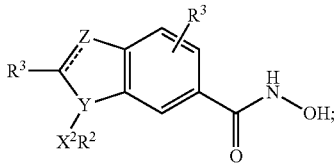

Formula IV wherein:
$Z$ is $CR^5$, N, O or S;
$Y$ is $CR^3$ or N;
⫽ represents a double bond when $Z$ is $CR^5$ or N; or is a single bond when $Z$ is O or S;
$X^2$ is a bond, or a substituted or unsubstituted group selected from among $C_1$-$C_6$alkylene, $C_2$-$C_6$alkenylene, $C_2$-$C_6$ alkynylene, $C_1$-$C_6$heteroalkylene; $C_1$-$C_6$alkoxy; $C_1$-$C_6$amine; $C_1$-$C_6$amide; $C_1$-$C_6$sulfide; $C_1$-$C_6$sulfoxide; $C_1$-$C_6$sulfonyl; $C_1$-$C_6$fluoroalkylene, $C_2$-$C_6$fluoroalkenylene, $C_1$-$C_6$haloalkylene, $C_2$-$C_6$haloalkenylene, —C(=O)—, and —C(=O)—$C_1$-$C_6$alkylene;
$R^2$ is a substituted or unsubstituted group selected from among aryl, heteroaryl, cycloalkyl, and heterocycloalkyl;
where if $R^2$ is substituted, then each substituent on $R^2$ is selected from among halogen, sulfonyl, thiol, substituted or unsubstituted $C_1$-$C_6$alkoxy, $C_1$-$C_6$ fluoroalkoxy, $C_1$-$C_6$aminoalkoxy, $C_1$-$C_6$alkylaminoalkoxy, $C_1$-$C_6$alkoxyaminoalkoxy, $C_1$-$C_6$hydroxyalkylaminoalkoxy, $C_1$-$C_6$heterocycloalkylalkoxy, substituted or unsubstituted heterocycloalkyl, substituted or unsubstituted heteroaryl; —CN, —$NO_2$, —$CO_2R^{10}$, —C(=O)$R^{11}$, —S—$R^{11}$, —S(=O)—$R^{11}$, —S(=O)$_2$—$R^{11}$, —$NR^{10}$C(=O)—$R^{11}$, —C(=O)N($R^{10}$)$_2$, —S(=O)$_2$N($R^{10}$)$_2$, —$NR^{10}$S(=O)$_2$—$R^{11}$, —OC(=O)N($R^{10}$)$_2$, —$NR^{10}$C(=O)O—$R^{11}$, —OC(=O)O—$R^{11}$, —NHC(=O)NH—$R^{11}$, —OC(=O)—$R^{11}$; —N($R^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_8$cycloalkyl, and substituted or unsubstituted aryl;
$R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;
$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

each $R^3$ is independently hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $C_1$-$C_6$aminoalkyl;
or an active metabolite, pharmaceutically acceptable solvate, pharmaceutically acceptable salt, pharmaceutically acceptable N-oxide, or pharmaceutically acceptable prodrug thereof.

In another embodiment, is a compound having a structure selected from among Formula (IVa):

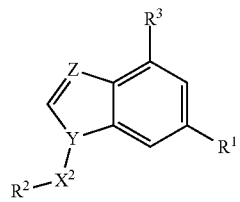

IVa wherein:
$Y$ is $CR^3$ or N;
$Z$ is $CR^3$;
$R^1$ is —C(O)NHOH;
$X^2$ is a bond, alkylene, alkenylene, or alkoxy;
$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;
$R^3$ is hydrogen, alkyl, substituted alkyl, alkenyl, substituted alkenyl, hydroxy, alkoxy, or haloalkoxy;
or an active metabolite, pharmaceutically acceptable solvate, pharmaceutically acceptable salt, pharmaceutically acceptable N-oxide, or pharmaceutically acceptable prodrug thereof.

In another embodiment, is a compound having a structure selected from among Formula (IVa):
wherein:
$Y$ is $CR^3$ or N;
$Z$ is $CR^3$;
$R^1$ is —C(O)NHOH;
$X^2$ is a bond, alkylene, or alkoxy;
$R^2$ is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

$R^3$ is hydrogen, alkenyl, substituted alkenyl, hydroxy, alkoxy, haloalkoxy, or —$X^6$—$R^6$ where $X^6$ is alkylene or alkenylene and $X^6$ is additionally optionally substituted with one, two, three, four, of five halo; and $R^6$ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where R$^a$ and R$^b$ are independently hydrogen, alkyl, substituted alkyl, alkenyl, alkynyl, substituted alkynyl, hydroxy, alkoxy, or alkenyloxy); or an active metabolite, pharmaceutically acceptable solvate, pharmaceutically acceptable salt, pharmaceutically acceptable N-oxide, or pharmaceutically acceptable prodrug thereof.

In one embodiment, is a compound of Formula (IVa).

For any and all of the embodiments, substituents are selected from among from a subset of the listed alternatives. For example, in some embodiments, $X^2$ is a bond, alkylene, alkoxy, or alkenylene where the alkylene or alkenylene is optionally substituted with one, two, three, four, or five halogens. In another embodiment, $X^2$ is alkylene or alkenylene. In other embodiments, $X^2$ is —CH$_2$—, —CH$_2$CH$_2$—, —CH(CH$_3$)—, —(CH$_2$)$_3$—, —OCH$_2$—, —OCH$_2$CH$_2$—, or —CH$_2$CH=CH—. In some embodiments, $X^2$ is —CH$_2$—. In other embodiments, $X^2$ is —OCH$_2$CH$_2$—.

In some embodiments, $R^2$ is aryl, cycloalkyl, heteroaryl, or heterocycloalkyl where the aryl, cycloalkyl, heteroaryl, and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro. In other embodiments, $R^2$ is aryl, cycloalkyl, heteroaryl, or heterocycloalkyl, where the aryl, cycloalkyl, heteroaryl, and heterocycloalkyl are optionally substituted with one, two, or three substituents selected from among alkyl, alkoxy, alkoxycarbonyl, halogen, and haloalkoxy. In some other embodiments, $R^2$ is aryl, cycloalkyl, heteroaryl, or heterocycloalkyl, where the aryl is optionally substituted with one, two, or three substituents selected from among alkyl, alkoxy, halo, and haloalkoxy, and the heterocycloalkyl is optionally substituted with alkoxycarbonyl. In further embodiments, $R^2$ is cyclohexyl, benzooxadiazolyl, naphth-2-yl, phenyl, or piperidinyl, where the phenyl is optionally substituted with one, two, or three substituents selected from among methyl, methoxy, chloro, fluoro, trifluoromethoxy, and difluoromethoxy, and the piperidinyl is optionally substituted with t-butoxycarbonyl. In yet other embodiments, $R^2$ is cyclohexyl, benzo[2,1,3]oxadiazol-5-yl, phenyl, naphth-2-yl, 2-methylphenyl, 3-methylphenyl, 4-methylphenyl, 3-methoxyphenyl, 4-methoxyphenyl, 3,5-dimethoxyphenyl, 3,4,5-trimethoxyphenyl, 2-chlorophenyl, 3-chlorophenyl, 4-chlorophenyl, 3,4-dichlorophenyl, 2-fluorophenyl, 3-fluorophenyl, 4-fluorophenyl, 4-(difluoromethoxy)-phenyl, 4-(trifluoromethoxy)-phenyl, 3-fluoro-4-methoxy-phenyl, piperidin-4-yl, or N-(t-butoxycarbonyl)piperidin-4-yl.

In some embodiments, $R^2$ is benzo[2,1,3]oxadiazol-5-yl, 4-methoxyphenyl, 4-chlorophenyl, 4-(difluoromethoxy)-phenyl, or 3-fluoro-4-methoxy-phenyl.

In other embodiments, $R^2$ is 3,4-dichlorophenyl, 2,4-dichlorophenyl, 2-chloro-4-fluorophenyl, 3-chloro-4-fluorophenyl, 2-fluoro-4-chlorophenyl, 3-fluoro-4-cholorophenyl, 2-chloro-4-methoxyphenyl, 2,3-dichlorophenyl, 3-methoxy-4-fluorophenyl, 3-methoxy-5-fluorophenyl, 3-methoxy-4-chlorophenyl, 3-(methylsulfonyl)phenyl, 4-(methylsulfonyl)phenyl, 2-thiophenyl, 3-thiophenyl, 2-pyridyl, 3-pyridyl, 4-pyridyl, 2,3-difluorophenyl, 2,4-difluorophenyl, 3,4-difluorophenyl.

In some embodiments, $R^3$ is hydrogen, alkyl, substituted alkyl, alkenyl, substituted alkenyl, hydroxy, alkoxy, or haloalkoxy. In other embodiments, $R^3$ is hydrogen.

In some embodiments, $R^2$ is aryl, cycloalkyl, heteroaryl, or heterocycloalkyl, where the aryl is substituted with one, two, or three substituents selected from among acyloxy, alkyl, substituted alkyl, alkenyl, substituted alkenyl, alkylamino, dialkylamino, and haloalkoxy; where the cycloalkyl is optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro; and where the heteroaryl and the heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, and nitro. In other embodiments, $R^2$ is aryl, cycloalkyl, heteroaryl, or heterocycloalkyl where the aryl is substituted with one, two, or three substituents selected from among alkyl and haloalkoxy, and the heterocycloalkyl is optionally substituted with alkoxycarbonyl. In yet other embodiments, $R^2$ is cyclohexyl; benzooxadiazolyl; phenyl substituted with one, two, or three substituents selected from among methyl, trifluoromethoxy, or difluoromethoxy; or piperidinyl optionally substituted with t-butoxycarbonyl.

In some embodiments, $R^2$ is cyclohexyl, benzo[2,1,3]oxadiazol-5-yl, 2-methylphenyl, 3-methylphenyl, 4-methylphenyl, 4-(difluoromethoxy)-phenyl, 4-(trifluoromethoxy)-phenyl, N-(t-butoxycarbonyl)piperidin-4-yl, or piperidin-4-yl. In yet other embodiments, $R^2$ is benzo[2,1,3]oxadiazol-5-yl or 4-(difluoromethoxy)-phenyl.

In some embodiments, $R^3$ is hydrogen, alkenyl, substituted alkenyl, hydroxy, alkoxy, haloalkoxy, or —$X^6$—$R^6$, where $X^6$ is alkylene or alkenylene and $X^6$ is additionally optionally substituted with one, two three, four, or five halogens; and $R^6$ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^a$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where R$^a$ and R$^b$ are independently hydrogen, alkyl, substituted alkyl, alkenyl, alkynyl, substituted alkynyl, hydroxy, alkoxy, or alkenyloxy). In some embodiments, $R^3$ is hydrogen.

In some embodiments, $R^3$ is hydrogen; $X^2$ is alkylene or alkenylene; and $R^2$ is aryl, cycloalkyl, or heteroaryl, where the aryl, cycloalkyl, and heteroaryl are optionally substituted with one, two, or three substituents selected from among alkyl, alkoxy, alkoxycarbonyl, halogen, and haloalkoxy. In other embodiments, $R^3$ is hydrogen; $X^2$ is alkylene or alkenylene; and $R^2$ is naphthyl, phenyl, cycloalkyl, heteroaryl, or heterocycloalkyl optionally substituted with methyl, methoxy, t-butoxycarbonyl, chloro, fluoro, trifluoromethoxy, or difluoromethoxy. In some other embodiments, $R^3$ is hydrogen; $X^2$ is alkylene or alkenylene; and $R^2$ is phenyl where the phenyl is optionally substituted with one, two, or three substituents selected from among methyl, methoxy, chloro, fluoro, trifluoromethoxy, and difluoromethoxy; or $R^2$ is benzooxadiazolyl.

In some embodiments, $R^3$ is hydrogen; $X^2$ is alkylene or alkenylene; and $R^2$ is cycloalkyl, aryl, heteroaryl, or heterocycloalkyl, where the cycloalkyl is optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro; where the aryl is substituted with one, two, or three substituents selected from among acyloxy, alkyl, substituted alkyl, alkenyl, substituted alkenyl, alkylamino, dialkylamino, and haloalkoxy; where the heteroaryl and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, and nitro.

In some embodiments, $R^3$ is hydrogen; $X^2$ is alkylene or alkenylene; and $R^2$ is cycloalkyl; phenyl substituted with one, two, or three alkyl or haloalkoxy; benzooxadiazolyl; or piperidinyl optionally substituted with alkoxycarbonyl. In some other embodiments, $R^3$ is hydrogen; $X^2$ is alkylene or alkenylene; and $R^2$ is benzooxadiazolyl or phenyl where the phenyl is substituted with one, two, or three substituents selected from among methyl, chloro, fluoro, trifluoromethoxy, or difluoromethoxy.

In some embodiments $R^2$ is a substituted aryl. In some embodiments the aryl substituted with a halogen to decrease oxidation. In one embodiment the $X^2$ is a bond. In another embodiment $R^2$ is phenyl. In further embodiments the phenyl is substituted with a halogen. In yet further embodiments the halogen is fluorine.

In some embodiments $R^2$ is a substituted or unsubstituted aryl. In some embodiments $X^2$ is a $C_1$-$C_6$ alkylene. In other embodiments $X^2$ is —$CH_2CH_2$—. In some embodiments $X^2$ is chosen from a methylene or ethylene. In further embodiments $X^2$ is chosen from a methylene or ethylene to decrease benzyl oxidation. In another embodiment $R^2$ is phenyl.

In some embodiments $R^2$ is a heterocycle. In some embodiments $R^2$ is a heterocycle to affect potency and metabolism of the composition. In one embodiment $X^2$ is a bond. In another embodiment $R^2$ is an aromatic heterocycle.

In some embodiments $R^2$ is a substituted aryl and $R^3$ is an amine. In one embodiment $X^2$ is a bond. In another embodiment $R^2$ is substituted phenyl. In further embodiments the phenyl is substituted with an alkoxy. In further embodiments $R^3$ is an amine. In yet further embodiments $R^3$ is an amine that affects selectivity of the composition.

Any combination of the groups described above for the various variables is contemplated herein. It is understood that substituents and substitution patterns on the compounds provided herein are selected to provide compounds that are chemically stable and that are synthesized by techniques set forth herein.

In one aspect, HDAC8 inhibitors compounds described herein include, but are not limited to, compounds in Table 1, 2, 3, 4, 5, 6 and 7.

TABLE 1

1,2-disubstituted-1H-benzimidazole-6-carboxylic acid hydroxyamides.

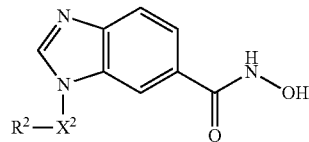

| Compound no. | $R^2$ | $X^2$ |
|---|---|---|
| 1 | Phenyl | —$CH_2$— |
| 2 | 3-methoxyphenyl | —$CH_2$— |
| 3 | 4-methoxyphenyl | —$CH_2$— |
| 4 | 2-methylphenyl | —$CH_2$— |
| 5 | 3-methylphenyl | —$CH_2$— |
| 6 | 4-methyl-phenyl | —$CH_2$— |
| 7 | 2-fluorophenyl | —$CH_2$— |
| 8 | 3-fluorophenyl | —$CH_2$— |
| 9 | 4-fluorophenyl | —$CH_2$— |
| 10 | 2-chlorophenyl | —$CH_2$— |
| 11 | 3-chlorophenyl | —$CH_2$— |
| 12 | 4-chlorophenyl | —$CH_2$— |
| 13 | 3-fluoro-4-methoxyphenyl | —$CH_2$— |
| 14 | 4-(trifluoromethoxy)-phenyl | —$CH_2$— |
| 15 | 3,4-dichlorophenyl | —$CH_2$— |
| 16 | 2,4-dichlorophenyl | —$CH_2$— |
| 17 | 2-chloro-4-fluorophenyl | —$CH_2$— |
| 18 | 2-chloro-4-methoxyphenyl | —$CH_2$— |
| 19 | 2,3-dichlorophenyl | —$CH_2$— |
| 20 | 3-methoxy-4-fluorophenyl | —$CH_2$— |
| 21 | 3-methoxy-5-fluorophenyl | —$CH_2$— |
| 22 | 3-methoxy-4-chlorophenyl | —$CH_2$— |
| 23 | 3-(methylsulfonyl)phenyl | —$CH_2$— |
| 24 | 4-(methylsulfonyl)phenyl | —$CH_2$— |
| 25 | 2-thiophenyl | —$CH_2$— |
| 26 | 3-thiophenyl | —$CH_2$— |
| 27 | 2-pyridyl | —$CH_2$— |
| 28 | 3-pyridyl | —$CH_2$— |
| 29 | 4-pyridyl | —$CH_2$— |
| 30 | phenyl | —$(CH_2)_2$— |
| 31 | phenyl | —$(CH_2)_3$— |
| 32 | phenyl | —$O(CH_2)_2$— |
| 33 | 2-fluorophenyl | —$O(CH_2)_2$— |
| 34 | 3-fluorophenyl | —$O(CH_2)_2$— |
| 35 | 4-fluorophenyl | —$O(CH_2)_2$— |
| 36 | 2-chlorophenyl | —$O(CH_2)_2$— |
| 37 | 3-chlorophenyl | —$O(CH_2)_2$— |
| 38 | 4-chlorophenyl | —$O(CH_2)_2$— |
| 39 | 2-chloro-4-fluorophenyl | —$O(CH_2)_2$— |
| 40 | 3-chloro-4-fluorophenyl | —$O(CH_2)_2$— |
| 41 | 2-fluoro-4-chlorophenyl | —$O(CH_2)_2$— |
| 42 | 3-fluoro-4-chlorophenyl | —$O(CH_2)_2$— |
| 43 | 2,3-difluorophenyl | —$O(CH_2)_2$— |
| 44 | 2,4-difluorophenyl | —$O(CH_2)_2$— |
| 45 | 3,4-difluorophenyl | —$O(CH_2)_2$— |
| 46 | 3-(methylsulfonyl)phenyl | —$O(CH_2)_2$— |
| 47 | 4-(methylsulfonyl)phenyl | —$O(CH_2)_2$— |
| 48 | 2-pyridyl | —$O(CH_2)_2$— |
| 49 | 3-pyridyl | —$O(CH_2)_2$— |
| 50 | 4-pyridyl | —$O(CH_2)_2$— |

Benzimidazole compounds in Table 1 are named: (Compound 1) 3-benzyl-N-hydroxy-3H-benzo[d]imidazole-5-carboxamide; (Compound 2) 3-(3-methoxybenzyl)-N-hydroxy-3H-benzo[d]imidazole-5-carboxamide; (Compound 3) 3-(4-methoxybenzyl)-N-hydroxy-3H-benzo[d]imidazole-5-carboxamide; (Compound 4) 3-(2-methylbenzyl)-N-hydroxy-3H-benzo[d]imidazole-5-carboxamide;

(Compound 5) 3-(3-methylbenzyl)-N-hydroxy-3H-benzo[d]imidazole-5-carboxamide; (Compound 6) 3-(4-methylbenzyl)-N-hydroxy-3H-benzo[d]imidazole-5-carboxamide; (Compound 7) 3-(2-fluorobenzyl)-N-hydroxy-3H-benzo[d]imidazole-5-carboxamide; (Compound 8) 3-(3-fluorobenzyl)-N-hydroxy-3H-benzo[c]imidazole-5-carboxamide; (Compound 9) 3-(4-fluorobenzyl)-N-hydroxy-3H-benzo[d]imidazole-5-carboxamide; (Compound 10) 3-(2-chlorobenzyl)-N-hydroxy-3H-benzo[d]imidazole-5-carboxamide; (Compound 11) 3-(3-chlorobenzyl)-N-hydroxy-3H-benzo[d]imidazole-5-carboxamide; (Compound 12) 3-(4-chlorobenzyl)-N-hydroxy-3H-benzo[d]imidazole-5-carboxamide; (Compound 13) 3-(3-fluoro-4-methoxybenzyl)-N-hydroxy-3H-benzo[d]imidazole-5-carboxamide; (Compound 14) 3-(4-(trifluoromethoxy)benzyl)-N-hydroxy-3H-benzo[d]imidazole-5-carboxamide; (Compound 15) 3-(3,4-dichlorobenzyl)-N-hydroxy-3H-benzo[d]imidazole-5-carboxamide; (Compound 16) 3-(2,4-dichlorobenzyl)-N-hydroxy-3H-benzo[d]imidazole-5-carboxamide; (Compound 17) 3-(2-chloro-4-fluorobenzyl)-N-hydroxy-3H-benzo[c]imidazole-5-carboxamide; (Compound 18) 3-(2-chloro-4-methoxybenzyl)-N-hydroxy-3H-benzo[d]imidazole-5-carboxamide; (Compound 19) 3-(2,3-dichlorobenzyl)-N-hydroxy-3H-benzo[c]imidazole-5-carboxamide; (Compound 20) 3-(3-methoxy-4-fluorobenzyl)-N-hydroxy-3H-benzo[d]imidazole-5-carboxamide; (Compound 21) 3-(3-methoxy-5-fluorobenzyl)-N-hydroxy-3H-benzo[d]imidazole-5-carboxamide; (Compound 22) 3-(3-methoxy-4-chlorobenzyl)-N-hydroxy-3H-benzo[d]imidazole-5-carboxamide; (Compound 23) 3-(3-(methylsulfonyl)benzyl)-N-hydroxy-3H-benzo[d]imidazole-5-carboxamide; (Compound 24) 3-(4-(methylsulfonyl)benzyl)-N-hydroxy-3H-benzo[d]imidazole-5-carboxamide; (Compound 25) N-hydroxy-3-((thiophen-2-yl)methyl)-3H-benzo[d]imidazole-5-carboxamide; (Compound 26) N-hydroxy-3-((thiophen-3-yl)methyl)-3H-benzo[d]imidazole-5-carboxamide; (Compound 27) N-hydroxy-3-((pyridine-2-yl)methyl)-3H-benzo[d]imidazole-5-carboxamide; (Compound 28) N-hydroxy-3-((pyridine-3-yl)methyl)-3H-benzo[d]imidazole-5-carboxamide; (Compound 29) N-hydroxy-3-((pyridine-4-yl)methyl)-3H-benzo[d]imidazole-5-carboxamide; (Compound 30) N-hydroxy-3-phenylethyl-3H-benzo[d]imidazole-5-carboxamide; (Compound 31) N-hydroxy-3-(3-phenylpropyl)-3H-benzo[d]imidazole-5-carboxamide; (Compound 32) N-hydroxy-3-(3-phenoxyethyl)-3H-benzo[d]imidazole-5-carboxamide; (Compound 33) 3-(2-(2-fluorophenoxy)ethyl)-N-hydroxy-3H-benzo[d]imidazole-5-carboxamide; (Compound 34) 3-(2-(3-fluorophenoxy)ethyl)-N-hydroxy-3H-benzo[d]imidazole-5-carboxamide; (Compound 35) 3-(2-(4-fluorophenoxy)ethyl)-N-hydroxy-3H-benzo[d]imidazole-5-carboxamide; (Compound 36) 3-(2-(2-chlorophenoxy)ethyl)-N-hydroxy-3H-benzo[d]imidazole-5-carboxamide; (Compound 37) 3-(2-(3-chlorophenoxy)ethyl)-N-hydroxy-3H-benzo[d]imidazole-5-carboxamide; (Compound 38) 3-(2-(4-chlorophenoxy)ethyl)-N-hydroxy-3H-benzo[d]imidazole-5-carboxamide; (Compound 39) 3-(2-(2-chloro-4-fluorophenoxy)ethyl-N-hydroxy-3H-benzo[d]imidazole-5-carboxamide; (Compound 40) 3-(2-(3-chloro-4-fluorophenoxy)ethyl-N-hydroxy-3H-benzo[d]imidazole-5-carboxamide; (Compound 41) 3-(2-(2-fluoro-4-chlorophenoxy)ethyl-N-hydroxy-3H-benzo[d]imidazole-5-carboxamide; (Compound 42) 3-(2-(3-fluoro-4-chlorophenoxy)ethyl-N-hydroxy-3H-benzo[d]imidazole-5-carboxamide; (Compound 43) 3-(2-(2,3-difluorophenoxy)ethyl)-N-hydroxy-3H-benzo[d]imidazole-5-carboxamide; (Compound 44) 3-(2-(2,4-difluorophenoxy)ethyl)-N-hydroxy-3H-benzo[d]imidazole-5-carboxamide; (Compound 45) 3-(2-(3,4-difluorophenoxy)ethyl)-N-hydroxy-3H-benzo[d]imidazole-5-carboxamide; (Compound 46) 3-(2-(3-(methylsulfonyl)phenoxy)ethyl)-N-hydroxy-3H-benzo[d]imidazole-5-carboxamide; (Compound 47) 3-(2-(4-(methylsulfonyl)phenoxy)ethyl)-N-hydroxy-3H-benzo[d]imidazole-5-carboxamide; (Compound 48) N-hydroxy-3-(2-(pyridin-2-yloxy)ethyl)-3H-benzo[d]imidazole-5-carboxamide; (Compound 49) N-hydroxy-3-(2-(pyridin-3-yloxy)ethyl)-3H-benzo[d]imidazole-5-carboxamide; and (Compound 50) N-hydroxy-3-(2-(pyridin-4-yloxy)ethyl)-3H-benzo[d]imidazole-5-carboxamide.

TABLE 2

1,3-disubstituted-azaindole-6-carboxylic acid hydroxyamides

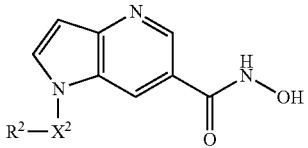

| Compound no. | R² | X² |
| --- | --- | --- |
| 51 | Phenyl | —CH₂— |
| 52 | 3-methoxyphenyl | —CH₂— |
| 53 | 4-methoxyphenyl | —CH₂— |
| 54 | 2-methylphenyl | —CH₂— |
| 55 | 3-methylphenyl | —CH₂— |
| 56 | 4-methyl-phenyl | —CH₂— |
| 57 | 2-fluorophenyl | —CH₂— |
| 58 | 3-fluorophenyl | —CH₂— |
| 59 | 4-fluorophenyl | —CH₂— |
| 60 | 2-chlorophenyl | —CH₂— |
| 61 | 3-chlorophenyl | —CH₂— |
| 62 | 4-chlorophenyl | —CH₂— |
| 63 | 3-fluoro-4-methoxyphenyl | —CH₂— |
| 64 | 4-(trifluoromethoxy)-phenyl | —CH₂— |
| 65 | 3,4-dichlorophenyl | —CH₂— |
| 66 | 2,4-dichlorophenyl | —CH₂— |
| 67 | 2-chloro-4-fluorophenyl | —CH₂— |
| 68 | 2-chloro-4-methoxyphenyl | —CH₂— |
| 69 | 2,3-dichlorophenyl | —CH₂— |
| 70 | 3-methoxy-4-fluorophenyl | —CH₂— |
| 71 | 3-methoxy-5-fluorophenyl | —CH₂— |
| 72 | 3-methoxy-4-chlorophenyl | —CH₂— |
| 73 | 3-(methylsulfonyl)phenyl | —CH₂— |
| 74 | 4-(methylsulfonyl)phenyl | —CH₂— |
| 75 | 2-thiophenyl | —CH₂— |
| 76 | 3-thiophenyl | —CH₂— |
| 77 | 2-pyridyl | —CH₂— |
| 78 | 3-pyridyl | —CH₂— |
| 79 | 4-pyridyl | —CH₂— |
| 80 | phenyl | —(CH₂)₂— |
| 81 | phenyl | —(CH₂)₃— |
| 82 | phenyl | —O(CH₂)₂— |
| 83 | 2-fluorophenyl | —O(CH₂)₂— |
| 84 | 3-fluorophenyl | —O(CH₂)₂— |
| 85 | 4-fluorophenyl | —O(CH₂)₂— |
| 86 | 2-chlorophenyl | —O(CH₂)₂— |
| 87 | 3-chlorophenyl | —O(CH₂)₂— |
| 88 | 4-chlorophenyl | —O(CH₂)₂— |
| 89 | 2-chloro-4-fluorophenyl | —O(CH₂)₂— |
| 90 | 3-chloro-4-fluorophenyl | —O(CH₂)₂— |
| 91 | 2-fluoro-4-ehlorophenyl | —O(CH₂)₂— |
| 92 | 3-fluoro-4-ehlorophenyl | —O(CH₂)₂— |
| 93 | 2,3-difluorophenyl | —O(CH₂)₂— |
| 94 | 2,4-difluorophenyl | —O(CH₂)₂— |
| 95 | 3,4-difluorophenyl | —O(CH₂)₂— |
| 96 | 3-(methylsulfonyl)phenyl | —O(CH₂)₂— |
| 97 | 4-(methylsulfonyl)phenyl | —O(CH₂)₂— |
| 98 | 2-pyridyl | —O(CH₂)₂— |
| 99 | 3-pyridyl | —O(CH₂)₂— |
| 100 | 4-pyridyl | —O(CH₂)₂— |

4-Azaindole compounds in Table 2 are named: (Compound 51) 1-benzyl-N-hydroxy-1H-pyrrolo[3,2-b]pyridine-6-carboxamide; (Compound 52) 1-(3-methoxybenzyl)-N-hydroxy-1H-pyrrolo[3,2-b]pyridine-6-carboxamide; (Compound 53) 1-(4-methoxybenzyl)-N-hydroxy-1H-pyrrolo[3,2-b]pyridine-6-carboxamide; (Compound 54) 1-(2-methylbenzyl)-N-hydroxy-1H-pyrrolo[3,2-b]pyridine-6-carboxamide; (Compound 55) 1-(3-methylbenzyl)-N-hydroxy-1H-pyrrolo[3,2-b]pyridine-6-carboxamide; (Compound 56) 1-(4-methylbenzyl)-N-hydroxy-1H-pyrrolo[3,2-b]pyridine-6-carboxamide; (Compound 57) 1-(2-fluorobenzyl)-N-hydroxy-1H-pyrrolo[3,2-b]pyridine-6-carboxamide; (Compound 58) 1-(3-fluorobenzyl)-N-hydroxy-1H-pyrrolo[3,2-b]pyridine-6-carboxamide; (Compound 59) 1-(4-fluorobenzyl)-N-hydroxy-1H-pyrrolo[3,2-b]pyridine-6-carboxamide; (Compound 60) 1-(2-chlorobenzyl)-N-hydroxy-1H-pyrrolo[3,2-b]pyridine-6-carboxamide; (Compound 61) 1-(3-chlorobenzyl)-N-hydroxy-1H-pyrrolo[3,2-b]pyridine-6-carboxamide; (Compound 62) 1-(4-chlorobenzyl)-N-hydroxy-1H-pyrrolo[3,2-b]pyridine-6-carboxamide; (Compound 63) 1-(3-fluoro-4-methoxybenzyl)-N-hydroxy-1H-pyrrolo[3,2-b]pyridine-6-carboxamide; (Compound 64) 1-(4-(trifluoromethoxy)benzyl)-N-hydroxy-1H-pyrrolo[3,2-b]pyridine-6-carboxamide; (Compound 65) 1-(3,4-dichlorobenzyl)-N-hydroxy-1H-pyrrolo[3,2-b]pyridine-6-carboxamide; (Compound 66) 1-(2,4-dichlorobenzyl)-N-hydroxy-1H-pyrrolo[3,2-b]pyridine-6-carboxamide; (Compound 67) 1-(2-chloro-4-fluorobenzyl)-N-hydroxy-1H-pyrrolo[3,2-b]pyridine-6-carboxamide; (Compound 68) 1-(2-chloro-4-methoxybenzyl)-N-hydroxy-1H-pyrrolo[3,2-b]pyridine-6-carboxamide; (Compound 69) 1-(2,3-dichlorobenzyl)-N-hydroxy-1H-pyrrolo[3,2-b]pyridine-6-carboxamide; (Compound 70) 1-(3-methoxy-4-fluorobenzyl)-N-hydroxy-1H-pyrrolo[3,2-b]pyridine-6-carboxamide; (Compound 71) 1-(3-methoxy-5-fluorobenzyl)-N-hydroxy-1H-pyrrolo[3,2-b]pyridine-6-carboxamide; (Compound 72) 1-(3-methoxy-4-chlorobenzyl)-N-hydroxy-1H-pyrrolo[3,2-b]pyridine-6-carboxamide; (Compound 73) 1-(3-(methylsulfonyl)benzyl)-N-hydroxy-1H-pyrrolo[3,2-b]pyridine-6-carboxamide; (Compound 74) 1-(4-(methylsulfonyl)benzyl)-N-hydroxy-1H-pyrrolo[3,2-b]pyridine-6-carboxamide; (Compound 75) N-hydroxy-1-((thiophen-2-yl)methyl)-1H-pyrrolo[3,2-b]pyridine-6-carboxamide; (Compound 76) N-hydroxy-1-((thiophen-3-yl)methyl)-1H-pyrrolo[3,2-b]pyridine-6-carboxamide; (Compound 77) N-hydroxy-1-((pyridine-2-yl)methyl)-1H-pyrrolo[3,2-b]pyridine-6-carboxamide; (Compound 78) N-hydroxy-1-((pyridine-3-yl)methyl)-1H-pyrrolo[3,2-b]pyridine-6-carboxamide; (Compound 79) N-hydroxy-1-((pyridine-4-yl)methyl)-1H-pyrrolo[3,2-b]pyridine-6-carboxamide; (Compound 80) N-hydroxy-1-phenethyl-1H-pyrrolo[3,2-b]pyridine-6-carboxamide; (Compound 81) N-hydroxy-1-(3-phenylpropyl)-1H-pyrrolo[3,2-b]pyridine-6-carboxamide; (Compound 82) N-hydroxy-(2-phenoxyethyl)-1H-pyrrolo[3,2-b]pyridine-6-carboxamide; (Compound 83) 1-(2-fluorophenoxy)ethyl)-N-hydroxy-1H-pyrrolo[3,2-b]pyridine-6-carboxamide; (Compound 84) 1-(3-fluorophenoxy)ethyl)-N-hydroxy-1H-pyrrolo[3,2-b]pyridine-6-carboxamide; (Compound 85) 1-(4-fluorophenoxy)ethyl)-N-hydroxy-1H-pyrrolo[3,2-b]pyridine-6-carboxamide; (Compound 86) 1-(2-chlorophenoxy)ethyl)-N-hydroxy-1H-pyrrolo[3,2-b]pyridine-6-carboxamide; (Compound 87) 1-(3-chlorophenoxy)ethyl)-N-hydroxy-1H-pyrrolo[3,2-b]pyridine-6-carboxamide; (Compound 88) 1-(4-chlorophenoxy)ethyl)-N-hydroxy-1H-pyrrolo[3,2-b]pyridine-6-carboxamide; (Compound 89) 1-(2-(2-chloro-4-fluorophenoxy)ethyl)-N-hydroxy-1H-pyrrolo[3,2-b]pyridine-6-carboxamide; (Compound 90) 1-(2-(3-chloro-4-fluorophenoxy)ethyl)-N-hydroxy-1H-pyrrolo[3,2-b]pyridine-6-carboxamide; (Compound 91) 1-(2-(2-fluoro-4-chlorophenoxy)ethyl)-N-hydroxy-1H-pyrrolo[3,2-b]pyridine-6-carboxamide; (Compound 92) 1-(2-(3-fluoro-4-chlorophenoxy)ethyl)-N-hydroxy-1H-pyrrolo[3,2-b]pyridine-6-carboxamide; (Compound 93) 1-(2-(2,3-difluorophenoxy)ethyl)-N-hydroxy-1H-pyrrolo[3,2-b]pyridine-6-carboxamide; (Compound 94) 1-(2-(2,4-difluorophenoxy)ethyl)-N-hydroxy-1H-pyrrolo[3,2-b]pyridine-6-carboxamide; (Compound 95) 1-(2-(3,4-difluorophenoxy)ethyl)-N-hydroxy-1H-pyrrolo[3,2-b]pyridine-6-carboxamide; (Compound 96) 1-(2-(3-(methylsulfonyl)phenoxy)ethyl)-N-hydroxy-1H-pyrrolo[3,2-b]pyridine-6-carboxamide; (Compound 97) 1-(2-(4-(methylsulfonyl)phenoxy)ethyl)-N-hydroxy-1H-pyrrolo[3,2-b]pyridine-6-carboxamide; (Compound 98) N-hydroxy-1-(2-(pyridine-2-yloxy)ethyl)-N-hydroxy-1H-pyrrolo[3,2-b]pyridine-6-carboxamide; (Compound 99) N-hydroxy-1-(2-(pyridine-3-yloxy)ethyl)-N-hydroxy-1H-pyrrolo[3,2-b]pyridine-6-carboxamide; and (Compound 100) N-hydroxy-1-(2-(pyridine-4-yloxy)ethyl)-N-hydroxy-1H-pyrrolo[3,2-b]pyridine-6-carboxamide.

TABLE 3

1,3-disubstituted-azaindole-6-carboxylic acid hydroxyamides

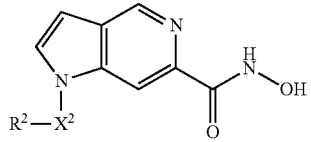

| Compound no. | $R^2$ | $X^2$ |
|---|---|---|
| 101 | Phenyl | —$CH_2$— |
| 102 | 3-methoxyphenyl | —$CH_2$— |
| 103 | 4-methoxyphenyl | —$CH_2$— |
| 104 | 2-methylphenyl | —$CH_2$— |
| 105 | 3-methylphenyl | —$CH_2$— |
| 106 | 4-methyl-phenyl | —$CH_2$— |
| 107 | 2-fluorophenyl | —$CH_2$— |
| 108 | 3-fluorophenyl | —$CH_2$— |
| 109 | 4-fluorophenyl | —$CH_2$— |
| 110 | 2-chlorophenyl | —$CH_2$— |
| 111 | 3-chlorophenyl | —$CH_2$— |
| 112 | 4-chlorophenyl | —$CH_2$— |
| 113 | 3-fluoro-4-methoxyphenyl | —$CH_2$— |
| 114 | 4-(trifluoromethoxy)-phenyl | —$CH_2$— |
| 115 | 3,4-dichlorophenyl | —$CH_2$— |
| 116 | 2,4-dichlorophenyl | —$CH_2$— |
| 117 | 2-chloro-4-fluorophenyl | —$CH_2$— |
| 118 | 2-chloro-4-methoxyphenyl | —$CH_2$— |
| 119 | 2,3-dichlorophenyl | —$CH_2$— |
| 120 | 3-methoxy-4-fluorophenyl | —$CH_2$— |
| 121 | 3-methoxy-5-fluorophenyl | —$CH_2$— |
| 122 | 3-methoxy-4-chlorophenyl | —$CH_2$— |
| 123 | 3-(methylsulfonyl)phenyl | —$CH_2$— |
| 124 | 4-(methylsulfonyl)phenyl | —$CH_2$— |
| 125 | 2-thiophenyl | —$CH_2$— |
| 126 | 3-thiophenyl | —$CH_2$— |
| 127 | 2-pyridyl | —$CH_2$— |
| 128 | 3-pyridyl | —$CH_2$— |
| 129 | 4-pyridyl | —$CH_2$— |
| 130 | phenyl | —$(CH_2)_2$— |
| 131 | phenyl | —$(CH_2)_3$— |
| 132 | phenyl | —$O(CH_2)_2$— |
| 133 | 2-fluorophenyl | —$O(CH_2)_2$— |
| 134 | 3-fluorophenyl | —$O(CH_2)_2$— |
| 135 | 4-fluorophenyl | —$O(CH_2)_2$— |
| 136 | 2-chlorophenyl | —$O(CH_2)_2$— |
| 137 | 3-chlorophenyl | —$O(CH_2)_2$— |
| 138 | 4-chlorophenyl | —$O(CH_2)_2$— |

TABLE 3-continued 1,3-disubstituted-azaindole-6-carboxylic acid hydroxyamides

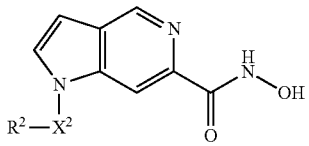

| Compound no. | R² | X² |
|---|---|---|
| 139 | 2-chloro-4-fluorophenyl | —O(CH₂)₂— |
| 140 | 3-chloro-4-fluorophenyl | —O(CH₂)₂— |
| 141 | 2-fluoro-4-chlorophenyl | —O(CH₂)₂— |
| 142 | 3-fluoro-4-chlorophenyl | —O(CH₂)₂— |
| 143 | 2,3-difluorophenyl | —O(CH₂)₂— |
| 144 | 2,4-difluorophenyl | —O(CH₂)₂— |
| 145 | 3,4-difluorophenyl | —O(CH₂)₂— |
| 146 | 3-(methylsulfonyl)phenyl | —O(CH₂)₂— |
| 147 | 4-(methylsulfonyl)phenyl | —O(CH₂)₂— |
| 148 | 2-pyridyl | —O(CH₂)₂— |
| 149 | 3-pyridyl | —O(CH₂)₂— |
| 150 | 4-pyridyl | —O(CH₂)₂— |

5-Azaindole compounds in Table 3 are named: (Compound 101) 1-benzyl-N-hydroxy-1H-pyrrolo[3,2-c]pyridine-6-carboxamide; (Compound 102) 1-(3-methoxybenzyl)-N-hydroxy-1H-pyrrolo[3,2-c]pyridine-6-carboxamide; (Compound 103) 1-(4-methoxybenzyl)-N-hydroxy-1H-pyrrolo[3,2-c]pyridine-6-carboxamide; (Compound 104) 1-(2-methylbenzyl)-N-hydroxy-1H-pyrrolo[3,2-c]pyridine-6-carboxamide; (Compound 105) 1-(3-methylbenzyl)-N-hydroxy-1H-pyrrolo[3,2-c]pyridine-6-carboxamide; (Compound 106) 1-(4-methylbenzyl)-N-hydroxy-1H-pyrrolo[3,2-c]pyridine-6-carboxamide; (Compound 107) 1-(2-fluorobenzyl)-N-hydroxy-1H-pyrrolo[3,2-c]pyridine-6-carboxamide; (Compound 108) 1-(3-fluorobenzyl)-N-hydroxy-1H-pyrrolo[3,2-c]pyridine-6-carboxamide; (Compound 109) 1-(4-fluorobenzyl)-N-hydroxy-1H-pyrrolo[3,2-c]pyridine-6-carboxamide; (Compound 110) 1-(2-chlorobenzyl)-N-hydroxy-1H-pyrrolo[3,2-c]pyridine-6-carboxamide; (Compound 111) 1-(3-chlorobenzyl)-N-hydroxy-1H-pyrrolo[3,2-c]pyridine-6-carboxamide; (Compound 112) 1-(4-chlorobenzyl)-N-hydroxy-1H-pyrrolo[3,2-d]pyridine-6-carboxamide; (Compound 113) 1-(3-fluoro-4-methoxybenzyl)-N-hydroxy-1H-pyrrolo[3,2-c]pyridine-6-carboxamide; (Compound 114) 1-(4-(trifluoromethoxy)benzyl)-N-hydroxy-1H-pyrrolo[3,2-c]pyridine-6-carboxamide; (Compound 115) 1-(3,4-dichlorobenzyl)-N-hydroxy-1H-pyrrolo[3,2-c]pyridine-6-carboxamide; (Compound 116) 1-(2,4-dichlorobenzyl)-N-hydroxy-1H-pyrrolo[3,2-c]pyridine-6-carboxamide; (Compound 117) 1-(2-chloro-4-fluorobenzyl)-N-hydroxy-1H-pyrrolo[3,2-c]pyridine-6-carboxamide; (Compound 118) 1-(2-chloro-4-methoxybenzyl)-N-hydroxy-1H-pyrrolo[3,2-e]pyridine-6-carboxamide; (Compound 119) 1-(2,3-dichlorobenzyl)-N-hydroxy-1H-pyrrolo[3,2-c]pyridine-6-carboxamide; (Compound 120) 1-(3-methoxy-4-fluorobenzyl)-N-hydroxy-1H-pyrrolo[3,2-c]pyridine-6-carboxamide; (Compound 121) 1-(3-methoxy-5-fluorobenzyl)-N-hydroxy-1H-pyrrolo[3,2-c]pyridine-6-carboxamide; (Compound 122) 1-(3-methoxy-4-chlorobenzyl)-N-hydroxy-1H-pyrrolo[3,2-c]pyridine-6-carboxamide; (Compound 123) 1-(3-(methylsulfonyl)benzyl)-N-hydroxy-1H-pyrrolo[3,2-c]pyridine-6-carboxamide; (Compound 124) 1-(4-(methylsulfonyl)benzyl)-N-hydroxy-1H-pyrrolo[3,2-c]pyridine-6-carboxamide; (Compound 125) N-hydroxy-1-((thiophen-2-yl)methyl)-1H-pyrrolo[3,2-c]pyridine-6-carboxamide; (Compound 126) N-hydroxy-1-((thiophen-3-yl)methyl)-1H-pyrrolo[3,2-c]pyridine-6-carboxamide; (Compound 127) N-hydroxy-1-((pyridine-2-yl)methyl)-1H-pyrrolo[3,2-c]pyridine-6-carboxamide; (Compound 128) N-hydroxy-1-((pyridine-3-yl)methyl)-1H-pyrrolo[3,2-c]pyridine-6-carboxamide; (Compound 129) N-hydroxy-1-((pyridine-4-yl)methyl)-1H-pyrrolo[3,2-c]pyridine-6-carboxamide; (Compound 130) N-hydroxy-1-phenethyl-1H-pyrrolo[3,2-c]pyridine-6-carboxamide; (Compound 131) N-hydroxy-1-(3-phenylpropyl)-1H-pyrrolo[3,2-c]pyridine-6-carboxamide; (Compound 132) N-hydroxy-(2-phenoxyethyl)-1H-pyrrolo[3,2-c]pyridine-6-carboxamide; (Compound 133) 1-(2-fluorophenoxy)ethyl)-N-hydroxy-1H-pyrrolo[3,2-c]pyridine-6-carboxamide; (Compound 134) 1-(3-fluorophenoxy)ethyl)-N-hydroxy-1H-pyrrolo[3,2-c]pyridine-6-carboxamide; (Compound 135) 1-(4-fluorophenoxy)ethyl)-N-hydroxy-1H-pyrrolo[3,2-c]pyridine-6-carboxamide; (Compound 136) 1-(2-chlorophenoxy)ethyl)-N-hydroxy-1H-pyrrolo[3,2-c]pyridine-6-carboxamide; (Compound 137) 1-(3-chlorophenoxy)ethyl)-N-hydroxy-1H-pyrrolo[3,2-c]pyridine-6-carboxamide; (Compound 138) 1-(4-chlorophenoxy)ethyl)-N-hydroxy-1H-pyrrolo[3,2-c]pyridine-6-carboxamide; (Compound 139) 1-(2-(2-chloro-4-fluorophenoxy)ethyl)-N-hydroxy-1H-pyrrolo[3,2-c]pyridine-6-carboxamide; (Compound 140) 1-(2-(3-chloro-4-fluorophenoxy)ethyl)-N-hydroxy-1H-pyrrolo[3,2-c]pyridine-6-carboxamide; (Compound 141) 1-(2-(2-fluoro-4-chlorophenoxy)ethyl)-N-hydroxy-1H-pyrrolo[3,2-c]pyridine-6-carboxamide; (Compound 142) 1-(2-(3-fluoro-4-chlorophenoxy)ethyl)-N-hydroxy-1H-pyrrolo[3,2-c]pyridine-6-carboxamide; (Compound 143) 1-(2-(2,3-difluorophenoxy)ethyl)-N-hydroxy-1H-pyrrolo[3,2-c]pyridine-6-carboxamide; (Compound 144) 1-(2-(2,4-difluorophenoxy)ethyl)-N-hydroxy-1H-pyrrolo[3,2-c]pyridine-6-carboxamide; (Compound 145) 1-(2-(3,4-difluorophenoxy)ethyl)-N-hydroxy-1H-pyrrolo[3,2-c]pyridine-6-carboxamide; (Compound 146) 1-(2-(3-(methylsulfonyl)phenoxy)ethyl)-N-hydroxy-1H-pyrrolo[3,2-c]pyridine-6-carboxamide; (Compound 147) 1-(2-(4-(methylsulfonyl)phenoxy)ethyl)-N-hydroxy-1H-pyrrolo[3,2-c]pyridine-6-carboxamide; (Compound 148) N-hydroxy-1-(2-(pyridine-2-yloxy)ethyl)-N-hydroxy-1H-pyrrolo[3,2-c]pyridine-6-carboxamide; (Compound 149) N-hydroxy-1-(2-(pyridine-3-yloxy)ethyl)-N-hydroxy-1H-pyrrolo[3,2-c]pyridine-6-carboxamide; and (Compound 150) N-hydroxy-1-(2-(pyridine-4-yloxy)ethyl)-N-hydroxy-1H-pyrrolo[3,2-c]pyridine-6-carboxamide.

TABLE 4

1,3-disubstituted-azaindole-6-carboxylic acid hydroxyamides

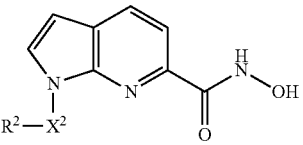

| Compound no. | R² | X² |
|---|---|---|
| 151 | Phenyl | —CH₂— |
| 152 | 3-methoxyphenyl | —CH₂— |
| 153 | 4-methoxyphenyl | —CH₂— |
| 154 | 2-methylphenyl | —CH₂— |
| 155 | 3-methylphenyl | —CH₂— |
| 156 | 4-methyl-phenyl | —CH₂— |
| 157 | 2-fluorophenyl | —CH₂— |
| 158 | 3-fluorophenyl | —CH₂— |
| 159 | 4-fluorophenyl | —CH₂— |

TABLE 4-continued 1,3-disubstituted-azaindole-6-carboxylic acid hydroxyamides

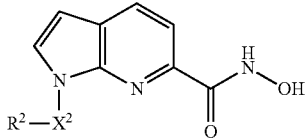

| Compound no. | R² | X² |
| --- | --- | --- |
| 160 | 2-chlorophenyl | —CH₂— |
| 161 | 3-chlorophenyl | —CH₂— |
| 162 | 4-chlorophenyl | —CH₂— |
| 163 | 3-fluoro-4-methoxyphenyl | —CH₂— |
| 164 | 4-(trifluoromethoxy)-phenyl | —CH₂— |
| 165 | 3,4-dichlorophenyl | —CH₂— |
| 166 | 2,4-dichlorophenyl | —CH₂— |
| 167 | 2-chloro-4-fluorophenyl | —CH₂— |
| 168 | 2-chloro-4-methoxyphenyl | —CH₂— |
| 169 | 2,3-dichlorophenyl | —CH₂— |
| 170 | 3-methoxy-4-fluorophenyl | —CH₂— |
| 171 | 3-methoxy-5-fluorophenyl | —CH₂— |
| 172 | 3-methoxy-4-chlorophenyl | —CH₂— |
| 173 | 3-(methylsulfonyl)phenyl | —CH₂— |
| 174 | 4-(methylsulfonyl)phenyl | —CH₂— |
| 175 | 2-thiophenyl | —CH₂— |
| 176 | 3-thiophenyl | —CH₂— |
| 177 | 2-pyridyl | —CH₂— |
| 178 | 3-pyridyl | —CH₂— |
| 179 | 4-pyridyl | —CH₂— |
| 180 | phenyl | —(CH₂)₂— |
| 181 | phenyl | —(CH₂)₃— |
| 182 | phenyl | —O(CH₂)₂— |
| 183 | 2-fluorophenyl | —O(CH₂)₂— |
| 184 | 3-fluorophenyl | —O(CH₂)₂— |
| 185 | 4-fluorophenyl | —O(CH₂)₂— |
| 185 | 2-chlorophenyl | —O(CH₂)₂— |
| 187 | 3-chlorophenyl | —O(CH₂)₂— |
| 188 | 4-chlorophenyl | —O(CH₂)₂— |
| 189 | 2-chloro-4-fluorophenyl | —O(CH₂)₂— |
| 190 | 3-chloro-4-fluorophenyl | —O(CH₂)₂— |
| 191 | 2-fluoro-4-chlorophenyl | —O(CH₂)₂— |
| 192 | 3-fluoro-4-chlorophenyl | —O(CH₂)₂— |
| 193 | 2,3-difluorophenyl | —O(CH₂)₂— |
| 194 | 2,4-difluorophenyl | —O(CH₂)₂— |
| 195 | 3,4-difluorophenyl | —O(CH₂)₂— |
| 196 | 3-(methylsulfonyl)phenyl | —O(CH₂)₂— |
| 197 | 4-(methylsulfonyl)phenyl | —O(CH₂)₂— |
| 198 | 2-pyridyl | —O(CH₂)₂— |
| 199 | 3-pyridyl | —O(CH₂)₂— |
| 200 | 4-pyridyl | —O(CH₂)₂— |

7-Azaindole compounds in Table 4 are named: (Compound 151) 1-benzyl-N-hydroxy-1H-pyrrolo[2,3-b]pyridine-6-carboxamide; (Compound 152) 1-(3-methoxybenzyl)-N-hydroxy-1H-pyrrolo[2,3-b]pyridine-6-carboxamide; (Compound 153) 1-(4-methoxybenzyl)-N-hydroxy-1H-pyrrolo[2,3-b]pyridine-6-carboxamide; (Compound 154) 1-(2-methylbenzyl)-N-hydroxy-1H-pyrrolo[2,3-b]pyridine-6-carboxamide; (Compound 155) 1-(3-methylbenzyl)-N-hydroxy-1H-pyrrolo[2,3-b]pyridine-6-carboxamide; (Compound 156) 1-(4-methylbenzyl)-N-hydroxy-1H-pyrrolo[2,3-b]pyridine-6-carboxamide; (Compound 157) 1-(2-fluorobenzyl)-N-hydroxy-1H-pyrrolo[2,3-b]pyridine-6-carboxamide; (Compound 158) 1-(3-fluorobenzyl)-N-hydroxy-1H-pyrrolo[2,3-b]pyridine-6-carboxamide; (Compound 159) 1-(4-fluorobenzyl)-N-hydroxy-1H-pyrrolo[2,3-b]pyridine-6-carboxamide; (Compound 160) 1-(2-chlorobenzyl)-N-hydroxy-1H-pyrrolo[2,3-b]pyridine-6-carboxamide; (Compound 161) 1-(3-chlorobenzyl)-N-hydroxy-1H-pyrrolo[2,3-b]pyridine-6-carboxamide; (Compound 162) 1-(4-chlorobenzyl)-N-hydroxy-1H-pyrrolo[2,3-b]pyridine-6-carboxamide; (Compound 163) 1-(3-fluoro-4-methoxybenzyl)-N-hydroxy-1H-pyrrolo[2,3-b]pyridine-6-carboxamide; (Compound 164) 1-(4-(trifluoromethoxy)benzyl)-N-hydroxy-1H-pyrrolo[2,3-b]pyridine-6-carboxamide; (Compound 165) 1-(3,4-dichlorobenzyl)-N-hydroxy-1H-pyrrolo[2,3-b]pyridine-6-carboxamide; (Compound 166) 1-(2,4-dichlorobenzyl)-N-hydroxy-1H-pyrrolo[2,3-b]pyridine-6-carboxamide; (Compound 167) 1-(2-chloro-4-fluorobenzyl)-N-hydroxy-1H-pyrrolo[2,3-b]pyridine-6-carboxamide; (Compound 168) 1-(2-chloro-4-methoxybenzyl)-N-hydroxy-1H-pyrrolo[2,3-b]pyridine-6-carboxamide; (Compound 169) 1-(2,3-dichlorobenzyl)-N-hydroxy-1H-pyrrolo[2,3-b]pyridine-6-carboxamide; (Compound 170) 1-(3-methoxy-4-fluorobenzyl)-N-hydroxy-1H-pyrrolo[2,3-b]pyridine-6-carboxamide; (Compound 171) 1-(3-methoxy-5-fluorobenzyl)-N-hydroxy-1H-pyrrolo[2,3-b]pyridine-6-carboxamide; (Compound 172) 1-(3-methoxy-4-chlorobenzyl)-N-hydroxy-1H-pyrrolo[2,3-b]pyridine-6-carboxamide; (Compound 173) 1-(3-(methylsulfonyl)benzyl)-N-hydroxy-1H-pyrrolo[2,3-b]pyridine-6-carboxamide; (Compound 174) 1-(4-(methylsulfonyl)benzyl)-N-hydroxy-1H-pyrrolo[2,3-b]pyridine-6-carboxamide; (Compound 175) N-hydroxy-1-((thiophen-2-yl)methyl)-1H-pyrrolo[2,3-b]pyridine-6-carboxamide; (Compound 176) N-hydroxy-1-((thiophen-3-yl)methyl)-1H-pyrrolo[2,3-b]pyridine-6-carboxamide; (Compound 177) N-hydroxy-1-((pyridine-2-yl)methyl)-1H-pyrrolo[2,3-b]pyridine-6-carboxamide; (Compound 178) N-hydroxy-1-((pyridine-3-yl)methyl)-1H-pyrrolo[2,3-b]pyridine-6-carboxamide; (Compound 179) N-hydroxy-1-((pyridine-4-yl)methyl)-1H-pyrrolo[2,3-b]pyridine-6-carboxamide; (Compound 180) N-hydroxy-1-phenethyl-1H-pyrrolo[2,3-b]pyridine-6-carboxamide; (Compound 181) N-hydroxy-1-(3-phenylpropyl)-1H-pyrrolo[2,3-b]pyridine-6-carboxamide; (Compound 182) N-hydroxy-(2-phenoxyethyl)-1H-pyrrolo[2,3-t]pyridine-6-carboxamide; (Compound 183) 1-(2-fluorophenoxy)ethyl)-N-hydroxy-1H-pyrrolo[2,3-b]pyridine-6-carboxamide; (Compound 184) 1-(3-fluorophenoxy)ethyl)-N-hydroxy-1H-pyrrolo[2,3-b]pyridine-6-carboxamide; (Compound 185) 1-(4-fluorophenoxy)ethyl)-N-hydroxy-1H-pyrrolo[2,3-b]pyridine-6-carboxamide; (Compound 186) 1-(2-chlorophenoxy)ethyl)-N-hydroxy-1H-pyrrolo[2,3-b]pyridine-6-carboxamide; (Compound 187) 1-(3-chlorophenoxy)ethyl)-N-hydroxy-1H-pyrrolo[2,3-b]pyridine-6-carboxamide; (Compound 188) 1-(4-chlorophenoxy)ethyl)-N-hydroxy-1H-pyrrolo[2,3-b]pyridine-6-carboxamide; (Compound 189) 1-(2-(2-chloro-4-fluorophenoxy)ethyl)-N-hydroxy-1H-pyrrolo[2,3-b]pyridine-6-carboxamide; (Compound 190) 1-(2-(3-chloro-4-fluorophenoxy)ethyl)-N-hydroxy-1H-pyrrolo[2,3-b]pyridine-6-carboxamide; (Compound 191) 1-(2-(2-fluoro-4-chlorophenoxy)ethyl)-N-hydroxy-1H-pyrrolo[2,3-b]pyridine-6-carboxamide; (Compound 192) 1-(2-(3-fluoro-4-chlorophenoxy)ethyl)-N-hydroxy-1H-pyrrolo[2,3-b]pyridine-6-carboxamide; (Compound 193) 1-(2-(2,3-difluorophenoxy)ethyl)-N-hydroxy-1H-pyrrolo[2,3-b]pyridine-6-carboxamide; (Compound 194) 1-(2-(2,4-difluorophenoxy)ethyl)-N-hydroxy-1H-pyrrolo[2,3-b]pyridine-6-carboxamide; (Compound 195) 1-(2-(3,4-difluorophenoxy)ethyl)-N-hydroxy-1H-pyrrolo[2,3-b]pyridine-6-carboxamide; (Compound 196) 1-(2-(3-(methylsulfonyl)phenoxy)ethyl)-N-hydroxy-1H-pyrrolo[2,3-b]pyridine-6-carboxamide; (Compound 197) 1-(2-(4-(methylsulfonyl)phenoxy)ethyl)-N-hydroxy-1H-pyrrolo[2,3-b]pyridine-6-carboxamide; (Compound 198) N-hydroxy-1-(2-(pyridine-2-yloxy)ethyl)-N-hydroxy-1H-pyrrolo[2,3-b]pyridine-6-carboxamide; (Compound 199) N-hydroxy-1-(2-(pyridine-3-yloxy)ethyl)-N-hydroxy-1H-pyrrolo[2,3-b]

pyridine-6-carboxamide; and (Compound 200) N-hydroxy-1-(2-(pyridine-4-yloxy)ethyl)-N-hydroxy-1H-pyrrolo[2,3-b]pyridine-6-carboxamide.

TABLE 5

Substituted-1H-pyrrole-2-yl-N-hydroxyacrylamide compounds.

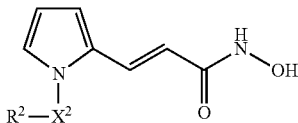

| Compound no. | R² | X² |
|---|---|---|
| 201 | Phenyl | —CH₂— |
| 202 | 3-methoxyphenyl | —CH₂— |
| 203 | 4-methoxyphenyl | —CH₂— |
| 204 | 2-methylphenyl | —CH₂— |
| 205 | 3-methylphenyl | —CH₂— |
| 206 | 4-methyl-phenyl | —CH₂— |
| 207 | 2-fluorophenyl | —CH₂— |
| 208 | 3-fluorophenyl | —CH₂— |
| 209 | 4-fluorophenyl | —CH₂— |
| 210 | 2-chlorophenyl | —CH₂— |
| 211 | 3-chlorophenyl | —CH₂— |
| 212 | 4-chlorophenyl | —CH₂— |
| 213 | 3-fluoro-4-methoxyphenyl | —CH₂— |
| 214 | 4-(trifluoromethoxy)-phenyl | —CH₂— |
| 215 | 3,4-dichlorophenyl | —CH₂— |
| 216 | 2,4-dichlorophenyl | —CH₂— |
| 217 | 2-chloro-4-fluorophenyl | —CH₂— |
| 218 | 2-chloro-4-methoxyphenyl | —CH₂— |
| 219 | 2,3-dichlorophenyl | —CH₂— |
| 220 | 3-methoxy-4-fluorophenyl | —CH₂— |
| 221 | 3-methoxy-5-fluorophenyl | —CH₂— |
| 222 | 3-methoxy-4-chlorophenyl | —CH₂— |
| 223 | 3-(methylsulfonyl)phenyl | —CH₂— |
| 224 | 4-(methylsulfonyl)phenyl | —CH₂— |
| 225 | 2-thiophenyl | —CH₂— |
| 226 | 3-thiophenyl | —CH₂— |
| 227 | 2-pyridyl | —CH₂— |
| 228 | 3-pyridyl | —CH₂— |
| 229 | 4-pyridyl | —CH₂— |
| 230 | phenyl | —(CH₂)₂— |
| 231 | phenyl | —(CH₂)₃— |
| 232 | phenyl | —O(CH₂)₂— |
| 233 | 2-fluorophenyl | —O(CH₂)₂— |
| 234 | 3-fluorophenyl | —O(CH₂)₂— |
| 235 | 4-fluorophenyl | —O(CH₂)₂— |
| 236 | 2-chlorophenyl | —O(CH₂)₂— |
| 237 | 3-chlorophenyl | —O(CH₂)₂— |
| 238 | 4-chlorophenyl | —O(CH₂)₂— |
| 239 | 2-chloro-4-fluorophenyl | —O(CH₂)₂— |
| 240 | 3-chloro-4-fluorophenyl | —O(CH₂)₂— |
| 241 | 2-fluoro-4-chlorophenyl | —O(CH₂)₂— |
| 242 | 3-fluoro-4-chlorophenyl | —O(CH₂)₂— |
| 243 | 2,3-difluorophenyl | —O(CH₂)₂— |
| 244 | 2,4-difluorophenyl | —O(CH₂)₂— |
| 245 | 3,4-difluorophenyl | —O(CH₂)₂— |
| 246 | 3-(methylsulfonyl)phenyl | —O(CH₂)₂— |
| 247 | 4-(methylsulfonyl)phenyl | —O(CH₂)₂— |
| 248 | 2-pyridyl | —O(CH₂)₂— |
| 249 | 3-pyridyl | —O(CH₂)₂— |
| 250 | 4-pyridyl | —O(CH₂)₂— |
| 251 | 2-(dimethylaminomethyl)phenyl | —O(CH₂)₂— |
| 252 | 3-(dimethylaminomethyl)phenyl | —O(CH₂)₂— |
| 253 | 4-(dimethylaminomethyl)phenyl | —O(CH₂)₂— |
| 254 | 2-(morpholin-4-ylmethyl)phenyl | —O(CH₂)₂— |
| 255 | 3-(morpholin-4-ylmethyl)phenyl | —O(CH₂)₂— |
| 256 | 4-(morpholin-4-ylmethyl)phenyl | —O(CH₂)₂— |

Pyrrole alkene compounds in Table 5 are named: (Compound 201) (E)-3-(1-benzyl-1H-pyrrol-2-yl)-N-hydroxyacrylamide; (Compound 202) (E)-3-(1-(3-methoxybenzyl)-1H-pyrrol-2-yl)-N-hydroxyacrylamide; (Compound 203) (E)-3-(1-(4-methoxybenzyl)-1H-pyrrol-2-yl)-N-hydroxyacrylamide; (Compound 204) (E)-3-(1-(2-methylbenzyl)-1H-pyrrol-2-yl)-N-hydroxyacrylamide; (Compound 205) (E)-3-(1-(3-methylbenzyl)-1H-pyrrol-2-yl)-N-hydroxyacrylamide; (Compound 206) (E)-3-(1-(4-methylbenzyl)-1H-pyrrol-2-yl)-N-hydroxyacrylamide; (Compound 207) (E)-3-(1-(2-fluorobenzyl)-1H-pyrrol-2-yl)-N-hydroxyacrylamide; (Compound 208) (E)-3-(1-(3-fluorobenzyl)-1H-pyrrol-2-yl)-N-hydroxyacrylamide; (Compound 209) (E)-3-(1-(4-fluorobenzyl)-1H-pyrrol-2-yl)-N-hydroxyacrylamide; (Compound 210) (E)-3-(1-(2-chlorobenzyl)-1H-pyrrol-2-yl)-N-hydroxyacrylamide; (Compound 211) (E)-3-(1-(3-chlorobenzyl)-1H-pyrrol-2-yl)-N-hydroxyacrylamide; (Compound 212) (E)-3-(1-(4-chlorobenzyl)-1H-pyrrol-2-yl)-N-hydroxyacrylamide; (Compound 213) (E)-3-(1-(3-fluoro-4-methoxybenzyl)-1H-pyrrol-2-yl)-N-hydroxyacrylamide; (Compound 214) (E)-3-(1-(4-(trifluoromethoxy)-benzyl)-1H-pyrrol-2-yl)-N-hydroxyacrylamide; (Compound 215) (E)-3-(1-(3,4-dichlorobenzyl)-1H-pyrrol-2-yl)-N-hydroxyacrylamide; (Compound 216) (E)-3-(1-(2,4-dichlorobenzyl)-1H-pyrrol-2-yl)-N-hydroxyacrylamide; (Compound 217) (E)-3-(1-(2-chloro-4-fluorobenzyl)-1H-pyrrol-2-yl)-N-hydroxyacrylamide; (Compound 218) (E)-3-(1-(2-chloro-4-methoxybenzyl)-1H-pyrrol-2-yl)-N-hydroxyacrylamide; (Compound 219) (E)-3-(1-(2,3-dichlorobenzyl)-1H-pyrrol-2-yl)-N-hydroxyacrylamide; (Compound 220) (E)-3-(1-(4-fluoro-3-methoxybenzyl)-1H-pyrrol-2-yl)-N-hydroxyacrylamide; (Compound 221) (E)-3-(1-(5-fluoro-3-methoxybenzyl)-1H-pyrrol-2-yl)-N-hydroxyacrylamide; (Compound 222) (E)-3-(1-(4-chloro-3-methoxybenzyl)-1H-pyrrol-2-yl)-N-hydroxyacrylamide; (Compound 223) (E)-3-(1-(3-(methylsulfonyl)benzyl)-1H-pyrrol-2-yl)-N-hydroxyacrylamide; (Compound 224) (E)-3-(1-(4-(methylsulfonyl)benzyl)-1H-pyrrol-2-yl)-N-hydroxyacrylamide; (Compound 225) (E)-N-hydroxy-3-((thiophen-2-yl)methyl)-1H-pyrrol-2-yl)-N-hydroxyacrylamide; (Compound 226) (E)-N-hydroxy-3-((thiophen-3-yl)methyl)-1H-pyrrol-2-yl)-N-hydroxyacrylamide; (Compound 227) (E)-N-hydroxy-3-(1-((pyridine-2-yl)methyl)-1H-pyrrol-2-yl)-N-hydroxyacrylamide; (Compound 228) (E)-N-hydroxy-3-(1-((pyridine-3-yl)methyl)-1H-pyrrol-2-yl)-N-hydroxyacrylamide; (Compound 229) (E)-N-hydroxy-3-(1-((pyridine-4-yl)methyl)-1H-pyrrol-2-yl)-N-hydroxyacrylamide; (Compound 230) (E)-N-hydroxy-3-(1-phenethyl-1H-pyrrol-2-yl)acrylamide; (Compound 231) (E)-N-hydroxy-3-(1-(3-phenylpropyl)-1H-pyrrol-2-yl)-N-hydroxyacrylamide; (Compound 232) (E)-N-hydroxy-3-(2-phenoxyethyl-1H-pyrrol-2-yl)acrylamide; (Compound 233) (E)-3-(1-(2-(2-fluorophenoxy)ethyl)-1H-pyrrol-2-yl)-N-hydroxyacrylamide; (Compound 234) (E)-3-(1-(2-(3-fluorophenoxy)ethyl)-1H-pyrrol-2-yl)-N-hydroxyacrylamide; (Compound 235) (E)-3-(1-(2-(4-fluorophenoxy)ethyl)-1H-pyrrol-2-yl)-N-hydroxyacrylamide; (Compound 236) (E)-3-(1-(2-(2-chlorophenoxy)ethyl)-1H-pyrrol-2-yl)-N-hydroxyacrylamide; (Compound 237) (E)-3-(1-(2-(3-chlorophenoxy)ethyl)-1H-pyrrol-2-yl)-N-hydroxyacrylamide; (Compound 238) (E)-3-(1-(2-(4-chlorophenoxy)ethyl)-1H-pyrrol-2-yl)-N-hydroxyacrylamide; (Compound 239) (E)-3-(1-(2-(2-chloro-4-fluorophenoxy)ethyl)-1H-pyrrol-2-yl)-N-hydroxyacrylamide; (Compound 240) (E)-3-(1-(2-(3-chloro-4-fluorophenoxy)ethyl)-1H-pyrrol-2-yl)-N-hydroxyacrylamide; (Compound 241) (E)-3-(1-(2-(2-fluoro-4-chlorophenoxy)ethyl)-1H-pyrrol-2-yl)-N-hydroxyacrylamide; (Compound 242) (E)-3-(1-(2-(3-fluoro-4-chlorophenoxy)ethyl)-1H-pyrrol-2-yl)-N-hydroxyacrylamide; (Compound 243) (E)-3-(1-(2-(2,3-difluorophenoxy)ethyl)-1H-pyrrol-2-yl)-N-hydroxyacrylamide; (Compound 244) (E)-3-(1-(2-(2,4- difluorophenoxy)ethyl)-1H-pyrrol-2-yl)-N-hydroxyacrylamide; (Compound 245) (E)-3-(1-(2-(3,4-difluorophenoxy)ethyl)-1H-pyrrol-2-yl)-N-hydroxyacrylamide; (Compound 246) (E)-3-(1-(2-(3-(methylsulfonyl)phenoxy)ethyl)-1H-pyrrol-2-yl)-N-hydroxyacrylamide; (Compound 247) (E)-3-(1-(2-(4-(methylsulfonyl)phenoxy)ethyl)-1H-pyrrol-2-yl)-N-hydroxyacrylamide; (Compound 248) (E)-N-hydroxy-3-(1-(2-(pyridine-2-yloxy)ethyl)-1H-pyrrol-2-yl)-N-hydroxyaryl amide; (Compound 249) (E)-N-hydroxy-3-(1-(2-(pyridine-3-yloxy)ethyl)-1H-pyrrol-2-yl)-N-hydroxyacrylamide; (Compound 250) (E)-N-hydroxy-3-(1-(2-(pyridine-4-yloxy)ethyl)-1H-pyrrol-2-yl)-N-hydroxyacrylamide; (Compound 251) (E)-3-(1-(2-(2-(dimethylaminomethyl)phenoxy)ethyl)-1H-pyrrol-2-yl)-N-hydroxyacrylamide; (Compound 252) (E)-3-(1-(2-(3-(dimethylaminomethyl)phenoxy)ethyl)-1H-pyrrol-2-yl)-N-hydroxyacrylamide; (Compound 253) (E)-3-(1-(2-(4-(dimethylaminomethyl)phenoxy)ethyl)-1H-pyrrol-2-yl)-N-hydroxyacrylamide; (Compound 254) (E)-3-(1-(2-(2-(morpholin-4-ylmethyl)phenoxy)ethyl)-1H-pyrrol-2-yl)-N-hydroxyacrylamide; (Compound 255) (E)-3-(1-(2-(3-(morpholin-4-ylmethyl)phenoxy)ethyl)-1H-pyrrol-2-yl)-N-hydroxyacrylamide; (Compound 256) (E)-3-(1-(2-(4-(morpholin-4-ylmethyl)phenoxy)ethyl)-1H-pyrrol-2-yl)-N-hydroxyacrylamide.

TABLE 6

Substituted benzofuran, benzothiopbene compounds.

Z is S or O

| Compound No. | R² | X² |
|---|---|---|
| 251 | Phenyl | —CH₂— |
| 252 | 3-methoxyphenyl | —CH₂— |
| 253 | 4-methoxyphenyl | —CH₂— |
| 254 | 2-methylphenyl | —CH₂— |
| 255 | 3-methylphenyl | —CH₂— |
| 256 | 4-methyl-phenyl | —CH₂— |
| 257 | 2-fluorophenyl | —CH₂— |
| 258 | 3-fluorophenyl | —CH₂— |
| 259 | 4-fluorophenyl | —CH₂— |
| 260 | 2-chlorophenyl | —CH₂— |

TABLE 6-continued

Substituted benzofuran, benzothiopbene compounds.

Z is S or O

| Compound No. | R² | X² |
|---|---|---|
| 261 | 3-chlorophenyl | —CH₂— |
| 262 | 4-chlorophenyl | —CH₂— |
| 263 | 3-fluoro-4-methoxyphenyl | —CH₂— |
| 264 | 4-(trifluoromethoxy)-phenyl | —CH₂— |
| 265 | 3,4-dichlorophenyl | —CH₂— |
| 266 | 2,4-dichlorophenyl | —CH₂— |
| 267 | 2-chloro-4-fluorophenyl | —CH₂— |
| 268 | 2-chloro-4-methoxyphenyl | —CH₂— |
| 269 | 2,3-dichlorophenyl | —CH₂— |
| 270 | 3-methoxy-4-fluorophenyl | —CH₂— |
| 271 | 3-methoxy-5-fluorophenyl | —CH₂— |
| 272 | 3-methoxy-4-chlorophenyl | —CH₂— |
| 273 | 3-(methylsulfonyl)phenyl | —CH₂— |
| 274 | 4-(methylsulfonyl)phenyl | —CH₂— |
| 275 | 2-thiophenyl | —CH₂— |
| 276 | 3-thiophenyl | —CH₂— |
| 277 | 2-pyridyl | —CH₂— |
| 278 | 3-pyridyl | —CH₂— |
| 279 | 4-pyridyl | —CH₂— |
| 280 | phenyl | —(CH₂)₂— |
| 281 | phenyl | —(CH₂)₃— |
| 282 | phenyl | —O(CH₂)₂— |
| 283 | 2-fluorophenyl | —O(CH₂)₂— |
| 284 | 3-fluorophenyl | —O(CH₂)₂— |
| 285 | 4-fluorophenyl | —O(CH₂)₂— |
| 286 | 2-chlorophenyl | —O(CH₂)₂— |
| 287 | 3-chlorophenyl | —O(CH₂)₂— |
| 288 | 4-chlorophenyl | —O(CH₂)₂— |
| 289 | 2-chloro-4-fluorophenyl | —O(CH₂)₂— |
| 290 | 3-chloro-4-fluorophenyl | —O(CH₂)₂— |
| 291 | 2-fluoro-4-chlorophenyl | —O(CH₂)₂— |
| 292 | 3-fluoro-4-chlorophenyl | —O(CH₂)₂— |
| 293 | 2,3-difluorophenyl | —O(CH₂)₂— |
| 294 | 2,4-difluorophenyl | —O(CH₂)₂— |
| 295 | 3,4-difluorophenyl | —O(CH₂)₂— |
| 296 | 3-(methylsulfonyl)phenyl | —O(CH₂)₂— |
| 297 | 4-(methylsulfonyl)phenyl | —O(CH₂)₂— |
| 298 | 2-pyridyl | —O(CH₂)₂— |
| 299 | 3-pyridyl | —O(CH₂)₂— |
| 300 | 4-pyridyl | —O(CH₂)₂— |

TABLE 7

1H-indole-6-carboxylic acid hydroxyamides.

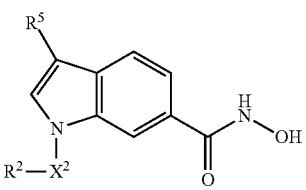

| Compound no. | R² | X² | R⁵ |
|---|---|---|---|
| 301 | phenyl | —CH₂— | H |
| 302 | phenyl | —CH₂CH₂— | H |
| 303 | phenyl | —CH₂CH₂CH₂— | H |
| 304 | 2-methoxyphenyl | —CH₂— | H |
| 305 | 3-methoxyphenyl | —CH₂— | H |
| 306 | 4-methoxyphenyl | —CH₂— | H |
| 307 | 4-methoxyphenyl | —CH₂— | dimethylaminomethyl |

TABLE 7-continued 1H-indole-6-carboxylic acid hydroxyamides.

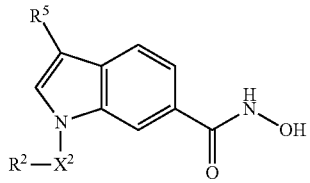

| Compound no. | R² | X² | R⁵ |
|---|---|---|---|
| 308 | 4-methoxyphenyl | —CH₂— | phenyl-CH₂—NH—CH₂— |
| 309 | 4-methoxyphenyl | —CH₂— | (pyridini-2-yl)-CH₂—NCH₃—CH₂— |
| 310 | 2-methoxypyridin-5-yl | —CH₂— | H |
| 311 | 4-(methoxyethoxy)phenyl | —CH₂— | H |
| 312 | 2-(phenylsulfonamido)phenyl | —CH₂— | H |
| 313 | 3-(phenylsulfonamido)phenyl | —CH₂— | H |
| 314 | 4-(phenylsulfonamido)phenyl | —CH₂— | H |
| 315 | benzo[d][1,3]dioxol-5-yl | —CH₂— | H |
| 316 | phenyl | —O(CH₂)₂— | H |
| 317 | 2-fluorophenyl | —O(CH₂)₂— | H |
| 318 | 3-fluorophenyl | —O(CH₂)₂— | H |
| 319 | 4-fluorophenyl | —O(CH₂)₂— | H |
| 320 | 2-chlorophenyl | —O(CH₂)₂— | H |
| 321 | 3-chlorophenyl | —O(CH₂)₂— | H |
| 322 | 4-chlorophenyl | —O(CH₂)₂— | H |
| 323 | 2-(dimethylaminomethyl)phenyl | —O(CH₂)₂— | H |
| 324 | 3-(dimethylaminomethyl)phenyl | —O(CH₂)₂— | H |
| 325 | 4-(dimethylaminomethyl)phenyl | —O(CH₂)₂— | H |
| 326 | 2-(morpholin-4-ylmethyl)phenyl | —O(CH₂)₂— | H |
| 327 | 3-(morpholin-4-ylmethyl)phenyl | —O(CH₂)₂— | H |
| 328 | 4-(morpholin-4-ylmethyl)phenyl | —O(CH₂)₂— | H |
| 329 | phenyl | —NHC(=O)CH₂— | H |
| 330 | 3-fluoro-4-methoxyphenyl | —CH₂— | H |
| 331 | 2-methylphenyl | —CH₂— | H |
| 332 | 3-methylphenyl | —CH₂— | H |
| 333 | 4-methylphenyl | —CH₂— | H |
| 334 | 2-fluorophenyl | —CH₂— | H |
| 335 | 3-fluorophenyl | —CH₂— | H |
| 336 | 4-fluorophenyl | —CH₂— | H |
| 337 | 2-chlorophenyl | —CH₂— | H |
| 338 | 3-chlorophenyl | —CH₂— | H |
| 339 | 4-chlorophenyl | —CH₂— | H |
| 340 | 3-fluoro-4-methoxyphenyl | —CH₂— | H |
| 341 | 4-(trifluoromethoxy)-phenyl | —CH₂— | H |
| 342 | 3,4-dichlorophenyl | —CH₂— | H |
| 343 | 2,4-dichlorophenyl | —CH₂— | H |
| 344 | 2-chloro-4-fluorophenyl | —CH₂— | H |
| 345 | 2-chloro-4-methoxyphenyl | —CH₂— | H |
| 346 | 2,3-dichlorophenyl | —CH₂— | H |
| 347 | 3-methoxy-4-fluorophenyl | —CH₂— | H |
| 348 | 3-methoxy-5-fluorophenyl | —CH₂— | H |
| 349 | 3-methoxy-4-chlorophenyl | —CH₂— | H |
| 350 | 3-(methylsulfonyl)phenyl | —CH₂— | H |
| 351 | 4-(methylsulfonyl)phenyl | —CH₂— | H |
| 352 | 2-thiophenyl | —CH₂— | H |
| 353 | 3-thiophenyl | —CH₂— | H |
| 354 | 2-pyridyl | —CH₂— | H |
| 355 | 3-pyridyl | —CH₂— | H |
| 356 | 4-pyridyl | —CH₂— | H |
| 357 | 2-chloro-4-fluorophenyl | —O(CH₂)₂— | H |
| 358 | 3-chloro-4-fluorophenyl | —O(CH₂)₂— | H |
| 359 | 2-fluoro-4-chlorophenyl | —O(CH₂)₂— | H |
| 360 | 3-fluoro-4-chlorophenyl | —O(CH₂)₂— | H |
| 361 | 2,3-difluorophenyl | —O(CH₂)₂— | H |
| 362 | 2,4-difluorophenyl | —O(CH₂)₂— | H |
| 363 | 3,4-difluorophenyl | —O(CH₂)₂— | H |
| 364 | 3-(methylsulfonyl)phenyl | —O(CH₂)₂— | H |
| 365 | 4-(methylsulfonyl)phenyl | —O(CH₂)₂— | H |
| 366 | 2-pyridyl | —O(CH₂)₂— | H |
| 367 | 3-pyridyl | —O(CH₂)₂— | H |
| 368 | 4-pyridyl | —O(CH₂)₂— | H |

1H-indole-6-carboxylic acid hydroxyamides in Table 7 are named: (Compound 301) N-hydroxy-1-benzyl-1H-indole-6-carboxamide; (Compound 302) N-hydroxy-1-(2-phenylethyl)-1H-indole-6-carboxamide; (Compound 303) N-hydroxy-1-(3-phenyl-propyl)-1H-indole-6-carboxamide; (Compound 304) N-hydroxy-1-(2-methoxybenzyl)-1H-indole-6-carboxamide; (Compound 305) N-hydroxy-1-(3-methoxybenzyl)-1H-indole-6-carboxamide; (Compound 306) N-hydroxy-1-(4-methoxybenzyl)-1H-indole-6-carboxamide; (Compound 307) N-hydroxy-1-(4-methoxybenzyl)-3-(dimethylaminomethyl)-1H-indole-6-carboxamide; (Compound 308) N-hydroxy-1-(4-methoxybenzyl)-3-((methyl(2-(pyridin-2-yl)ethyl)amino)methyl)-1H-indole-6-carboxamide; (Compound 309) 3-((benzylamino)methyl)-N-hydroxy-1-(4-methoxybenzyl)-1H-indole-6-carboxamide; (Compound 310) N-hydroxy-1-(2-methoxylpyridin-5-ylmethyl)-1H-indole-6-carboxamide; (Compound 311) N-hydroxy-1-(4-(methoxyethoxy)benzyl)-1H-indole-6-carboxamide; (Compound 312) N-hydroxy-1-(2-(phenylsulfonamido)benzyl)-1H-indole-6-carboxamide; (Compound 313) N-hydroxy-1-(3-(phenylsulfonamido)benzyl)-1H-indole-6-carboxamide; (Compound 314) N-hydroxy-1-(4-(phenylsulfonamido)benzyl)-1H-indole-6-carboxamide; (Compound 315) N-hydroxy-1-(benzo[d][1,3]dioxol-5-ylmethyl)-1H-indole-6-carboxamide; (Compound 316) N-hydroxy-1-(2-phenoxyethyl)-1H-indole-6-carboxamide; (Compound 317) N-hydroxy-1-(2-(2-fluorophenoxy)ethyl)-1H-indole-6-carboxamide; (Compound 318) N-hydroxy-1-(2-(3-fluorophenoxy)ethyl)-1H-indole-6-carboxamide; (Compound 319) N-hydroxy-1-(2-(4-fluorophenoxy)ethyl)-1H-indole-6-carboxamide; (Compound 320) N-hydroxy-1-(2-(2-chlorophenoxy)ethyl)-1H-indole-6-carboxamide; (Compound 321) N-hydroxy-1-(2-(3-chlorophenoxy)ethyl)-1H-indole-6-carboxamide; (Compound 322) N-hydroxy-1-(2-(4-chlorophenoxy)ethyl)-1H-indole-6-carboxamide; (Compound 323) N-hydroxy-1-(2-(2-(dimethylaminomethyl)phenoxy)ethyl)-1H-indole-6-carboxamide; (Compound 324) N-hydroxy-1-(2-(3-(dimethylaminomethyl)phenoxy)ethyl)-1H-indole-6-carboxamide; (Compound 325) N-hydroxy-1-(2-(4-(dimethylaminomethyl)phenoxy)ethyl)-1H-indole-6-carboxamide; (Compound 326) N-hydroxy-1-(2-(2-(morpholin-4-ylmethyl)phenoxy)ethyl)-1H-indole-6-carboxamide; (Compound 327) N-hydroxy-1-(2-(3-(morpholin-4-ylmethyl)phenoxy)ethyl)-1H-indole-6-carboxamide; (Compound 328) N-hydroxy-1-(2-(4-(morpholin-4-ylmethyl)phenoxy)ethyl)-1H-indole-6-carboxamide; (Compound 329) N-hydroxy-1-(2-oxo-2-(phenylamino)ethyl)-1H-indole-6-carboxamide; (Compound 330) N-hydroxy-1-(3-fluoro-4-methoxybenzyl)-1H-indole-6-carboxamide; (Compound 331) N-hydroxy-1-(2-methylbenzyl)-1H-indole-6-carboxamide; (Compound 332) N-hydroxy-1-(3-methylbenzyl)-1H-indole-6-carboxamide; (Compound 333) N-hydroxy-1-(4-methylbenzyl)-1H-indole-6-carboxamide; (Compound 334) N-hydroxy-1-(2-fluorobenzyl)-1H-indole-6-carboxamide; (Compound 335) N-hydroxy-1-(3-fluorobenzyl)-1H-indole-6-carboxamide; (Compound 336) N-hydroxy-1-(4-fluorobenzyl)-1H-indole-6-carboxamide; (Compound 337) N-hydroxy-1-(2-chlorobenzyl)-1H-indole-6-carboxamide; (Compound 338) N-hydroxy-1-(3-chlorobenzyl)-1H-indole-6-carboxamide; (Compound 339) N-hydroxy-1-(4-chlorobenzyl)-1H-indole-6-carboxamide; (Compound 340) N-hydroxy-1-(3-fluoro-4-methoxybenzyl)-1H-indole-6-carboxamide; (Compound 341) N-hydroxy-1-(4-(trifluoromethoxy)-benzyl)-1H-indole-6-carboxamide; (Compound 342) N-hydroxy-1-(3,4-dichlorobenzyl)-1H-indole-6-carboxamide; (Compound 343) N-hydroxy-1-(2,4-dichlorobenzyl)-1H-indole-6-carboxamide; (Compound 344) N-hydroxy-1-(2-chloro-4-fluorobenzyl)-1H-indole-6-carboxamide; (Compound 345) N-hydroxy-1-(2-chloro-4-methoxybenzyl)-1H-indole-6-carboxamide; (Compound 346) N-hydroxy-1-(2,3-dichlorobenzyl)-1H-indole-6-carboxamide; (Compound 347) N-hydroxy-1-(3-methoxy-4-fluorobenzyl)-1H-indole-6-carboxamide; (Compound 348) N-hydroxy-1-(3-methoxy-5-fluorobenzyl)-1H-indole-6-carboxamide; (Compound 349) N-hydroxy-1-(3-methoxy-4-chlorobenzyl)-1H-indole-6-carboxamide; (Compound 350) N-hydroxy-1-(3-(methylsulfonyl)benzyl)-1H-indole-6-carboxamide; (Compound 351) N-hydroxy-1-(4-(methylsulfonyl)benzyl)-1H-indole-6-carboxamide; (Compound 352) N-hydroxy-1-(2-thiophenylmethyl)-1H-indole-6-carboxamide; (Compound 353) N-hydroxy-1-(3-thiophenylmethyl)-1H-indole-6-carboxamide; (Compound 354) N-hydroxy-1-(2-pyridylmethyl)-1H-indole-6-carboxamide; (Compound 355) N-hydroxy-1-(3-pyridylmethyl)-1H-indole-6-carboxamide; (Compound 356) N-hydroxy-1-(4-pyridylmethyl)-1H-indole-6-carboxamide; (Compound 357) N-hydroxy-1-(2-chloro-4-fluorophenoxyethyl)-1H-indole-6-carboxamide; (Compound 358) N-hydroxy-1-(3-chloro-4-fluorophenoxyethyl)-1H-indole-6-carboxamide; (Compound 359) N-hydroxy-1-(2-fluoro-4-chlorophenoxyethyl)-1H-indole-6-carboxamide; (Compound 360) N-hydroxy-1-(3-fluoro-4-chlorophenoxyethyl)-1H-indole-6-carboxamide; (Compound 361) N-hydroxy-1-(2,3-difluorophenoxyethyl)-1H-indole-6-carboxamide; (Compound 362) N-hydroxy-1-(2,4-difluorophenoxyethyl)-1H-indole-6-carboxamide; (Compound 363) N-hydroxy-1-(3,4-difluorophenoxyethyl)-1H-indole-6-carboxamide; (Compound 364) N-hydroxy-1-(3-(methylsulfonyl)phenoxyethyl)-1H-indole-6-carboxamide; (Compound 365) N-hydroxy-1-(4-(methylsulfonyl)phenoxyethyl)-1H-indole-6-carboxamide; (Compound 356) N-hydroxy-1-(2-pyridyloxyethyl)-1H-indole-6-carboxamide; (Compound 357) N-hydroxy-1-(3-pyridyloxyethyl)-1H-indole-6-carboxamide; (Compound 358) N-hydroxy-1-(4-pyridyloxyethyl)-1H-indole-6-carboxamide; (Compound 365) N-hydroxy-1-(2,4-difluorophenoxyethyl)-1H-indole-6-carboxamide.

Throughout the specification, groups and substituents thereof are chosen to provide stable moieties and compounds.

Further Forms of Compounds

In some embodiments, compounds described herein possess one or more stereocenters and each center exists in the R or S configuration. The compounds presented herein include all diastereomeric, enantiomeric, and epimeric forms as well as the appropriate mixtures thereof. In some embodiments, separation of stereoisomers are performed by chromatography. In other embodiments, individual stereoisomers are obtained by reacting a racemic mixture of the compound with an optically active resolving agent to form a pair of diastereoisomeric compounds, separating the diastereomers and recovering the optically pure enantiomers. In one embodiment the resolution of enantiomers are carried out using covalent diastereomeric derivatives of the compounds described herein, dissociable complexes are also possible (e.g., crystalline diastereomeric salts). Diastereomers have distinct physical properties (e.g., melting points, boiling points, solubilities, reactivity, etc.) and are readily separated by taking advantage of these dissimilarities. In some embodiments, the diastereomers are separated by chiral chromatography, or by separation/resolution techniques based upon differences in solubility. The optically pure enantiomer(s) is/are then recovered, along with the resolving agent, by any practical means that would not result in racemization. A more detailed description of the techniques applicable to the resolution of stereoisomers of compounds from their racemic mixture is found in Jean Jacques, Andre Collet, Samuel H. Wilen, "Enantiomers, Racemates and Resolutions", John Wiley And Sons, Inc., 1981, herein incorporated by reference for such disclosure. In further embodiments, stereoisomers are obtained by stereoselective synthesis.

In some situations, compounds exist as tautomers. All tautomers are included within the formulas described herein.

The methods and formulations described herein include the use of N-oxides, crystalline forms (also known as polymorphs), or pharmaceutically acceptable salts of compounds described herein, as well as active metabolites of these compounds having the same type of activity. In some situations, compounds exist as tautomers. All tautomers are included within the scope of the compounds presented herein. In addition, the compounds described herein exist in unsolvated as well as solvated forms with pharmaceutically acceptable solvents such as water, ethanol, and the like. The solvated forms of the compounds presented herein are also considered to be disclosed herein.

In some embodiments, the compounds described herein in unoxidized form are prepared from the corresponding N-oxides compounds by treating with a reducing agent, such as, but not limited to, sulfur, sulfur dioxide, triphenyl phosphine, lithium borohydride, sodium borohydride, phosphorus trichloride, phosphorus tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they are easier to administer than the parent drug. In some embodiments, prodrugs are bioavailable by oral administration whereas the parent is not. In other embodiments, the prodrug has improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. In some embodiments, the prodrug is designed to alter the metabolic stability or the transport characteristics of a drug, to mask side effects or toxicity, to improve the flavor of a drug or to alter other characteristics or properties of a drug. In some embodiments, once a pharmaceutically active compound is known, knowledge of pharmacodynamic processes and drug metabolism in vivo, aids in the design of prodrugs of the compound. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews,* 56:53-102, 2004; Miller et al., *J. Med. Chem.* Vol. 46, no. 24, 5097-5116, 2003; Aesop Cho, "Recent Advances in Oral Prodrug Discovery", *Annual Reports in Medicinal Chemistry*, Vol. 41, 395-407, 2006).

Prodrug forms of the herein described compounds, wherein the prodrug is metabolized in vivo to produce a derivative as set forth herein are included within the scope of the claims. In some embodiments, some of the herein-described compounds are a prodrug for another derivative or active compound.

In some embodiments prodrugs are easier to administer than the parent drug. In some embodiments the prodrug is bioavailable by oral administration whereas the parent is not. In other embodiments the prodrug has improved solubility in pharmaceutical compositions over the parent drug. In further embodiments, prodrugs are designed as reversible drug derivatives, for use as modifiers to enhance drug transport to site-specific tissues. In some embodiments, the design of a prodrug increases the effective water solubility. See, e.g., Fedorak et al., *Am. J. Physiol.,* 269:G210-218 (1995); McLoed et al., *Gastroenterol,* 106:405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure.

Sites on the aromatic ring portion of compounds described herein are susceptible to various metabolic reactions, therefore incorporation of appropriate substituents on the aromatic ring structures, such as, by way of example only, halogens reduces, minimizes or eliminates this metabolic pathway.

In some embodiments the compounds described herein are labeled isotopically (e.g. with a radioisotope) or by other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

In some embodiments, compounds described herein are formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, nitric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion. In some embodiments, compounds described herein form a coordinate with an organic base, such as, but not limited to, ethanolamine, diethanolamine, triethanolamine, tromethamine, N-methylglucamine, dicyclohexylamine, tris(hydroxymethyl)methylamine. In other embodiments, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. In some embodiments, solvates contain either stoichiometric or non-stoichiometric amounts of a solvent, and form during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein exist in unsolvated as well as solvated forms. In general, the solvated forms are considered equivalent to the unsolvated forms for the purposes of the compounds and methods provided herein.

In some embodiments, compounds described herein are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. In some embodiments, various factors such as the recrystallization solvent, rate of crystallization, and storage temperature cause a single crystal form to dominate.

In other embodiments, the screening and characterization of the pharmaceutically acceptable salts, polymorphs and/or solvates is accomplished by using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof are chosen to provide stable moieties and compounds.

Synthesis of Compounds

The synthesis of compounds described herein are accomplished using means described in the chemical literature, using the methods described herein, or by a combination thereof. In addition, solvents, temperatures and other reaction conditions presented herein vary according to the means described in the chemical literature, using the methods described herein, or by a combination thereof.

The starting materials and reagents used for the synthesis of the compounds described herein are synthesized or are obtained from commercial sources, such as, but not limited to, Sigma-Aldrich, Fluka, Acros Organics, Alfa Aesar, Bachem and the like.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001), and Green and Wuts, PROTECTIVE GROUPS IN ORGANIC SYNTHESIS $3^{rd}$ Ed., (Wiley 1999) (all of which are incorporated by reference for such disclosure). General methods for the preparation of compound as disclosed herein are modified by the use of appropriate reagents and conditions, for the introduction of the various moieties found in the formulae as provided herein. As a guide the following synthetic methods are utilized.

Compounds described herein are synthesized starting from compounds that are available from commercial sources or that are prepared using procedures outlined herein.

Using the reaction conditions described herein, 1,2-disubstituted-1H-benzimidazole-6-carboxylic acid hydroxyamides, 1,3-disubstituted-azaindole-6-carboxylic acid hydroxyamides, substituted 1H-pyrrol-2-yl-N-hydroxyacrylamide and substituted benzofuran, thiphene and indole compositions as disclosed herein are obtained in good yields and purity. The compounds prepared by the methods disclosed herein are purified by conventional means such as, filtration, recrystallization, chromatography, distillation, and combinations thereof.

Schemes presented herein are merely illustrative of some methods by which the compounds described herein are synthesized, and various modifications to these schemes are made based on this disclosure.

Formation of Covalent Linkages by Reaction of an Electrophile with a Nucleophile The compounds described herein are modified using various electrophiles and/or nucleophiles to form new functional groups or substituents. Table A entitled "Examples of Covalent Linkages and Precursors Thereof" lists selected non-limiting examples of covalent linkages and precursor functional groups which yield the covalent linkages. Table 7 is used as guidance toward the variety of electrophiles and nucleophiles combinations available that provide covalent linkages. Precursor functional groups are shown as electrophilic groups and nucleophilic groups.

TABLE A

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In the reactions described, it is necessary in certain cases to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group is removable by a different means. Protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

General Syntheses

Benzimidazole Compounds:

Benzimidazole compounds described herein are prepared from commercially available materials.

In one embodiment, compounds of structure 1 are used as starting materials for the synthesis of compounds described herein.

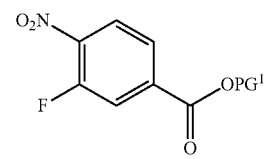

1

$PG^1$ represents carboxylic acid protecting groups. In one embodiment, $PG^1$ represents a substituted or unsubstituted alkyl group, such as, but not limited to, methyl, ethyl, propyl, benzyl, and p-methoxybenzyl.

In another embodiment, the 3-position of the 3-fluoro-4-nitrobenzoate described herein is functionalized as outlined in Scheme 1.

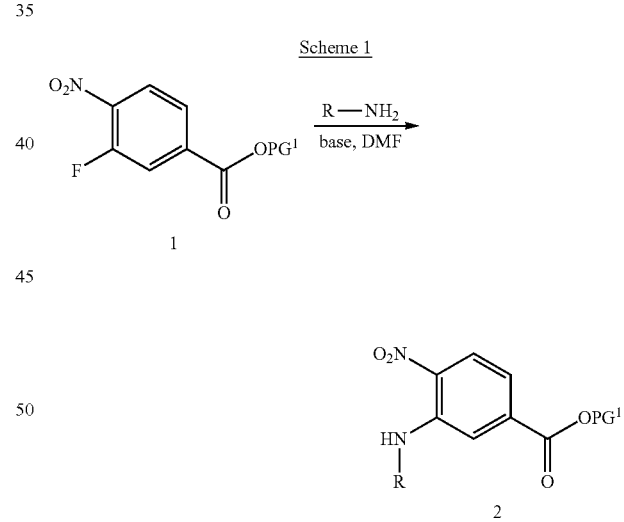

3-Amino-4-nitrobenzoates of general structure 2 (where $R=X^2$—$R^2$) are obtained from the nucleophilic aromatic substitution reactions of 3-fluoro-4-nitrobenzoates of structure 1 with, for example, an aromatic amine (e.g. benzylamine or phenethylamine) in a solvent such as tetrahydrofuran (THF) or dimethylformamide (DMF) in the presence of a base, such as, for example, NaH or potassium carbonate or sodium carbonate, triethylamine or diisopropylethylamine.

In another embodiment, the 4-position of the 3-fluoro-4-nitrobenzoate described herein is reduced as outlined in Scheme 2.

Scheme 2

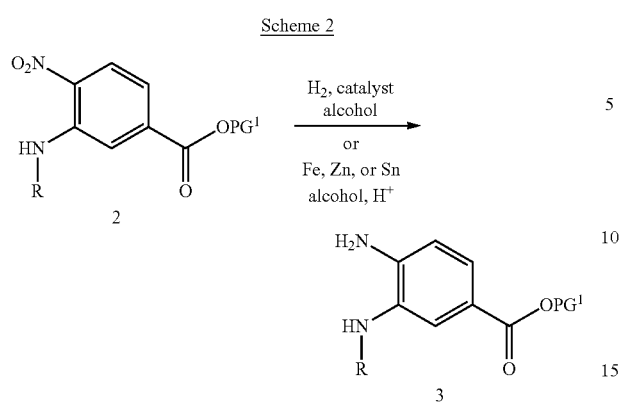

3-Amino-4-nitrobenzoates of general structure 2 is reduced to the 3,4-diaminobenzoate of general structure 3 by catalytic hydrogenation using hydrogen gas, a catalyst (e.g. Pd—C, Pd(OH)$_2$, Raney Ni, or PtO$_2$) in an alcoholic solvent such as methanol, ethanol or isopropanol. In another embodiment, the reduction is carried out by treatment of structure 2 with a metal (e.g. Zn, Fe, or Sn) in an alcoholic solvent such as methanol, ethanol or isopropanol and an appropriate acid source (e.g. HCl, acetic acid or propionic acid).

In another embodiment, the benzimidazoles are synthesized as outlined in Scheme 3.

Scheme 3

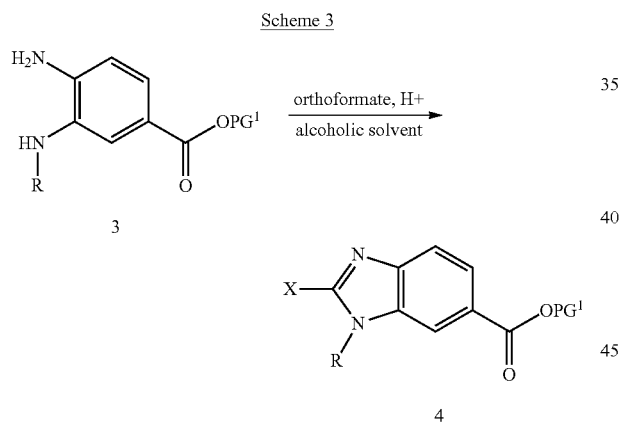

Benzimidazoles of structure 4 are synthesized by treating 3,4-diaminobenzoates 3 with an orthoformate (e.g. triethylorthoformate or trimethylorthoacetate) and an acid (e.g. HCl) in an alcoholic solvent.

In another embodiment, benzimidazoles of structure 4 are synthesized as outlined in

Scheme 4

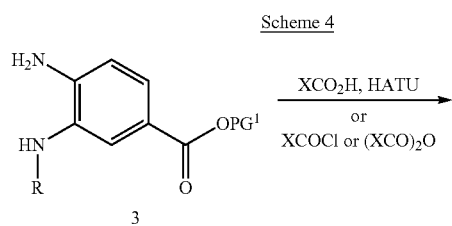

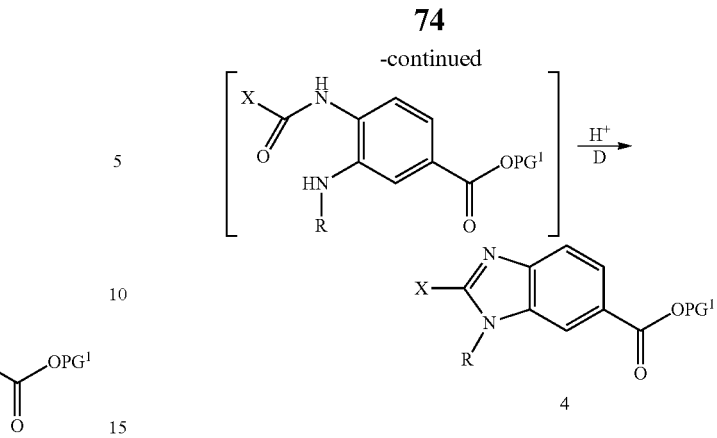

Benzimidazoles of structure 4 are synthesized by first forming an amide bond using a carboxylic acid and a coupling agent such as, but not limited to, 2-(7-Aza-1H-benzotriazole-1-yl)-1,1,3,3-tetramethyluronium hexafluorophosphate (HATU), dicyclohexyl carbodiimide (DCC), and the like, in the presence of a base such as, but not limited to, diisopropylethylamine, triethylamine in a solvent such as, but not limited to, DMF and THF. The amide bond is formed with an acid chloride or anhydride (e.g. acetyl chloride or acetic anhydride) in a solvent such as THF and in the presence of a base such as triethylamine or diisopropylethylamine. The resulting intermediate amide is then be treated with an appropriate acid (e.g. HCl) with heating in a solvent such as ethanol to provide the benzimidazole 4.

Conversion of the benzimidazoles of general structure 4 (where R=—X$^2$—R$^2$) to the corresponding N-hydroxy-3H-benzo[d]imidazole-5-carboxamide is shown in Scheme 5.

Scheme 5

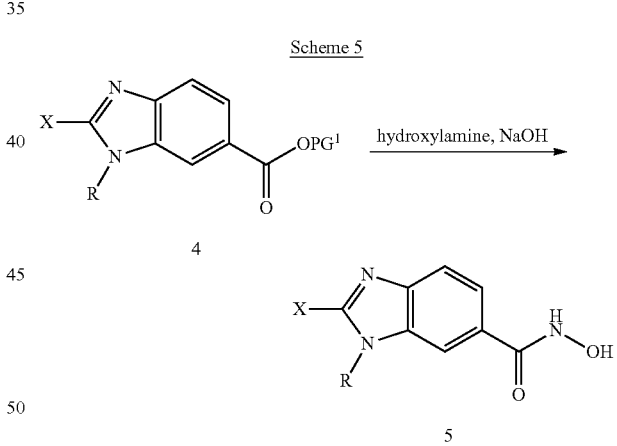

Benzimidazoles of structure 4, where PG$^1$ is an alkyl group such as methyl or ethyl, are treated with sodium hydroxide and an aqueous solution of hydroxylamine to provide the corresponding N-hydroxy-3H-benzo[d]imidazole-5-carboxamide. In embodiments where PG$^1$ is H in structure 4, the carboxylic acid is reacted with hydroxylamine hydrochloride salt using a coupling agent such as, but not limited to, 2-(7-Aza-1H-benzotriazole-1-yl)-1,1,3,3-tetramethyluronium hexafluorophosphate (HATU), dicyclohexyl carbodiimide (DCC), and the like, in the presence of a base such as, but not limited to, N,N-diisopropylethylamine, triethylamine, and the like, in a solvent such as, but not limited to, DMF, THY, and the like. In another embodiment, where PG$^1$ is H in structure 4, the carboxylic acid is reacted with thionyl chloride or oxalyl chloride to provide the acid chloride, which is treated with hydroxylamine to furnish the indole hydroxamic acid compounds.

4-Azaindole Compounds:

1H-Pyrrolo[3,2-b]pyridine compounds described herein are prepared from commercially available materials.

In one embodiment, compounds of structure 6 are used as starting materials for the synthesis of compounds described herein.

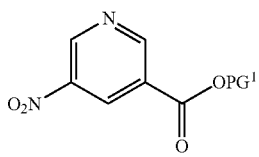

6

PG¹ represents carboxylic acid protecting groups. In one embodiment, PG¹ represents a substituted or =substituted alkyl group, such as, but not limited to, methyl, ethyl, propyl, benzyl, and p-methoxybenzyl.

In another embodiment, the 6-position of the 5-nitropyridine-3-carboxylate described herein is functionalized as outlined in Scheme 6.

Scheme 6

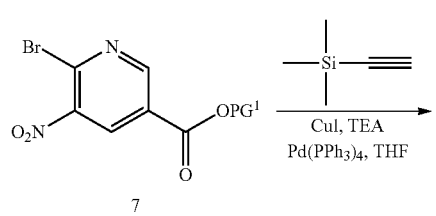

6-Bromo-5-nitropyridine-3-carboxylate of general structure 7 are obtained from the bromination of 5-nitropyridine-3-carboxylates of structure 6 as described in Berrie, *J. Chem. Soc.*, 1951, p. 2590.

In another embodiment, the 6-bromo-5-nitropyridine-3-carboxylate 7, is functionalized as outlined in Scheme 7.

Scheme 7

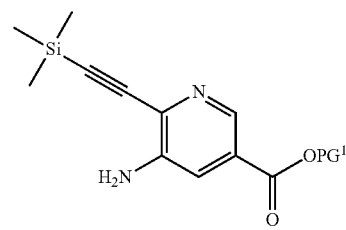

-continued

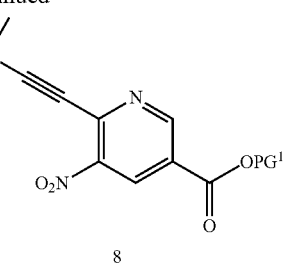

8

6-Bromo-5-nitropyridine-3-carboxylates of general structure 7 is functionalized on the 6-position to form compounds of general structure 8 by the Sonogashira reaction using (trimethylsilyl)acetylene, copper(I) iodide, a suitable base such as triethylamine or diisopropylethylamine and a catalyst (e.g. Pd(PPh₃)₄, Pd(OAc)₂, or PdCl₂(PPh₃)₂) in a solvent such as THF, CH₂Cl₂ or DMF.

In another embodiment, the 5-position of the compounds of general structure 8 described herein are reduced as outlined in Scheme 8.

Scheme 8

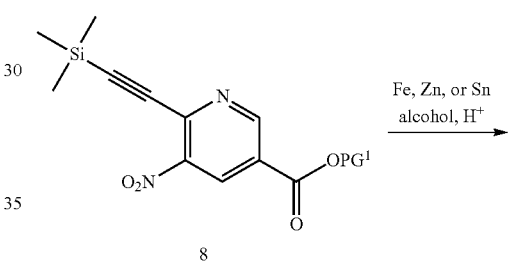

6-Ethynyl-5-nitropyridine-3-carboxylates of general structure 8 is reduced to the 5-amino-6-ethynylpyridine-3-carboxylates of general structure 9 by treatment of structure 8 with a metal (e.g. Zn, Fe, or Sn) in an alcoholic solvent such as methanol, ethanol or isopropanol and an appropriate acid source (e.g. HCl, acetic acid or propionic acid).

In another embodiment, the 5-amino-6-ethynylpyridine-3-carboxylates of general structure 9 is cyclized as outlined in Scheme 9.

Scheme 9

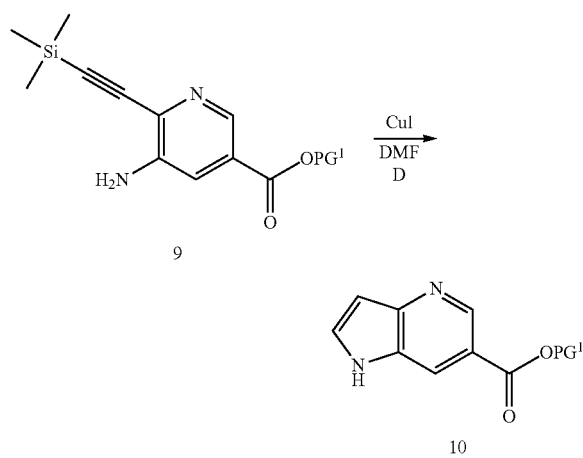

5-Amino-6-ethynylpyridine-3-carboxylates of general structure 9 is cyclized to the 1H-pyrrolo[3,2-b]pyridine-6-carboxylates of general structure 10 by treatment with a catalyst such as CuI or Cu(OAc)$_2$ and heating in an appropriate solvent such as DMF, THF or 1,2-dichloroethane.

In another embodiment, the 1H-pyrrolo[3,2-b]pyridine-6-carboxylates of general structure 10 is N-alkylated as outlined in Scheme 10.

Scheme 10

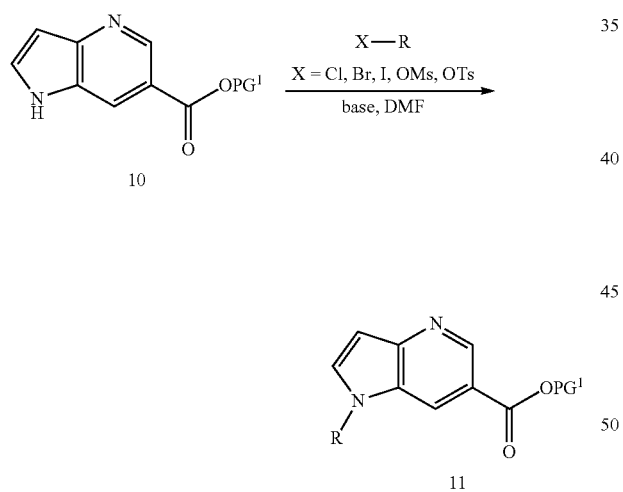

1H-pyrrolo[3,2-b]pyridine-6-carboxylates of structure 11 (R or —X$^2$—R$^2$) are obtained from the N-alkylation of 1H-pyrrole-2-carbaldehyde of structure 10 with, for example, an alkyl halide (or benzyl halide, or tosylate (OTs) or mesylate (OMs)) in a solvent such as tetrahydrofuran (THF) or dimethylformamide (DMF) in the presence of a base, such as, for example, NaH or potassium carbonate, sodium carbonate, triethylamine, or diisopropylethylamine.

Conversion of the 1H-pyrrolo[3,2-b]pyridine-6-carboxylates of general structure 11 to the corresponding N-hydroxy-1H-pyrrolo[3,2-b]pyridine-6-carboxamide of general structure 12 is shown in Scheme 11.

Scheme 11

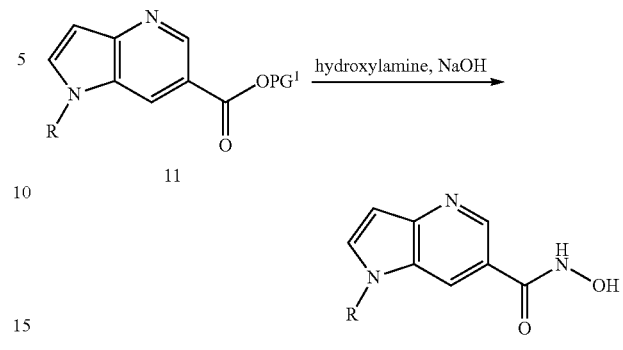

1H-Pyrrolo[3,2-b]pyridine-6-carboxylates of structure 11, where PG$^1$ is an alkyl group such as methyl or ethyl, are treated with sodium hydroxide and an aqueous solution of hydroxylamine to provide the corresponding N-hydroxy-1H-pyrrolo[3,2-b]pyridine-6-carboxamide. In embodiments where PG$^1$ is H in structure 11, the carboxylic acid is reacted with hydroxylamine hydrochloride salt using a coupling agent such as, but not limited to, 2-(7-Aza-1H-benzotriazole-1-yl)-1,1,3,3-tetramethyluronium hexafluorophosphate (HATU), dicyclohexyl carbodiimide (DCC), and the like, in the presence of a base such as, but not limited to, N,N-diisopropylethylamine, triethylamine, and the like, in a solvent such as, but not limited to, DMF, THF, and the like. In another embodiment, where PG$^1$ is H in structure 11, the carboxylic acid is reacted with thionyl chloride or oxalyl chloride to provide the acid chloride, which is treated with hydroxylamine to furnish the indole hydroxamic acid compounds.

Pyrrole Compounds:

Pyrrole compounds described herein are prepared from commercially available materials.

In one embodiment, compounds of structure 13 are used as starting materials for the synthesis of compounds described herein.

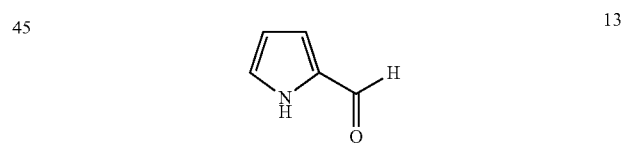

In another embodiment, the 1-position of the 1H-pyrrole-2-carbaldehyde described herein is functionalized as outlined in Scheme 12.

Scheme 12

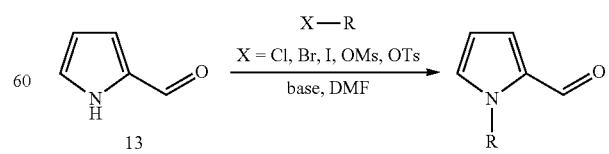

1H-pyrrole-2-carbaldehyde of structure 14 (R or —X$^2$—R$^2$) are obtained from the N-alkylation of 1H-pyrrole-2-carbaldehyde of structure 13 with, for example, an alkyl halide (or benzyl halide, or tosylate (OTs) or mesylate (OMs)) in a solvent such as tetrahydrofuran (THF) or dimethylformamide (DMF) in the presence of a base, such as, for example, NaH or potassium carbonate, sodium carbonate, triethylamine, or diisopropylethylamine.

In another embodiment, the 2-carbaldehyde of the 1H-pyrrole-2-carbaldehyde described herein is functionalized as outlined in Scheme 13.

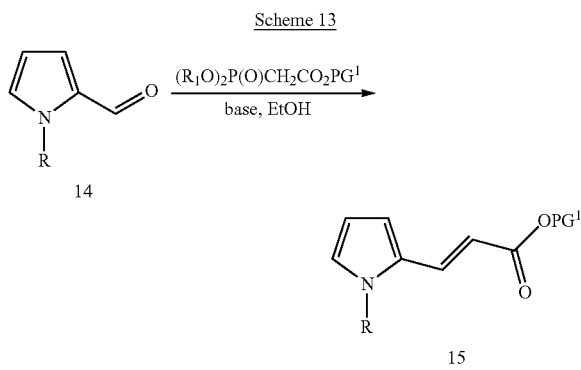

1H-pyrrole-2-carbaldehyde of general structure 14 is functionalized to the (E)-3-(1H-pyrrol-2-yl)acrylate of general structure 15 by the Witting reaction using a trialkyl phosphonoacetate (e.g. triethyl phosphonoacetate, $R_1$=ethyl), and a suitable base such as potassium carbonate, sodium carbonate or sodium hydride in an appropriate solvent such as ethanol, methanol, THF or DMF. $PG^1$ represents a substituted or unsubstituted alkyl group, such as, but not limited to, methyl, ethyl, propyl, benzyl, and p-methoxybenzyl.

Conversion of the pyrroles of general structure 15 to the corresponding (E)-3-(1H-pyrrol-2-yl)-N-hydroxyacrylamide of general structure 16 is shown in Scheme 14.

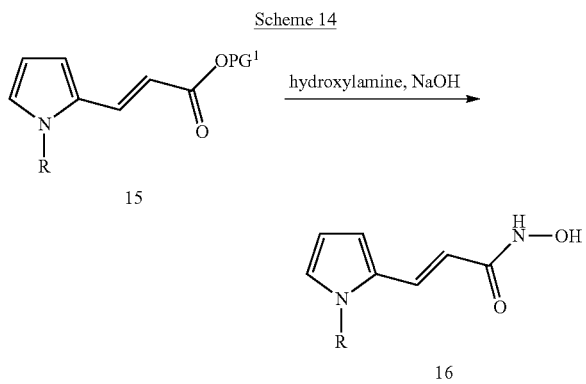

Pyrroles of structure 15, where $PG^1$ is an alkyl group such as methyl or ethyl, are treated with sodium hydroxide and an aqueous solution of hydroxylamine to provide the corresponding N-hydroxy-3H-benzo[d]imidazole-5-carboxamide. In embodiments where $PG^1$ is H in structure 15, the carboxylic acid is reacted with hydroxylamine hydrochloride salt using a coupling agent such as, but not limited to, 2-(7-Aza-1H-benzotriazole-1-yl)-1,1,3,3-tetramethyluronium hexafluorophosphate (HATU), dicyclohexyl carbodiimide (DCC), and the like, in the presence of a base such as, but not limited to, N,N-diisopropylethylamine, triethylamine, and the like, in a solvent such as, but not limited to, DMF, THF, and the like. In another embodiment, where $PG^1$ is H in structure 15, the carboxylic acid is reacted with thionyl chloride or oxalyl chloride to provide the acid chloride, which is treated with hydroxylamine to furnish the indole hydroxamic acid compounds.

Throughout the specification, groups and substituents thereof are chosen to provide stable moieties and compounds.

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry terms are found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology are employed. In addition, nucleic acid and amino acid sequences for HDAC8 are disclosed in, e.g., U.S. Pat. No. 6,875,598. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are used for chemical syntheses, chemical analyses, pharmaceutical preparation, formulation, and delivery, and treatment of patients. Standard techniques are used for recombinant DNA, oligonucleotide synthesis, and tissue culture and transformation (e.g., electroporation, lipofection). Reactions and purification techniques are performed e.g., using kits of manufacturer's specifications or as described herein. The foregoing techniques and procedures are generally performed by conventional methods and as described in various general and more specific references that are cited and discussed throughout the present specification.

It is to be understood that the methods and compositions described herein are not limited to the particular methodology, protocols, cell lines, constructs, and reagents described herein and as such vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ . . . $C_1$-$C_x$, $C_1$-$C_x$ refers to the number of carbon atoms that make up the moiety to which it designates (excluding optional substitutents).

An "alkyl" group refers to an aliphatic hydrocarbon group. In some embodiments, the alkyl moiety is a "saturated alkyl" group, which means that it does not contain any alkene or alkyne moieties. In other embodiments, the alkyl moiety is an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, is branched, straight chain, or cyclic.

The "alkyl" moiety has 1 to 10 carbon atoms (whenever it appears herein, a numerical range such as "1 to 10" refers to each integer in the given range; e.g., "1 to 10 carbon atoms" means that the alkyl group consists of 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein are designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, t-butyl, pentyl, iso-pentyl, neo-pentyl, and hexyl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. In some embodiments alkyl groups are substituted or unsubstituted. Depending on the structure, an alkyl group is either a monoradical or a diradical (i.e., an alkylene group).

An "alkoxy" group refers to a (alkyl)O— group, where alkyl is as defined herein. Examples of alkoxy groups include, but are not limited to, methoxy, ethoxy, propoxy, isopropoxy, buytloxy, cyclopropyloxy, cyclopentyloxy, cyclohexyloxy, and the like.

"Hydroxyalkyl" refers to an alkyl group substituted with hydroxy group(s).

"Hydroxyalkoxy" refers to an alkoxy substituted with hydroxy group(s).

"Hydroxyalkylaminoalkoxy" refers to an alkoxy substituted with an amino group with the amino group substituted with a hydroxyalkyl group as defined herein.

"Alkoxyalkyl" refers to alkyl group substituted with alkoxy group(s).

"Alkoxyalkyloxy" refers to an alkoxy group as defined herein substituted with alkoxy group as defined herein.

"Alkoxycarbonyl" refers to a —C(=O)O-(alkyl) group, where alkyl as defined herein. Non-limiting examples of alkoxycarbonyl groups include, e.g., methoxycarbonyl, ethoxycarbonyl, and the like.

"Alkoxycarbonylamino" refers to a —NR(C=O)—O-(alkyl), where alkyl is as defined herein and R is H, alkyl, heteroalkyl, haloalkyl, and the like.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which are the same or different. Non-limiting examples of an alkenyl group include —CH=CH$_2$, —C(CH$_3$)=CH$_2$, —CH=CHCH$_3$ and —C(CH$_3$)=CHCH$_3$. The alkenyl moiety is branched, straight chain, or cyclic (in which case, it would also be known as a "cycloalkenyl" group). Alkenyl groups have 2 to 6 carbons. In some embodiments alkenyl groups are substituted or unsubstituted. Depending on the structure, an alkenyl group is either a monoradical or a diradical (i.e., an alkenylene group).

"Alkenylcarbonyl" refers to a —C(O)-(alkenyl) group, where alkenyl is as defined herein.

"Alkenylcarbonyloxy" refers to a —OC(O)-(alkenyl) group, where alkenyl is as defined herein.

"Alkenyloxy" refers to a —O-(alkenyl) group, where alkenyl is as defined herein.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CH$_3$, —C≡CCH$_2$CH$_3$ and —C≡CCH$_2$CH$_2$CH$_3$. The "R" portion of the alkynyl moiety is branched, straight chain, or cyclic. In some embodiments an alkynyl group has 2 to 6 carbons. In other embodiments, alkynyl groups are substituted or unsubstituted. Depending on the structure, an alkynyl group is either a monoradical or a diradical (i.e., an alkynylene group).

"Amino" or "amine" refers to a —NH$_2$ group, an N-oxide derivative, an aliphatic amine or an aromatic amine. Aliphatic amines include: primary amines wherein one of hydrogen atoms is replaced by an organic substituent; secondary amines wherein two of hydrogen atoms are replaced by two organic substituents; and tertiary amines wherein all three substituents on the N atom are organic substituents.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, optionally form a cyclic ring system. The term "alkylamine" also refers to an amino group substituted with an alkyl group. "Dialkylamino" refers to a —N(alkyl)$_2$ group, where alkyl is as defined herein.

"Aminoalkyl" refers to an alkyl group as is defined herein that is substituted with an amino group.

"Aminoalkoxy" refers to an alkoxy group substituted with an amino group.

"Aminocarbonyl" refers to a —CONH$_2$ group.

"Aminosulfonyl" means an —S(O)$_2$NH$_2$ radical.

The term "alkylaminoalkyl" refers to an alkyl group, as is defined herein, substituted with an alkylamine as is defined herein. "Dialkylaminoalkyl" refers to an alkyl group that is substituted with a dialkylamino group.

"Alkylaminoalkoxy" refers to a alkoxy substituted with an alkylamine.

"Alkylaminocarbonyl" means a —C(O)R radical where R is alkylamino as defined herein.

"Alkylaminocarbonylamino" refers to —NHC(=O)-(alkylamino).

"Alkylaminocarbonyloxy" refers to —OC(=O)-(alkylamino).

"Alkylaminosulfonyl" refers to —S(=O)$_2$NHR radical where R is alkyl, as defined herein.

"Alkylcarbonyl" means a —C(=O)R radical where R is alkyl as defined herein.

"Alkylcarbonylamino" means a —NR'C(=O)-(alkyl), where R' is hydrogen, alkyl, haloalkyl, heteroalkyl.

"Alkylcarbonyloxy" means a —OC(=O)R radical where R is alkyl as defined herein.

"Dialkylaminoalkyloxy" refers to a alkoxy substituted with a dialkylamino.

"Dialkylaminocarbonyl" refers to —C(=O)R, where R is dialkylamino.

"Dialkylaminocarbonylamino" refers to —NR'—C(=O)-(diallylamino), where R' is hydrogen, alkyl, heteroalkyl, haloalkyl, and dialkylaminocarbonyl as defined herein.

"Dialkylaminocarbonyloxy" means an —O(C=O)-(dialkylamino), dialkylaminocarbonyl as defined herein.

"Dialkylaminosulfonyl" refers to —S(O)$_2$NR$_2$, where R is alkyl as defined herein.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). In some embodiments, rings are optionally substituted. In other embodiments rings are monocyclic or polycyclic.

The term "membered ring" refers to any cyclic structure. The term "membered" is meant to denote the number of skeletal atoms that constitute the ring. Thus, for example, cyclohexyl, phenyl, pyridine, piperidine, morpholine, piperazine, pyridazine, pyrimidine, pyrazine, pyran and thiopyran are 6-membered rings; and cyclopentyl, pyrrolidine, imidazole, oxazole, thiazole, pyrrole, furan, and thiophene are 5-membered rings.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e. a heteroatom). Heterocycle includes heteroaryl and heterocycloalkyl. In some embodiments carbocycles and heterocycles are optionally substituted.

The term "aromatic" refers to a planar ring having a delocalized π-electron system containing 4n+2 π electrons, where n is an integer. In some embodiments aromatic rings are formed from five, six, seven, eight, nine, or more than nine atoms. In other embodiments aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. In some embodiments, aryl rings are formed by five, six, seven, eight, nine, ten or more than ten carbon atoms. In some embodiments, aryl groups are optionally substituted. In some embodiments, an aryl is a $C_6$-$C_{10}$ aryl. Examples of aryl groups include, but are not limited to phenyl, and naphthalenyl. In one aspect, an aryl is a phenyl. Depending on the structure, an aryl group is either a monoradical or a diradical (i.e., an arylene group).

"Aralkyl" or "arylalkyl" refers to an alkyl group as is defined herein substituted with an aryl group as is defined herein.

"Phenylalkyl" refers to an alkyl substituted with a phenyl.

The term "cycloalkyl" refers to a monocyclic or polycyclic non-aromatic radical, wherein each of the atoms forming the ring (i.e. skeletal atoms) is a carbon atom. Cycloalkyls are saturated, or partially unsaturated. In some embodiments, cycloalkyls are fused with an aromatic ring. Cycloalkyl groups include groups having from 3 to 10 ring atoms. Illustrative examples of cycloalkyl groups include, but are not limited to, the following:

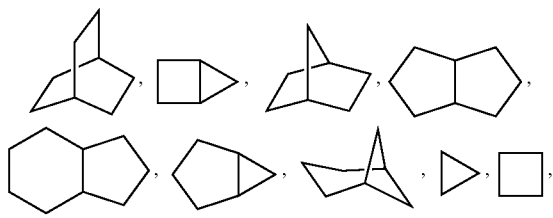

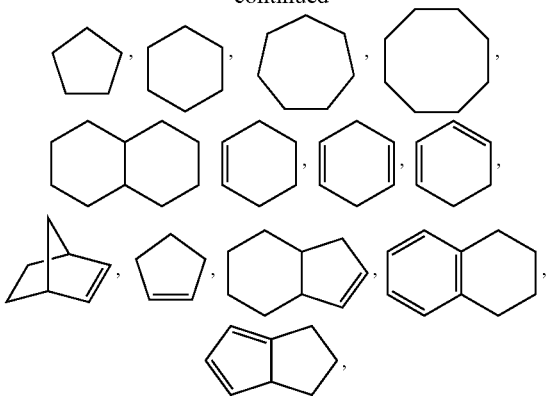

and the like. Cycloalkyls include, but are not limited to, cyclopropyl, cyclobutyl, cyclopentyl, cyclohexyl, cycloheptyl, and cyclooctyl. In one aspect, a cycloalkyl is a $C_3$-$C_6$ cycloalkyl.

"Cycloalkylalkyl" refers to an alkyl, as is defined herein, substituted with a cycloalkyl, as is defined herein.

"Cycloalkylcarbonyl" refers to —C(=O)-cycloalkyl.

The term "heterocycle" refers to heteroaromatic and heteroalicyclic groups containing one to four ring heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are C-attached or N-attached where such is possible. For example, a group derived from pyrrole is named pyrrol-1-yl (N-attached) or pyrrol-3-yl (C-attached). Further, a group derived from imidazole is named imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups are fused or non-fused. Illustrative examples of heteroaryl groups include the following moieties:

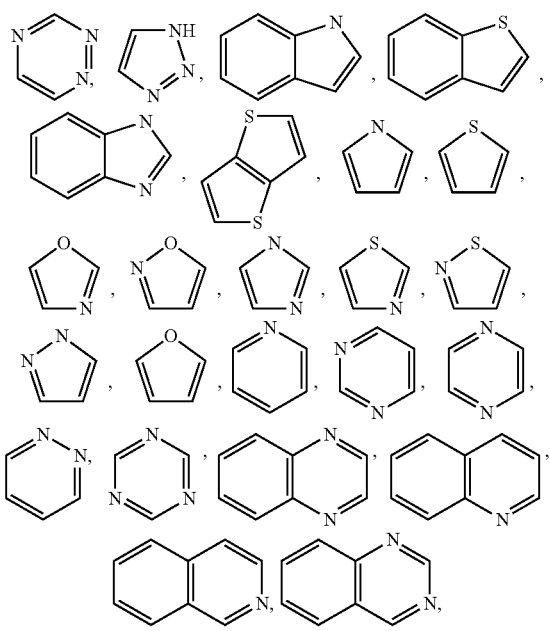

and the like. In one aspect, a heteroaryl includes 0-3 N atoms. In one aspect, a heteroaryl includes 1-3 N atoms. In one aspect, a heteroaryl includes 0-3 N atoms, 0-1 O atoms, and 0-1 S atoms. In one aspect, a heteroaryl is a monocyclic or bicyclic heteroaryl. In one aspect, a heteroaryl is a monocyclic heteroaryl. In one aspect, the heteroaryl is a $C_1$-$C_{10}$heteroaryl. In another aspect, the heteroaryl is a $C_2$-$C_9$heteroaryl. In one aspect, monocyclic heteroaryl is a $C_1$-$C_5$heteroaryl. In one aspect, bicyclic heteroaryl is a $C_5$-$C_{10}$heteroaryl. Depending on the structure, a heteroaryl group can be a monoradical or a diradical (i.e., a heteroarylene group).

In some embodiments, substituted or unsubstituted heteroaryl groups are selected from among pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, 4-azaindolyl, 5-azaindolyl, 6-azaindolyl, 7-azaindolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothienyl, benzothiazolyl, benzoxazolyl, quinazolinyl, quinoxalinyl, imidazo[1,2-a]pyridinyl, thiophenopyridinyl, and furopyridinyl. In other embodiments, substituted or unsubstituted heteroaryl groups are selected from among pyridinyl, pyrimidinyl, pyrazinyl, quinolinyl, isoquinolinyl, indolyl, benzimidazolyl, benzofuranyl, cinnolinyl, indozolyl, indolizinyl, phthalazinyl, pyridazinyl, isoindolyl, pteridinyl, purinyl, oxadiazolyl, thiadiazolyl, furazanyl, benzofurazanyl, benzothienyl, benzothiazolyl, benzoxazolyl, quinazolinyl, quinoxalinyl, naphthyridinyl, imidazo[1,2-a]pyridinyl, thiophenopyridinyl, and furopyridinyl. In yet other embodiments, substituted or unsubstituted heteroaryl groups are selected from among pyridinyl, pyrimidinyl, pyrazinyl, quinolinyl, isoquinolinyl, pyridazinyl, quinazolinyl, quinoxalinyl. In still other embodiments, substituted or unsubstituted heteroaryl groups are selected from among pyridinyl, and quinolinyl.

"Heteroaralkyl" or "heteroarylalkyl" refers to an alkyl, as is defined herein, substituted with a heteroaryl as is defined herein.

A "heteroalicyclic" group or "heterocycloalkyl" group refers to a cycloalkyl group, wherein at least one skeletal ring atom is a heteroatom selected from nitrogen, oxygen and sulfur. The radicals are fused with an aryl or heteroaryl. Illustrative examples of heterocycloalkyl groups, also referred to as non-aromatic heterocycles, include:

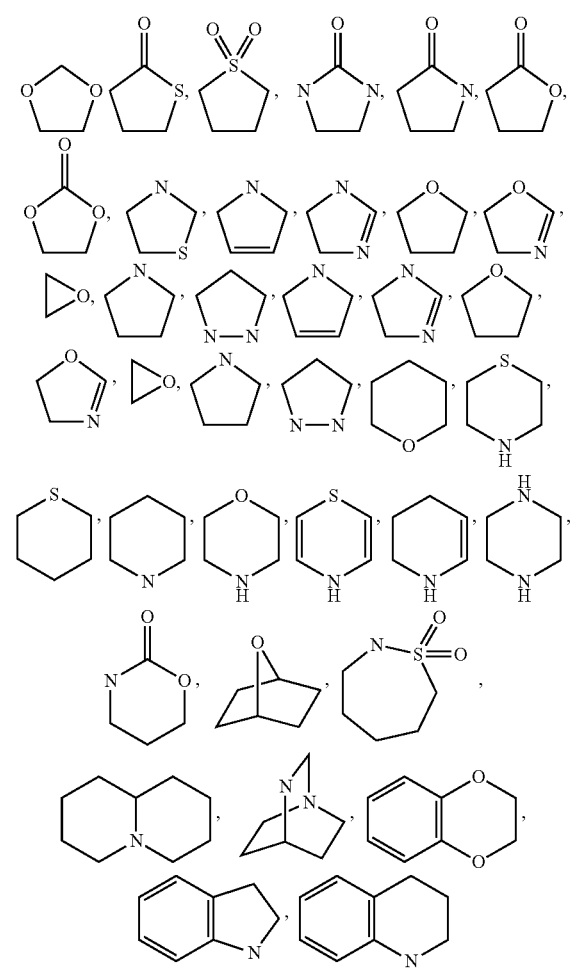

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In one aspect, a heterocycloalkyl is a $C_2$-$C_{10}$heterocycloalkyl. In another aspect, a heterocycloalkyl is a $C_4$-$C_{10}$heterocycloalkyl.

In some embodiments, substituted or unsubstituted heterocycloalkyl groups are selected from among quinolizinyl, dioxinyl, piperidinyl, morpholinyl, thiomorpholinyl, thiazinyl, tetrahydropyridinyl, piperazinyl, oxazinanonyl, dihydropyrrolyl, dihydroimidazolyl, tetrahydrofuranyl, tetrahydropyranyl, dihydrooxazolyl, oxiranyl, pyrrolidinyl, pyrazolidinyl, dihydrothienyl, imidazolidinonyl, pyrrolidinonyl, dihydrofuranonyl, dioxolanonyl, thiazolidinyl, piperidinonyl, indolinyl, tetrahydroquinolinyl, tetrahydroisoquinolinyl, and tetrahydrothienyl. In other embodiments, substituted or unsubstituted heterocycloalkyl groups are selected from among piperidinyl, morpholinyl, piperazinyl, dihydropyrrolyl, dihydroimidazolyl, tetrahydrofuranyl, dihydrooxazolyl, pyrrolidinyl, pyrazolidinyl, dihydrothienyl, imidazolidinonyl, pyrrolidinonyl, piperidinonyl, indolinyl, tetrahydroquinolinyl, tetrahydroisoquinolinyl, and tetrahydrothienyl. In yet other embodiments, substituted or unsubstituted heterocycloalkyl groups are selected from among piperidinyl, morpholinyl, piperazinyl, tetrahydrofuranyl, pyrrolidinyl, pyrrolidinonyl, piperidinonyl, indolinyl, tetrahydroquinolinyl, and tetrahydrothienyl. In some embodiments, substituted or unsubstituted heterocycloalkyl groups are selected from among piperidinyl, morpholinyl, thiomorpholinyl, piperazinyl, and pyrrolidinyl.

"Heterocycloalkylalkyl" refers to an alkyl, as defined herein, substituted with a heterocycloalkyl, as defined herein.

"Heterocycloalkylalkoxy" refers to an alkoxy, as defined herein, substituted with a heterocycloalkyl, as defined herein wherein heterocycloalkyl includes alkyl substituents.

"1,2-substituted-1H-benzimidazole-6-carboxylic acid hydroxyamide" or "1,2-substituted-1H-benzimidazole-6-hydroxamic acid" refers to:

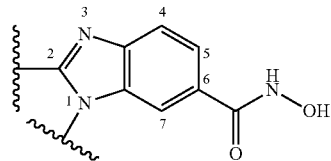

"1,3-substituted-4-azaindole-6-carboxylic acid hydroxyamide" or "1,3-substituted-4-azaindole-6-hydroxamic acid" refers to:

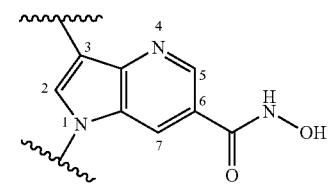 [SMILES: *c1cn(*)c2cc(C(=O)NO)cnc12]

"1,3-substituted-5-azaindole-6-carboxylic acid hydroxyamide" refers to:

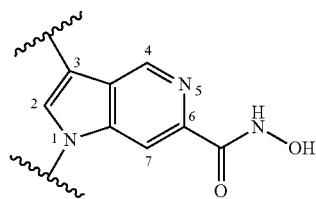 [SMILES: *c1cn(*)c2cc(C(=O)NO)ncc12]

"1,3-substituted-7-azaindole-6-carboxylic acid hydroxyamide" refers to:

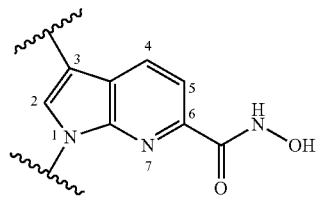 [SMILES: *c1cn(*)c2nc(C(=O)NO)ccc12]

As used herein, "substituted-1H-pyrrol-2-yl-N-hydroxyacrylamide" refers to:

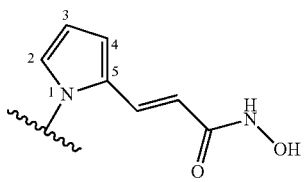 [SMILES: *n1cccc1/C=C/C(=O)NO]

As used herein, "1,3-substituted-1H-indole-6-carboxylic acid hydroxyamide" or "1,3-substituted-1H-indole-6-hydroxamic acid" refers to:

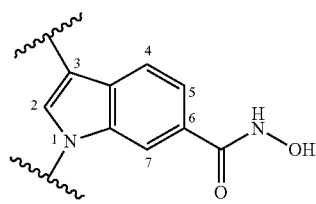 [SMILES: *c1cn(*)c2cc(C(=O)NO)ccc12]

The term "hydroxamate", "hydroxamic acid", "N-hydroxycarboxamide" or "carboxylic acid hydroxyamide" refers to:

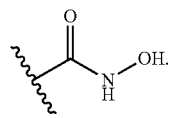

The term "halo" or, alternatively, "halogen" means fluoro, chloro, bromo and iodo.

The terms "haloalkyl," "haloalkenyl," "haloalkynyl" and "haloalkoxy" include alkyl, alkenyl, alkynyl and alkoxy structures that are substituted with one or more halogens. In some embodiments, the halogens are the same or are different. The terms "fluoroalkyl" and "fluoroalkoxy" include haloalkyl and haloalkoxy groups, respectively, in which the halo is fluorine. Non-limiting examples of haloalkyls include —CH$_2$Cl, —CF$_3$, —CHF$_2$, —CH$_2$CF$_3$, —CF$_2$CF$_3$, —CF(CH$_3$)$_3$, and the like. Non-limiting examples of fluoroalkyls include —CF$_3$, —CHF$_2$, —CH$_2$F, —CH$_2$CF$_3$, —CF$_2$CF$_3$, —CF$_2$CF$_2$CF$_3$, —CF(CH$_3$)$_3$, and the like. Non-limiting examples of haloalkoxy groups include —OCF$_3$, —OCHF$_2$, —OCH$_2$F, —OCH$_2$CF$_3$, —OCF$_2$CF$_3$, —OCF$_2$CF$_2$CF$_3$, —OCF(CH$_3$)$_3$, and the like.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus, silicon, or combinations thereof. The heteroatom(s) are placed at any position of the heteroalkyl group. In some embodiments, up to two heteroatoms are consecutive, such as, by way of example, —CH$_2$—NH—OCH$_3$ and —CH$_2$—O—Si(CH$_3$)$_3$. Excluding the number of heteroatoms, a "heteroalkyl" includes from 1 to 6 carbon atoms, a "heteroalkenyl" includes from 2 to 6 carbons atoms, and a "heteroalkynyl" includes from 2 to 6 carbon atoms.

The term "moiety" refers to a specific segment or functional group of a molecule. Chemical moieties are often recognized chemical entities embedded in or appended to a molecule.

"Cyanoalkylaminocarbonyl" refers to a —C(=O)NR'(cyanoalkyl) group, where R' is hydrogen, alkyl, heteroalkyl, haloalkyl, as is defined herein, cyanoalkyl is as defined herein.

An "isothiocyanato" group refers to a —NCS group.

"Alkylthio" means an —SR radical where R is alkyl as defined herein.

"Acylamino" refers to a RC(=O)N(R')— group, where R' is hydrogen, hydroxy, alkyl, or alkoxy. In some embodiments, R' is H or R.

"Alkylsulfinyl" means an —S(O)R radical where R is alkyl as defined herein.

"Alkylsulfonyl" means a —SO$_2$R radical where R is alkyl as defined herein.

"Alkylsulfonylamino" means a —N(R')SO$_2$R group, where R' is hydrogen, alkyl, heteroalkyl, haloalkyl, as is defined herein, and R is alkyl as is defined herein.

"Phenylsulfonyl" refers to means a —S(=O)$_2$-phenyl moiety.

"Phenylsulfonylamino" refers to a —NR'SO$_2$— (phenyl) where R' is hydrogen, alkyl, heteroalkyl, haloalkyl, as is defined herein.

"Heteroarylaminocarbonyl" refers to a —C(=O)NR'(heteroaryl) group, where R' is hydrogen, alkyl, heteroalkyl, haloalkyl, as is defined herein, and heteroaryl is as defined herein.

"Arylaminocarbonyl" refers to a —C(=O)NR'(aryl) group, where R' is hydrogen, alkyl, heteroalkyl, haloalkyl, as is defined herein, and aryl is as defined herein.

"Arylcarbonylamino" refers to —NR'C(=O)-(aryl) group, where R' is hydrogen, alkyl, heteroalkyl, haloalkyl, as is defined herein, and aryl is as defined herein.

As used herein, the substituent "R" appearing by itself and without a number designation refers to a substituent selected from among from alkyl, haloalkyl, heteroalkyl, alkenyl, cycloalkyl, cycloalkylalkyl, aryl, arylalkyl, heteroaryl (bonded through a ring carbon), heteroarylalkyl, heterocycloalkyl, and heterocycloalkylalkyl.

The term "optionally substituted" or "substituted" means that the referenced group is substituted with one or more additional group(s) individually and independently selected from alkyl, cycloalkyl, aryl, heteroaryl, heterocycloalkyl, hydroxy, alkoxy, aryloxy, alkylthio, arylthio, alkylsulfoxide, arylsulfoxide, alkylsulfone, arylsulfone, cyano, halo, acyl, acyloxy, isocyanato, thiocyanato, isothiocyanato, nitro, haloalkyl, fluoroalkyl, and amino, including mono- and di-substituted amino groups (e.g. —NH$_2$, —NHR, —N(R)$_2$), and the protected derivatives thereof. By way of example, an optional substituent is L$^s$R$^s$, wherein each L$^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —(C$_1$-C$_6$alkyl)-, or —(C$_2$-C$_6$alkenyl)-; and each Its is independently selected from among H, (C$_1$-C$_6$alkyl), (C$_3$-C$_8$cycloalkyl), aryl, heteroaryl, heterocycloalkyl, and C$_1$-C$_6$heteroalkyl. In one aspect, substituted groups are substituted with one or more substituents selected from halogen, —OH, —OC$_1$-C$_4$alkyl, C$_1$-C$_4$alkyl, C$_1$-C$_4$heteroalkyl, C$_1$-C$_4$fluoroalkyl and —OC$_1$-C$_4$fluoroalkyl. In yet other aspect, substituted groups are substituted with one or more substituents selected from F, Cl, Br, —OH, —OCH$_3$, —CH$_3$, and —CF$_3$. In yet other embodiments, substituted groups are substituted with one or more substituents selected from F, Cl, and Br. In one aspect, substituted groups are substituted with one of the preceding groups. The protecting groups that form the protective derivatives of the above substituents are found in references such as Greene and Wuts, above.

The compounds presented herein possess one or more stereocenters and each center exists in the R or S configuration. The compounds presented herein include all diastereomeric, enantiomeric, and epimeric forms as well as the appropriate mixtures thereof. Stereoisomers are obtained, if desired, by separation of stereoisomers by chiral chromatographic columns.

The methods and formulations described herein include the use of N-oxides, crystalline forms (also known as polymorphs), or pharmaceutically acceptable salts of compounds having the structure of Formula (A), as well as active metabolites of these compounds having the same type of activity. In some situations, compounds exist as tautomers. All tautomers are included within the scope of the compounds presented herein. In addition, the compounds described herein exist in unsolvated as well as solvated forms with pharmaceutically acceptable solvents such as water, ethanol, and the like. The solvated forms of the compounds presented herein are also considered to be disclosed herein.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "selective HDAC8 inhibitor," as used herein, refers to a compound that has an $IC_{50}$ for inhibition of HDAC8 deacetylase activity that is at least about 5 fold to more than about 500 fold lower than the $IC_{50}$ for inhibition of deacetylase activity of another HDAC. In some embodiments, the selective HDAC8 inhibitor has an $IC_{50}$ for inhibition of HDAC8 deacetylase activity that is about 5, about 10, about 50, about 100, about 150, about 200, about 250, about 300, about 350, about 400, about 450 or more than about 500 fold lower than the $IC_{50}$ for inhibition of deacetylase activity of another HDAC. In one embodiment, the selective HDAC8 inhibitor has an $IC_{50}$ for inhibition of HDAC8 deacetylase activity that is at least about 10 fold lower than the $IC_{50}$ for inhibition of deacetylase activity of at least one of HDAC1, HDAC2, HDAC3, HDAC6, HDAC10, and HDAC11; in another embodiment at least two of HDAC1, HDAC2, HDAC3, HDAC6, HDAC10, and HDAC11; in another embodiment all of HDAC1, HDAC2, HDAC3, HDAC6, HDAC10, and HDAC11. In another embodiment, the selective HDAC8 inhibitor has an $IC_{50}$ for HDAC8 deacetylase activity that is at least about 20 fold lower than the $IC_{50}$ for inhibition of deacetylase activity of at least one of HDAC1, HDAC2, HDAC3, HDAC6, HDAC10, and HDAC11; in another embodiment at least two of HDAC1, HDAC2, HDAC3, HDAC6, HDAC10, and HDAC11; in another embodiment all of HDAC1, HDAC2, HDAC3, HDAC6, HDAC10, and HDAC11.

As used herein, the term "target protein" refers to a protein or a portion of a protein capable of being bound by a selective binding compound. In certain embodiments, a target protein is HDAC8.

As used herein, the term "selective binding compound" refers to a compound that selectively binds to any portion of one or more target proteins.

As used herein, the term "selectively binds" refers to the ability of a selective binding compound to bind to a target protein, such as, for example, HDAC8, with greater affinity than it binds to a non-target protein. In certain embodiments, specific binding refers to binding to a target with an affinity that is at least about 10, about 50, about 100, about 250, about 500, about 1000 or more times greater than the affinity for a non-target.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that is attributed to or associated with administration of the compound or composition.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a target. For example, a modulator causes an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target. In certain embodiments, a modulator is an activator, which increases the magnitude of at least one activity of a target. In certain embodiments the presence of a modulator results in an activity that does not occur in the absence of the modulator.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "inhibits", "inhibiting", or "inhibitor" of HDAC, as used herein, refer to inhibition of histone deacetylase activity.

The term "acceptable" with respect to a formulation, composition or ingredient, as used herein, means having no persistent detrimental effect on the general health of the subject being treated.

By "pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that the active ingredients, e.g. an idole compound described herein, and a co-agent, are both administered to a patient simultaneously in the form of a single entity or dosage. The term "non-fixed combination" means that the active ingredients, e.g. a compound described herein, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of the compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound include but are not limited to: intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result is reduction and/or alleviation of the signs, symptoms, or causes of a disease, or any other desired alteration of a biological system. For example, an "effective amount" for therapeutic uses is the amount of the composition comprising a HDAC8 inhibiting compound as disclosed herein required to provide a clinically significant decrease in disease symptoms. An appropriate "effective" amount in any individual case is determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "co-administration" or the like, as used herein, are meant to encompass administration of the selected therapeutic agents to a single patient, and are intended to include treatment regimens in which the agents are administered by the same or different route of administration or at the same or different time.

The term "carrier," as used herein, refers to relatively non-toxic chemical compounds or agents that facilitate the incorporation of a compound into cells or tissues.

The term "diluent" refers to chemical compounds that are used to dilute the compound of interest prior to delivery. Diluents are also used to stabilize compounds because they provide a more stable environment. Salts dissolved in buffered solutions (which also provide pH control or maintenance) are utilized, including, but not limited to a phosphate buffered saline solution.

The term "enzymatically cleavable linker," as used herein refers to unstable or degradable linkages which are degraded by one or more enzymes.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism is obtained from The Pharmacological Basis of Therapeutics, 9th Edition, McGraw-Hill (1996). Metabolites of the compounds disclosed herein are identified either by administration of compounds to a host and analysis of tissue samples from the host, or by incubation of compounds with hepatic cells in vitro and analysis of the resulting compounds.

"Bioavailability" refers to the percentage of the weight of compounds disclosed herein, that is delivered into the general circulation of the animal or human being studied. The total exposure (AUC(0-∞)) of a drug when administered intravenously is usually defined as 100% bioavailable (F %). "Oral bioavailability" refers to the extent to which the compounds disclosed herein, are absorbed into the general circulation when the pharmaceutical composition is taken orally as compared to intravenous injection.

"Blood plasma concentration" refers to the concentration of the compounds disclosed herein, in the plasma component of blood of a subject. It is understood that the plasma concentration of the compounds described herein vary significantly between subjects, due to variability with respect to metabolism and/or possible interactions with other therapeutic agents. In accordance with one embodiment disclosed herein, the blood plasma concentration of the compounds disclosed herein vary from subject to subject. Likewise, values such as maximum plasma concentration ($C_{max}$) or time to reach maximum plasma concentration ($T_{max}$), or total area under the plasma concentration time curve (AUC(0-∞)) varies from subject to subject. Due to this variability, the amount necessary to constitute "a therapeutically effective amount" of a compound varies from subject to subject.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

A "measurable serum concentration" or "measurable plasma concentration" describes the blood serum or blood plasma concentration, typically measured in mg, µg, or ng of therapeutic agent per ml, dl, or 1 of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

As used herein, the term "subject" is used to mean an animal, in some embodiments, a mammal, including a human or non-human. The terms patient and subject are used interchangeably.

Examples of Pharmaceutical Compositions and Methods of Administration

Suitable routes of administration include, but are not limited to, oral, intravenous, rectal, aerosol, parenteral, ophthalmic, pulmonary, transmucosal, transdermal, vaginal, otic, nasal, intramuscular injection, subcutaneous injection, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In certain embodiments, a compound as described herein is administered in a local rather than systemic manner. In other embodiments, the compound as described herein is provided in the form of a rapid release formulation, in the form of an extended release formulation, or in the form of an intermediate release formulation. In yet other embodiments, the compound described herein is administered topically.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A pharmaceutical composition refers to a mixture of a HDAC8 inhibitor compound described herein with other chemical components, such as carriers, stabilizers, diluents, dispersing agents, suspending agents, thickening agents, and/or excipients. In certain embodiments, the pharmaceutical composition facilitates administration of the compound to a mammal.

In one embodiment, HDAC8 inhibitor compounds described herein are formulated in an aqueous solution. In specific embodiments, the aqueous solution is selected from, by way of example only, a physiologically compatible buffer, such as Hank's solution, Ringer's solution, or physiological saline buffer. In other embodiments, HDAC8 inhibitor compounds described herein are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions.

In another embodiment, compounds described herein are formulated for oral administration. The compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or pills. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

Oral dosage forms also include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the HDAC8 inhibitor compounds described herein are administered topically. Topically administrable compositions include solutions, suspensions, lotions, gels, pastes, medicated sticks, balms, creams or ointments.

In other embodiments, the HDAC8 inhibitor compounds described herein are formulated for administration by inhalation. Various forms suitable for administration by inhalation include, but are not limited to, aerosols, mists or powders.

The active ingredient in the pharmaceutical compositions is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions comprising the compounds described herein are administered to a patient susceptible to or otherwise at risk of a particular disease, disorder or condition. In this use, the precise amounts also depend on the patient's state of health, weight, and the like.

In some embodiments pharmaceutical compositions are formulated in a conventional manner using one or more physiologically acceptable carriers including excipients and auxiliaries which facilitate processing of the active compounds into preparations which are used pharmaceutically. Proper formulation is dependent upon the route of administration chosen.

Examples of Methods of Dosing and Treatment Regimens

The compounds described herein are used in the preparation of medicaments for the inhibition of HDAC8, or for the treatment of diseases or conditions that would benefit, at least in part, from inhibition of HDAC8. In addition, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein are administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. One determines such therapeutically effective amounts by, e.g., a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. One determines such prophylactically effective amounts by e.g., a dose escalation clinical trial. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds are given continuously; alternatively, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. In some embodiments, the dose reduction during a drug holiday is from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. Some patients require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but will be determined according to the particular circumstances surrounding the case, including, e.g., the specific agent being administered, the route of administration, the condition being treated, and the subject or host being treated. In general, however, doses employed for adult human treatment will typically be in the range of about 0.02 to about 5000 mg per day, in other embodiments about 1 to about 1500 mg per day. In some embodiments the desired dose is presented in a single dose or as divided doses administered simultaneously (or over a short period of time) or at appropriate intervals, for example as two, three, four or more sub-doses per day.

The pharmaceutical composition described herein is in unit dosage forms suitable for single administration of precise dosages. In unit dosage form, the formulation is divided into unit doses containing appropriate quantities of one or more compound. The unit dosage is in the form of a package containing discrete quantities of the formulation. Non-limiting examples are packaged tablets or capsules, and powders in vials or ampoules. Aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi-dose containers, with an added preservative.

The daily dosages appropriate for the compounds described herein described herein are from about 0.01 to about 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 to about 50 mg active ingredient. The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are contemplated herein. The data obtained from cell culture assays and animal studies is used in formulating a range of dosage for use in human. In some embodiments, the dosage of such compounds lies within a range of circulating concentrations that include the ED50 with minimal toxicity. The dosage varies within this range depending upon the dosage form employed and the route of administration utilized.

Combination Treatments

The compounds and compositions described herein are also used in combination with other therapeutic agents that are selected for their therapeutic value for the condition to be treated. In general, the compositions described herein and, in embodiments where combinational therapy is employed, other agents are not administered in the same pharmaceutical composition, and are administered by different routes because of different physical and chemical characteristics. The initial administration is made according to established protocols and based upon the observed effects, the dosage, modes of administration and times of administration.

In certain instances, it is appropriate to administer at least one compound described herein in combination with another therapeutic agent. By way of example only, if one of the side effects experienced by a patient upon receiving one of the compounds herein, such as a hydroxamic acid compound described herein, is nausea, then it is appropriate to administer an anti-nausea agent in combination with the initial therapeutic agent. Or, by way of example only, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by a patient is increased by administering one of the compounds described herein with another therapeutic agent (which also includes a therapeutic regimen) that also has therapeutic benefit. In any case, regardless of the disease, disorder or condition being treated, the overall benefit experienced by the patient is additive of the two therapeutic agents or the patient experiences a synergistic benefit.

The particular choice of compounds used will depend upon the diagnosis of the attending physicians and their judgment of the condition of the patient and the appropriate treatment protocol. The compounds are administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is determined after evaluation of the disease being treated and the condition of the patient.

For combination therapies described herein, dosages of the co-administered compounds will vary depending on the type of co-drug employed, on the specific drug employed, on the disease or condition being treated and so forth. In addition, when co-administered with one or more biologically active agents, the compound provided herein is administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a HDAC8 selective compound described herein) are administered in any order or even simultaneously. If simultaneously, the multiple therapeutic agents are provided in a single, unified form, or in multiple forms (by way of example only, either as a single pill or as two separate pills). In some embodiments the therapeutic agents are given in multiple doses, or both are given as multiple doses. If not simultaneous, the timing between the multiple doses varies from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, is modified in accordance with a variety of factors. These factors include the disorder or condition from which the subject suffers, as well as the age, weight, sex, diet, and medical condition of the subject. Thus, the dosage regimen actually employed varies widely and therefore deviates from the dosage regimens set forth herein.

The pharmaceutical agents which make up the combination therapy disclosed herein are a combined dosage form or in separate dosage forms intended for substantially simultaneous administration. The pharmaceutical agents that make up the combination therapy are administered sequentially, with either therapeutic compound being administered by a regimen calling for two-step administration. The two-step administration regimen calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration also determines the optimal dose interval.

In addition, the compounds described herein are used in combination with procedures that provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies are administered before, during or after the occurrence of a disease or condition, and the timing of administering the composition containing a compound varies. Thus, for example, the compounds are used as a prophylactic and are administered continuously to subjects with a propensity to develop conditions or diseases in order to prevent the occurrence of the disease or condition. The compounds and compositions are administered to a subject during or as soon as possible after the onset of the symptoms. The administration of the compounds are initiated within the first 48 hours of the onset of the symptoms, in other embodiments, within the first 48 hours of the onset of the symptoms, in further embodiments, within the first 6 hours of the onset of the symptoms, and in yet further embodiments within 3 hours of the onset of the symptoms. The initial administration is via any route practical, such as, for example, an intravenous injection, a bolus injection, infusion over 5 minutes to about 5 hours, a pill, a capsule, transdermal patch, buccal delivery, and the like, or combination thereof. In some embodiments, a compound is administered as soon as is practicable after the onset of a disease or condition is detected or suspected, and for a length of time necessary for the treatment of the disease, such as, for example, from about 1 month to about 3 months. The length of treatment varies for each subject, and the length is determined using the known criteria. For example, the compound or a formulation containing the compound is administered for at least 2 weeks, in some embodiments, about 1 month to about 5 years, and in other embodiments from about 1 month to about 3 years.

Anti-Cancer Agents

Combinations of selective HDAC8 inhibitors described herein with other anti-cancer or chemotherapeutic agents are described herein. Examples of such anti-cancer or chemotherapeutic agents are found in *Cancer Principles and Practice of Oncology* by V. T. Devita and S. Hellman (editors), $6^{th}$ edition (Feb. 15, 2001), Lippincott Williams & Wilkins Publishers. Combinations of agents are determined based on the particular characteristics of the drugs and the cancer involved.

In one aspect, HDAC inhibitors disclosed herein are administered in combination with an agent selected from anthrocyclins, fludarabine, flavopiridol, imatinib, bortezomib, anti-angiogenesis agents and nuclear receptor ligands, such as, all-trans retinoic acid and tumor necrosis factor-related apoptosis-inducing ligand.

Anti-cancer agents and/or agents used in chemotherapy include, but are not limited to, the following: estrogen receptor modulators, androgen receptor modulators, retinoid receptor modulators, cytotoxic/cytostatic agents, antiproliferative agents, prenyl-protein transferase inhibitors, nitrogen mustards, nitroso ureas, angiogenesis inhibitors, inhibitors of cell proliferation and survival signaling pathway, apoptosis inducing agents, agents that interfere with cell cycle checkpoints, agents that interfere with receptor tyrosine kinases (RTKs), integrin blockers, NSAIDs, inhibitors of inherent multidrug resistance (MDR), anti-emetic agents, agents useful in the treatment of anemia, agents useful in the treatment of neutropenia, immunologic-enhancing drugs, biphosphonates, aromatase inhibitors, agents inducing terminal differencation of neoplastic cells, γ-secretase inhibitors, cancer vaccines, and any combination thereof.

Where the subject is suffering from a cancer (e.g., a T-cell lymphoma), a selective HDAC8 inhibitor is used in any combination with one or more other anti-cancer agents. Examples of anti-cancer agents include, but are not limited to, any of the following: 5-aza-2'-deoxycytidine, all trans retinoic acid, doxorabicin, vincristine, etoposide, gemcitabine, imatinib, 17-N-allylamino-17-demethoxygeklanamycin (17-AAG), flavopiridol, LY294002, bortezomib, trastuzumab, BAY 11-7082, PKC412, or PD184352.

Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and are useful for treating cancer in combination with the compounds described herein.

Other anti-cancer agents that are employed in combination with a selective HDAC8 inhibitor include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that are employed in combination with a selective HDAC8 inhibitor include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin IR derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin;

levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, macroalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that are employed in combination with a selective HDAC8 inhibitor include alkylating agents, antimetabolites, natural products, or hormones, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a selective HDAC8 inhibitor include but are not limited to ulna alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that are employed in combination a selective HDAC8 inhibitor include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with a selective HDAC8 inhibitor include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide, SPD-424).

In another embodiment, Dynepo gene activated erythropoietin (Anti-anemic; human erythropoietin) is administered in combination with selective HDAC8 inhibitor compounds.

"Estrogen receptor modulators" refers to compounds that interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646. In some embodiments, estrogen receptor modulators are tamoxifen and raloxifene.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

Other agents that are used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which are used in combination with a selective HDAC8 inhibitor include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianoiide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans,trans,trans)-bis-mu-(hexane-1,6-diamine)-mu-[diamine-platinum(II)]bis[diamine-(chloro)platinum(II)]-tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MENI0755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)-benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)-ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]-carbazole-1-carboxamide, asulacrine, (5a, 5aB,8aa,9b)-9-[2-[N-[2-(dimethylamino)ethyl]-N-methylamino]ethyl]-5-[4-hydroxy-3,5-dimethoxyphenyl]-5,5a,6, 8,8a,9-hexohydrofuro(3',4':6,7)colchic(2,3-d)-1,3-dioxol-6-one, 2,3-(methylenedioxy)-5-methyl-7-hydroxy-8- methoxybenzo[c]-phenanthridinium, 6,9-bis[(2-aminoethyl)-amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2-,1-c]quinolin-7-one, and dimesna.

"Antiproliferative agents" include antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxy-cytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]-glycylamino]-L-glycero-B-L-manno-heptopyranosyl]-adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetra cyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which are delivered via recombinant virus-mediated gene transfer (see U.S. Pat. No. 6,069,134, for example).

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-1), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl-1)(1-methyl-1H-imidazol-5-yl)methyl]-4-(3-chlorophenyl)-1-methyl-2(1H)-quinolinone, (±)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethyl-phenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)-methyl)-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]-piperidine, 4-{5-[4-hydroxymethyl-4-(4-chloropyridin-2-ylmethyl)-piperidine-1-ylmethyl]-2-methylimidazol-1-ylmethyl]benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl}-3H-imidazol-4-ylmethyl}benzonitrile, 4-{3-[4-(5-chloro-2-oxo-2H-[1,2]bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6, 10:12,16-dimetheno-1H-imidazo[4,3-c][1,11,4]dioxa-azacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]-oxatriaza-cyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacyclo-eicosine-9-carbonitrile, and (±)-19,20-dihydro-3-methyl-19-oxo-5H-18,21-ethano-12,14-etheno-6,10-metheno-22H-benzo[d]imidazo[4, 3-1c][1,6,9,12]oxa-triazacyclooctadecine-9-carbonitrile.

For an example of the role of a prenyl-protein transferase inhibitor on angiogenesis see *J. Of Cancer*, Vol. 35, No. 9, pp. 1394-1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232, 632. Examples of reverse transcriptase inhibitors include delaviridine, efavirenz, GS-840, HBY097, lamivudine, nevirapine, AZT, 3TC, ddC, and ddI. It has been reported (*Nat. Med.;* 8(3):225-32, 2002) that HIV protease inhibitors, such as indinavir or saquinavir, have potent anti-angiogenic activities and promote regression of Kaposi sarcoma.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib, valecoxib, and rofecoxib, carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105: 141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxas-piro[2,5]oct-6-yl(chloroacetyl)carbamate, acetyldinanaline, 5-amino-1-[[3,5-dichloro-4-(4-chlorobenzoyl)phenyl]-methyl]-1H-1,2,3-triazole-4-carboxamide, CM101, squalamine, combretastatin, RP14610, NX31838, sulfated mannopentose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PDK (for example LY294002), serine/threonine kinases, inhibitors of Raf kinase (for example BAY-43-9006), inhibitors of MEK (for example CI-1040 and PD-098059) and inhibitors of mTOR (for example Wyeth CCI-779 and Ariad AP23573), Such agents include small molecule inhibitor compounds and antibody antagonists.

"Apoptosis inducing agents" include, but not limited to, activators of TNF receptor family members (including the TRAIL receptors).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include, but not limited to, tyrosine kinase inhibitors such as inhibitors of c-Kit, Eph, PDGF, Flt3, Lck, Btk, and c-Met. Further agents include inhibitors of RTKs shown as described by Bume-Jensen and Hunter, 2001, Nature 411: 355-365. Examples of "tyrosine kinase inhibitors" include, but not limited to, N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]-quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg: 3',2',1'-kl]pyrrolo[3,4-i][1,6]benzodiazocin-1-one, SH268, genistein, ST1571, CEP2563, 4-(3-chlorophenylamino)-5,6-dimethyl-7-H-pyrrolo[2,3-d]pyrimidinemethane sulfonate, 4-(3-bromo-4-hydroxyphenyl)amino-6,7-dimethoxyquinazoline, 4-(4'-hydroxyphenyl) amino-6,7-dimethoxyquinazoline, SU6668, SU11248, STI571A, N-4-chlorophenyl-4-(4-pyridylmethyl)-1-phthalazinamine, and EMD121974.

HDAC inhibitors are also useful in combination with platelet fibrinogen receptor (GP Iib/IIIa) antagonists, such as tirofiban, to inhibit metastasis of cancerous cells. Tumor cells activate platelets largely via thrombin generation. This activation is associated with the release of VEGF. The release of VEGF enhances metastasis by increasing extravasation at points of adhesion to vascular endothelium (Amirkhosravi, 1999, Platelets 10: 285-292). Therefore, HDAC inhibitors serve to inhibit metastasis, in combination with GP Iib/IIIa) antagonists. Examples of other fibrinogen receptor antagonists include abciximab, eptifibatide, sibrafiban, lamifiban, lotrafiban, cromofiban, and CT50352.

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$; $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Commercially available anti-cancer agents which are used in combination with an HDAC8 selective agent disclosed herein include, but are not limited to: abarelix (Plenaxis®); aldesleukin (Prokine®); Aldesleukin (Proleukin®); Alemtuzumab (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacizumab (Avastin®); bexarotene (Targretin®); bleomycin (Blenoxane®); bortezomib (Velcade®); busulfan (Busulfex®); busulfan (Myleran®); calusterone (Methosarb®); capecitabine Xeloda®); carboplatin Paraplatin®); carmustine (BCNU, BiCNU); carmustine (Gliadel®); celecoxib (Celebrex®); cetuximab (Erbitux®); chlorambucil (Leukeran®); cisplatin (Platinol®); cladribine (Leustatin®); clofarabine (Clolar®); cyclophosphamide (Cytoxan®); cytarabine (Cytosar-U®); cytarabine liposomal (DepoCyt); dacarbazine (DTIC-Dome); dactinomycin (actinomycin D, Cosmegen®); Darbepoetin alfa (Aranesp®); dasatinib (Sprycel®); daunorubicin liposomal (DanuoXome); daunorubicin (daunomycin, Daunorubicin®); daunorubicin (daunomycin, Cerubidine®); decitabine (Dacogen®); denileukin (Ontak®); dexrazoxane (Zinecard®); docetaxel (Taxotere®); doxorubicin (Adriamycin®); doxorubicin liposomal (Doxil®); dromostanolone propionate; epirubicin (Ellence®); Epirubicin; Epoetin alfa (EPOGEN®); erlotinib (Tarceva®); estramustine (Emcyt®); etoposide phosphate (Etopophos®); etoposide (VP-16; Vepesid®); exemestane (AROMASIN®); fentanyl citrate (Fentora®); Filgrastim (Neupogen®); floxuridine (FUDR); fludarabine (Fludara®); fluorouracil (5-FU, Adrucil®); fulvestrant (Faslodex®); gefitinib (Iressa®); gemcitabine (Gemzar®); gemtuzumab ozogamicin (Mylotarg®); goserelin acetate (Zoladex®); histrelin acetate (Histrelin®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Leucovorin®); Leuprolide Acetate (Eligard®); levamisole (Ergamisol®); lomustine, CCNU CeeBU®); meclorethamine (nitrogen mustard, Mustargen®); megestrol acetate (Megace®); melphalan (Alkeran; mercaptopurine (6-MP, Purinethol®); mesna (Mesnex®); methotrexate (Rheumatrex®, Trexall®); methoxsalen (Uvadex®); mitomycin C (Mutamycin®); mitomycin C (Mitozytrex®); mitotane (Lysodren®); mitoxantrone (Novantrone®); nandrolone phenpropionate (Durabolin-50); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pegademase (Adagen®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); rituximab (Rituxan®); sargramostim (Leukine®); Sargramostim (Prokine®); sorafenib (Nexavar®); streptozocin (Zanosar®); sunitinib maleate (Sutent®); talc (Sclerosol); tamoxifen (Nolvadex®); temozolomide (Temodar®); teniposide (VM-26, Vumon®); testolactone (Teslac®); thalidomide (Thalomid®); thioguanine (6-TG, Thioguanine®); thiotepa (Thioplex®); topotecan (Hycamtin®); toremifene (Fareston®); Tositumomab (Bexxar®); Tositumomab/I-131 tositumomab (Bexxar®); trastuzumab (Herceptin®); tretinoin (ATRA, Vesanoid®); Uracil Mustard; valrubicin (Valstar®); vinblastine (Velban®); vincristine (Oncovin®); vinorelbine (Navelbine®); vorinostat (Zolinza®); zoledronate (Zometa®); and zoledronic acid (Zometa®).

In some embodiments, the HDAC8 selective compounds described herein are used in combination with gene therapy for the treatment of cancer. For an overview of genetic strategies to treating cancer see Hall et al. (*Am J Hum Genet.* 61:785-789, 1997) and Kufe et al. (*Cancer Medicine,* 5th Ed, pp 876-889, B C Decker, Hamilton 2000). Gene therapy is used to deliver any tumor suppressing gene. Examples of such genes include, but are not limited to, p53, which are delivered via recombinant virus-mediated gene transfer, Duc-4, NF-I, NF-2, RB, WT1, BRCA1, BRCA2, a uPA/uPAR antagonist ("Adenoviras-Mediated Delivery of a uPA/uPAR Antagonist Suppresses Angiogenesis-Dependent Tumor Growth and Dissemination in Mice," Gene Therapy, Aug. 1998, 5(8): 1105-13), and interferon-γ (*J. Immunol.* 2000; 164:217-222).

In other embodiments, the HDAC8 selective compounds described herein are administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

In some embodiments, the HDAC8 selective compounds described herein are employed in conjunction with anti-emetic agents to treat nausea or emesis, including acute, delayed, late-phase, and anticipatory emesis, which result from the use of a HDAC8 selective compound described herein, alone or with radiation therapy. For the prevention or treatment of emesis, a HDAC8 selective compound described herein is used in conjunction with anti-emetic agents, such as, but not limited to: neurokinin-1 receptor antagonists, 5HT3 receptor antagonists (such as ondansetron, granisetron, tropisetron, Palonosetron, and zatisetron), $GABA_B$ receptor agonists (such as baclofen), corticosteroids (such as dexamethasone, prednisone, prednisolone, dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In one embodiment, an anti-emesis agent selected from among a neurokinin-1 receptor antagonist, a 5HT3 receptor antagonist and a corticosteroid is administered as an adjuvant for the treatment or prevention of emesis that results upon administration of the instant compounds.

In other embodiments, the HDAC8 selective compounds described herein are administered with an agent useful in the treatment of anemia. Such an anemia treatment agent is, for example, a continuous eythropoiesis receptor activator (such as epoetin-α).

In other embodiments, the HDAC8 selective compounds described herein are administered with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, the HDAC8 selective compounds described herein are administered with an immunologic-enhancing drug, such as levamisole, bacillus Calmette-Guerin, octreotide, isoprinosine and Zadaxin.

In other embodiments, the HDAC8 selective compounds described herein are useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel®), pamidronate (Aredia®), alendronate (Fosamax®), risedronate (Actonel®), zoledronate (Zometa®), ibandronate (Boniva®), incadronate or cimadronate, clodronate, EB-1053, minodronate, neridronate, piridronate and tiludronate including any and all pharmaceutically acceptable salts, derivatives, hydrates and mixtures thereof.

In other embodiments, the HDAC8 selective compounds described herein are useful for treating breast cancer in combination with aromatase inhibitors. Examples of aromatase inhibitors include but are not limited to: anastrozole, letrozole and exemestane.

In some embodiments, the HDAC8 selective compounds described herein are useful for treating or preventing cancer in combination with siRNA or RNAi therapeutics.

"DNA methyltransferase inhibitor" refers to compounds which inhibit the methylation of the DNA base cytosine at the C-5 position of that base by the DNA methyltransferase enzyme. In some embodiments, DNA methyltransferase inhibitors include 5-azacytosine and Zebularine®.

Radiation Therapy

Radiotherapy, also called radiation therapy, is the treatment of cancer and other diseases with ionizing radiation. Ionizing radiation deposits energy that injures or destroys cells in an area being treated (a "target tissue") by damaging their genetic material, making it impossible for these cells to continue to grow. Although radiation damages both cancer cells and normal cells, the latter are better able to repair themselves and function properly. Radiotherapy is used to treat localized solid tumors, such as cancers of the skin, tongue, larynx, brain, breast, prostate, colon, uterus and/or cervix. It is also used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultra violet light. Radiotherapy with or without concurrent or sequential chemotherapy is an effective modality for head and neck, breast, skin, anogenital cancers, and certain nonmalignant diseases such as keloid, desmoid tumor, hemangioma, arteriovenous malformation, and histocytosis X.

Provided are methods of using at least one histone deacetylase inhibitor to reduce side effect caused by at least one other therapeutic treatment, such as radiation-induced normal tissue fibrosis or chemotherapy-induced tissue necrosis, and the methods provided herein also synergistically inhibit tumor cell growth with radiotherapy and other anti-cancer agents.

Growth Hormone Secretagogues

In some embodiments, a selective inhibitor of HDAC8 is used in combination with one or more growth hormone secretagogues including, but not limited to, arginine, L-3,4-dihydroxyphenylalanine (1-Dopa), glucagon, vasopressin, PACAP (pituitary adenylyl cyclase activating peptide), muscarinic receptor agonists and a synthetic hexapeptide, GHRP (growth hormone releasing peptide).

Agents for Treating Autoimmune Diseases, Inflammatory Diseases, or Allergy Diseases In one embodiment, where the subject is suffering from or at risk of suffering from an autoimmune disease, an inflammatory disease, or an allergy disease, a selective HDAC8 inhibitor compound is administered in any combination with one or more of the following therapeutic agents: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

In one embodiment, selective HDAC8 inhibitor compounds described herein, or compositions and medicaments that include the selective HDAC8 inhibitor compounds described herein, are administered to a patient in combination with an anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketolorac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, CS-502, JTE-522, L-745,337 and NS398).

Combinations with NSAIDs, which are selective COX-2 inhibitors, are contemplated herein.

Compounds that have been described as selective COX-2 inhibitors and are therefore useful in the methods or pharmaceutical compositions described herein include, but are not limited to, celecoxib, rofecoxib, lumiracoxib, etoricoxib, valdecoxib, and parecoxib, or a pharmaceutically acceptable salt thereof.

Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, HDAC8 selective inhibitors are administered in combination with leukotriene receptor antagonists including, but are not limited to, BAY u9773, Cuthbert et al EP 00791576 (published 27 Aug. 1997), DUO-LT (Tsuji et al, *Org. Biomol. Chem.*, 1, 3139-3141, 2003), zafirlukast (Accolate®), montelukast (Singulair®), prankulast (Onon®), and derivatives or analogs thereof.

Kits/Articles of Manufacture

For use in the therapeutic applications described herein, kits and articles of manufacture are also described herein. Such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers are formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of HDAC activity, or in which HDAC is a mediator or contributor to the symptoms or cause.

For example, the container(s) include one or more compounds described herein, optionally in a composition or in combination with another agent as disclosed herein. The container(s) optionally have a sterile access port (for example a container that is an intravenous solution bag or a vial having a stopper pierceable by a hypodermic injection needle). Such kits optionally comprising a compound with an identifying description or label or instructions relating to its use in the methods described herein.

A kit will include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also be included.

A label is attached on or associated with the container. A label is attached on a container when letters, numbers or other characters forming the label are attached, molded or etched into the container itself; a label is associated with a container when it is present within a receptacle or carrier that also holds the container, e.g., as a package insert. A label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. The pack or dispenser device is accompanied by instructions for administration. The pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. Compositions containing a compound provided herein formulated in a compatible pharmaceutical carrier are also prepared, placed in an appropriate container, and labeled for treatment of an indicated condition.

EXAMPLES

These examples are provided for illustrative purposes only and not to limit the scope of the claims provided herein. The starting materials and reagents used for the synthesis of the compounds described herein are synthesized or obtained from commercial sources, such as, Sigma-Aldrich, Fluka, Acros Organics, Alfa Aesar, Bachem and the like.

Example 1

Synthesis of Compound 1

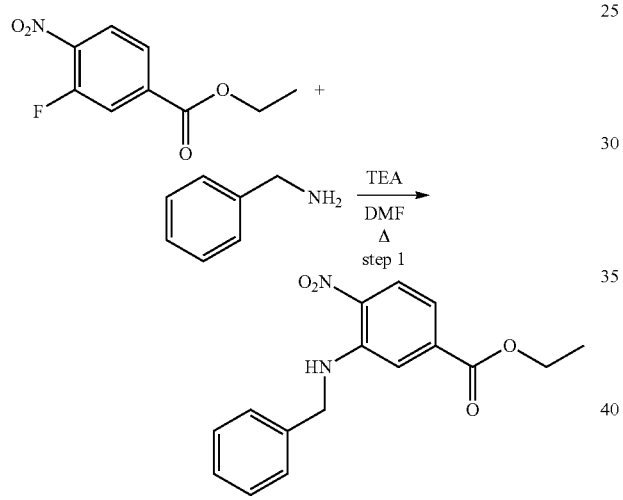

Step 1

A solution of benzylamine (0.77 mL, 7.0 mmol), ethyl 3-fluoro-4-nitrobenzoate (1.0 g, 4.7 mmol) and TEA (2 mL) was heated in DMF (10 mL) for 18 hr at 70° C. The solution was cooled to room temperature, diluted with ethyl acetate (200 mL) and washed with H$_2$O (2×100 mL) then 1N HCl (2×100 mL). The organic layer was dried (MgSO$_4$), filtered and then concentrated to provide 1.52 g (~100%) of crude ethyl 3-(benzylamino)-4-nitrobenzoate as an orange solid. This material was used without further purification.

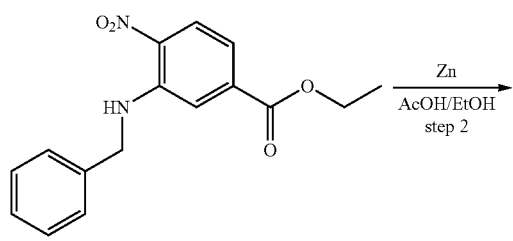

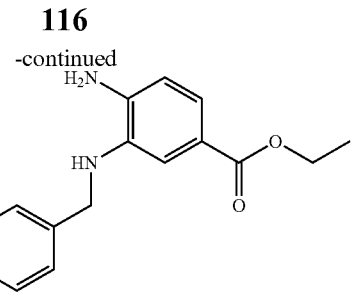

Step 2

To a stirring solution of ethyl 3-(benzylamino)-4-nitrobenzoate (1.52 g, 5 mmol) in ethanol (50 mL) and acetic acid (7 mL) was added zinc dust (2.3 g, 35 mmol). After 1 hr at room temperature, the solids were filtered and the remaining solution was concentrated. The resulting residue was diluted with ethyl acetate (200 mL) and washed with dilute aq. NaHCO$_3$ (1×100 mL), then the organic layer was dried (MgSO$_4$), filtered and then concentrated to provide 1.44 g (~100%) of crude ethyl 4-amino-3-(benzylamino)benzoate as an orange/brown oil. This material was used without further purification.

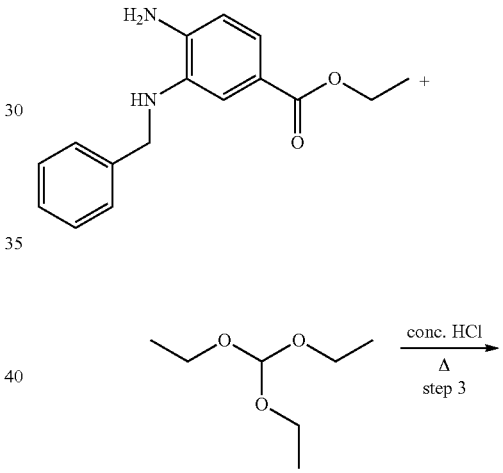

Step 3

A solution of ethyl 4-amino-3-(benzylamino)benzoate (0.24 g, 0.89 mmol) and triethyl orthoformate (0.8 mL, 4.8 mmol) in ethanol (10 mL) and conc. HCl (7 drops) was heated to reflux for 24 hr. The solution was cooled to room temperature and concentrated, then diluted with ethyl acetate (100 mL) and washed with dilute aq. NaHCO$_3$ (1×100 mL). Then organic layer was dried (MgSO$_4$), filtered and then concentrated and the resulting residue was purified by flash chromatography (50% ethyl acetate/hexane then ethyl acetate) to provide 0.12 g (48%) of ethyl 3-benzyl-3H-benzo[d]imidazole-5-carboxylate as an off white solid.

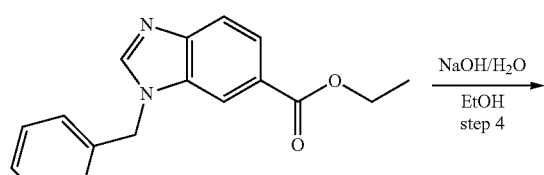

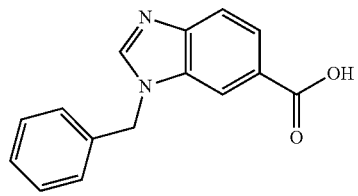

Step 4

To a stirred solution of ethyl 3-benzyl-3H-benzo[d]imidazole-5-carboxylate (0.12 g, 0.43 mmol) in ethanol (10 mL) was added NaOH (0.12 g in 2 mL of H$_2$O) and then the solution was stirred for 24 hr at room temperature. The reaction solution was then concentrated, diluted with water (10 mL) and then the pH was adjusted to using 1N HCl. The aqueous layer was then saturated with NaCl and extracted with ethyl acetate (2×50 mL). Then organic layer was dried (MgSO$_4$), filtered and then concentrated to provide 0.1 g (93%) of 3-benzyl-3H-benzo[d]imidazole-5-carboxylic acid as an off-white solid.

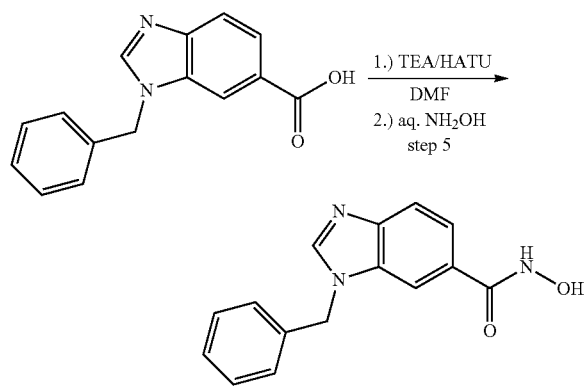

Step 5

To a solution of 3-benzyl-3H-benzo[d]imidazole-5-carboxylic acid (0.1 g, 0.4 mmol) and TEA (0.16 mL, 1.2 mmol) in DMF (7 mL) was added HATU (0.15 g, 0.4 mmol). After stirring the solution for 30 min at room temperature, aq. NH$_2$OH (50% wt/wt: 1 mL) was added. After stirring an additional 1 hr at room temperature, the solution was diluted with ethyl acetate (75 mL) and then washed with water (2×50 mL). The aqueous layer was saturated with NaCl and extracted with ethyl acetate (2×50 mL). The organic layers were combined, dried (MgSO$_4$), filtered and then concentrated to provide 0.14 g of a colorless residue. The residue was triturated in ethyl acetate (2 mL) and allowed to sit at room temperature overnight. The resulting solid was collected by filtration to provide 37 mg (35%) of 3-benzyl-N-hydroxy-3H-benzo[d]imidazole-5-carboxamide as a white solid. $^1$H NMR (300 MHz, DMSO) δ 11.17 (s, 1H), 8.97 (s, 1H), 8.54 (s, 1H), 7.97 (s, 1H), 7.68 (d, 1H, J=8.2 Hz), 7.59 (d, 1H, J=8.2 Hz), 7.37-7.27 (m, 5H), 5.53 (s, 2H). EM (calc.): 267.1; MS (M+1H): 267.88.

Example 2

Synthesis of Compound 203

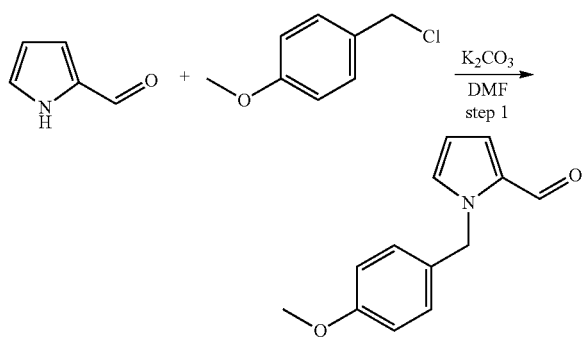

Step 1

To a solution of 1H-pyrrole-2-carbaldehyde (0.58 g, 6.1 mmol) and 1-(chloromethyl)-4-methoxybenzene (1.0 mL, 7.3 mmol) in DMF (15 mL) was added K$_2$CO$_3$ (3.4 g, 24.5 mmol). After stirring 16 hr at room temperature, the mixture was diluted with ethyl acetate (200 mL) and washed with H$_2$O (2×100 mL) then brine (100 mL). The organic layer was dried (MgSO$_4$), filtered and then concentrated to provide 1.45 g (~100%) of crude 1-(4-methoxybenzyl)-1H-pyrrole-2-carbaldehyde. This material was used without further purification.

Step 2

A mixture of 1-(4-methoxybenzyl)-1H-pyrrole-2-carbaldehyde (1.44 g, 6.7 mmol) triethyl phosphonoacetate (1.5 mL, 74. mmol) and K$_2$CO$_3$ (4.6 g, 33 mmol) was heated to reflux in ethanol (30 mL) for 24 hr. The mixture was then cooled to room temperature, filtered and concentrated. The residue was diluted with ethyl acetate (100 mL) and washed with water (100 mL). The organic layer was dried (MgSO$_4$), filtered and then concentrated to provide 1.54 g of a light yellow oil. The ¹H NMR showed the product, (E)-ethyl 3-(1-(4-methoxybenzyl)-1H-pyrrol-2-yl)acrylate, in ~2:1 ratio with the starting 1-(4-methoxybenzyl)-1H-pyrrole-2-carbaldehyde. The material was used without further purification.

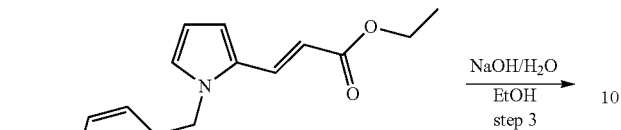

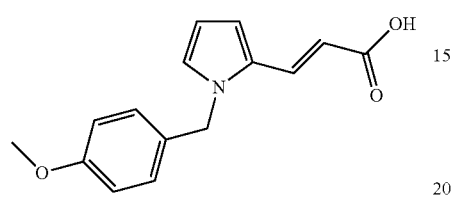

Step 3

To a solution of crude (E)-ethyl 3-(1-(4-methoxybenzyl)-1H-pyrrol-2-yl)acrylate in ethanol (50 mL) was added NaOH (1 g in 5 mL of H₂O). After stirring 4 hr at room temperature, the solution was concentrated and then diluted with H₂O (100 mL) and washed with TBME (2×75 mL). The aqueous base layer was the acidified with 1N HCl and extracted with ethyl acetate (100 mL). Then organic layer was dried (MgSO₄), filtered and then concentrated to provide 0.92 g (59% for 3 steps) of (E)-3-(1-(4-methoxybenzyl)-1H-pyrrol-2-yl)acrylic acid as a light yellow solid.

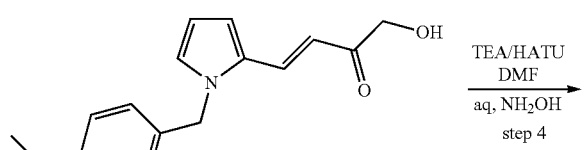

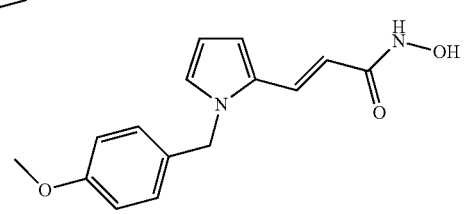

Step 4

To a solution of (E)-3-(1-(4-methoxybenzyl)-1H-pyrrol-2-yl)acrylic acid (0.92 g, 3.4 mmol) and TEA (1.5 mL, 10.7 mmol) in DMF (30 mL) was added HATU (1.36 g, 3.58 mmol). After stirring the solution for 30 min at room temperature, aq. NH₂OH (50% wt/wt: 3 mL) was added. After stirring an additional 2 hr at room temperature, the solution was diluted with ethyl acetate (200 mL) and then washed with 1N HCl (3×100 mL) and then dilute aq. NaHCO₃ (100 mL). The organic layer was dried (MgSO₄), filtered and then concentrated to provide 0.84 g of a light yellow solid. The solid was heated to reflux in ethyl acetate (~150 mL) and reduced to a ~20 mL volume. The cloudy solution was allowed to cool to room temperature and sit overnight. The resulting light yellow crystalline solid was collected by filtration to provide 0.68 g (35%) of (E)-3-(1-(4-methoxybenzyl)-1H-pyrrol-2-yl)-N-hydroxyacrylamide. ¹H NMR (300 MHz, DMSO) δ 10.49 (s, 1H), 8.83 (s, 1H), 7.30 (d, 1H, J=15.2 Hz), 7.05 (m, 1H), 6.98 (d, 2H, J=8.5 Hz), 6.87 (d, 2H, J=8.5 Hz), 6.53 (m, 1H), 6.13 (m, 1H), 6.06 (d, 1H, J=15.2 Hz), 5.20 (s, 2H), 3.70 (s, 3H). EM (calc.): 272.21; MS (2M+Na): 566.78.

Example 4

Synthesis of Compound 309

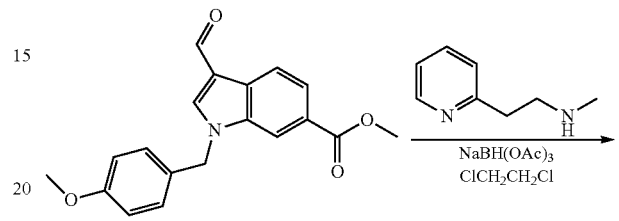

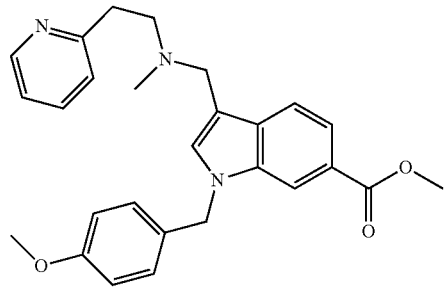

Step 1

To a solution of crude methyl 1-(4-methoxybenzyl)-3-formyl-1H-indole-6-carboxylate (0.50 g, 1.6 mmol) and N-methyl-2-(pyridin-2-yl)ethylamine (0.24 mL, 1.7 mmol) in 1,2-dichloroethane (20 mL) was added NaBH(OAc)₃ (0.66 g, 3.1 mmol). After stirring the solution for 24 hr at room temperature, the solution was concentrated and then diluted with ethyl acetate (100 mL) and washed with H₂O (100 mL). The organic layer was dried (MgSO₄), filtered and then concentrated to provide 0.77 g (100%) of methyl 1-(4-methoxybenzyl)-3-(2-(pyridin-2-yl)ethylamino)N-methyl)-1H-indole-6-carboxylate as an orange oil.

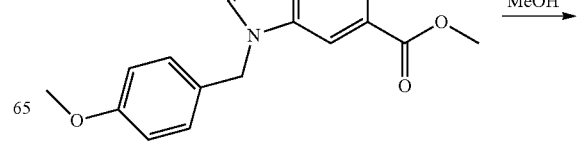

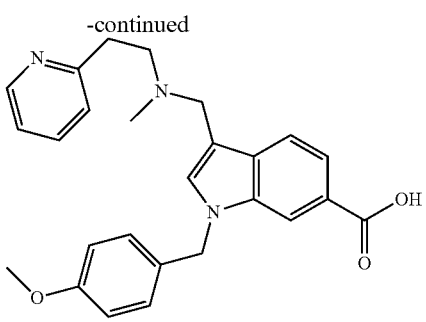

Step 2

To a solution of methyl 1-(4-methoxybenzyl)-3-(2-(pyridin-2-yl)ethylamino)N-methyl)-1H-indole-6-carboxylate (0.69 g, 1.55 mmol) in methanol (15 mL) was added NaOH (0.5 g in 2 mL H₂O) and heated to 60 T for 6 hr. The solution was then cool and concentrated and then stirred in methanol (10 mL) and 4.0M HCl/Dioxane (5 mL) was added, then the solid (NaCl) was filtered off and the solution was concentrated again, then slurried in ethyl acetate (200 mL) and stirred for 24 hr. The resulting precipitate was collected by filtration to provide 0.66 g (85%) of 1-(4-methoxybenzyl)-3-(2-(pyridin-2-yl)ethylamino)N-methyl)-1H-indole-6-carboxylate as the 2×HCl salt.

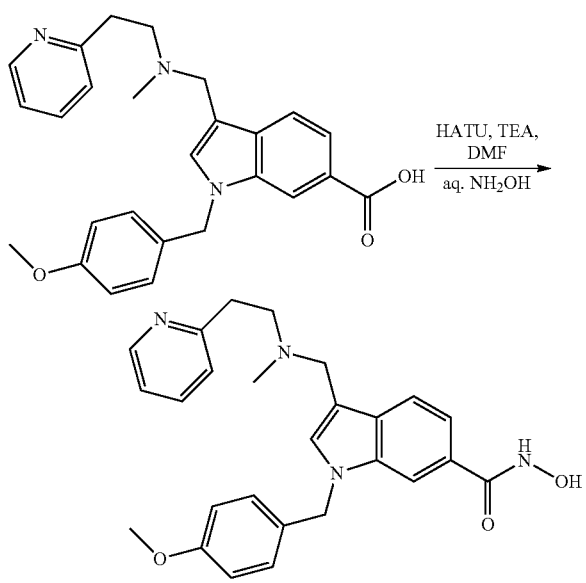

Step 3

To a solution of 1-(4-methoxybenzyl)-3-(2-(pyridin-2-yl)ethylamino)N-methyl)-1H-indole-6-carboxylate (0.66 g, 1.31 mmol) and TEA (0.92 mL, 6.6 mmol) in DMF (10 mL) was added HATU (0.52 g, 1.37 mmol). The solution was stirred 40 min at room temperature, then NH₂OH (50% wt/wt in H₂O; 3 mL) was added and the solution was stirred 20 min. The reaction solution was then diluted with ethyl acetate (100 mL) and washed with H₂O (2×100 mL). Then organic layer was dried (MgSO₄), filtered and then concentrated to provide 0.62 g of a tan solid. This was stirred in methylene chloride (7 mL) for 24 hr, then filtered to collect 0.23 g (39%) of 1-(4-methoxybenzyl)-3-(2-(pyridin-2-yl)ethylamino)N-methyl)-N-hydroxy-1H-indole-6-carboxamide as a tan solid.

¹H NMR (300 MHz, DMSO) δ 11.07 (s, 1H), 8.90 (s, 1H), 8.43 (d, 1H, J=4.6 Hz), 7.87 (s, 1H), 7.64 (dd, 1H, J=7.3 Hz, J=1.5 Hz), 7.47 (m, 2H), 7.35 (m, 1H), 7.25-7.18 (m, 2H), 7.14 (d, 1H, J=8.5 Hz), 6.84 (d, 1H, J=8.5 Hz), 5.31 (s, 2H), 3.68 (s, 3H), 3.65 (s, 2H), 2.90 (m, 2H), 2.71 (m, 2H), 2.16 (s, 3H). EM (calc.): 444.22; MS (M+H): 444.89.

Example 5

Synthesis of Compound 313

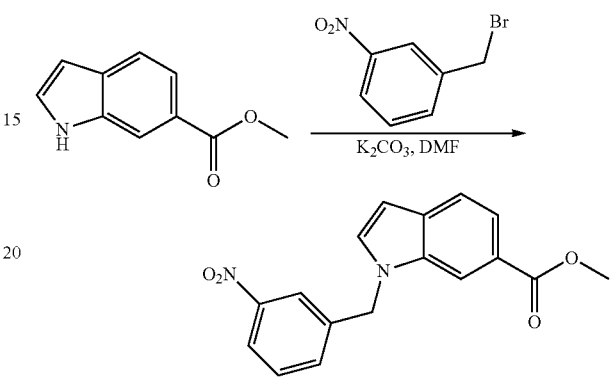

Step 1

To a solution of 1H-indole-6-carboxylic acid methyl ester (1.0 g, 5.7 mmol) and 3-nitrobenzyl bromide (1.48 g, 6.8 mmol) in DMF (15 mL) was added K₂CO₃ (1.6 g, 11.4 mmol). After stirring at room temperature for 16 hr, the solution was diluted with ethyl acetate (100 ml) and washed with water (3×50 ml). The organic layer was dried (MgSO₄), filtered and concentrated. The remaining residue was recrystallized with ethyl acetate/hexane to provide 1.34 g (76% yield) of 1-(3-nitrobenzyl)-1H-indole-6-carboxylic acid methyl ester as light orange crystals.

¹H NMR (300 MHz, DMSO) δ 8.13 (m, 2H), 8.03 (s, 1H), 7.81 (d, 1H, J=3.0 Hz), 7.67-7.54 (m, 4H, J=9.0 Hz), 6.65 (d, 1H, J=3.0 Hz), 5.73 (s, 2H), 3.81 (s, 3H).

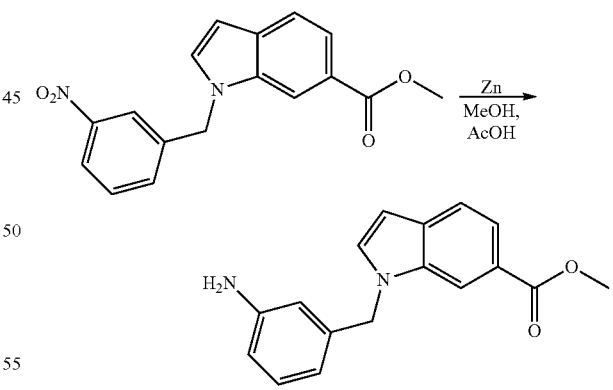

Step 2

To a solution of 1-(3-nitrobenzyl)-1H-indole-6-carboxylic acid methyl ester (1.3 g, 4.2 mmol) in MeOH (40 mL) and AcOH (3 ml) was added Zinc dust (1.9 g, 29 mmol). After stirring at room temperature for 3 hr, the solids were filtered and the filtrate was diluted with ethyl acetate (150 ml) and washed with sat. NaHCO₃ (200 ml). The organic layer was dried (MgSO₄), filtered and concentrated to collect 1.24 g (100% yield) of 1-(3-aminobenzyl)-1H-indole-6-carboxylic acid methyl ester.

¹H NMR (300 MHz, DMSO) δ 8.02 (s, 1H), 7.64 (m, 3H), 6.92 (t, 1H, J=7.6 Hz), 6.58 (d, 1H, J=3.0 Hz), 6.40 (d, 1H, J=7.6 Hz), 6.27 (m, 2H), 5.36 (s, 2H), 5.07 (s, 2H), 3.81 (s, 3H).

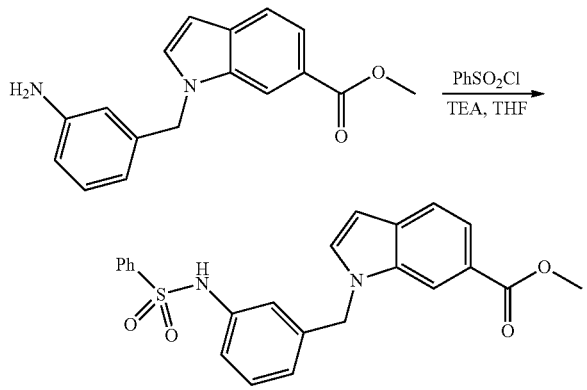

Step 3

To a solution of 1-(3-aminobenzyl)-1H-indole-6-carboxylic acid methyl ester (0.50 g, 1.78 mmol) and benzenesulfonyl chloride (0.25 ml, 2.0 mmol) in THF (15 mL) was added TEA (1.2 mL). After stirring at 20 hr at room temperature, the mixture was diluted with ethyl acetate (100 mL) and washed with 1N HCl (150 mL). The organic layer was dried (MgSO₄), filtered and concentrated to collect 1.93 g of crude 1-(3-phenylsulfonamide-benzyl)-1H-indole-6-carboxylic acid methyl ester as a brown oil.

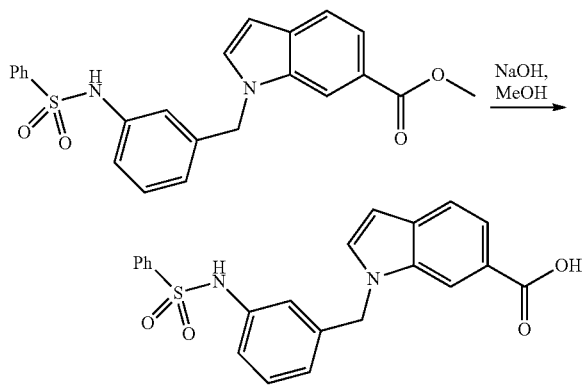

Step 4

1-(3-phenylsulfonamide-benzyl)-1H-indole-6-carboxylic acid methyl ester was hydrolyzed as described in Example 4, Step 2 to provide 1-(3-phenylsulfonamide-benzyl)-1H-indole-6-carboxylic acid.

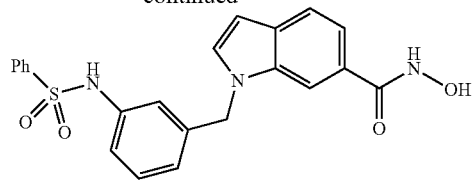

Step 5

1-(3-phenylsulfonamide-benzyl)-1H-indole-6-carboxylic acid has activated and coupled to NH₂OH as described in Example 4, Step 3 to provide 1-(3-phenylsulfonamide-benzyl)-1H-indole-6-carboxylic acid hydroxyamide as a tan solid.

¹H NMR (300 MHz, DMSO) δ 11.07 (s, 1H), 10.26 (s, 1H), 8.91 (s, 2H), 7.84 (s, 1H), 7.61-7.36 (m, 8H), 7.12 (t, 2H, J=7.9 Hz), 6.90-6.83 (m, 3H), 6.54 (d, 1H, J=3.1 Hz), 5.38 (s, 2H).

Example 6

Synthesis of Compound 310

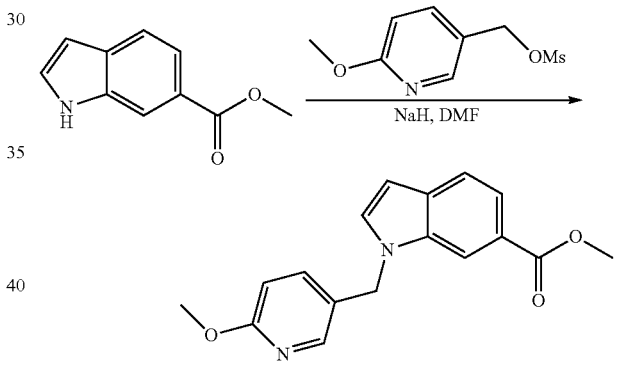

Step 1

To a solution of 1H-indole-6-carboxylic acid methyl ester (0.54 g, 3.1 mmol) and (6-methoxypyridin-3-yl)methyl methanesulfonate (0.73 g, 3.4 mmol) in DMF (15 mL) was added NaH (0.9 g, 3.7 mmol). After stirring at room temperature for 1 hr, the solution was diluted with ethyl acetate (100 ml) and washed with water (100 ml). The organic layer was dried (MgSO₄), filtered and concentrated. The remaining residue was subjected to flash chromatography (40% ethyl acetate/hexane) to provide 0.68 g (75%) of methyl 14(6-methoxypyridin-3-yl)methyl)-1H-indole-6-carboxylate as a colorless oil.

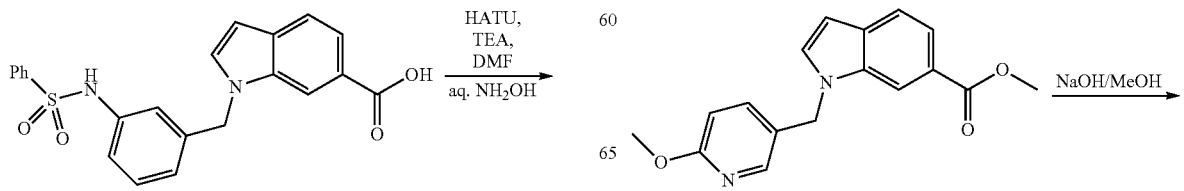

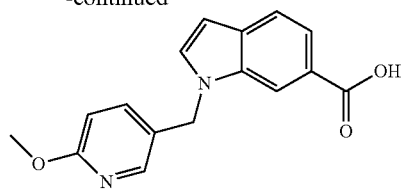

Step 2

Methyl 1((6-methoxypyridin-3-yl)methyl)-1H-indole-6-carboxylate was hydrolyzed as described in Example 4, Step 2 to provide 1-((6-methoxypyridin-3-yl)methyl)-1H-indole-6-carboxylic acid as a light yellow solid.

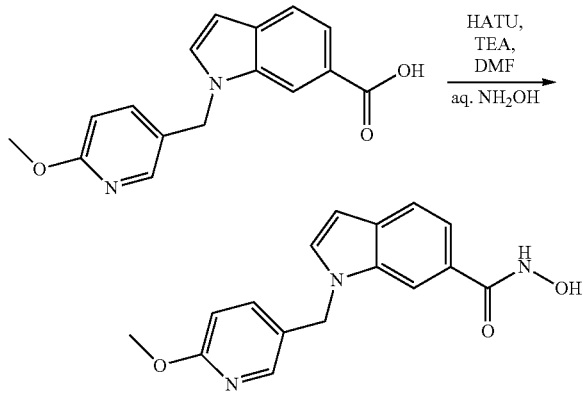

Step 3

1-((6-Methoxypyridin-3-yl)methyl)-1H-indole-6-carboxylic acid was activated and coupled with NH$_2$OH as described in Example 4, Step 3 to provide N-hydroxy-1-((6-methoxypyridin-3-yl)methyl)-1H-indole-6-carboxamide as a tan solid.

$^1$H NMR (300 MHz, DMSO) δ 11.12 (s, 1H), 8.93 (s, 1H), 8.18 (s, 1H, J=2.1 Hz), 7.99 (s, 1H), 7.67 (d, 1H, J=3.1 Hz), 7.59-7.55 (m, 2H), 7.44 (dd, 1H, J=8.2 Hz, J=1.0 Hz), 6.75 (d, 1H, J=8.6 Hz), 6.51 (d, 1H, J=2.7 Hz), 5.39 (s, 2H), 3.78 (2, 3H). EM (calc.): 297.11; MS (M+H): 297.92.

Example 7

Synthesis of Compound 328

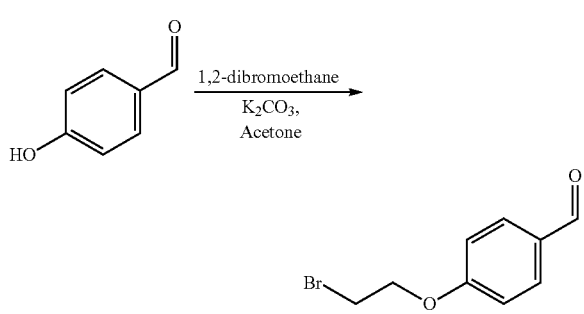

Step 1

A mixture of 1,2-dibromoethane (3.9 mL, 45 mmol), 4-hydroxybenzaldehyde (1.8 g, 15 mmol) and K$_2$CO$_3$ (10.4 g, 75 mmol) in acetone (40 mL) was heated to reflux for 18 hr. The mixture was cooled, diluted with ethyl acetate (200 mL) and washed with brine (200 mL). Then organic layer was dried (MgSO$_4$), filtered and then concentrated. The resulting residue was subjected to flash chromatography (25% ethyl acetate/hexane) to provide 1.51 g (44%) of 4-(2-bromoethoxy)benzaldehyde.

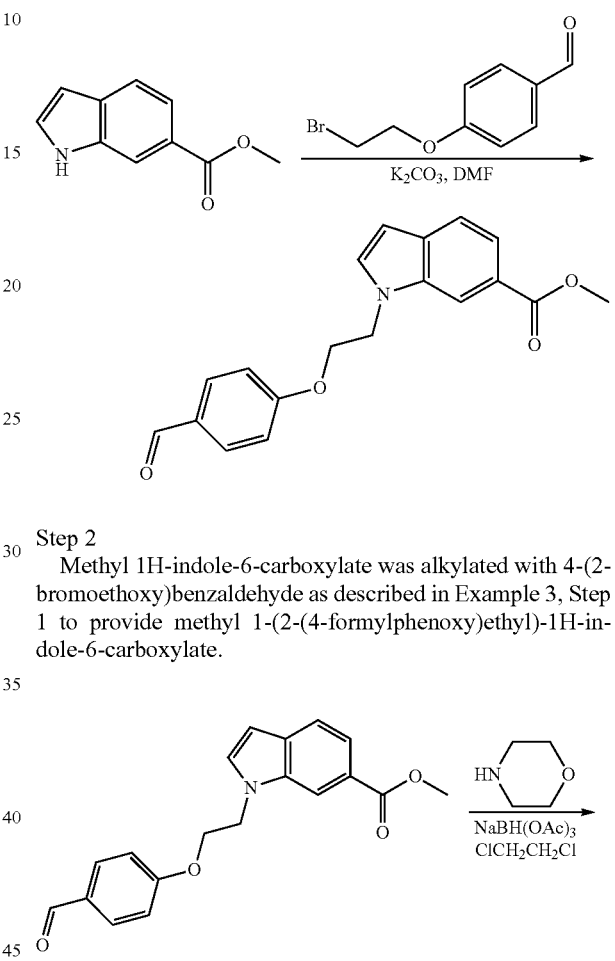

Step 2

Methyl 1H-indole-6-carboxylate was alkylated with 4-(2-bromoethoxy)benzaldehyde as described in Example 3, Step 1 to provide methyl 1-(2-(4-formylphenoxy)ethyl)-1H-indole-6-carboxylate.

Step 3

Methyl 1-(2-(4-formylphenoxy)ethyl)-1H-indole-6-carboxylate was subjected to reductive amination conditions as described in Example 4, Step 1 to provide methyl 1-(2-(4-(morpholinomethyl)phenoxy)ethyl)-1H-indole-6-carboxylate.

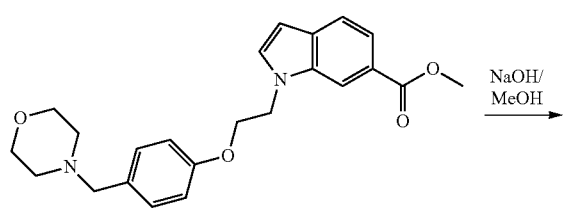

Step 4

Methyl 1-(2-(4-(morpholinomethyl)phenoxy)ethyl)-1H-indole-6-carboxylate was hydrolyzed as described in Example 4, Step 2 to provide 1-(2-(4-(morpholinomethyl)phenoxy)ethyl)-1H-indole-6-carboxylate.

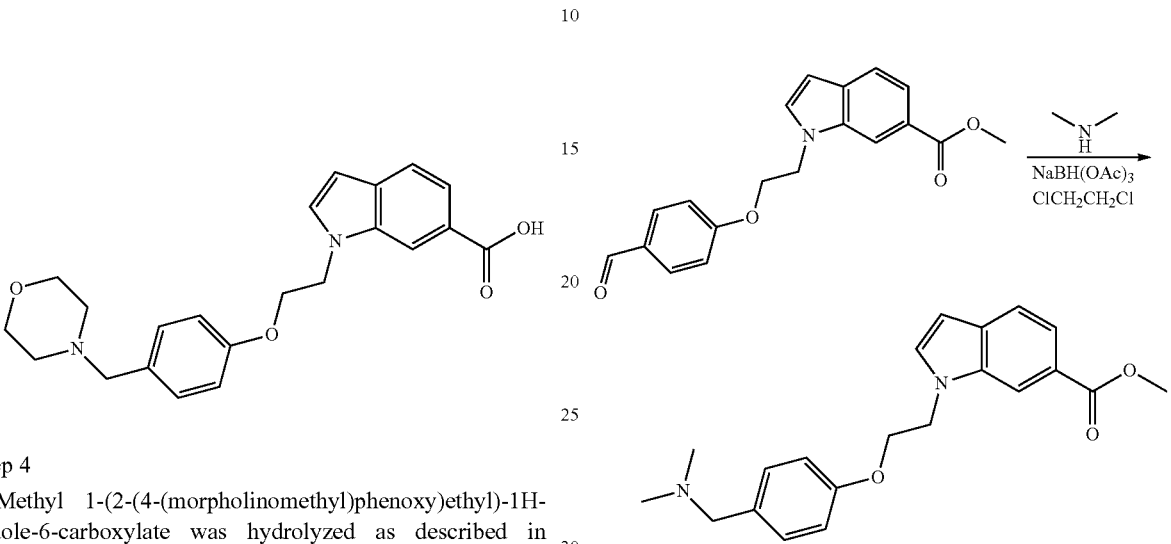

Step 5

1-(2-(4-(morpholinomethyl)phenoxy)ethyl)-1H-indole-6-carboxylate was activated and coupled with NH$_2$OH as described in Example 4, Step 3 to provide 1-(2-(4-(morpholinomethyl)phenoxy)ethyl)-N-hydroxy-1H-indole-6-carboxamide as a tan solid.

Example 8

Synthesis of Compound 325

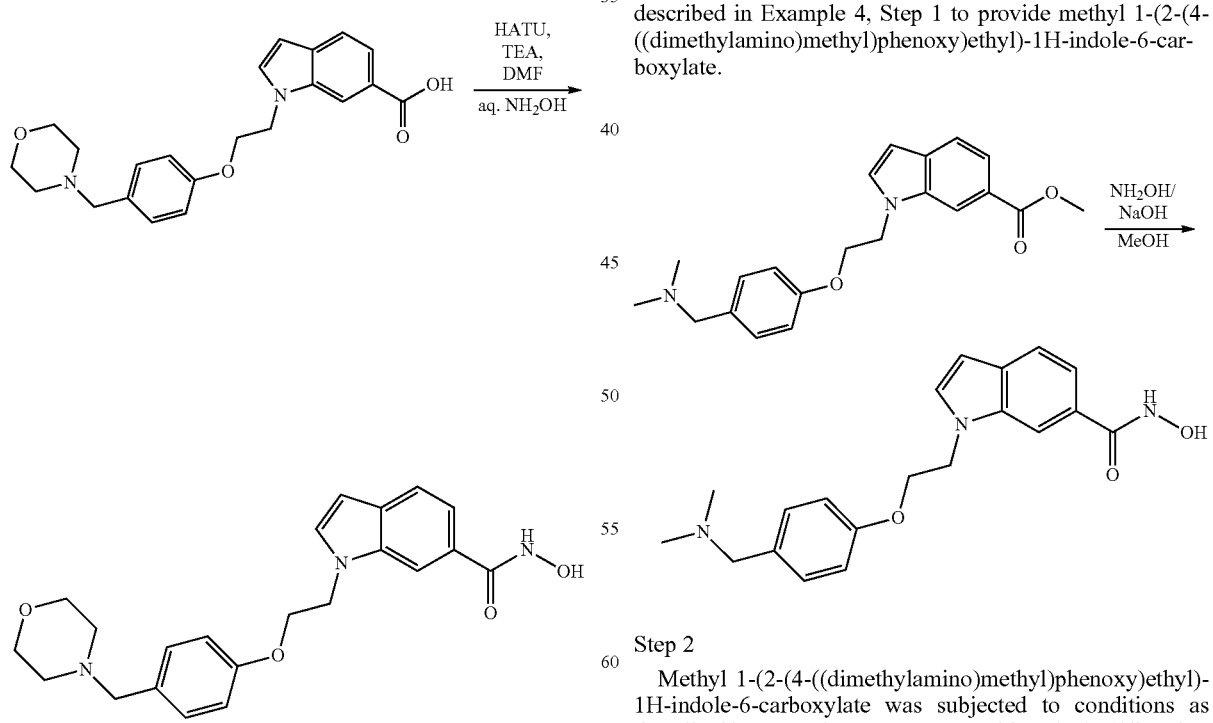

Step 1

Methyl 1-(2-(4-formylphenoxy)ethyl)-1H-indole-6-carboxylate was subjected to reductive amination conditions as described in Example 4, Step 1 to provide methyl 1-(2-(4-((dimethylamino)methyl)phenoxy)ethyl)-1H-indole-6-carboxylate.

Step 2

Methyl 1-(2-(4-((dimethylamino)methyl)phenoxy)ethyl)-1H-indole-6-carboxylate was subjected to conditions as described in Example 3, Step 3 to provide 1-(2-(4-((dimethylamino)methyl)phenoxy)ethyl)-N-hydroxy-1H-indole-6-carboxamide.

$^1$H NMR (300 MHz, DMSO) δ 8.05 (s, 1H), 7.56 (m, 2H), 7.44 (dd, 1H, J=8.2 Hz, J=1.0 Hz), 7.12 (d, 2H, J=8.5 Hz), 6.80 (d, 2H, J=8.5 Hz), 6.48 (d, 1H, J=3.1 Hz), 4.60 (t, 2H, J=4.9 Hz), 4.28 (t, 1H, J=4.9 Hz), 3.24 (s, 2H), 2.05 (s, 6H).

Example 9

Synthesis of Compound 327

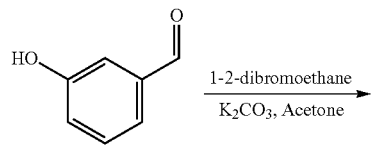

Step 1

3-Hydroxybenzaldehyde was subjected to the conditions described in Example 7, Step 1 to provide 3-(2-bromoethoxy) benzaldehyde.

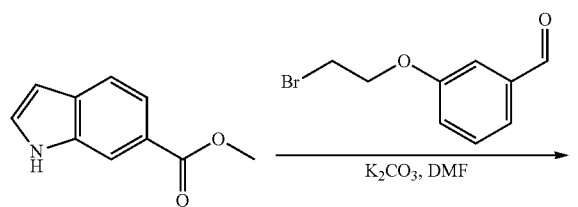

Step 2

Methyl 1H-indole-6-carboxylate was alkylated with 3-(2-bromoethoxy)benzaldehyde as described in Example 5, Step 1 to provide methyl 1-(2-(3-formylphenoxy)ethyl)-1H-indole-6-carboxylate.

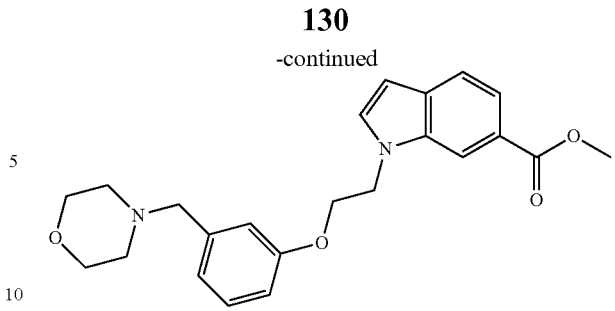

Step 3

Methyl 1-(2-(3-formylphenoxy)ethyl)-1H-indole-6-carboxylate was subjected to reductive amination conditions as described in Example 4, Step 1 to provide methyl 1-(2-(3-(morpholinomethyl)phenoxy)ethyl)-1H-indole-6-carboxylate.

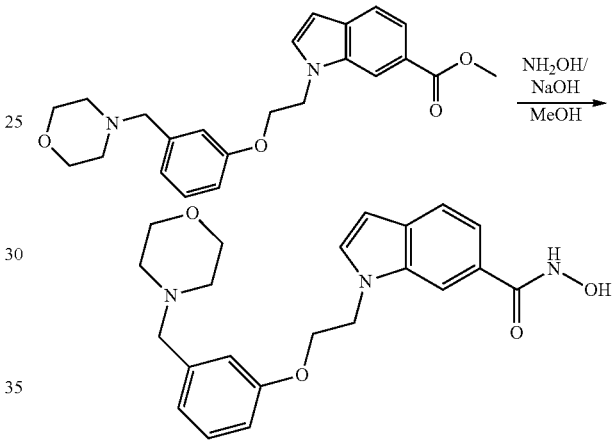

Step 4

Methyl 1-(2-(3-(morpholinomethyl)phenoxy)ethyl)-1H-indole-6-carboxylate was subjected to conditions as described in Example 4, Step 3 to provide 1-(2-(3-(morpholinomethyl)phenoxy)ethyl)-N-hydroxy-1H-indole-6-carboxamide.

$^1$H NMR (300 MHz, DMSO) δ 11.11 (s, 1H), 8.95 (s, 1H), 8.05 (s, 1H), 7.56 (m, 2H), 7.44 (dd, 1H, J=8.2 Hz, J=1.2 Hz), 7.17 (t, 1H, J=7.9 Hz), 6.78 (m, 3H), 6.48 (d, 1H, J=3.1 Hz), 4.60 (t, 2H, J=5.2 Hz), 4.29 (t, 1H, J=5.2 Hz), 3.52 (m, 4H), 3.35 (s, 2H), 2.29 (m, 4H).

Example 10

Synthesis of Compound 324

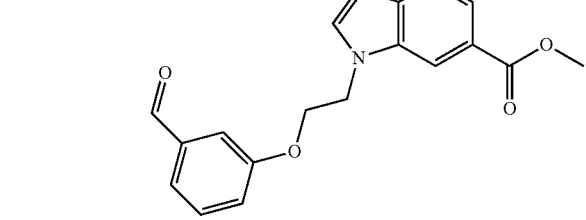

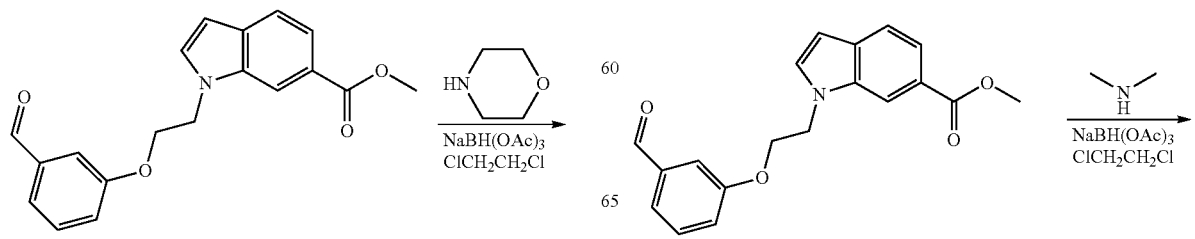

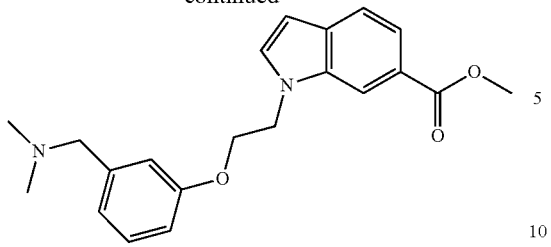

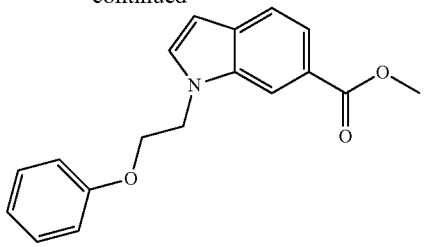

Step 1

Methyl 1-(2-(3-formylphenoxy)ethyl)-1H-indole-6-carboxylate was subjected to reductive amination conditions as described in Example 4, Step 1 to provide methyl 1-(2-(3-((dimethylamino)methyl)phenoxy)ethyl)-1H-indole-6-carboxylate

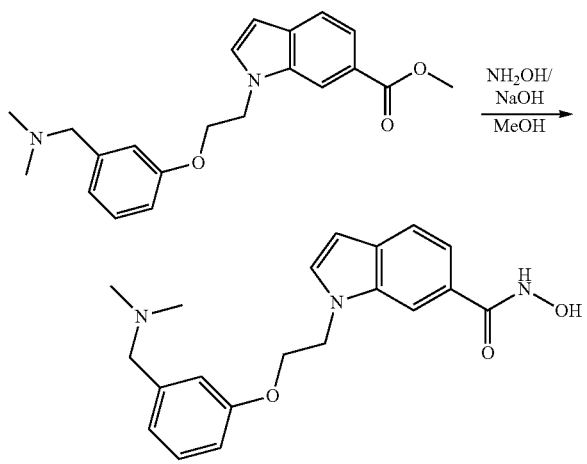

Step 2

Methyl 1-(2-(3-((dimethylamino)methyl)phenoxy)ethyl)-1H-indole-6-carboxylate was subjected to conditions as described in Example 3, Step 3 to provide 1-(2-(3-((dimethylamino)methyl)phenoxy)ethyl)-N-hydroxy-1H-indole-6-carboxamide.

$^1$H NMR (300 MHz, DMSO) δ 11.10 (s, 1H), 8.95 (s, 1H), 8.05 (s, 1H), 7.56 (m, 2H), 7.44 (dd, 1H, J=8.5 Hz, J=1.5 Hz), 7.16 (t, M, J=7.6 Hz), 6.77 (m, 3H), 6.48 (d, 1H, J=2.7 Hz), 4.60 (t, 2H, J=4.9 Hz), 4.28 (t, 1H, J=4.9 Hz), 3.28 (s, 2H), 2.08 (s, 6H).

Example 11

Synthesis of Compound 316

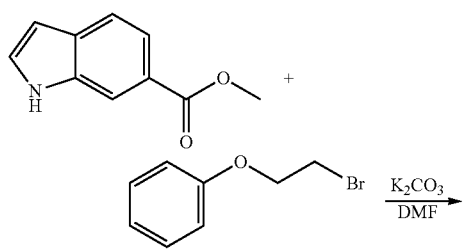

Step 1

To a solution of 1H-indole-6-carboxylic acid methyl ester (0.5 g, 2.9 mmol) and 1-(2-bromoethoxy)benzene (0.74 g, 3.7 mmol) in DMF (15 mL) was added K$_2$CO$_3$ (1.2 g, 8.6 mmol). After stirring at room temperature for 16 hr, the mixture was heated to 55° C. for 5 hr then cooled to room temperature and diluted with ethyl acetate (100 ml) and washed with water (3×50 ml). The organic layer was dried (MgSO$_4$), filtered and concentrated. The remaining residue was subjected to flash chromatography (20% ethyl acetate/hexane, then ethyl acetate) to provide 0.63 g (75%) of methyl 1-(2-phenoxyethyl)-1H-indole-6-carboxylate. $^1$H NMR (300 MHz, DMSO) δ 8.26 (d, 1H, J=1.0 Hz), 7.67-7.62 (m, 3H), 7.23 (td, 2H, J=7.6 Hz, J=1.0 Hz), 6.92-6.84 (m, 3H), 6.55 (dd, 1H, J=3.0 Hz, J=0.6 Hz), 4.66 (t, 2H, J=4.9 Hz), 4.28 (t, 2H, J=4.9 Hz), 3.86 (s, 3H).

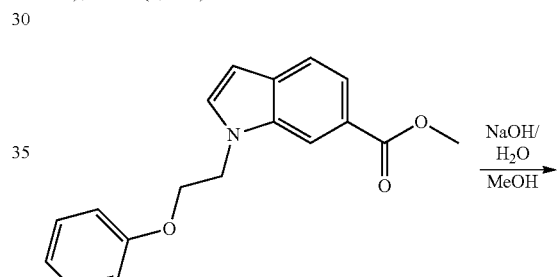

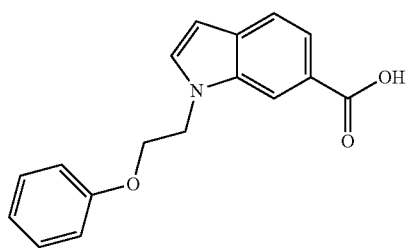

Step 2

To a solution of methyl 1-(2-phenoxyethyl)-1H-indole-6-carboxylate (0.63 g, 2.1 mmol) in methanol (15 mL) was added NaOH (0.6 g in 5 mL H$_2$O) and heated to 60° C. for 16 hr. The solvent was removed in vacuo and the residue was portioned between ethyl acetate (100 mL) and 1N HCl (100 mL). The organic layer was dried (MgSO$_4$), filtered and concentrated to collect 0.58 (97%) of 1-(2-phenoxyethyl)-1H-indole-6-carboxylic acid as a light yellow solid.

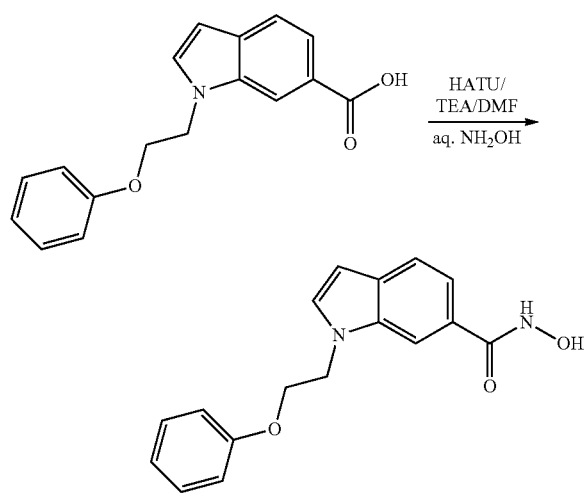

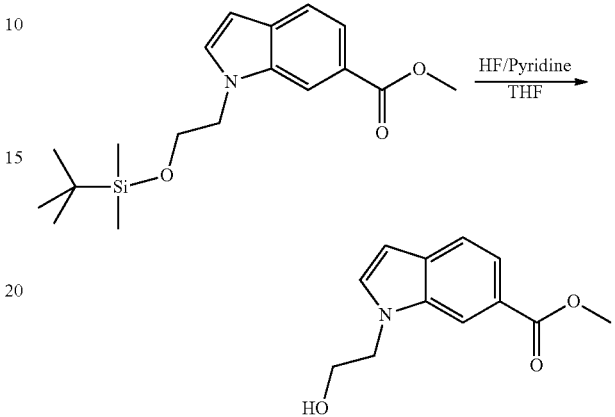

K₂CO₃ (14.6 g, 106 mmol). The mixture was heated to 60° C. for 24 hr then cooled to room temperature and diluted with ethyl acetate (300 ml) and washed with H₂O (2×200 ml). Then organic layer was dried (MgSO₄), filtered and then concentrated to provide 8.2 g of crude methyl 1-(2-ethoxy-tert-butyldimethylsilane)-1H-indole-6-carboxylate as an orange brown oil.

Step 3

To a solution of 1(2-phenoxyethyl)-1H-indole-6-carboxylic acid (0.66 g, 1.31 mmol) and TEA (0.92 mL, 6.6 mmol) in DMF (10 mL) was added HATU (0.52 g, 1.37 mmol). The solution was stirred 1 hr at room temperature, then NH₂OH (50% wt/wt in H₂O; 2 mL) was added and the solution was stirred 1 hr. The reaction solution was then diluted with ethyl acetate (150 mL) and washed with 1N HCl (100 mL) and then aq. NaHCO₃ (100 mL). Then organic layer was dried (MgSO₄), filtered and then concentrated to provide 0.57 g (93%) of N-hydroxy-1-(2-phenoxyethyl)-1H-indole-6-carboxamide a light yellow solid. ¹H NMR (300 MHz, DMSO) δ 11.11 (s, 1H), 8.94 (s, 1H), 8.06 (s, 1H), 7.56 (m, 2H), 7.66 (dd, 1H, J=8.5 Hz, J=1.5 Hz), 7.24 (m, 2H), 6.88 (m, 3H), 6.48 (d, 1H, J=3.0 Hz), 4.61 (t, 2H, J=5.2 Hz), 4.30 (t, 2H, J=5.2 Hz). EM (calc.): 296.12; MS (M+H): 297.06.

Step 2

To a solution of methyl 1-(2-ethoxy-tert-butyldimethylsilane)-1H-indole-6-carboxylate (21.2 mmol) in THF (50 mL) cooled with an ice bath was added HF/Pyridine (70% wt., ~2 mL). The solution was stirred for 1 hr with ice cooling, then 4 hr at room temperature. The solvent was removed in vacuo, then the residue was dissolved in ethyl acetate (200 mL) and washed with H₂O (2×200 mL). Then organic layer was dried (MgSO₄), filtered and then concentrated to provide 4.67 g (~100%) of crude methyl 1-(2-hydroxyethyl)-1H-indole-6-carboxylate as an orange solid. ¹H NMR (300 MHz, DMSO) δ 8.14 (s, 1H), 7.60 (m, 3H), 6.52 (d, 1H, J=3.0 Hz), 4.29 (t, 2H, J=5.5 Hz), 3.85 (s, 3H), 3.71 (t, 2H, J=5.5 Hz).

Example 12

Synthesis of Compound 318

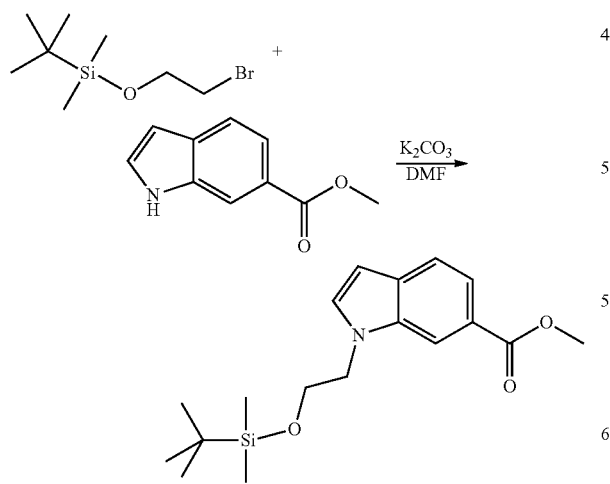

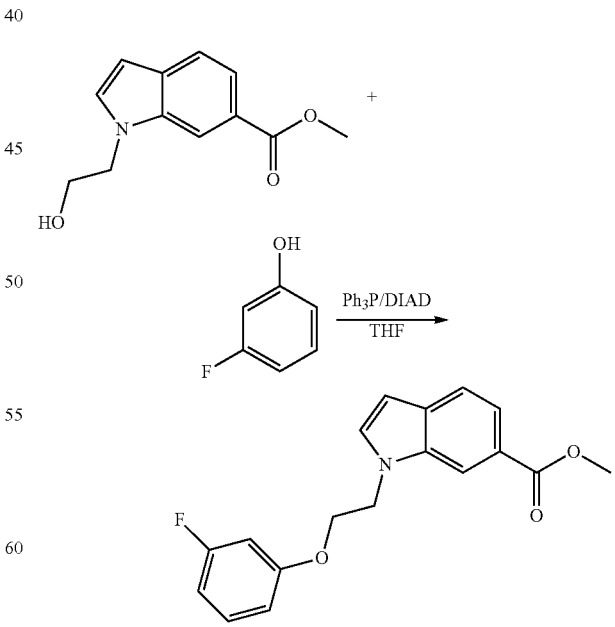

Step 1

To a solution of 1H-indole-6-carboxylic acid methyl ester (3.7 g, 21.2 mmol) and (2-bromoethoxy)(tert-butyl)dimethylsilane (5.6 g, 23.3 mmol) in DMF (40 mL) was added

Step 3

To a solution of methyl 1-(2-hydroxyethyl)-1H-indole-6-carboxylate (0.14 g, 0.64 mmol) and Ph₃P (0.25 mL, 0.96 mmol) and 3-fluorophenol (0.11 g, 0.96 mmol) in THF (10 mL) was added DIAD (0.19 mL, 0.96 mmol). The solution was stirred 1 hr at room temperature, then concentrated and subjected to flash chromatography (25% ethyl acetate/hexane) to provide 0.22 g (~100%) of methyl 1-(2-(3-fluorophenoxy)ethyl)-1H-indole-6-carboxylate as a colorless oil.

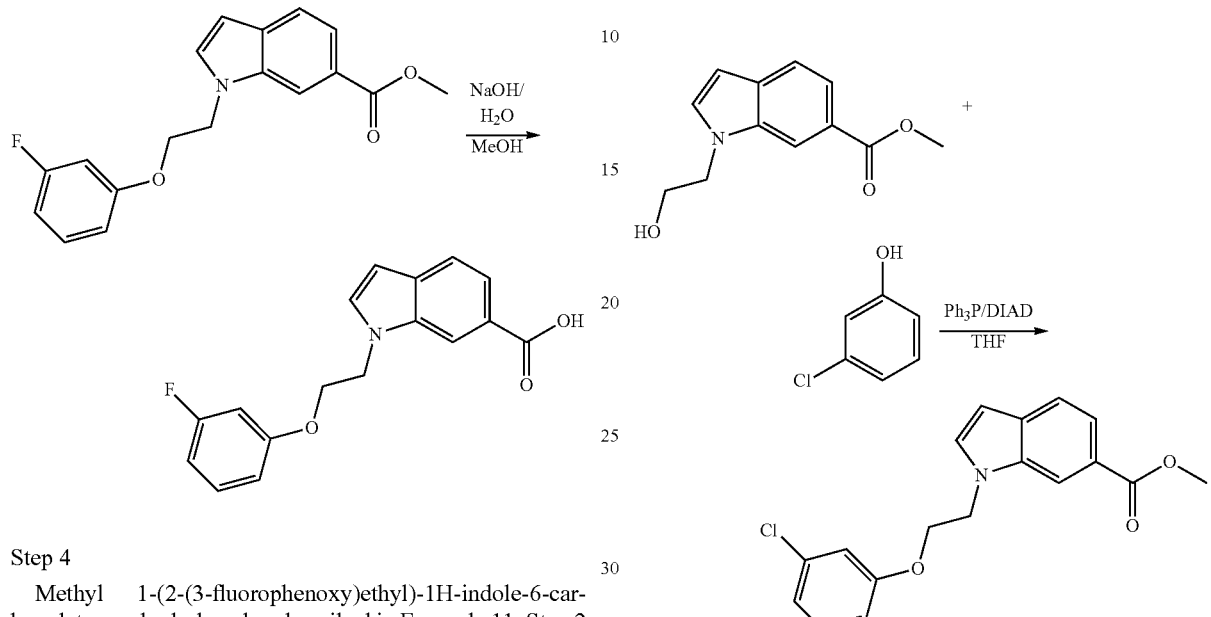

Step 4

Methyl 1-(2-(3-fluorophenoxy)ethyl)-1H-indole-6-carboxylate was hydrolyzed as described in Example 11, Step 2 to provide 1-(2-(3-fluorophenoxy)ethyl)-1H-indole-6-carboxylic acid as a white solid.

Step 5

1-(2-(3-fluorophenoxy)ethyl)-1H-indole-6-carboxylic acid was converted to the hydroxamic acid as described in Example 11, Step 3 to provide 1-(2-(3-fluorophenoxy)ethyl)-N-hydroxy-1H-indole-6-carboxamide. $^1$H NMR (300 MHz, DMSO) δ 11.09 (s, 1H), 8.94 (s, 1H), 8.05 (s, 1H), 7.56 (m, 2H), 7.44 (m, 1H), 7.27 (m, 1H), 6.76 (m, 3H), 6.49 (d, 1H, J=2.7 Hz), 4.60 (t, 2H, J=5.2 Hz), 4.33 (t, 2H, J=5.2 Hz). EM (calc.): 314.11; MS (M+H): 314.95.

Example 13

Synthesis of Compound 321

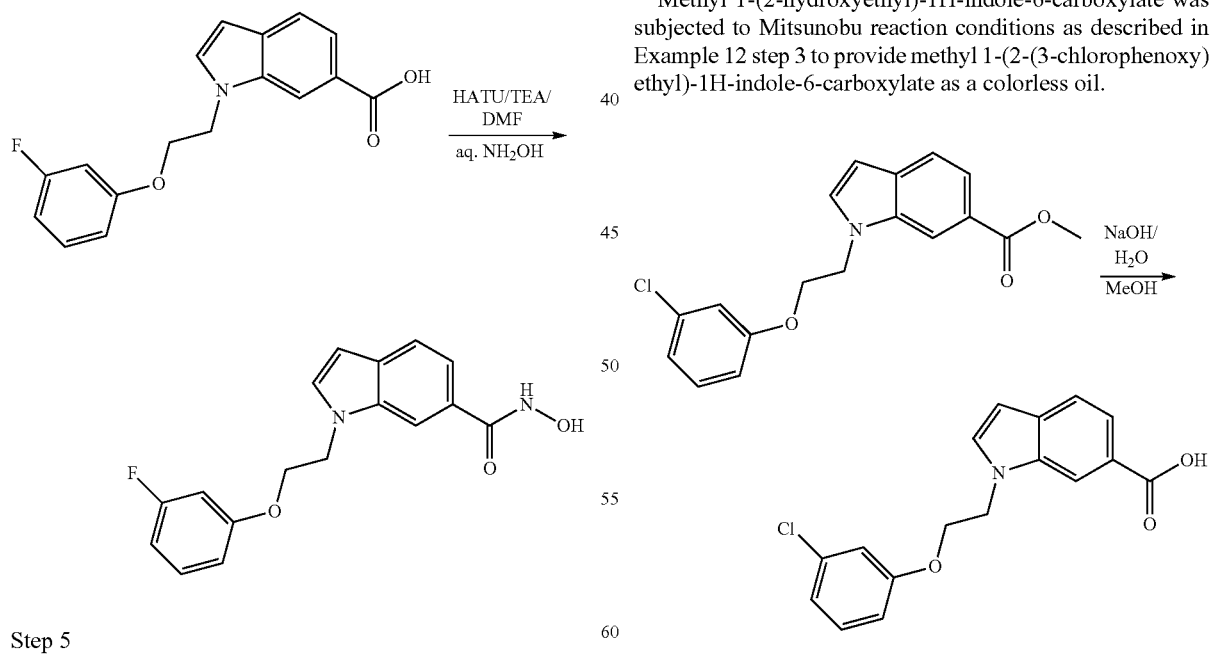

Step 1

Methyl 1-(2-hydroxyethyl)-1H-indole-6-carboxylate was subjected to Mitsunobu reaction conditions as described in Example 12 step 3 to provide methyl 1-(2-(3-chlorophenoxy)ethyl)-1H-indole-6-carboxylate as a colorless oil.

Step 2

Methyl 1-(2-(3-chorophenoxy)ethyl)-1H-indole-6-carboxylate was hydrolyzed as described in Example 11, Step 2 to provide 1-(2-(3-chlorophenoxy)ethyl)-1H-indole-6-carboxylic acid as a white solid.

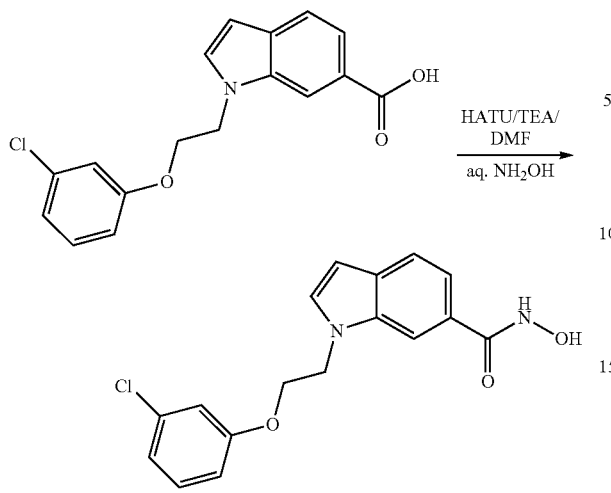

Step 3

1-(2-(3-Chlorophenoxy)ethyl)-1H-indole-6-carboxylic acid was converted to the hydroxamic acid as described in Example 11, Step 3 to provide 1-(2-(3-chlorophenoxy)ethyl)-N-hydroxy-1H-indole-6-carboxamide as a tan solid. $^1$H NMR (300 MHz, DMSO) δ 11.09 (s, 1H), 8.93 (s, 1H), 8.04 (s, 1H), 7.55 (m, 2H), 7.44 (m, 1H), 7.25 (m, 1H), 6.96 (m, 2H), 6.86 (m, 1H), 6.49 (d, 1H, J=3.0 Hz), 4.60 (t, 2H, J=5.5 Hz), 4.34 (t, 2H, J=5.5 Hz). EM (calc.): 330.08; MS (M+H): 330.94.

Example 14

Synthesis of Compound 317

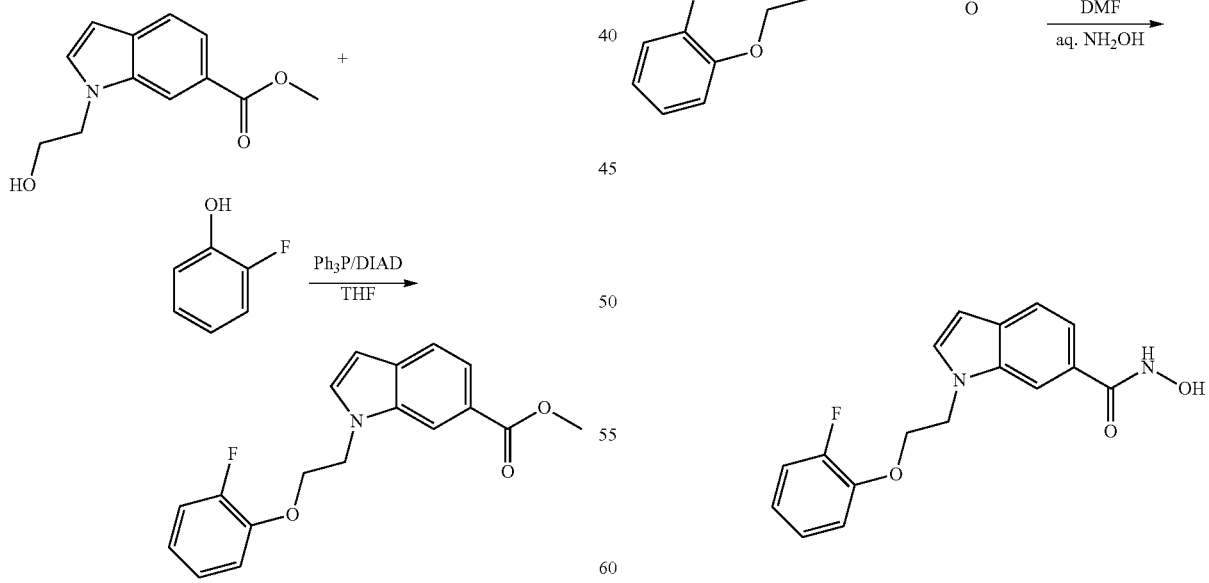

Step 1

Methyl 1-(2-hydroxyethyl)-1H-indole-6-carboxylate was subjected to Mitsunobu reaction conditions as described in Example 12 step 3 to provide methyl 1-(2-(2-fluorophenoxy)ethyl)-1H-indole-6-carboxylate as a colorless oil.

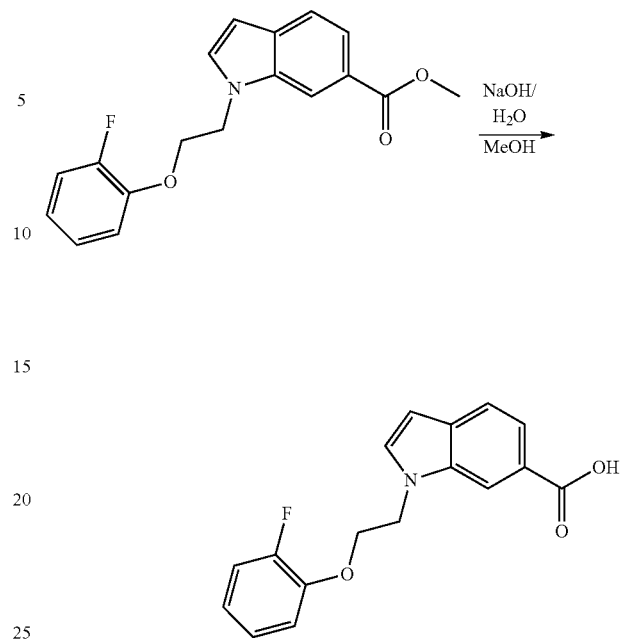

Step 2

Methyl 1-(2-(2-fluorophenoxy)ethyl)-1H-indole-6-carboxylate was hydrolyzed as described in Example 11, Step 2 to provide 1-(2-(2-fluorophenoxy)ethyl)-1H-indole-6-carboxylic acid as a white solid.

Step 3

1-(2-(2-fluorophenoxy)ethyl)-1H-indole-6-carboxylic acid was converted to the hydroxamic acid as described in Example 11, Step 3 to provide 1-(2-(2-fluorophenoxy)ethyl)-N-hydroxy-1H-indole-6-carboxamide as a tan solid. $^1$H NMR (300 MHz, DMSO) δ 11.07 (s, 1H), 8.92 (s, 1H), 8.03 (s, 1H), 7.55 (m, 2H), 7.43 (m, 1H), 7.16-7.06 (m, 3H), 6.90

(m, 1H), 6.49 (d, 1H, J=3.0 Hz), 4.63 (t, 2H, J=4.9 Hz), 4.38 (t, 2H, J=4.9 Hz). EM (calc.): 314.11; MS (M+H): 315.03.

Example 15

Synthesis of Compound 320

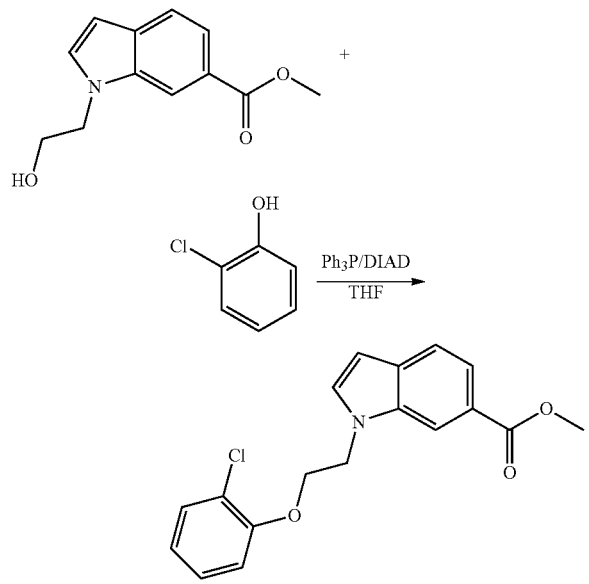

Step 1

Methyl 1-(2-hydroxyethyl)-1H-indole-6-carboxylate was subjected to Mitsunobu reaction conditions as described in Example 12 step 3 to provide methyl 1-(2-(2-chlorophenoxy)ethyl)-1H-indole-6-carboxylate.

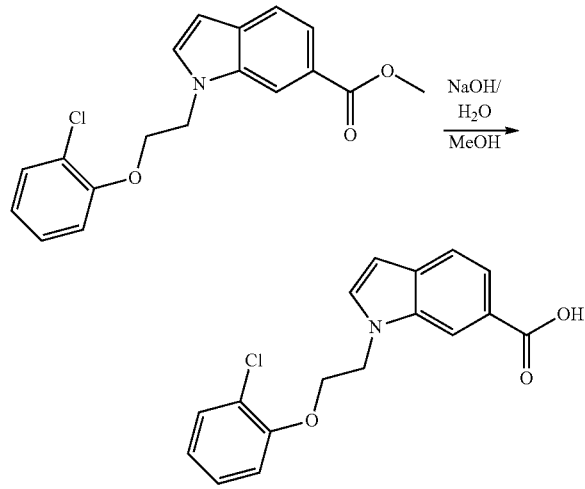

Step 2

Methyl 1-(2-(2-chlorophenoxy)ethyl)-1H-indole-6-carboxylate was hydrolyzed as described in Example 11, Step 2 to provide 1-(2-(2-chlorophenoxy)ethyl)-1H-indole-6-carboxylic acid as a white solid.

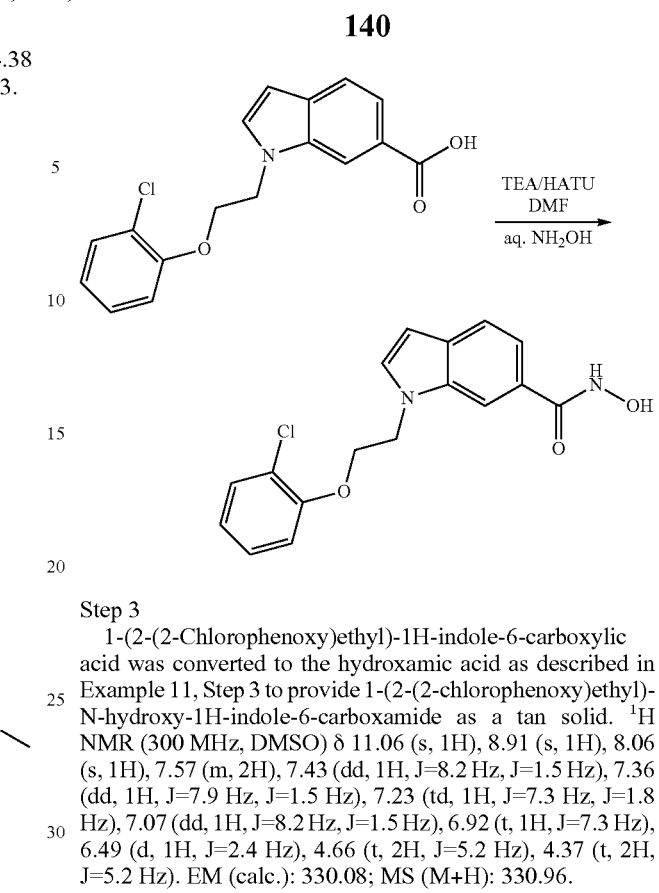

Step 3

1-(2-(2-Chlorophenoxy)ethyl)-1H-indole-6-carboxylic acid was converted to the hydroxamic acid as described in Example 11, Step 3 to provide 1-(2-(2-chlorophenoxy)ethyl)-N-hydroxy-1H-indole-6-carboxamide as a tan solid. $^1$H NMR (300 MHz, DMSO) δ 11.06 (s, 1H), 8.91 (s, 1H), 8.06 (s, 1H), 7.57 (m, 2H), 7.43 (dd, 1H, J=8.2 Hz, J=1.5 Hz), 7.36 (dd, 1H, J=7.9 Hz, J=1.5 Hz), 7.23 (td, 1H, J=7.3 Hz, J=1.8 Hz), 7.07 (dd, 1H, J=8.2 Hz, J=1.5 Hz), 6.92 (t, 1H, J=7.3 Hz), 6.49 (d, 1H, J=2.4 Hz), 4.66 (t, 2H, J=5.2 Hz), 4.37 (t, 2H, J=5.2 Hz). EM (calc.): 330.08; MS (M+H): 330.96.

Example 16

Synthesis of Compound 326

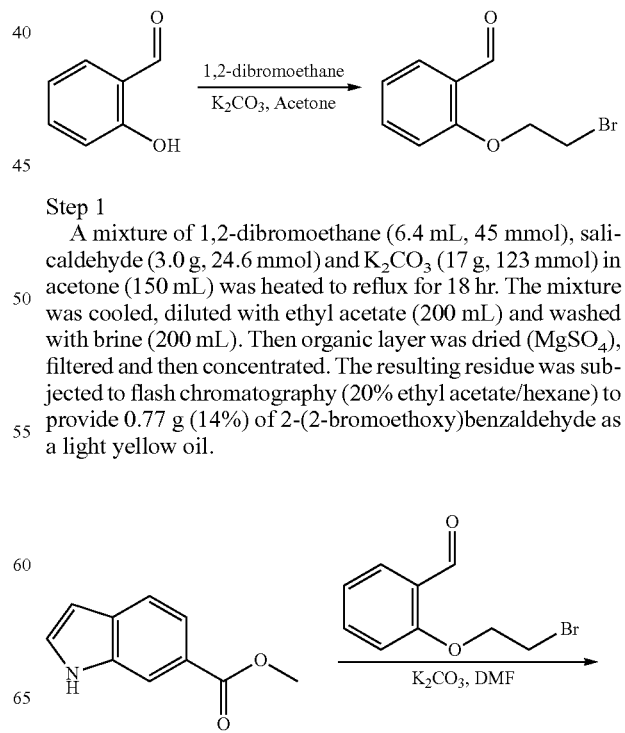

Step 1

A mixture of 1,2-dibromoethane (6.4 mL, 45 mmol), salicaldehyde (3.0 g, 24.6 mmol) and K$_2$CO$_3$ (17 g, 123 mmol) in acetone (150 mL) was heated to reflux for 18 hr. The mixture was cooled, diluted with ethyl acetate (200 mL) and washed with brine (200 mL). Then organic layer was dried (MgSO$_4$), filtered and then concentrated. The resulting residue was subjected to flash chromatography (20% ethyl acetate/hexane) to provide 0.77 g (14%) of 2-(2-bromoethoxy)benzaldehyde as a light yellow oil.

141

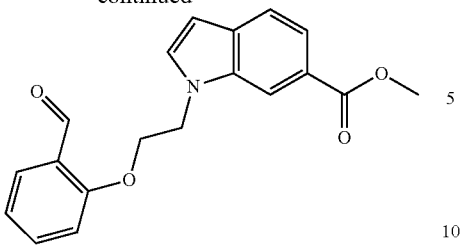

142

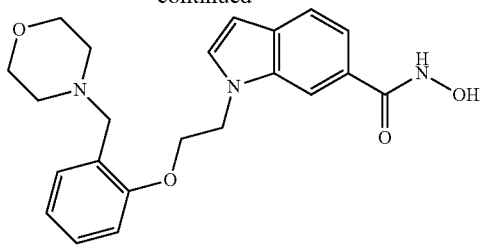

Step 2

1H-indole-6-carboxylic acid methyl ester was subjected to alkylation conditions as described in Example 11, step 1 to provide methyl 1-(2-(2-formylphenoxy)ethyl)-1H-indole-6-carboxylate as a light yellow oil. $^1$H NMR (300 MHz, DMSO) δ 10.17 (s, 1H), 8.23 (s, 1H), 7.75 (d, 1H, J=3.0 Hz), 7.63-7.56 (m, 4H), 7.17 (d, 1H, J=8.2 Hz), 7.03 (t, 2H, J=7.6 Hz), 6.56 (d, 1H, J=3.0 Hz), 4.77 (t, 2H, J=4.9 Hz), 4.44 (t, 2H, J=4.9 Hz), 3.85 (s, 3H).

Step 4

To a solution of methyl 1-(2-(2-(morpholinomethyl)phenoxy)ethyl)-1H-indole-6-carboxylate (0.3 g, 0.83 mmol) in methanol (25 mL) was added a premixed (5 min) solution of NaOH (0.24 g, 6 mmol) and NH$_2$OH (50% wt/wt in H$_2$O, 1 mL) and H$_2$O (2 mL). After stirring 5 hr at room temperature, the solution was concentrated and then diluted with H$_2$O (30 mL) and the pH was adjusted to ~9 with 1N HCl. The mixture was then extracted with ethyl acetate (100 mL) and concentrated to ~3 mL and allowed to sit at room temperature for 16 hr. The resulting solid was isolated by filtration to provide 96 mg (29%) of 1-(2-(2-(morpholinomethyl)phenoxy)ethyl)-N-hydroxy-1H-indole-6-carboxamide as a tan solid. $^1$H NMR (300 MHz, DMSO) δ 11.11 (s, 1H), 8.90 (s, 1H), 8.03 (s, 1H), 7.62-7.55 (m, 2H), 7.44 (d, 1H, J=8.2 Hz), 7.19 (m, 2H), 6.90 (m, 2H), 6.50 (d, 1H, J=3.0 Hz), 4.63 (t, 2H, J=5.2 Hz), 4.30 (t, 2H, J=5.2 Hz), 3.43 (m, 4H), 3.18 (s, 2H), 2.12 (m, 4H). EM (calc.): 395.18; MS (M+H): 396.04.

Example 17

Synthesis of Compound 232

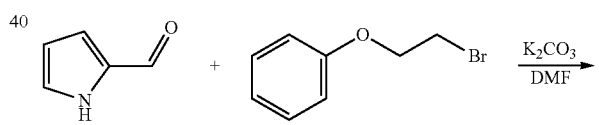

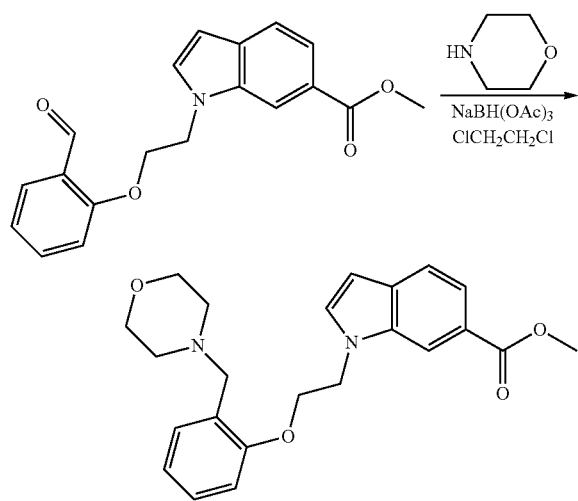

Step 3

To a solution of methyl 1-(2-(2-formylphenoxy)ethyl)-1H-indole-6-carboxylate (0.27 g, 0.84 mmol) and morpholine (0.22 mL, 2.5 mmol) in 1,2-dichloroethane (20 mL) was added NaBH(OAc)$_3$ (0.35 g, 1.7 mmol). After stirring the solution for 4 hr at room temperature, the solution was concentrated and then diluted with ethyl acetate (100 mL) and washed with H$_2$O (100 mL). The organic layer was dried (MgSO$_4$), filtered and then concentrated to provide 0.33 g (~100%) of methyl 1-(2-(2-(morpholinomethyl)phenoxy)ethyl)-1H-indole-6-carboxylate as an orange oil.

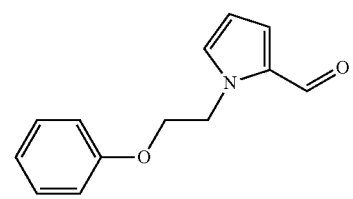

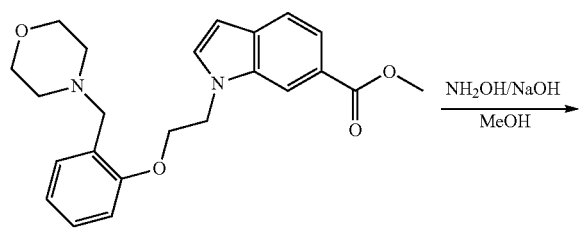

Step 1

To a solution of 1H-pyrrole-2-carbaldehyde (0.45 g, 4.8 mmol) and 1-(2-bromoethoxy)benzene (1.1 g, 5.3 mmol) in DMF (20 mL) was added K$_2$CO$_3$ (3.3 g, 24 mmol). After stirring 16 hr at room temperature, the mixture was diluted with ethyl acetate (200 mL) and washed with H$_2$O (2×100 mL) then brine (100 mL). The organic layer was dried (MgSO$_4$), filtered and then concentrated to provide 1.1 g (~100%) of crude 1-(2-phenoxyethyl)-1H-pyrrole-2-carbaldehyde as a light yellow oil.

6.93-6.84 (m, 3H), 6.50 (d, 1H, J=1.8 Hz), 6.10 (m, 2H), 4.41 (t, 2H, J=4.9 Hz), 4.14 (t, 2H, J=4.9 Hz).

Example 18

Synthesis of Compound 234

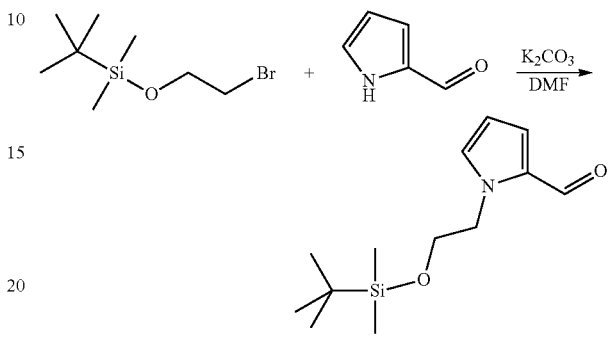

Step 1

1H-Pyrrole-2-carbaldehyde was alkylated with (2-bromoethoxy)(tert-butyl)dimethylsilane as described in Example 12, step 1 to provide 1-(2-ethoxy-tert-butyldimethylsilane-1H-pyrrole-2-carbaldehyde as a light yellow oil.

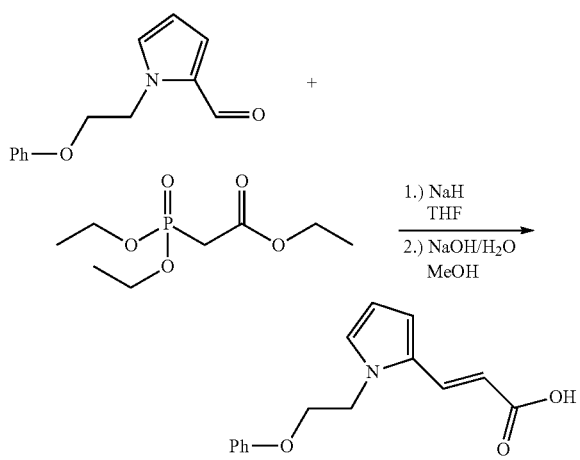

Step 2

To a solution of 1-(2-phenoxyethyl)-1H-pyrrole-2-carbaldehyde (0.68 g, 3.2 mmol) triethyl phosphonoacetate (0.76 mL, 3.8 mmol) in THF (20 mL) was added NaH (91 mg, 3.8 mmol. 60% wt.). The mixture was stirred for 2 hr at room temperature then diluted with ethyl acetate (100 mL) and washed with water (100 mL). The organic layer was dried (MgSO₄), filtered and then concentrated. The crude ethyl ester was stirred in MeOH (20 mL) and NaOH (0.9 g, 22 mmol/dissolved in 10 mL H₂O) was added. After stirring at room temperature for 24 hr, the solution was concentrated and then diluted with H₂0 (50 mL) and extracted with ether (2×100 mL). The aqueous layer was acidified (1N HCl) to pH=2-3 and then extracted with ethyl acetate (100 mL). The organic layer was dried (MgSO4), filtered and then concentrated to provide 0.47 g (58%) of (E)-3-(1-(2-phenoxyethyl)-1H-pyrrol-2-yl)acrylic acid as a light yellow solid.

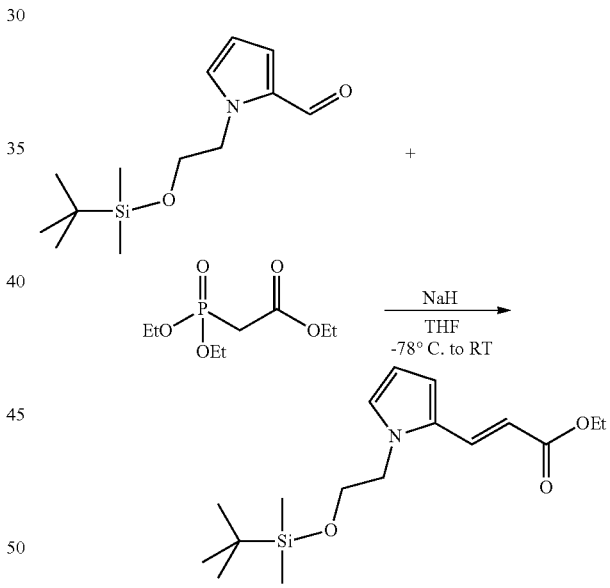

Step 2

To a solution of 1-(2-ethoxy-tert-butyldimethylsilane-1H-pyrrole-2-carbaldehyde (0.87 g, 3.4 mmol), triethyl phosphonoacetate (0.76 mL, 3.8 mmol) in THF (15 mL) cooled to −78° C. was added NaH (91 mg, 3.8 mmol. 60% wt.). The mixture was stirred at −78° C. for 5 min and then the cooling bath was removed and the reaction solution was stirred at room temperature for 16 hr. The solution was diluted with ethyl acetate 9100 mL) and washed with 1N HCl (100 mL). The organic layer was dried (MgSO₄), filtered and then concentrated. The residue was subjected to flash chromatography (5% ethyl acetate/hexane) to provide 0.72 g (65%) of (E)-ethyl-3-(1-(2-ethoxy-tert-butyldimethylsilane)-1H-pyrrol-2-yl)acrylate.

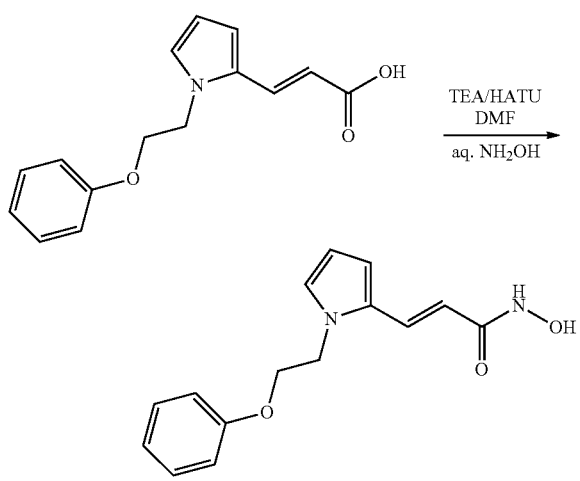

Step 3

(E)-3-(1-(2-phenoxyethyl)-1H-pyrrol-2-yl)acrylic was converted to (E)-N-hydroxy-3-(1-(2-phenoxyethyl)-1H-pyrrol-2-yl)acrylamide hydroxamic acid as described in Example 11, Step 3 to provide as a light yellow solid. ¹H NMR (300 MHz, DMSO) δ 10.55 (s, 1H), 8.90 (s, 1H), 7.54 (d, 1H, J=15.3 Hz), 7.24 (t, 2H, J=7.9 Hz), 7.01 (s, 1H),

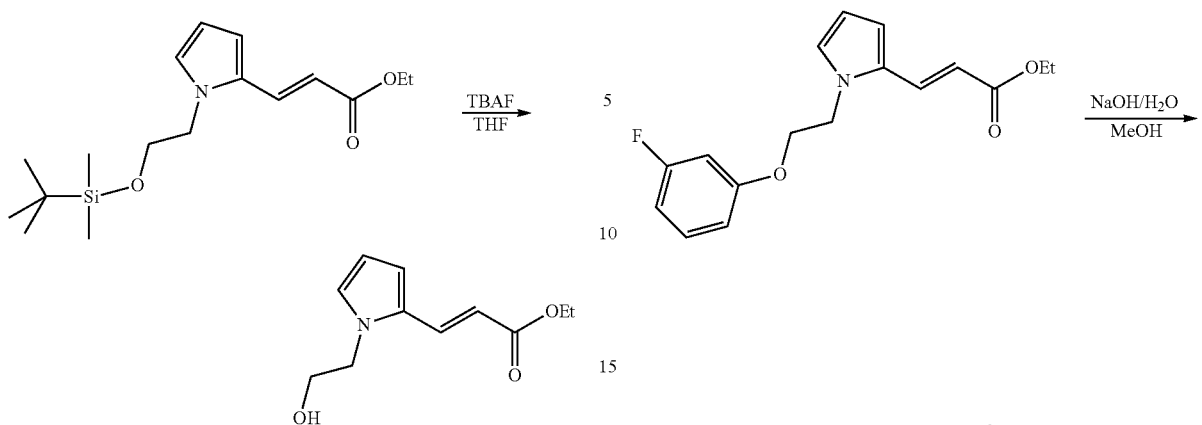

Step 3

To a solution of (E)-ethyl-3-(1-(2-ethoxy-tert-butyldimethylsilane)-1H-pyrrol-2-yl)acrylate (0.72 g, 2.2 mmol) in THF (15 mL) was added TBAF (1.0M solution in THF, 2.2 mL, 2.2 mmol) and the solution was stirred for 2 hr at room temperature, then concentrated, diluted with ethyl acetate (75 mL) and washed with 1N HCl (75 mL). The organic layer was dried (MgSO$_4$), filtered and then concentrated to provide 0.48 g (~100%) of (E)-ethyl 3-(1-(2-hydroxyethyl)-1H-pyrrol-2-yl)acrylate. $^1$H NMR (300 MHz, DMSO) δ 7.56 (d, 1H, J=15.6 Hz), 7.02 (t, 1H, J=1.5 Hz), 6.78 (dd, 1H, J=4.0 Hz, J=1.5 Hz), 6.19 (d, 1H, J=15.6 Hz), 6.11 (m, 1H), 4.94 (t, 1H, J=6.0 Hz), 4.13 (q, 2H, J=6.0 Hz), 4.06 (t, 2H, J=6.0 Hz), 4.14 (t, 2H, J=4.9 Hz), 3.58 (q, 2H, J=7.0 Hz), 1.22 (t, 3H, J=7.0 Hz).

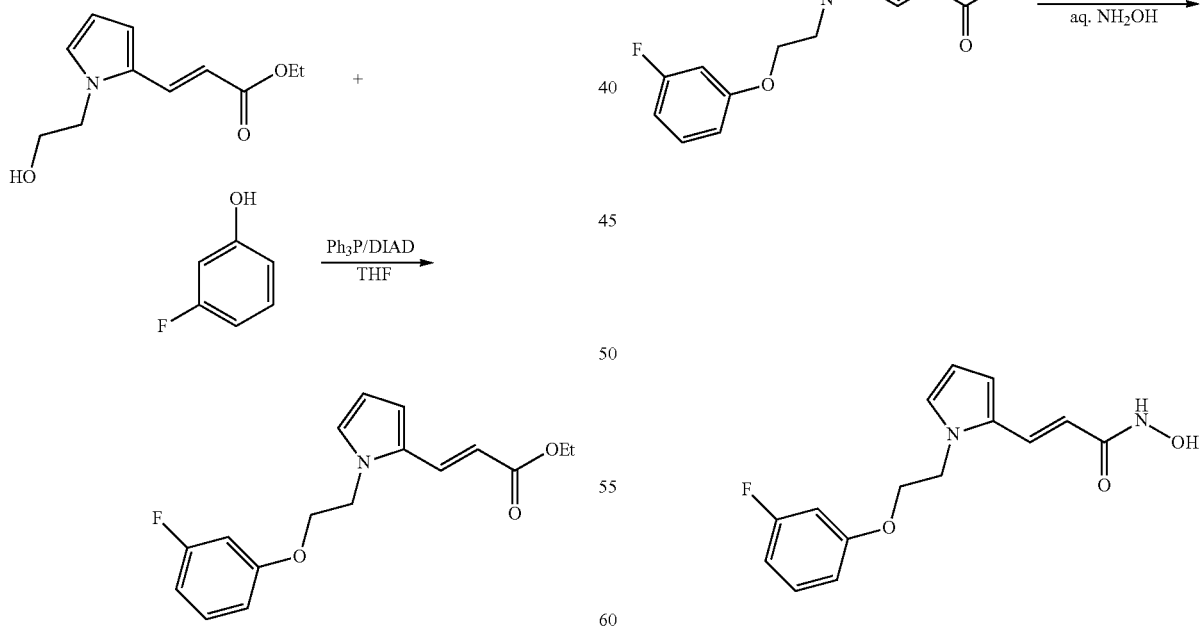

Step 4

(E)-Ethyl 3-(1-(2-hydroxyethyl)-1H-pyrrol-2-yl)acrylate was subjected to Mitsunobu reaction conditions as described in Example 12 step 3 to provide (E)-ethyl 3-(1-(2-(3-fluorophenoxy)ethyl)-1H-pyrrol-2-yl)acrylate.

Step 5

(E)-Ethyl 3-(1-(2-(3-fluorophenoxy)ethyl)-1H-pyrrol-2-yl)acrylate was hydrolyzed as described in Example 11, Step 2 to provide (E)-3-(1-(2-(3-fluorophenoxy)ethyl)-1H-pyrrol-2-yl)acrylic acid as a yellow oil/solid.

Step 6

(E)-3-(1-(2-(3-fluorophenoxy)ethyl)-1H-pyrrol-2-yl) acrylic acid was converted to the hydroxamic acid as described in Example 11, Step 3 to provide (E)-3-(1-(2-(3-fluorophenoxy)ethyl)-1H-pyrrol-2-yl)-N-hydroxyacrylamide as a light yellow solid. $^1$H NMR (300 MHz, DMSO) δ 10.54 (s, 1H), 8.89 (s, 1H), 7.53 (d, 1H, J=15.6 Hz), 7.27 (q, 1H, J=5.5 Hz), 7.44 (m, 1H), 7.00 (s, 1H), 6.77-6.69 (m, 3H), 6.50 (d, 1H, J=2.4 Hz), 6.15-6.09 (m, 2H), 4.41 (t, 2H, J=4.9 Hz), 4.17 (t, 2H, J=4.9 Hz).

Example 19

Synthesis of Compound 255

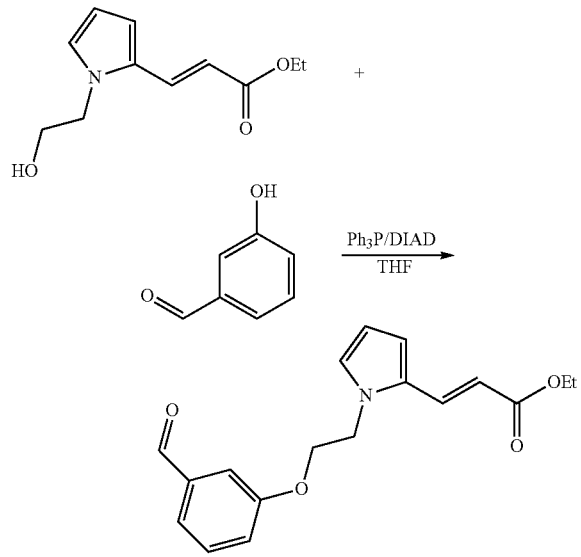

Step 1

(E)-Ethyl 3-(1-(2-hydroxyethyl)-1H-pyrrol-2-yl)acrylate was subjected to Mitsunobu reaction conditions as described in Example 12 step 3 to provide (E)-ethyl 3-(1-(2-(3-formylphenoxy)ethyl)-1H-pyrrol-2-yl)acrylate. $^1$H NMR (300 MHz, DMSO) δ 9.93 (s, 1H), 7.71 (d, 1H, J=15.6 Hz), 7.49 (d, 2H, J=4.9 Hz), 7.34 (d, 1H, J=2.8 Hz), 7.18 (m, 1H), 7.11 (t, 1H, J=1.8 Hz), 6.81 (dd, 1H, J=3.7 Hz, J=1.2 Hz), 6.22 (d, 1H, J=15.6 Hz), 6.14 (dd, 1H, J=3.7 Hz, J=2.8 Hz), 4.47 (t, 2H, J=4.9 Hz), 4.14 (q, 2H, J=7.0 Hz), 1.23 (t, 3H, J=7.0 Hz).

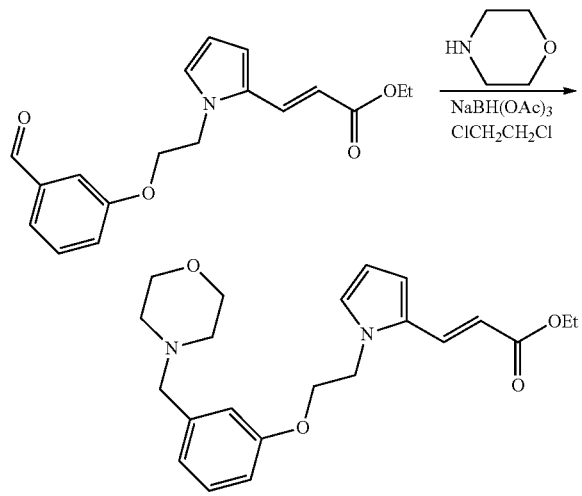

Step 2

(E)-ethyl 3-(1-(2-(3-formylphenoxy)ethyl)-1H-pyrrol-2-yl)acrylate was subjected to reductive amination conditions as described in Example 16, step 3 to provide (E)-ethyl 3-(1-(2-(3-(morpholinomethyl)phenoxy)ethyl)-1H-pyrrol-2-yl) acrylate.

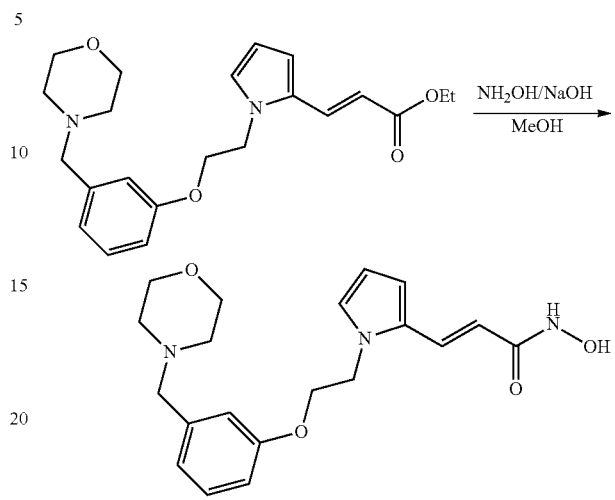

Step 3

(E)-Ethyl 3-(1-(2-(3-(morpholinomethyl)phenoxy)ethyl)-1H-pyrrol-2-yl)acrylate, was subjected to hydrolysis conditions as described in Example 16, step 4 to provide (E)-3-(1-(2-(3-(morpholinomethyl)phenoxy)ethyl)-1H-pyrrol-2-yl)-N-hydroxyacrylamide as a light yellow solid. $^1$H NMR (300 MHz, DMSO) δ 10.54 (s, 1H), 8.90 (s, 1H), 7.52 (d, 1H, J=15.6 Hz), 7.18 (t, 1H, J=7.6 Hz), 7.01 (s, 1H), 6.85 (d, 1H, J=7.6 Hz), 6.75 (m, 2H), 6.50 (d, 1H, J=2.5 Hz), 6.10 (m, 2H), 4.40 (t, 2H, J=4.9 Hz), 4.13 (t, 2H, J=4.9 Hz), 3.55 (m, 4H), 3.38 (s, 2H), 2.30 (m, 4H).

Biological Examples

Cell Lines and Reagents

Cell lines were obtained from DSMZ (Braunschweig, Germany) or ATCC (Manassas, Va.). Cells were grown in RPMI 1640 with 10% fetal bovine serum in a 5% $CO_2$/air incubator at 37° C. Thapsigargin and BAPTA-AM were from Calbiochem (San Diego, Calif.). 3-((dimethylamino)methyl)-N-(2-(4-(hydroxycarbamoyl)phenoxy)ethyl)benzofuran-2-carboxamide is a broad-spectrum HDAC inhibitor which was synthesized as previously described. Other analogs with varying degrees of specificity towards the HDAC isoforms were synthesized as described herein.

Example 20

Histone Deacetylase Activity

HDAC activity was measured using a continuous trypsin-coupled assay that has been described in detail previously (US 20070281934; Schultz et. al., *Biochemistry*, 43 (34), 11083-11091, 2004; Kim et al. (2006), *Methods Mol. Biol.*, 325:273-283). For inhibitor characterization, measurements were performed in a reaction volume of 100 μL using 96-well assay plates in a fluorescence plate reader. For each isozyme, the HDAC protein in reaction buffer (50 mM HEPES, 100 mM KCl, 0.001% Tween-20, 5% DMSO, pH 7.4, supplemented with bovine serum albumin at concentrations of 0-0.05%, was mixed with inhibitor at various concentrations and allowed to incubate for 15 minutes. Trypsin was added to a final concentration of 50 nM, and acetyl-Gly-Ala-(N-acetyl-Lys)-AMC was added to a final concentration of 25-100 µM to initiate the reaction. After a 30 minute lag time, the fluorescence was measured over a 30 minute time frame using an excitation wavelength of 355 nm and a detection wavelength of 460 nm. The increase in fluorescence with time was used as the measure of the reaction rate. Inhibition constants $K_i(app)$ were obtained using the program BatchKi (Biokin, Pullman, Wash.). The results are summarized in Table 8 below.

TABLE 8

Comparison of HDAC $IC_{50}$ values of Representative HDAC8-selective inhibitors

| Compound No. | HDAC1 $IC_{50}$ | HDAC2 $IC_{50}$ | HDAC3 $IC_{50}$ | HDAC6 $IC_{50}$ | HDAC8 $IC_{50}$ | HDAC10 $IC_{50}$ |
|---|---|---|---|---|---|---|
| 307 | ND | C  | ND | ND | A | ND |
| 311 | ND | C  | ND | ND | A | ND |
| 315 | ND | C  | ND | ND | A | ND |
| 309 | ND | C  | ND | ND | A | ND |
| 310 | ND | C  | ND | ND | A | ND |
| 313 | ND | B  | ND | ND | A | ND |
| 316 | C  | ND | ND | C  | A | ND |
| 325 | C  | C  | C  | B  | A | C  |
| 327 | C  | C  | C  | B  | A | C  |
| 324 | C  | C  | C  | B  | A | C  |
| 329 | C  | C  | C  | C  | A | C  |
| 326 | C  | ND | ND | C  | A | C  |
| 318 | C  | ND | ND | B  | A | ND |
| 321 | C  | ND | ND | B  | A | ND |
| 317 | C  | ND | ND | B  | A | ND |
| 320 | C  | ND | ND | B  | A | ND |
| 1   | C  | ND | ND | B  | A | ND |
| 203 | C  | ND | ND | B  | A | ND |
| 232 | C  | ND | ND | B  | A | ND |
| 255 | C  | ND | ND | B  | A | ND |
| 234 | B  | ND | ND | B  | A | ND |

ND = not determined
A = less than 1 µM
B = greater than 1 µM but less than 10 µM
C = greater than 10 µM The data presented above show that compounds described herein are selective inhibitors of HDAC8.

Example 21

Cell Proliferation Assay

Tumor cell lines and human umbilical vein endothelial cells (HUVEC) were cultured for at least two doubling times, and growth was monitored at the end of compound exposure using an Alamar Blue™ (Biosource, Camarillo, Calif.) fluorometric cell proliferation assay as recommended by the manufacturer. Compounds were assayed in triplicate wells in 96-well plates. The concentration required to inhibit cell growth by 50% ($GI_{50}$) and 95% confidence intervals were estimated from nonlinear regression using a 4-parameter logistic equation. The effect of HDAC8 selective inhibitor compounds on cell proliferation in Jurkat cells was measured. Apoptosis was measured by Annexin-V flow cytometry. Growth inhibition was measured by Alamar Blue assay. Growth Inhibition of Jurkat Cells measured by Alamar Blue assay is shown in Table 9. Cells were treated with compound for 3 days.

TABLE 9

Growth Inhibition of Jurkat Cells measured by Alamar Blue assay

| Compound | GI50 (µM) |
|---|---|
| 316 | 2.8 |
| 306 | 3.6 |
| 232 | 4.98 |
| 255 | 20.46 |
| 234 | 4.3 |
| 329 | 20.7 |
| 328 | 12.5 |
| 327 | 4.95 |
| 325 | 13.4 |
| 324 | 7.4 |
| 308 | 5.2 |
| 313 | 5.2 |
| 310 | 16 |
| 309 | 19.2 |
| 303 | 3.5 |
| 330 | 4.7 |
| 302 | 25.2 |

Example 22

Western Blotting

Cells were washed with PBS and resuspended in triple-detergent lysis buffer [50 mM Tris-Cl (pH 8.0), 150 mM NaCl, 0.1% SDS, 0.5% deoxycholic acid, 1.0% NP-40, supplemented with 1 mM EDTA, 1 mM PMSF, 1 mM $Na_3VO_4$, 2 mM β-glycerophosphate and the COMPLETE protease inhibitor cocktail (Roche Molecular Biochemicals, Indianapolis, Ind.)] on ice for 10 minutes. After centrifugation, equal quantities of protein were resolved on SDS-polyacrylamide gels (Bio-Rad Laboratories, Hercules, Calif.). Gels were transferred to polyvinylidene difluoride membrane using a Semi-dry Transfer Cell (Bio-Rad Laboratories, Hercules, Calif.) and Western blotted, using an anti-Hsc70 antibody to control for loading and transfer. Bands were imaged and quantified in the linear range and normalized to Hsc70, using the Odyssey Infrared Imaging System (LICOR, Lincoln, Nebr.).

Example 23

Apoptosis Assays

Cytotoxicity was evaluated after 2 or 3 days of treatment with Compound G alone and in combination with qVD, BAPTA-AM, thapsigargin and phospholipase C inhibitor (as described in the figure legends) using annexin-V staining. Annexin-V binding was assayed with a FACSCalibur instrument (Becton-Dickinson, San Jose, Calif.) using reagents from BioVision (Mountain View, Calif.) per manufacturer's protocol.

Example 24

Caspase Activation Assays

Caspase enzyme activity was measured in Jurkat cells using the Apotarget Caspase Colorimetric Protease Assay (BioSource International, Camarillo, Calif.) as per manufacturer's protocol following treatment with Compound G.

Example 25

Intracellular Calcium Measurements

Figure 3:
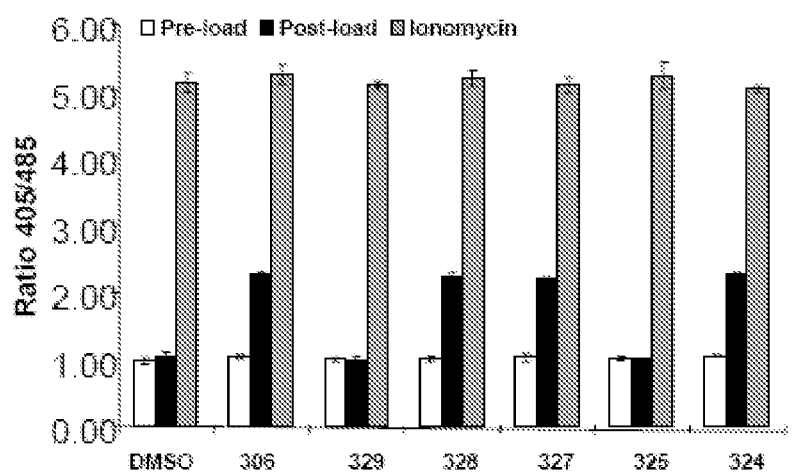
FIG. 3 is an illustrative bar graph showing the effect of Set 3 HDAC 8 selective inhibitor analogs on Calcium Flux in Jurkat cells. A calcium flux response correlates with a high percentage of apoptosis.
Figure 4:
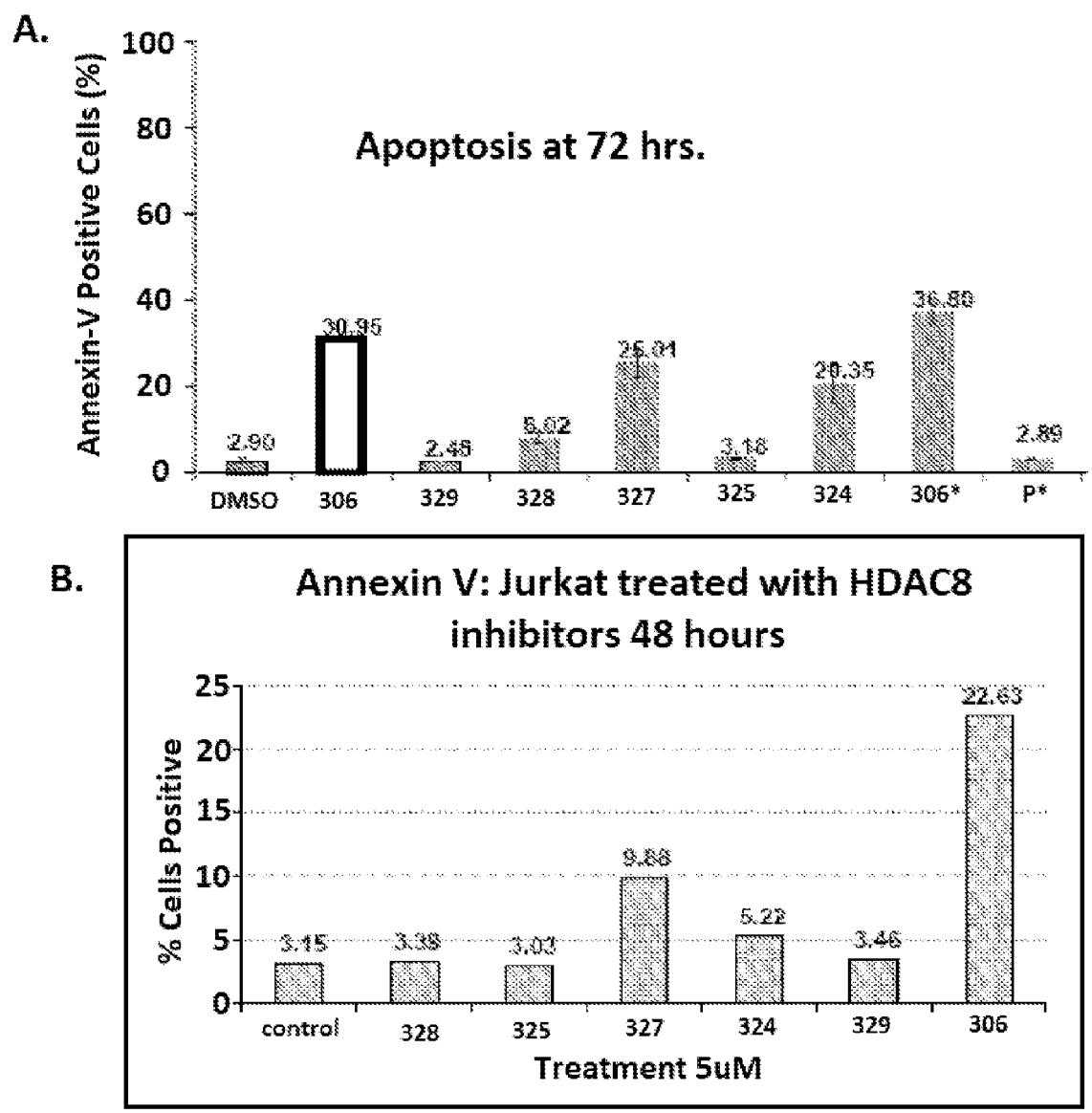
FIG. 4(A) illustrates that the same Set 3 HDAC8 selective inhibitors that induced Calcium Flux in FIG. 3 also induce apoptosis at a much later time point (72 hrs following drug addition). Apoptosis was measured by Annexin-V flow cytommetry. Compound 306* was provided unlabeled and later determined to be Compound 306. Compound P* is a fluorescent control. 4(B) is an illustrative bar graph that confirms apoptosis at an intermediate time point of 48 hrs following drug addition.

For the spectrofluorimetric measurements, cells ($1\times10^6$ cells/mL) were incubated for 1 h in Hanks' Balanced Salt Solution (HBSS; Invitrogen) containing 10% Fetal Bovine Serum and 5 µM Indol-AM (Invitrogen) at 37° C. in the dark. Cells were then harvested, centrifuged (200×g for 5 min) and washed three times with HBSS to remove extracellular Indol, and readjusted to $1\times10^6$ cells/mL in HESS. Fluorescence was monitored throughout each experiment at 37° C. with a fluorescent plate reader (Fluoroskan Ascent FL; Thermo Scientific). After a 5 min temperature equilibration period, samples were excited at 338 nm and emission was collected at 405 and 485 nm, corresponding to the $Ca^{2+}$-bound and -free Indol fluorescence emitted respectively, at 6-sec intervals over a 1 minute period. Drug (or control) was then added, and acquisition was continued for 5 minutes. Maximal ratio values were determined by the addition of 10 µM ionomycin at the end of the measurements. Intracellular $[Ca^{2+}]$ changes are shown as changes in the ratio of $Ca^{2+}$-bound and -free Indol. Results for representative compounds disclosed herein is shown in FIG. 3.

Example 26

Pharmacokinetic Analysis of HDAC Inhibitor Compounds

This study, performed in male rats with test compounds (Compound 303 and Compound 316), was designed to provide preliminary information on their pharmacokinetics. The test compounds were administered in combination by oral gavage.

The specifications for rats used on this study are as follows:
Strain: CD® IGS rats (Sprague-Dawley derived)
Source: Charles River Laboratories
Surgical modification for oral dosing: One portal vein cannula and one jugular vein cannula
Body weight range at dosing 350 to 375 g The rats were acclimatized to laboratory conditions for at least 24 hours before dosing. The evening before dosing, food was withheld from the rats and was returned immediately following the 3-hour blood collection time point. Water was provided ad libitum. The rats were housed individually in translucent polycarbonate cages.

Test compounds were prepared as 3.0 mg/ml solutions (1% MC/0.4% Cr EL in WFI).

Rats were administered a single dose of test compound in combination by oral gavage. Dose volumes were adjusted based on body weight data collected immediately prior to dosing.

The dose volume was 1 ml/kg and the nominal dosage was 3 mg/kg.

Blood samples were collected at 5 minutes, 20 minutes, 1 hour, 3 hours, 6 hours, 9 hours, and 24 hours post-dosing from orally dosed rats. The samples were collected into plasma separator Microtainer tubes with anticoagulant (lithium heparin). Plasma samples were prepared by centrifugation (5 min at 5000×g), and at least 100 µL were transferred to storage tubes and frozen on dry ice. Samples were maintained at approximately −75 C until prepared for analysis.

Plasma samples were thawed and 75 uL aliquots were transferred to centrifuge tubes to which 10 µL aliquots of internal standard solution (0.5 µg/mL) were added. The samples were not diluted with blank plasma prior to further processing. Soluble proteins were precipitated by the addition of 300 µL of methanol, followed by centrifugation (20 min at 16,000×g). The samples were evaporated to dryness and reconstituted in 100 µL of water containing 0.2% formic acid and 10% methanol. All samples were loaded onto an autosampler maintained at 6° C. and evaluated for concentrations of test compound using LC-MS/MS. lasma concentration data were evaluated using the computer program Win-Nonlin (Professional Edition, Pharsight Corporation, version 5.01). The analyses were performed using nominal sample times and a noncompartmental method with uniform weighting. Pharmacokinetic parameter estimates included terminal half-life, volume of distribution at steady state, and area under the concentration-time curve (AUC).

Pan HDAC inhibitor 3-((dimethylamino)methyl)-N-(2-(4-(hydroxycarbamoyl)phenoxy)ethyl)benzofuran-2-carboxamide was added to the cassette to serve as a standard since the pharmacokinetics of this compound have been determined previously in rats. The UC's determined for rats administered Compound 303 and Compound 316 orally at 3 mg/kg were 1.42, and 5.36 µg·h/mL, respectively. The Cmax for Compound 303 and Compound 316 were 0.310 and 0.828 µg/ml, respectively. Indole HDAC inhibitor compounds with heteroalkyl groups appear to provide better pk than indole HDAC inhibitor compounds without heteroalkyl groups.

Example 27a

Parenteral Composition

To prepare a parenteral pharmaceutical composition suitable for administration by injection, 100 mg of a water-soluble salt of a selective HDAC8 inhibitor compound described herein is dissolved in DMSO and then mixed with 10 mL of 0.9% sterile saline. The mixture is incorporated into a dosage unit form suitable for administration by injection.

In another embodiment, the following ingredients are mixed to form an injectable formulation.

| Ingredient | Amount |
| --- | --- |
| Selective HDAC8 inhibitor compound described herein | 1.2 g |
| sodium acetate buffer solution (0.4M) | 2.0 mL |
| HCl (1N) or NaOH (1M) | q.s. to suitable pH |
| water (distilled, sterile) | q.s. to 20 mL |

All of the above ingredients, except water, are combined and heated to 60-70° C. with stirring. A sufficient quantity of water at 60° C. is then added with vigorous stirring to emulsify the ingredients, and water then added q.s. to 100 g.

Example 27b

Oral Composition

To prepare a pharmaceutical composition for oral delivery, 100 mg of a selective HDAC8 inhibitor compound described herein is mixed with 750 mg of starch. The mixture is incorporated into an oral dosage unit for, such as a hard gelatin capsule, which is suitable for oral administration.

In another embodiment, the following ingredients are mixed intimately and pressed into single scored tablets.

| Ingredient | Quantity per tablet, mg |
| --- | --- |
| selective HDAC8 inhibitor compound described herein | 400 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
| --- | --- |
| selective HDAC8 inhibitor compound described herein | 200 |
| lactose, spray-dried | 148 |
| magnesium stearate | 2 |

In yet another embodiment, the following ingredients are mixed to form a suspension for oral administration.

| Ingredient | Amount |
| --- | --- |
| selective HDAC8 inhibitor compound described herein | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| distilled water | q.s. to 100 mL |

Example 27c

Sublingual (Hard Lozenge) Composition

To prepare a pharmaceutical composition for buccal delivery, such as a hard lozenge, mix 100 mg of a selective HDAC8 inhibitor compound described herein with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 27d

Inhalation Composition

To prepare a pharmaceutical composition for inhalation delivery, 20 mg of a selective HDAC8 inhibitor compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 27e

Rectal Gel Composition

To prepare a pharmaceutical composition for rectal delivery, 100 mg of a selective HDAC8 inhibitor compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 27f

Suppository Formulation

A suppository of total weight 2.5 g is prepared by mixing a selective HDAC8 inhibitor compound described herein with Witepsol™ H-15 (triglycerides of saturated vegetable fatty acid; Riches-Nelson, Inc., New York), and has the following composition:

| Ingredient | Quantity per suppository (mg) |
| --- | --- |
| selective HDAC8 inhibitor compound described herein | 500 |
| Witepsol ® H-15 | balance |

Example 27g

Topical Gel Composition

To prepare a pharmaceutical topical gel composition, 100 mg of a selective HDAC8 inhibitor compound described herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 27h

Ophthalmic Solution Composition

To prepare a pharmaceutical ophthalmic solution composition, 100 mg of a selective HDAC8 inhibitor compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and various modifications or changes are to be included within the spirit and purview of disclosure and scope of the appended claims.

What is claimed is:

1. A compound of Formula B:

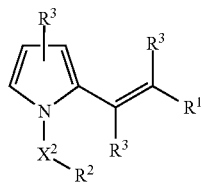

Formula B wherein:

$R^1$ is —C(=O)NHOH;

$X^2$ is a bond, —$C_1$-$C_6$alkylene-, —$C_2$-$C_6$alkenylene-, —$C_2$-$C_6$alkynylene-, —$C_1$-$C_6$heteroalkylene-, $C_1$-$C_6$-fluoroalkylene, $C_2$-$C_6$-fluoroalkenylene, $C_1$-$C_6$haloalkylene, $C_2$-$C_6$haloalkenylene, —$C_1$-$C_6$alkylene-O—, —$C_1$-$C_3$alkylene-O—$C_1$-$C_3$alkylene-, —$C_1$-$C_6$alkylene-NH—, —$C_1$-$C_3$alkylene-NH—$C_1$-$C_3$alkylene-, —$C_1$-$C_6$alkylene-C(=O)NH—, —$C_1$-$C_3$alkylene-C(=O)NH—$C_1$-$C_3$alkylene-, —$C_1$-$C_6$alkylene-NHC(=O)—, —$C_1$-$C_3$alkylene-NHC(=O)—$C_1$-$C_3$alkylene-, —$C_1$-$C_6$alkylene-S—, —$C_1$-$C_3$alkylene-S—$C_1$-$C_3$alkylene-, —$C_1$-$C_6$alkylene-S(=O)—, —$C_1$-$C_3$alkylene-S(=O)—$C_1$-$C_3$alkylene, —$C_1$-$C_6$alkylene-S(=O)$_2$—, —$C_1$-$C_3$alkylene-S(=O)$_2$—$C_1$-$C_3$alkylene, —C(=O)—, or —C(=O)—, or —C(=O)—$C_1$-$C_6$alkylene;

$R^2$ is a substituted or unsubstituted group selected from aryl, heteroaryl, $C_3$-$C_{10}$cycloalkyl, and $C_2$-$C_{10}$heterocycloalkyl; where if $R^2$ is substituted, then $R^2$ is substituted with 1, 2, or 3 groups selected from among halogen, $C_1$-$C_6$alkoxy, $C_1$-$C_6$-fluoroalkoxy, amino$C_1$-$C_6$alkoxy, $C_1$-$C_3$alkylamino$C_1$-$C_3$alkoxy, hydroxy$C_1$-$C_3$alkylamino$C_1$-$C_3$alkoxy, $C_2$-$C_8$heterocycloalkyl$C_1$-$C_3$alkoxy, $C_2$-$C_8$heterocycloalkyl$C_1$-$C_2$alkyl, —CN, —NO$_2$, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=O)$_2$—R$^{11}$, —OC(=O)N(R$^{10}$)$_2$, —NR$^{10}$C(=O)O—R$^{11}$, —OC(=O)O—R$^{11}$, —NHC(=O)NH—R$^{11}$, —OC(=O)—R$^{11}$, —N(R$^{10}$)$_2$, —$C_1$-$C_2$alkylN(R$^{10}$)$_2$, $C_1$-$C_6$alkyl, $C_1$-$C_6$-fluoroalkyl, $C_2$-$C_6$alkenyl, $C_2$-$C_6$alkynyl, $C_1$-$C_6$heteroalkyl, $C_3$-$C_8$cycloalkyl, substituted or unsubstituted $C_2$-$C_{10}$heterocycloalkyl, substituted or unsubstituted aryl, substituted or unsubstituted heteroaryl;

$R^{10}$ is hydrogen, or a substituted or unsubstituted group selected from among $C_1$-$C_6$alkyl, $C_1$-$C_6$-fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

each $R^3$ is independently hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $C_1$-$C_6$aminoalkyl;

or a pharmaceutically acceptable salt, pharmaceutically acceptable N-oxide, or pharmaceutically acceptable thereof.

2. The compound of claim 1, wherein:
each $R^3$ is independently hydrogen or $C_1$-$C_4$alkyl.

3. The compound of claim 2, wherein:
each $R^3$ is hydrogen.

4. The compound of claim 3 having the structure of Formula IIIb:

Formula IIIb

5. The compound of claim 4, wherein:
$X^2$ is a bond, —$C_1$-$C_6$alkylene-, —$C_1$-$C_6$alkylene-O—, —$C_1$-$C_3$alkylene-O—$C_1$-$C_3$alkylene-, —$C_1$-$C_6$alkylene-NH—, —$C_1$-$C_3$alkylene-NH—$C_1$-$C_3$alkylene-, —$C_1$-$C_6$alkylene-C(=O)NH—, —$C_1$-$C_3$alkylene-C(=O)NH—$C_1$-$C_3$alkylene-, —$C_1$-$C_6$alkylene-NHC(=O)—, —$C_1$-$C_3$alkylene-NHC(=O)—$C_1$-$C_3$alkylene-, —$C_1$-$C_6$alkylene-S—, —$C_1$-$C_3$alkylene-S—$C_1$-$C_3$alkylene-, —$C_1$-$C_6$alkylene-S(=O)—, —$C_1$-$C_3$alkylene-S(=O)—$C_1$-$C_3$alkylene, —$C_1$-$C_6$alkylene-S(=O)$_2$—, —$C_1$-$C_3$alkylene-S(=O)$_2$—$C_1$-$C_3$alkylene, —C(=O)—, or —C(=O)—$C_1$-$C_6$alkylene.

6. The compound of claim 5, wherein:
$R^2$ is a substituted or unsubstituted group selected from phenyl, monocyclic heteroaryl, $C_3$-$C_6$cycloalkyl, and monocyclic $C_2$-$C_6$heterocycloalkyl; where if $R^2$ is substituted, then $R^2$ is substituted with 1 or 2 groups selected from among halogen, $C_1$-$C_4$alkoxy, $C_1$-$C_4$fluoroalkoxy, $C_3$-$C_6$heterocycloalkyl$C_1$-$C_2$alkyl, —CN, —NO$_2$, —CO$_2$R$^{10}$, —C(=O)R$^{11}$, —S—R$^{11}$, —S(=O)—R$^{11}$, —S(=O)$_2$—R$^{11}$, —NHC(=O)—R$^{11}$, —C(=O)N(R$^{10}$)$_2$, —S(=O)$_2$N(R$^{10}$)$_2$, —NHS(=O)$_2$—R$^{11}$, —OC(=O)N(R$^{10}$)$_2$, —NHC(=O)O—R$^{11}$, —OC(=O)O—R$^{11}$, —NHC(=O)NH—R$^{11}$, —OC(=O)—R$^{11}$, —N(R$^{10}$)$_2$, —$C_1$-$C_2$alkylN(R$^{10}$)$_2$, $C_1$-$C_4$alkyl, $C_1$-$C_4$fluoroalkyl, $C_1$-$C_4$heteroalkyl, $C_3$-$C_6$cycloalkyl, substituted or unsubstituted $C_2$-$C_6$heterocycloalkyl, substituted or unsubstituted phenyl, substituted or unsubstituted monocyclic heteroaryl.

7. The compound of claim 6, wherein:
$X^2$ is a bond, —$C_1$-$C_4$alkylene-, —$C_1$-$C_4$alkylene-O—, —$C_1$-$C_4$alkylene-C(=O)NH—, —$C_1$-$C_4$alkylene-NHC(=O)—, —$C_1$-$C_4$alkylene-S—, —$C_1$-$C_4$alkylene-S(=O)—, —$C_1$-$C_4$alkylene-S(=O)$_2$—, —C(=O)—, or —C(=O)—$C_1$-$C_4$alkylene.

8. The compound of claim 7, wherein:
$X^2$ is —$C_1$-$C_4$alkylene- or —$C_1$-$C_4$alkylene-O—;
$R^2$ is a substituted or unsubstituted group selected from among phenyl and monocyclic heteroaryl.

9. The compound of claim 8, wherein:
$R^2$ is a substituted or unsubstituted phenyl, or a substituted or unsubstituted 5- or 6-membered monocyclic heteroaryl group; where if $R^2$ is substituted, then $R^2$ is substituted with 1 or 2 groups selected from among halogen, $C_1$-$C_4$alkoxy, $C_1$-$C_4$fluoroalkoxy, $C_3$-$C_6$heterocycloalkyl$C_1$-$C_2$alkyl, —CN, —CO$_2$R$^{10}$, —C(=O)R$^{11}$, —NHC(=O)—R$^{11}$, —C(=OC)N(R$^{10}$)$_2$, —S(=O)$_2$N(R$^{10}$)$_2$, —NHS(=O)$_2$—R$^{11}$, —N(R$^{10}$)$_2$,—$C_1$-$C_2$alkylN(R$^{10}$)$_2$, $C_1$-$C_4$alkyl, $C_1$-$C_4$fluoroalkyl, and $C_1$-$C_4$heteroalkyl.

10. The compound of claim 9, wherein:
$R^2$ is a substituted or unsubstituted group selected from phenyl, pyridinyl, pyrimidinyl, triazinyl, pyrrolyl, thiophenyl, and furanyl.

11. The compound of claim 9, wherein:
$R^2$ is a substituted or unsubstituted 5- or 6-membered monocyclic heteroaryl group.

12. The compound of claim 9, wherein:
R² is a substituted or unsubstituted phenyl.

13. The compound of claim 12, wherein:
X² is —C₁-C₄alkylene-.

14. The compound of claim 12, wherein:
X² is C₁-C₄alkylene-O—.

15. A pharmaceutical composition comprising a compound of claim 1 or an active metabolite, pharmaceutically acceptable solvate, pharmaceutically acceptable salt, pharmaceutically acceptable N-oxide, or pharmaceutically acceptable thereof and a pharmaceutically acceptable diluent, excipient, or carrier.

16. The pharmaceutical composition of claim 15, wherein the pharmaceutical composition is formulated for intravenous injection, subcutaneous injection, oral administration, inhalation, nasal administration, topical administration, ophthalmic administration or otic administration.

17. The pharmaceutical composition of claim 16, wherein the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

\* \* \* \* \*